(12) United States Patent
Kao et al.

(10) Patent No.: US 11,744,785 B2
(45) Date of Patent: Sep. 5, 2023

(54) USE OF VOLATILE COMPOSITIONS TO LIMIT OR ELIMINATE THE PERCEPTION OF MALODOR

(71) Applicant: Firmenich SA, Satigny (CH)

(72) Inventors: Huey-Ling Kao, Plainsboro, NJ (US); Stefan Alexander Ruider, Rumlang (CH); Ben Smith, Plainsboro, NJ (US); Gary Marr, Plainsboro, NJ (US); Matthew Rogers, Plainsboro, NJ (US); Mushhood Sheikh, Plainsboro, NJ (US); Zhenan Wu, Plainsboro, NJ (US); Patrick Pfister, Plainsboro, NJ (US); Anthony Alexander Birkbeck, Satigny (CH); Julien Coulomb, Satigny (CH)

(73) Assignee: FIRMENICH SA, Satigny (CH)

( * ) Notice: Subject to any disclaimer, the term of this patent is extended or adjusted under 35 U.S.C. 154(b) by 0 days.

(21) Appl. No.: 16/760,031

(22) PCT Filed: Nov. 21, 2018

(86) PCT No.: PCT/EP2018/082132
§ 371 (c)(1),
(2) Date: Apr. 28, 2020

(87) PCT Pub. No.: WO2019/101821
PCT Pub. Date: May 31, 2019

(65) Prior Publication Data
US 2020/0345601 A1    Nov. 5, 2020

Related U.S. Application Data

(60) Provisional application No. 62/589,857, filed on Nov. 22, 2017, provisional application No. 62/589,862,
(Continued)

(30) Foreign Application Priority Data

Jan. 23, 2018   (EP) .................................... 18153067
Feb. 9, 2018    (EP) .................................... 18156134
(Continued)

(51) Int. Cl.
*A61Q 15/00*     (2006.01)
*A61K 8/33*      (2006.01)
(Continued)

(52) U.S. Cl.
CPC ............... *A61K 8/33* (2013.01); *A61K 8/31* (2013.01); *A61K 8/347* (2013.01); *A61K 8/35* (2013.01);
(Continued)

(58) Field of Classification Search
CPC ........ A61L 9/01; A61L 15/46; A61L 2101/00; A61Q 15/00; A61K 8/4926; A61K 8/4973; C11B 9/0057
(Continued)

(56) References Cited

U.S. PATENT DOCUMENTS 5,268,356 A      12/1993  Decorzant et al.
2004/0072721 A1   4/2004  Vial et al.
(Continued)

FOREIGN PATENT DOCUMENTS

CN    107072911 A    8/2017
EP      2612923 A1   7/2013
(Continued)

OTHER PUBLICATIONS

STIC Search Report dated Feb. 16, 2022.*
(Continued)

*Primary Examiner* — Eisa B Elhilo

(57) ABSTRACT

The various aspects presented herein relate to the perfumery industry. More particularly, the various aspects presented
(Continued)

herein relate to the use of volatile compositions to limit, decrease or eliminate the perception of malodor. Such compositions include at least one malodor antagonist optionally combined with perfuming ingredients. Such compositions, their use in combination with delivery systems and their applications in consumer products are also objects of the present disclosure.

11 Claims, 9 Drawing Sheets

Related U.S. Application Data filed on Nov. 22, 2017, provisional application No. 62/589,841, filed on Nov. 22, 2017, provisional application No. 62/589,947, filed on Nov. 22, 2017, provisional application No. 62/754,860, filed on Nov. 2, 2018, provisional application No. 62/754,875, filed on Nov. 2, 2018, provisional application No. 62/754,849, filed on Nov. 2, 2018, provisional application No. 62/754,899, filed on Nov. 2, 2018.

(30) Foreign Application Priority Data

Feb. 21, 2018 (EP) .................................. 18157790
Feb. 22, 2018 (EP) .................................. 18158074

(51) Int. Cl.
| | | |
|---|---|---|
| *A61K 8/31* | (2006.01) | |
| *A61K 8/34* | (2006.01) | |
| *A61K 8/368* | (2006.01) | |
| *A61K 8/41* | (2006.01) | |
| *A61K 8/49* | (2006.01) | |
| *C11B 9/00* | (2006.01) | |
| *C11C 5/00* | (2006.01) | |
| *A61K 8/35* | (2006.01) | |

(52) U.S. Cl.
CPC .............. *A61K 8/368* (2013.01); *A61K 8/41* (2013.01); *A61K 8/4926* (2013.01); *A61K 8/4973* (2013.01); *C11B 9/0034* (2013.01); *C11B 9/0042* (2013.01); *C11B 9/0057* (2013.01); *C11C 5/002* (2013.01)

(58) Field of Classification Search
USPC ....................................................... 424/76.1
See application file for complete search history.

(56) References Cited

U.S. PATENT DOCUMENTS

| | | | |
|---|---|---|---|
| 2013/0216492 A1* | 8/2013 | Kato | ..................... A61Q 15/00 424/76.1 |
| 2016/0090557 A1 | 3/2016 | Frankenbach et al. | |
| 2017/0107455 A1 | 4/2017 | Frankenbach | |
| 2017/0290757 A1 | 10/2017 | Fadel et al. | |
| 2018/0021647 A1* | 1/2018 | Wrigg | ................ G09B 19/0038 434/247 |
| 2018/0361004 A1 | 12/2018 | Rogers et al. | |

FOREIGN PATENT DOCUMENTS

| | | |
|---|---|---|
| JP | 2012250958 A | 12/2012 |
| JP | 2017176134 A | 10/2017 |
| WO | 2014191047 A1 | 12/2014 |
| WO | 2016/049394 A1 | 3/2016 |

OTHER PUBLICATIONS

International Search Report and Written Opinion for International Application No. PCT/EP2018/082132, dated Sep. 13, 2019; 26 pages.

* cited by examiner $4-(2,6,6-trimethylcyclohexen-1-yl)but-3-en-2-one;
4-(2,6,6-trimethylcyclohex-2-en-1-yl)but-3-en-2-one
(+-)-(2E)-1-(2,6,6-trimethyl-2-cyclohexen-1-yl)-2-buten-1-one
*4-(2,6,6-trimethylcyclohex-2-en-1-yl)but-3-en-2-one

US 11,744,785 B2

USE OF VOLATILE COMPOSITIONS TO LIMIT OR ELIMINATE THE PERCEPTION OF MALODOR

CROSS REFERENCE TO RELATED APPLICATIONS

This application is the national phase of PCT/EP2018/082132, filed on Nov. 21, 2018, which claims priority to U.S. Provisional Patent Application Ser. No. 62/589,947, filed on Nov. 22, 2017, European Patent Application Serial No. 18157790.9, filed on Feb. 21, 2018, U.S. Provisional Patent Application Ser. No. 62/754,899, filed on Nov. 2, 2018, U.S. Provisional Patent Application Ser. No. 62/589,841, filed on Nov. 22, 2017, European Patent Application Serial No. 18156134.1, filed on Feb. 9, 2018, U.S. Provisional Patent Application Ser. No. 62/754,849, filed on Nov. 2, 2018, U.S. Provisional Patent Application Ser. No. 62/589,862, filed on Nov. 22, 2017, European Patent Application Serial No. 18153067.6, filed on Jan. 23, 2018, U.S. Provisional Patent Application Ser. No. 62/754,875, filed on Nov. 2, 2018, U.S. Provisional Patent Application Ser. No. 62/589,857, filed on Nov. 22, 2017, European Patent Application Serial No. 18158074.7, filed on Feb. 22, 2018, and U.S. Provisional Patent Application Ser. No. 62/754,860, filed on Nov. 2, 2018, the entire contents of which are hereby incorporated by reference in their entirety.

FIELD OF THE INVENTION

The various aspects presented herein relate to the perfumery industry. More particularly, the various aspects presented herein relate to the use of volatile compositions to limit, decrease or eliminate the perception of malodor. Such compositions include at least one malodor antagonist optionally combined with perfuming ingredients. Such compositions, their use in combination with delivery systems and their applications in consumer products are also objects of the present disclosure.

BACKGROUND

Malodorous smells exist in many environments and are experienced in our daily life. Such odors are created in any environment. Malodorous smells include the commercial and residential environment malodors generated by, for example, waste products, trash receptacles, toilets, cat litter, and food handling and processing. Other examples include environmental sources, such as bathroom (including feces or urine), laundry, kitchen and body malodors. Malodors are frequently complex mixtures of more than one malodorant compound which may typically include various amines, thiols, sulfides, short chain aliphatic and olefinic acids, e.g. fatty acids, and derivatives thereof. For example, residential or body related malodors typically include indole, skatole, dimethyl trisulfide (DMTS), p-cresol, and methanethiol (found in feces malodor); piperidine and morpholine (found in urine malodor); 1-octen-3-ol, geonol, butyric acid, nonene-1-ol, and borneol (found in laundry or mold malodors), pyridine and triethyl amine (found in kitchen and garbage malodors); and short chain fatty acids, such as 3-methyl-3-hydroxyhexanoic acid, 3-methylhexanoic acid, 3-2-methyl-2-hexenoic acid, 3-methyl-3-hydroxyhexanoic acid, 3-methyl-2-hexenoic acid, or 3-methyl-3-sulphanylhexanol (transpirol) (found in axilla malodors).

Malodors are not pleasant for humans and therefore there is a constant need for malodor counteracting (MOC) compositions and/or ingredients for decreasing or suppressing the perception of malodors. Various approaches exist to achieve such goal with MOC compositions and/or ingredients, and include masking, which relates to the suppression or decrease of the perception of a malodor by various mechanisms such as, for example by the MOC compositions and/or ingredients having an olfactory receptor antagonist activity.

The present disclosure provides methods to counteract malodor using volatile compositions that limit, decrease or eliminate the perception of malodor. Such compositions include at least one malodor antagonist optionally combined with perfuming ingredients. Such compositions, their use in combination with delivery systems and their applications in consumer products are also objects of the present disclosure.

SUMMARY

One aspect presented herein provides a method to inhibit, reduce, or suppress the perception of a malodor in a subject, comprising contacting the subject with at least one compound selected from the group consisting of: (1RS,6RS,11RS)-2,2,9,11-tetramethylspiro[5.5]undec-8-en-1-yl acetate, (+−)-2,2,7,11-tetramethylspiro[5.5]undec-8-en-1-yl-acetate, (+−)-2,3,7,7-tetramethylspiro[4.5]dec-2-en-6-yl acetate, (+−)-2,3,7,7-tetramethylspiro[4.5]dec-6-yl acetate, 1,5,10,10-tetramethylspiro[5.5]undec-3-en-11-yl acetate, 2,3,9,9-tetramethylspiro[4.5]decan-10-yl)acetate, (5,10,10-trimethylspiro[5.5]undec-2-en-11-yl) formate, (3,5,10,10-tetramethylspiro[5.5]undec-2-en-11-yl) acetate, (2,3,9,9-tetramethylspiro[4.5]dec-2-en-10-yl)acetate, (9,9-dimethylspiro[4.5]dec-2-en-10-yl)acetate, 10-methoxy-9,9-dimethylspiro[4.5]dec-2-ene, 4,10,10,11-tetramethylspiro[5.5]undec-2-en-11-ol, 5,10,10,11-tetramethylspiro[5.5]undec-3-en-11-ol, a mixture of 4,10,10,11-tetramethylspiro[5.5]undec-2-en-11-ol and 5,10,10,11-tetramethylspiro[5.5]undec-3-en-11-ol, 2,4,8-trimethylspiro[5.5]undec-3-en-11-ol, 2,9,11-trimethylspiro[5.5]undec-9-en-5-ol, a mixture of 2,4,8-trimethylspiro[5.5]undec-3-en-11-ol and 2,9,11-trimethylspiro[5.5]undec-9-en-5-ol, 3-methyl-5-propan-2-yl-spiro[5.5]undec-2-en-11-ol, 11-methylspiro[5.5]undecan-5-ol, 3,10,10-trimethylspiro[5.5]undec-3-en-11-ol, 4,10,10-trimethylspiro[5.5]undec-3-en-11-ol, a mixture of 3,10,10-trimethylspiro[5.5]undec-3-en-11-ol and 4,10,10-trimethylspiro[5.5]undec-3-en-11-ol [2,2-dimethyl-1-(2,4,6-trimethylcyclohex-3-en-1-yl)propyl] acetate, [2,2-dimethyl-1-(2,4,6-trimethylcyclohexyl)propyl] acetate, (1RS)-2,2-dimethyl-1-[(1SR,2SR)-2-methylcyclohexyl]propyl acetate, 9,9-dimethylspiro[4.5]dec-2-en-10-ol, 2,3,9,9-tetramethylspiro[4.5]decan-10-ol, (2,2,3,3,9,9-hexamethylspiro[4.5]decan-10-yl) acetate, 9-methoxy-8,8-dimethylspiro[4.4]non-2-ene, (8,8-dimethylspiro[4.4]non-2-en-9-yl) acetate, 2,3,8,8-tetramethylspiro[4.4]non-2-en-9-one, 2,3,9,9-tetramethylspiro[4.5]dec-2-en-10-ol, 4-methoxy-3,3-dimethylspiro[4.4]nonane, (4,9,9-trimethylspiro[4.5]dec-2-en-10-yl) acetate, 2,4,9,9-tetramethylspiro[4.5]dec-2-en-10-ol, (2,3,9,9-tetramethylspiro[4.5]dec-2-en-10-yl) formate, (2,4,9,9-tetramethylspiro[4.5]dec-2-en-10-yl) acetate, (+−)-2,3-dimethylspiro[4.5]dec-2-en-6-yl acetate, (4~{S},5~{R},6~{S},11~{S})-4,11-dimethylspiro[5.5]undecan-5-ol, 9,9-dimethylspiro[4.5]dec-2-en-10-one, 2,3,9,9-tetramethylspiro[4.5]dec-2-en-10-one, 2,4,9,9-tetramethylspiro[4.5]dec-2-en-10-one, 1,1',1',5-tetramethyl-2'-methylidenespiro[6-oxabicyclo[3.1.0]hexane-3,3'-cyclohexane], 4,9,9-trimethylspiro[4.5]dec-2-en-10-one, 2,2-dimethyl-6,6-bis(2-methylprop-2-enyl)cyclohexan-1-one, 2,2-dimethyl-5,5-bis(2-methylprop-2-enyl)cyclopentan-1-one, 2-but-3-en-2-yl-6,6-dimethyl-2-prop-2-enylcyclohexan-1-one, 2,2-bis(2-methyl-2-propen-1-yl)cyclohexanone, a mixture of 2-but-3-en-2-yl-6,6-dimethyl-2-prop-2-enylcyclohexan-1-one and 2,2-bis(2-methyl-2-propen-1-yl)cyclohexanone, 2,2-dimethyl-1-(2-methylcyclohexyl)propan-1-ol, 2,2-dimethyl-1-(3-methylcyclohexyl)propan-1-ol, a mixture of 2,2-dimethyl-1-(2-methylcyclohexyl)propan-1-ol and 2,2-dimethyl-1-(3-methylcyclohexyl)propan-1-ol, 2,2-dimethyl-6,6-bis(2-methylprop-2-enyl)cyclohexan-1-ol, 1-methoxy-2,6-dimethyl-1-prop-2-enylcyclohexane, methyl 1-(3-methylbut-2-enyl)cyclohex-2-ene-1-carboxylate, methyl 1-(3-methylbut-2-enyl)cyclohex-3-ene-1-carboxylate, a mixture of methyl 1-(3-methylbut-2-enyl)cyclohex-2-ene-1-carboxylate and methyl 1-(3-methylbut-2-enyl)cyclohex-3-ene-1-carboxylate, 2,2-dimethyl-5,5-bis(2-methylprop-2-enyl)cyclopentan-1-ol, 1-(2,6-dimethylcyclohex-3-en-1-yl)-2,2-dimethylpropan-1-ol, 1-(2-methyl-4-tricyclo[5.2.1.0$^{1,5}$]decanyl)ethyl acetate, 1-(2,4-dimethyl-4-tricyclo[5.2.1.0$^{1,5}$]decanyl)ethyl acetate, 1-((1R,3S,3aS,6S)-1,2,3-trimethyloctahydro-3a,6-methanoinden-1-yl)ethan-1-one, 1-(2,4-dimethyl-4-tricyclo[5.2.1.0ˆ{1,5}]decanyl)ethanone, 2,3,4-trimethyltricyclo[5.2.1.0ˆ{1,5}]decane-4-carbaldehyde, (2,3,4-trimethyl-4-tricyclo[5.2.1.0ˆ{1,5}]decanyl) methyl acetate, 1-((3aS,6S)-2,3-dimethyloctahydro-3a,6-methanoinden-1-yl)ethan-1-one oxime, 1,3-dimethyloctahydro-3a,6-methanoindene-1-carbaldehyde oxime, ~{N}-[1-[(1~{R},7~{R})-2,3,4-trimethyl-4-tricyclo[5.2.1.0$^{1,5}$]decanyl]ethylidene]hydroxylamine, (+-)-1-(2,4-dimethyltricyclo[5.2.1.0$^{1,5}$]dec-4-yl)ethanone, (+-)-1-(2,4-dimethyltricyclo[5.2.1.0$^{1,5}$~]dec-4-yl) ethyl acetate, 1-[(1RS,2RS,4SR,7RS)-2,3,4-trimethyltricyclo[5.2.1.0$^{1,}$~]dec-4-yl) ethanone, (E/Z)-1-[(1RS,7RS)-2,3-dimethyltricyclo[5.2.1.0$^{1,5}$]dec-4-yl) ethanone oxime, (E/Z)-1-[(1S,7S)-2,3,4-trimethyltricyclo[5.2.1.0~1.5~]dec-4-yl) ethanone oxime, (E/Z)-1-((3aS,6S)-1,2,3-trimethyloctahydro-3a,6-methanoinden-1-yl)ethanone oxime, (+-)-1-(3-methyloctahydro-3a,6-methanoinden-1-yl)ethyl acetate, [1R-(1R*,4R*,6R*,10S*)]-4,12,12-trimethyl-9-methylene-5-oxatricyclo[8.2.0.0$^{4,6}$]dodecane, 1-2,6,6-trimethyl-3-cyclohexen-1-yl-2-buten-1-one, 2-tertbutyl phenol, 5-Methyl-2-(propan-2-yl)phenol, nona-2,6-dienal, 1,1-diethoxy-3,7-dimethylocta-2,6-diene, 3-(4-hydroxy-4-methylpentyl)cyclohex-3-ene-1-carbaldehyde; 4-(4-hydroxy-4-methylpentyl)cyclohex-3-ene-1-carbaldehyde, 1,4,8-trimethyl-13-oxabicyclo[10.1.0]trideca-4,8-diene, 1,5,8-trimethyl-13-oxabicyclo[10.1.0]trideca-4,8-diene, 3-(4-tert-butylphenyl)propanal, (4R,4aS,6R)-4,4a-dimethyl-6-prop-1-en-2-yl-3,4,5,6,7,8-hexahydronaphthalen-2-one, geranyl acetate, 1-(3,3-dimethylcyclohexen-1-yl)pent-4-en-1-one; 1-(5,5-dimethylcyclohexen-1-yl)pent-4-en-1-one, 1-(3,3-dimethylcyclohexen-1-yl)pent-4-en-1-one; 1-(5,5-dimethylcyclohexen-1-yl)pent-4-en-1-one, 2-ethoxy-5-prop-1-enylphenol, 2,6,6,8-tetramethyl-9-oxatetracyclo[5.4.1.0ˆ{1,5}.0ˆ{8,10}]dodecane, nonylenic aldehyde, isobutylquinoline, cyclopentadec-4-en-1-one, (-)-(R)-3,7-dimethyl-6-octenenitrile, 2-methyl-5-propan-2-ylphenol, isopropyl quinolone, 5-hexyl-2-methylpyridine, (2,5-dimethyl-1,3-dihydroinden-2-yl)methanol, 2-pentylcyclopentan-1-one, 4-(2,6,6-trimethylcyclohexen-1-yl)but-3-en-2-one; 4-(2,6,6-trimethylcyclohex-2-en-1-yl)but-3-en-2-one, 3-methyl-4-(2,6,6-trimethylcyclohex-2-en-1-yl)but-3-en-2-one; 1-(2,6,6-trimethylcyclohex-2-en-1-yl)pent-1-en-3-one, 2,4-dimethylcyclohex-3-enecarbaldehyde, phenethylol, 3,7-dimethylocta-2,6-dienal, (2,2,2-trichloro-1-phenylethyl) acetate, 4-(2,6,6-trimethylcyclohexen-1-yl)but-3-en-2-one, phenyl ethyl acetate, 7-hydroxy-3,7-dimethyloctanal, methyl citral, 6,10-dimethylundeca-5,9-dien-2-one, 2-ethoxy-5-prop-1-enylphenol, (4-methyl-4-phenylpentan-2-yl) acetate, (+-)-3-methylcyclopentadecanone, 1-(4,8-dimethyl-12-methylidenecyclododeca-4,8-dien-1-yl)ethanone; 1-(2,6,10-trimethylcyclododeca-1,5,9-trien-1-yl)ethanone; 1-(2,6,10-trimethylcyclododeca-2,5,9-trien-1-yl)ethanone, cyclododecanone, (Z)-3,4,5,6,6-pentamethylhept-3-en-2-one, 1,4-dioxacyclohexadecane-5,16-dione, pentanol, oxacyclohexadecan-2-one, 1,1,2,3,3-pentamethyl-2,5,6,7-tetrahydroinden-4-one, (+-)-perhydro-5,5,8A-trimethyl-2-trans-naphthalenone, 2,3,3-trimethyl-2H-inden-1-one, 4-(4,8-dimethylnona-3,7-dienyl)pyridine, 4-[(1~{R},3~{R},6~{R})-2,2,3,6-tetramethylcyclohexyl]but-3-en-2-one; 4-[(1~{S},3~{S},6~{R})-2,2,3,6-tetramethylcyclohexyl]but-3-en-2-one, (+)-(1R,7R)-10,10-dimethyl-tricyclo[7.1.1.0(2,7)]undec-2-en-4-one, (9<I>E</I>)-cycloheptadec-9-en-1-one, 8,8-dimethyl-2,3,4,6,7,8~{a}-hexahydro-1~{H}-naphthalene-2-carbaldehyde; 8,8-dimethyl-2,3,5,6,7,8~{a}-hexahydro-1~{H}-naphthalene-2-carbaldehyde; 8,8-dimethyl-2,3,4,5,6,7-hexahydro-1~{H}-naphthalene-2-carbaldehyde; 2,2-dimethyloctahydro-1~{H}-2,4-~{a}-methanonaphthalen-8-one, 2,4~{a},8,8-tetramethyl-1~{a},2,4,5,6,7-hexahydro-1~{H}-cycloprop[j]naphthalen-3-one; 2,6,6,8-tetramethyltricyclo[5.3.1.0$^{1,5}$]undecan-9-one, (+-)-(3E)-4-(2,6,6-trimethyl-2-cyclohexen-1-yl)-3-buten-2-one, (+-)-3,6,8,8-tetramethyloctahydro-1H-3a,7-methanoazulen-6-ol, (1RS,2SR,5RS,7RS,8SR)-5-methyltricyclo[6.2.1.0~2,7~]undecan-4-one (A)+(1RS,2SR,5SR,7RS,8SR)-5-methyltricyclo[6.2.1.0~2,7~]undecan-4-one (B), ethyl 2,6,6-trimethyl-1,3-cyclohexadiene-1-carboxylate, ethyl 4,6,6-trimethyl-1,3-cyclohexadiene-1-carboxylate, (2-methyl-2-indanyl)methyl acetate, 2-pentylcyclopentan-1-one, (+-)-1-(2,5-dimethyl-2,3-dihydro-1H-inden-2-yl)ethanone, 4-(1,1-dimethylpropyl)-1-cyclohexanone, phenethyl alcohol, diethyl 1,4-cyclohexanedicarboxylate, (+)-(R)-3,7-dimethyl-6-octenal, 3,5,6-trimethyl-3-cyclohexene-1-carbaldehyde (A)+2,4,6-trimethyl-3-cyclohexene-1-carbaldehyde (B), 3,7-dimethylocta-2,6-dienal, 3-(4-methyl-3-pentenyl)-3-cyclohexene-1-carbaldehyde (A)+4-(4-methyl-3-pentenyl)-3-cyclohexene-1-carbaldehyde, (4<I>Z</I>,8<I>E</I>)-13-oxabicyclo[10.1.0]trideca-4,8-diene, (4E,8E)-4,8-cyclododecadien-1-one (A)+(4E,8Z)-4,8-cyclododecadien-1-one (B)+(4Z,8E)-4,8-cyclododecadien-1-one (C), 13-oxabicyclo[10.1.0]trideca-4,8-diene 2,2,7,7-tetramethyltricyclo[6.2.1.0~1,6~]undecan-6-ol, (+)-(1S,2S,3S,5R)-2,6,6-trimethylspiro[bicyclo[3.1.1]heptane-3,1'-cyclohexane]-2'-en-4'-one, (5RS,6RS)-2,6,10,10-tetramethyl-1-oxaspiro[4.5]decan-6-ol, (2,2,2-trichloro-1-phenylethyl) acetate, patchouli oil, (1~{S},3~{S},6~{R},7~{R},8~{S})-2,2,6,8-tetramethyltricyclo[5.3.1.0$^{3,8}$]undecan-3-ol, (4S,4aS,8aR)-4,8a-dimethyl-1,2,3,4,5,6,7-octahydronaphthalen-4a-ol, benzyl formate, (+-)-1-phenylethyl acetate, 3-phenyl-1-propanol, [cis-4-(2-propanyl)cyclohexyl]methanol, 2-methyl-2-indanmethanol, (2-methyl-2-indanyl)methyl acetate, (+-)-5-ethyl-2-methyl-2-indanmethanol, 5-methyl-2-indanmethanol, (+-)-2-methoxymethyl-2,5-dimethylindan, 2,5,6-trimethyl-2-indanmethanol, (+-)-(2,4,5-trimethyl-2,3-dihydro-1H-inden-2-yl)methanol, (+-)-2-ethyl-5-methyl-2-indanmethanol, (+-)-2,4-dimethyl-2-indanmethanol, (+-)-2,4,6-trimethyl-2-indanmethanol, (+-)(2,7-dimethyl-1,2,3,4-tetrahydro-2-naphthalenyl)methanol, (+-)-(2,6-dimethyl-1,2,3,4-tetrahydro-2-naphthalenyl)methanol, (+-)-(5-methoxy-2-methyl-2,3-dihydro-1H-inden-2-YL)methanol, 2,2-dimethyl-3-phenyl-1-propanol alcohol, (+-)-1,2,6-trimethyl-2-indanmethanol, (+-)-2,4-dimethyl-4,4a,5,9b- tetrahydroindeno[1,2-d][1,3]dioxine (ISOMER A)+(+−)-2,4-dimethyl-4,4a,5,9b-tetrahydroindeno[1,2-d][1,3]dioxine (ISOMER B) (A+B), 4-t-butylcyclohexanone, 1-(2,2-dimethyl-6-methylidenecyclohexyl)pent-1-en-3-one; 3-methyl-4-(2,6,6-trimethylcyclohex-2-en-1-yl)but-3-en-2-one; 1-(2,6,6-trimethylcyclohexen-1-yl)pent-1-en-3-one; 1-(2,6,6-trimethylcyclohex-2-en-1-yl)pent-1-en-3-one, 2,2-dimethyl-4-phenyl-1,3-dioxolane, (+−)-2-((methoxymethoxy)methyl)-2,5-dimethyl-2,3-dihydro-1H-indene, amyl phenylacetate, 3-phenylbutanal, 2,4-dimethyl-4-phenyloxolane, 1-(5,5-dimethylcyclohexen-1-yl)pent-4-en-1-one, 2-methyl-3-(4-methylphenyl)propanal, 3-methyl-5-phenylpentanal, (+−)-(2E)-1-(2,6,6-trimethyl-2-cyclohexen-1-yl)-2-buten-1-one, 4-(2,6,6-trimethylcyclohexen-1-yl)but-3-en-2-one; 4-(2,6,6-trimethylcyclohex-2-en-1-yl)but-3-en-2-one, 4,5,6,7,8,9,10,11,12,13-decahydrocyclododeca[d][1,3]oxazole, and combinations thereof, wherein the at least one compound is contacted in an amount sufficient to inhibit, reduce, or suppress the subject's perception of the malodor.

In one aspect, the contacting inhibits at least one olfactory receptor in the subject.

In one aspect, the at least one olfactory receptor is a butyric acid olfactory receptor.

In one aspect, the at least one olfactory receptor is a geonol olfactory receptor.

In one aspect, the at least one olfactory receptor is a 1-octen-3-ol olfactory receptor.

In one aspect, the at least one olfactory receptor is an indole/skatole olfactory receptor.

In one aspect, the at least one olfactory receptor is a DMTS olfactory receptor.

One aspect presented herein provides a method to inhibit at least one olfactory receptor in a subject, comprising contacting the subject with at least one compound selected from the group consisting of: (1RS,6RS,11RS)-2,2,9,11-tetramethylspiro[5.5]undec-8-en-1-yl acetate, (+−)-2,2,7,11-tetramethylspiro[5.5]undec-8-en-1-yl-acetate, (+−)-2,3,7,7-tetramethylspiro[4.5]dec-2-en-6-yl acetate, (+−)-2,3,7,7-tetramethylspiro[4.5]dec-6-yl acetate, 1,5,10,10-tetramethylspiro[5.5]undec-3-en-11-yl acetate, 2,3,9,9-tetramethylspiro[4.5]decan-10-yl) acetate, (5,10,10-trimethylspiro[5.5]undec-2-en-11-yl) formate, (3,5,10,10-tetramethylspiro[5.5]undec-2-en-11-yl) acetate, (2,3,9,9-tetramethylspiro[4.5]dec-2-en-10-yl)acetate, (9,9-dimethylspiro[4.5]dec-2-en-10-yl)acetate, 10-methoxy-9,9-dimethylspiro[4.5]dec-2-ene, 4,10,10,11-tetramethylspiro[5.5]undec-2-en-11-ol, 5,10,10,11-tetramethylspiro[5.5]undec-3-en-11-ol, a mixture of 4,10,10,11-tetramethylspiro[5.5]undec-2-en-11-ol and 5,10,10,11-tetramethylspiro[5.5]undec-3-en-11-ol, 2,4,8-trimethylspiro[5.5]undec-3-en-11-ol, 2,9,11-trimethylspiro[5.5]undec-9-en-5-ol, a mixture of 2,4,8-trimethylspiro[5.5]undec-3-en-11-ol and 2,9,11-trimethylspiro[5.5]undec-9-en-5-ol, 3-methyl-5-propan-2-yl-spiro[5.5]undec-2-en-11-ol, 11-methylspiro[5.5]undecan-5-ol, 3,10,10-trimethylspiro[5.5]undec-3-en-11-ol, 4,10,10-trimethylspiro[5.5]undec-3-en-11-ol, a mixture of 3,10,10-trimethylspiro[5.5]undec-3-en-11-ol and 4,10,10-trimethylspiro[5.5]undec-3-en-11-ol [2,2-dimethyl-1-(2,4,6-trimethylcyclohex-3-en-1-yl)propyl] acetate, [2,2-dimethyl-1-(2,4,6-trimethylcyclohexyl)propyl] acetate, (1RS)-2,2-dimethyl-1-[(1SR,2SR)-2-methylcyclohexyl]propyl acetate, 9,9-dimethylspiro[4.5]dec-2-en-10-ol, 2,3,9,9-tetramethylspiro[4.5]decan-10-ol, (2,2,3,3,9,9-hexamethylspiro[4.5]decan-10-yl) acetate, 9-methoxy-8,8-dimethylspiro[4.4]non-2-ene, (8,8-dimethylspiro[4.4]non-2-en-9-yl) acetate, 2,3,8,8-tetramethylspiro[4.4]non-2-en-9-one, 2,3,9,9-tetramethylspiro[4.5]dec-2-en-10-ol, 4-methoxy-3,3-dimethylspiro[4.4]nonane, (4,9,9-trimethylspiro[4.5]dec-2-en-10-yl) acetate, 2,4,9,9-tetramethylspiro[4.5]dec-2-en-10-ol, (2,3,9,9-tetramethylspiro[4.5]dec-2-en-10-yl) formate, (2,4,9,9-tetramethylspiro[4.5]dec-2-en-10-yl) acetate, (+−)-2,3-dimethylspiro[4.5]dec-2-en-6-yl acetate, (4~{S},5~{R},6~{S},11~{S})-4,11-dimethylspiro[5.5]undecan-5-ol, 9,9-dimethylspiro [4.5]dec-2-en-10-one, 2,3,9,9-tetramethylspiro[4.5]dec-2-en-10-one, 2,4,9,9-tetramethylspiro [4.5]dec-2-en-10-one, 1,1',1',5-tetramethyl-2'-methylidenespiro[6-oxabicyclo[3.1.0]hexane-3,3'-cyclohexane],4,9,9-trimethylspiro[4.5]dec-2-en-10-one, 2,2-dimethyl-6,6-bis(2-methylprop-2-enyl)cyclohexan-1-one, 2,2-dimethyl-5,5-bis(2-methylprop-2-enyl)cyclopentan-1-one, 2-but-3-en-2-yl-6,6-dimethyl-2-prop-2-enylcyclohexan-1-one, 2,2-bis(2-methyl-2-propen-1-yl)cyclohexanone, a mixture of 2-but-3-en-2-yl-6,6-dimethyl-2-prop-2-enylcyclohexan-1-one and 2,2-bis(2-methyl-2-propen-1-yl)cyclohexanone, 2,2-dimethyl-1-(2-methylcyclohexyl)propan-1-ol, 2,2-dimethyl-1-(3-methylcyclohexyl)propan-1-ol, a mixture of 2,2-dimethyl-1-(2-methylcyclohexyl)propan-1-ol and 2,2-dimethyl-1-(3-methylcyclohexyl)propan-1-ol, 2,2-dimethyl-6,6-bis(2-methylprop-2-enyl)cyclohexan-1-ol, 1-methoxy-2,6-dimethyl-1-prop-2-enylcyclohexane, methyl 1-(3-methylbut-2-enyl)cyclohex-2-ene-1-carboxylate, methyl 1-(3-methylbut-2-enyl)cyclohex-3-ene-1-carboxylate, a mixture of methyl 1-(3-methylbut-2-enyl)cyclohex-2-ene-1-carboxylate and methyl 1-(3-methylbut-2-enyl)cyclohex-3-ene-1-carboxylate, 2,2-dimethyl-5,5-bis(2-methylprop-2-enyl)cyclopentan-1-ol, 1-(2,6-dimethylcyclohex-3-en-1-yl)-2,2-dimethylpropan-1-ol, 1-(2-methyl-4-tricyclo[5.2.1.0$^{1,5}$]decanyl)ethyl acetate, 1-(2,4-dimethyl-4-tricyclo[5.2.1.0$^{1,5}$]decanyl) acetate, 1-((1R,3S,3aS,6S)-1,2,3-trimethyloctahydro-3a,6-methanoinden-1-yl)ethan-1-one, 1-(2,4-dimethyl-4-tricyclo[5.2.1.0ˆ{1,5}]decanyl)ethanone, 2,3,4-trimethyltricyclo[5.2.1.0ˆ{1,5}]decane-4-carbaldehyde, (2,3,4-trimethyl-4-tricyclo[5.2.1.0ˆ{1,5}]decanyl) methyl acetate, 1-((3aS,6S)-2,3-dimethyloctahydro-3a,6-methanoinden-1-yl)ethan-1-one oxime, 1,3-dimethyloctahydro-3a,6-methanoindene-1-carbaldehyde oxime, ~{N}-[1-[(1~{R},7~{R})-2,3,4-trimethyl-4-tricyclo[5.2.1.0$^{1,5}$]decanyl]ethylidene]hydroxylamine, (+−)-1-(2,4-dimethyltricyclo[5.2.1.0$^{1.5}$]dec-4-yl)ethanone, (+−)-1-(2,4-dimethyltricyclo[5.2.1.0~1.5~]dec-4-yl) ethyl acetate, 1-[(1RS,2RS,4SR,7RS)-2,3,4-trimethyltricyclo[5.2.1.0$^{1.}$~] dec-4-yl) ethanone, (E/Z)-1-[(1RS,7RS)-2,3-dimethyltricyclo[5.2.1.0$^{1.5}$]dec-4-yl) ethanone oxime, (E/Z)-1-[(1S,7S)-2,3,4-trimethyltricyclo[5.2.1.0~1.5~]dec-4-yl) ethanone oxime, (E/Z)-1-((3aS,6S)-1,2,3-trimethyloctahydro-3a,6-methanoinden-1-yl)ethanone oxime, (+−)-1-(3-methyloctahydro-3a,6-methanoinden-1-yl)ethyl acetate, [1R-(1R*,4R*,6R*,10S*)]-4,12,12-trimethyl-9-methylene-5-oxatricyclo[8.2.0.0$^{4,6}$]dodecane, 1-2,6,6-trimethyl-3-cyclohexen-1-yl-2-buten-1-one, 2-tertbutyl phenol, 5-Methyl-2-(propan-2-yl)phenol, nona-2,6-dienal, 1,1-diethoxy-3,7-dimethylocta-2,6-diene, 3-(4-hydroxy-4-methylpentyl)cyclohex-3-ene-1-carbaldehyde; 4-(4-hydroxy-4-methylpentyl)cyclohex-3-ene-1-carbaldehyde, 1,4,8-trimethyl-13-oxabicyclo[10.1.0]trideca-4,8-diene; 1,5,8-trimethyl-13-oxabicyclo[10.1.0]trideca-4,8-diene, 3-(4-tert-butylphenyl)propanal, (4R,4aS,6R)-4,4a-dimethyl-6-prop-1-en-2-yl-3,4,5,6,7,8-hexahydronaphthalen-2-one, geranyl acetate, 1-(3,3-dimethylcyclohexen-1-yl)pent-4-en-1-one; 1-(5,5-dimethylcyclohexen-1-yl)pent-4-en-1-one, 1-(3,3-dimethylcyclohexen-1-yl)pent-4-en-1-one; 1-(5,5-dimethylcyclohexen-1-yl)pent-4-en-1-one, 2-ethoxy-5-prop-1-enylphenol, 2,6,6,8-tetramethyl-9-oxatetracyclo[5.4.1.0^{1,5}.0^{8,10}]dodecane, nonylenic aldehyde, isobutylquinoline, cyclopentadec-4-en-1-one, (−)-(R)-3,7-dimethyl-6-octenenitrile, 2-methyl-5-propan-2-ylphenol, isopropyl quinolone, 5-hexyl-2-methylpyridine, (2,5-dimethyl-1,3-dihydroinden-2-yl)methanol, 2-pentylcyclopentan-1-one, 4-(2,6,6-trimethylcyclohexen-1-yl)but-3-en-2-one; 4-(2,6,6-trimethylcyclohex-2-en-1-yl)but-3-en-2-one, 3-methyl-4-(2,6,6-trimethylcyclohex-2-en-1-yl)but-3-en-2-one; 1-(2,6,6-trimethylcyclohex-2-en-1-yl)pent-1-en-3-one, 2,4-dimethylcyclohex-3-enecarbaldehyde, phenylethylol, 3,7-dimethylocta-2,6-dienal, (2,2,2-trichloro-1-phenylethyl) acetate, 4-(2,6,6-trimethylcyclohexen-1-yl)but-3-en-2-one, phenyl ethyl acetate, 7-hydroxy-3,7-dimethyloctanal, methyl citral, 6,10-dimethylundeca-5,9-dien-2-one, 2-ethoxy-5-prop-1-enylphenol, (4-methyl-4-phenylpentan-2-yl) acetate, (+−)-3-methylcyclopentadecanone, 1-(4,8-dimethyl-12-methylidenecyclododeca-4,8-dien-1-yl)ethanone; 1-(2,6,10-trimethylcyclododeca-1,5,9-trien-1-yl)ethanone; 1-(2,6,10-trimethylcyclododeca-2,5,9-trien-1-yl)ethanone, cyclododecanone, (Z)-3,4,5,6,6-pentamethylhept-3-en-2-one, 1,4-dioxacyclohexadecane-5,16-dione, pentanol, oxacyclohexadecan-2-one, 1,1,2,3,3-pentamethyl-2,5,6,7-tetrahydroinden-4-one, (+−)-perhydro-5,5,8A-trimethyl-2-trans-naphthalenone, 2,3,3-trimethyl-2H-inden-1-one, 4-(4,8-dimethylnona-3,7-dienyl)pyridine, 4-[(1~{R},3~{R},6~{R})-2,2,3,6-tetramethylcyclohexyl]but-3-en-2-one; 4-[(1{S},3~{S},6~{R})-2,2,3,6-tetramethylcyclohexyl]but-3-en-2-one, (+)-(1R,7R)-10,10-dimethyl-tricyclo[7.1.1.0(2,7)]undec-2-en-4-one, (9<I>E</I>)-cycloheptadec-9-en-1-one, 8,8-dimethyl-2,3,4,6,7,8~{a}-hexahydro-1~{H}-naphthalene-2-carbaldehyde; 8,8-dimethyl-2,3,5,6,7,8~{a}-hexahydro-1~{H}-naphthalene-2-carbaldehyde; 8,8-dimethyl-2,3,4,5,6,7-hexahydro-1~{H}-naphthalene-2-carbaldehyde; 2,2-dimethyl-octahydro-1~{H}-2,4~{a}-methanonaphthalen-8-one, 2,4~{a},8,8-tetramethyl-1~{a},2,4,5,6,7-hexahydro-1~{H}-cycloprop[j]naphthalen-3-one; 2,6,6,8-tetramethyl-tricyclo[5.3.1.0^{1,5}]undecan-9-one, (+−)-(3E)-4-(2,6,6-trimethyl-2-cyclohexen-1-yl)-3-buten-2-one, (+−)-3,6,8,8-tetramethyloctahydro-1H-3a,7-methanoazulen-6-ol, (1RS,2SR,5RS,7RS,8SR)-5-methyltricyclo[6.2.1.0~2,7~]undecan-4-one (A)+(1RS,2SR,5SR,7RS,8SR)-5-methyltricyclo[6.2.1.0~2,7~]undecan-4-one (B), ethyl 2,6,6-trimethyl-1,3-cyclohexadiene-1-carboxylate, ethyl 4,6,6-trimethyl-1,3-cyclohexadiene-1-carboxylate, (2-methyl-2-indanyl)methyl acetate, 2-pentylcyclopentan-1-one, (+−)-1-(2,5-dimethyl-2,3-dihydro-1H-inden-2-yl)ethanone, 4-(1,1-dimethylpropyl)-1-cyclohexanone, phenethyl alcohol, diethyl 1,4-cyclohexanedicarboxylate, (+)-(R)-3,7-dimethyl-6-octenal, 3,5,6-trimethyl-3-cyclohexene-1-carbaldehyde (A)+2,4,6-trimethyl-3-cyclohexene-1-carbaldehyde (B), 3,7-dimethylocta-2,6-dienal, 3-(4-methyl-3-pentenyl)-3-cyclohexene-1-carbaldehyde (A)+4-(4-methyl-3-pentenyl)-3-cyclohexene-1-carbaldehyde, (4<I>Z</I>,8<I>E</I>)-13-oxabicyclo[10.1.0]trideca-4,8-diene, (4E,8E)-4,8-cyclododecadien-1-one (A)+(4E,8Z)-4,8-cyclododecadien-1-one (B)+(4Z,8E)-4,8-cyclododecadien-1-one (C), 13-oxabicyclo[10.1.0]trideca-4,8-diene 2,2,7,7-tetramethyltricyclo[6.2.1.0~1,6~]undecan-6-ol, (+)-(1S,2S,3S,5R)-2,6,6-trimethylspiro[bicyclo[3.1.1]heptane-3,1'-cyclohexane]-2'-en-4'-one, (5RS,6RS)-2,6,10,10-tetramethyl-1-oxaspiro[4.5]decan-6-ol, (2,2,2-trichloro-1-phenylethyl) acetate, patchouli oil, (1{S},3~{S},6~{R},7~{R},8~{S})-2,2,6,8-tetramethyltricyclo[5.3.1.0^{3,8}]undecan-3-ol, (4S,4aS,8aR)-4,8a-dimethyl-1,2,3,4,5,6,7-octahydronaphthalen-4a-ol, benzyl formate, (+−)-1-phenylethyl acetate, 3-phenyl-1-propanol, [cis-4-(2-propanyl)cyclohexyl]methanol, 2-methyl-2-indanmethanol, (2-methyl-2-indanyl)methyl acetate, (+−)-5-ethyl-2-methyl-2-indanmethanol, 5-methyl-2-indanmethanol, (+−)-2-methoxymethyl-2,5-dimethylindan, 2,5,6-trimethyl-2-indanmethanol, (+−)-(2,4,5-trimethyl-2,3-dihydro-1H-inden-2-yl)methanol, (+−)-2-ethyl-5-methyl-2-indanmethanol, (+−)-2,4-dimethyl-2-indanmethanol, (+−)-2,4,6-trimethyl-2-indanmethanol, (+−)(2,7-dimethyl-1,2,3,4-tetrahydro-2-naphthalenyl)methanol, (+−)-(2,6-dimethyl-1,2,3,4-tetrahydro-2-naphthalenyl)methanol, (+−)-(5-methoxy-2-methyl-2,3-dihydro-1H-inden-2-YL)methanol, 2,2-dimethyl-3-phenyl-1-propanol alcohol, (+−)-1,2,6-trimethyl-2-indanmethanol, (+−)-2,4-dimethyl-4,4a,5,9b-tetrahydroindeno[1,2-d][1,3]dioxine (ISOMER A)+(+−)-2,4-dimethyl-4,4a,5,9b-tetrahydroindeno[1,2-d][1,3]dioxine (ISOMER B) (A+B), 4-t-butylcyclohexanone, 1-(2,2-dimethyl-6-methylidenecyclohexyl)pent-1-en-3-one; 3-methyl-4-(2,6,6-trimethylcyclohex-2-en-1-yl)but-3-en-2-one; 1-(2,6,6-trimethylcyclohexen-1-yl)pent-1-en-3-one; 1-(2,6,6-trimethylcyclohex-2-en-1-yl)pent-1-en-3-one, 2,2-dimethyl-4-phenyl-1,3-dioxolane, (+−)-2-((methoxymethoxy)methyl)-2,5-dimethyl-2,3-dihydro-1H-indene, amyl phenylacetate, 3-phenylbutanal, 2,4-dimethyl-4-phenyloxalane, 1-(5,5-dimethylcyclohexen-1-yl)pent-4-en-1-one, 2-methyl-3-(4-methylphenyl)propanal, 3-methyl-5-phenylpentanal, (+−)-(2E)-1-(2,6,6-trimethyl-2-cyclohexen-1-yl)-2-buten-1-one, 4-(2,6,6-trimethylcyclohexen-1-yl)but-3-en-2-one; 4-(2,6,6-trimethylcyclohex-2-en-1-yl)but-3-en-2-one, 4,5,6,7,8,9,10,11,12,13-decahydrocyclododeca[d][1,3]oxazole, and combinations thereof, wherein the at least one olfactory receptor is selected from the group consisting of: a butyric acid olfactory receptor, a geonol olfactory receptor, a 1-octen-3-ol olfactory receptor, and indole/skatole olfactory receptor, and a DMTS olfactory receptor, and wherein the at least one compound is contacted in an amount sufficient to inhibit the at least one olfactory receptor.

In one aspect, the inhibition of the at least one olfactory receptor inhibits, reduces, suppresses, the perception of a malodor in a subject.

In one aspect, the malodor is selected from the group consisting of: latrine malodor, laundry malodor, moldy malodor, and sweat malodor.

In one aspect, the at least one olfactory receptor is a butyric acid olfactory receptor. In one aspect, the butyric acid olfactory receptor is selected from the group consisting of: the OR51E1 olfactory receptor and the Olfr558 olfactory receptor.

In one aspect, the at least one compound that inhibits the butyric acid olfactory receptor is selected from the group consisting of: (1RS,6RS,11RS)-2,2,9,11-tetramethylspiro[5.5]undec-8-en-1-yl acetate, (+−)-2,2,7,11-tetramethylspiro[5.5]undec-8-en-1-yl-acetate, (+−)-2,3,7,7-tetramethylspiro[4.5]dec-2-en-6-yl acetate, (+−)-2,3,7,7-tetramethylspiro[4.5]dec-6-yl acetate, 1,5,10,10-tetramethylspiro[5.5]undec-3-en-11-yl acetate, 2,3,9,9-tetramethylspiro[4.5]decan-10-yl)acetate, (5,10,10-trimethylspiro[5.5]undec-2-en-11-yl) formate, (3,5,10,10-tetramethylspiro[5.5]undec-2-en-11-yl) acetate, (2,3,9,9-tetramethylspiro[4.5]dec-2-en-10-yl)acetate, (9,9-dimethylspiro[4.5]dec-2-en-10-yl)acetate, 10-methoxy-9,9-dimethylspiro[4.5]dec-2-ene, 4,10,10,11-tetramethylspiro[5.5]undec-2-en-11-ol, 5,10,10,11-tetramethylspiro[5.5]undec-3-en-11-ol, a mixture of 4,10,10,11- tetramethylspiro[5.5]undec-2-en-11-ol and 5,10,10,11-tetramethylspiro[5.5]undec-3-en-11-ol, 2,4,8-trimethylspiro[5.5]undec-3-en-11-ol, 2,9,11-trimethylspiro[5.5]undec-9-en-5-ol, a mixture of 2,4,8-trimethylspiro[5.5]undec-3-en-11-ol and 2,9,11-trimethylspiro[5.5]undec-9-en-5-ol, 3-methyl-5-propan-2-ylspiro[5.5]undec-2-en-11-ol, 11-methylspiro[5.5]undecan-5-ol, 3,10,10-trimethylspiro[5.5]undec-3-en-11-ol, 4,10,10-trimethylspiro[5.5]undec-3-en-11-ol, a mixture of 3,10,10-trimethylspiro[5.5]undec-3-en-11-ol and 4,10,10-trimethylspiro[5.5]undec-3-en-11-ol [2,2-dimethyl-1-(2,4,6-trimethylcyclohex-3-en-1-yl)propyl] acetate, [2,2-dimethyl-1-(2,4,6-trimethylcyclohexyl)propyl] acetate, (1RS)-2,2-dimethyl-1-[(1SR,2SR)-2-methylcyclohexyl]propyl acetate, 9,9-dimethylspiro[4.5]dec-2-en-10-ol, 2,3,9,9-tetramethylspiro[4.5]decan-10-ol, (2,2,3,3,9,9-hexamethylspiro[4.5]decan-10-yl)acetate, 9-methoxy-8,8-dimethylspiro[4.4]non-2-ene, (8,8-dimethylspiro[4.4]non-2-en-9-yl) acetate, 2,3,8,8-tetramethylspiro[4.4]non-2-en-9-one, 2,3,9,9-tetramethylspiro[4.5]dec-2-en-10-ol, 4-methoxy-3,3-dimethylspiro[4.4]nonane, (4,9,9-trimethylspiro[4.5]dec-2-en-10-yl) acetate, 2,4,9,9-tetramethylspiro[4.5]dec-2-en-10-ol, (2,3,9,9-tetramethylspiro[4.5]dec-2-en-10-yl) formate, (2,4,9,9-tetramethylspiro[4.5]dec-2-en-10-yl) acetate, (+−)-2,3-dimethylspiro[4.5]dec-2-en-6-yl acetate, (4~{S},5~{R},6~{S},11~{S})-4,11-dimethylspiro[5.5]undecan-5-ol, 9,9-dimethylspiro[4.5]dec-2-en-10-one, 2,3,9,9-tetramethylspiro[4.5]dec-2-en-10-one, 2,4,9,9-tetramethylspiro[4.5]dec-2-en-10-one, 1,1',1',5-tetramethyl-2'-methylidenespiro[6-oxabicyclo[3.1.0]hexane-3,3'-cyclohexane],4,9,9-trimethylspiro[4.5]dec-2-en-10-one, 2,2-dimethyl-6,6-bis(2-methylprop-2-enyl)cyclohexan-1-one, 2,2-dimethyl-5,5-bis(2-methylprop-2-enyl)cyclopentan-1-one, 2-but-3-en-2-yl-6,6-dimethyl-2-prop-2-enylcyclohexan-1-one, 2,2-bis(2-methyl-2-propen-1-yl) cyclohexanone, a mixture of 2-but-3-en-2-yl-6,6-dimethyl-2-prop-2-enylcyclohexan-1-one and 2,2-bis(2-methyl-2-propen-1-yl)cyclohexanone, 2,2-dimethyl-1-(2-methylcyclohexyl)propan-1-ol, 2,2-dimethyl-1-(3-methylcyclohexyl)propan-1-ol, a mixture of 2,2-dimethyl-1-(2-methylcyclohexyl)propan-1-ol and 2,2-dimethyl-1-(3-methylcyclohexyl)propan-1-ol, 2,2-dimethyl-6,6-bis(2-methylprop-2-enyl)cyclohexan-1-ol, 1-methoxy-2,6-dimethyl-1-prop-2-enylcyclohexane, methyl 1-(3-methylbut-2-enyl)cyclohex-2-ene-1-carboxylate, methyl 1-(3-methylbut-2-enyl)cyclohex-3-ene-1-carboxylate, a mixture of methyl 1-(3-methylbut-2-enyl)cyclohex-2-ene-1-carboxylate and methyl 1-(3-methylbut-2-enyl)cyclohex-3-ene-1-carboxylate, 2,2-dimethyl-5,5-bis(2-methylprop-2-enyl)cyclopentan-1-ol, 1-(2,6-dimethylcyclohex-3-en-1-yl)-2,2-dimethylpropan-1-ol, 1-(2-methyl-4-tricyclo[5.2.1.0$^{1,5}$] decanyl)ethyl acetate, 1-(2,4-dimethyl-4-tricyclo[5.2.1.0$^{1,5}$] decanyl)ethyl acetate, 1-((1R,3S,3aS,6S)-1,2,3-trimethyloctahydro-3a,6-methanoinden-1-yl)ethan-1-one, 1-(2,4-dimethyl-4-tricyclo[5.2.1.0^{1,5}]decanyl)ethanone, 2,3,4-trimethyltricyclo[5.2.1.0^{1,5}]decane-4-carbaldehyde, (2,3,4-trimethyl-4-tricyclo[5.2.1.0^{1,5}]decanyl) methyl acetate, 1-((3aS,6S)-2,3-dimethyloctahydro-3a,6-methanoinden-1-yl)ethan-1-one oxime, 1,3-dimethyloctahydro-3a,6-methanoindene-1-carbaldehyde oxime, ~{N}-[1-[(1~{R},7~{R})-2,3,4-trimethyl-4-tricyclo[5.2.1.0$^{1,5}$]decanyl]ethylidene]hydroxylamine, (+−)-1-(2,4-dimethyltricyclo[5.2.1.0$^{1,5}$]dec-4-yl) ethanone, (+−)-1-(2,4-dimethyltricyclo[5.2.1.0~1.5~]dec-4-yl) ethyl acetate, 1-[(1RS,2RS,4SR,7RS)-2,3,4-trimethyltricyclo[5.2.1.0$^{1,}$~] dec-4-yl) ethanone, (E/Z)-1-[(1RS,7RS)-2,3-dimethyltricyclo[5.2.1.0$^{1,5}$]dec-4-yl) ethanone oxime, (E/Z)-1-[(1S,7S)-2,3,4-trimethyltricyclo[5.2.1.0~1.5~]dec-4-yl) ethanone oxime, (E/Z)-1-((3aS,6S)-1,2,3-trimethyloctahydro-3a,6-methanoinden-1-yl)ethanone oxime, (+−)-1-(3-methyloctahydro-3a,6-methanoinden-1-yl)ethyl acetate, and combinations thereof.

In one aspect, at least one olfactory receptor is a geonol olfactory receptor. In one aspect, the geonol olfactory receptor is selected from the group consisting of: the OR11A1 olfactory receptor, the OR2M3 olfactory receptor, the OR1A1 olfactory receptor, the OR2W1 olfactory receptor, the OR1A1 olfactory receptor, the OR2J3 olfactory receptor, the OR4Q3 olfactory receptor, and the OR5K1 olfactory receptor.

In one aspect, the at least one compound that inhibits the geonol olfactory receptor is selected from the group consisting of: [1R-(1R*,4R*,6R*,10S*)]-4,12,12-trimethyl-9-methylene-5-oxatricyclo[8.2.0.0$^{4,6}$]dodecane, 1-(2,6,6-trimethyl-1-cyclohex-3-enyl)but-2-en-1-one, 2-tertbutyl phenol, 5-Methyl-2-(propan-2-yl)phenol, nona-2,6-dienal, 1,1-diethoxy-3,7-dimethylocta-2,6-diene, 3-(4-hydroxy-4-methylpentyl)cyclohex-3-ene-1-carbaldehyde; 4-(4-hydroxy-4-methylpentyl)cyclohex-3-ene-1-carbaldehyde, 1,4,8-trimethyl-13-oxabicyclo[10.1.0]trideca-4,8-diene; 1,5,8-trimethyl-13-oxabicyclo[10.1.0]trideca-4,8-diene, 3-(4-tert-butylphenyl)propanal, (4R,4aS,6R)-4,4a-dimethyl-6-prop-1-en-2-yl-3,4,5,6,7,8-hexahydronaphthalen-2-one, geranyl acetate, 1-(3,3-dimethylcyclohexen-1-yl)pent-4-en-1-one; 1-(5,5-dimethylcyclohexen-1-yl)pent-4-en-1-one, 1-(3,3-dimethylcyclohexen-1-yl)pent-4-en-1-one; 1-(5,5-dimethylcyclohexen-1-yl)pent-4-en-1-one, 2-ethoxy-5-prop-1-enylphenol, 2,6,6,8-tetramethyl-9-oxatetracyclo[5.4.1.0^{1,5}].0^{8,10}]dodecane, nonylenic aldehyde, isobutylquinoline, cyclopentadec-4-en-1-one, (−)-(R)-3,7-dimethyl-6-octenenitrile, 2-methyl-5-propan-2-ylphenol, isopropyl quinolone, 5-hexyl-2-methylpyridine, (2,5-dimethyl-1,3-dihydroinden-2-yl)methanol, 2-pentylcyclopentan-1-one, 4-(2,6,6-trimethylcyclohexen-1-yl)but-3-en-2-one; 4-(2,6,6-trimethylcyclohex-2-en-1-yl)but-3-en-2-one, 3-methyl-4-(2,6,6-trimethylcyclohex-2-en-1-yl)but-3-en-2-one; 1-(2,6,6-trimethylcyclohex-2-en-1-yl)pent-1-en-3-one, 2,4-dimethylcyclohex-3-enecarbaldehyde, phenylethylol, 3,7-dimethylocta-2,6-dienal, (2,2,2-trichloro-1-phenylethyl) acetate, 4-(2,6,6-trimethylcyclohexen-1-yl)but-3-en-2-one, phenyl ethyl acetate, 7-hydroxy-3,7-dimethyloctanal, methyl citral, 6,10-dimethylundeca-5,9-dien-2-one, 2-ethoxy-5-prop-1-enylphenol, and combinations thereof.

In one aspect, the at least one olfactory receptor is a 1-octen-3-ol olfactory receptor. In one aspect, the 1-octen-3-ol olfactory receptor is selected from the group consisting of: the OR2W1 olfactory receptor, the OR1A1 olfactory receptor, the OR2J3 olfactory receptor, the OR4Q3 olfactory receptor, and the OR5K1 olfactory receptor.

In one aspect, the at least one compound that inhibits the 1-octen-3-ol olfactory receptor is selected from the group consisting of: isobutylquinoline, 2-tertbutyl phenol, [1R-(1R*,4R*,6R*,10S*)]-4,12,12-trimethyl-9-methylene-5-oxatricyclo[8.2.0.0$^{4,6}$]dodecane, (4-methyl-4-phenylpentan-2-yl)acetate, (+−)-3-methylcyclopentadecanone, 1-(4,8-dimethyl-12-methylidenecyclododeca-4,8-dien-1-yl) ethanone; 1-(2,6,10-trimethylcyclododeca-1,5,9-trien-1-yl) ethanone; 1-(2,6,10-trimethylcyclododeca-2,5,9-trien-1-yl) ethanone, cyclopentadec-4-en-1-one, cyclododecanone, 2,4-dimethylcyclohex-3-enecarbaldehyde, 1,4-dioxacyclohexadecane-5,16-dione, pentanol, oxacyclohexadecan-2-one, 1,1,2,3,3-pentamethyl-2,5,6,7-tetrahydroinden-4-one, (+−)-perhydro-5,5,8A-trimethyl-2-trans-naphthalenone, 2,3,3-trimethyl-2H-inden-1-one, 4-(4,8-dimethylnona-3,7-dienyl)pyridine, 4-[(1~{R},3~{R}, 6~{R})-2,2,3,6-tetramethylcyclohexyl]but-3-en-2-one; 4-[(1~{S},3~{S},6~{R})-2,2,3,6-tetramethylcyclohexyl]but-3-en-2-one, (+)-(1R,7R)-10,10-dimethyl-tricyclo[7.1.1.0(2,7)]undec-2-en-4-one, (9<I>E</I>)-cycloheptadec-9-en-1-one, 8,8-dimethyl-2,3,4,6,7,8~{a}-hexahydro-1~{H}-naphthalene-2-carbaldehyde; 8,8-dimethyl-2,3,5,6,7,8~{a}-hexahydro-1~{H}-naphthalene-2-carbaldehyde; 8,8-dimethyl-2,3,4,5,6,7-hexahydro-1~{H}-naphthalene-2-carbaldehyde; 2,2-dimethyl-octahydro-1~{H}-2,4~{a}-methanonapthalen-8-one, 2,4~{a},8,8-tetramethyl-1~{a},2,4,5,6,7-hexahydro-1~{H}-cycloprop[j]naphthalen-3-one; 2,6,6,8-tetramethyltricyclo[5.3.1.0^{1,5}]undecan-9-one, methyl citral, and combinations thereof.

In one aspect, the at least one olfactory receptor is a DMTS olfactory receptor. In one aspect, the DMTS olfactory receptor is selected from the group consisting of: the OR4S2 olfactory receptor, the OR52N5 olfactory receptor, the OR2L13 olfactory receptor, the OR2AJ1 olfactory receptor, the OR4C15 olfactory receptor, the OR5AC2 olfactory receptor, the OR8H3 olfactory receptor, the OR11G2 olfactory receptor, the OR52N2 olfactory receptor, the OR5T1 olfactory receptor, the OR2W1 olfactory receptor, the Olfr1193 olfactory receptor, the Olfr1093 olfactory receptor, the Olfr1097 olfactory receptor, the Olfr166 olfactory receptor, the Olfr169 olfactory receptor, the Olfr738 olfactory receptor, the Olfr742 olfactory receptor, the Olfr207 olfactory receptor, the Olfr665 olfactory receptor, the Olfr669 olfactory receptor, and the Olfr1211 olfactory receptor.

In one aspect, the at least one compound that inhibits the DMTS olfactory receptor is selected from the group consisting of: (+−)-(3E)-4-(2,6,6-trimethyl-2-cyclohexen-1-yl)-3-buten-2-one, (+−)-3,6,8,8-tetramethyloctahydro-1H-3a,7-methanoazulen-6-ol, nona-2,6-dienal, (+−)-perhydro-5,5,8A-trimethyl-2-trans-naphthalenone, (1RS,2SR,5RS,7RS,8SR)-5-methyltricyclo[6.2.1.0~2,7~]undecan-4-one (A)+(1RS,2SR,5SR,7RS,8SR)-5-methyltricyclo[6.2.1.0~2,7~]undecan-4-one (B), ethyl2,6,6-trimethyl-1,3-cyclohexadiene-1-carboxylate, 1,4,8-trimethyl-13-oxabicyclo[10.1.0]trideca-4,8-diene; 1,5,8-trimethyl-13-oxabicyclo[10.1.0]trideca-4,8-diene, ethyl 4,6,6-trimethyl-1,3-cyclohexadiene-1-carboxylate, (2-methyl-2-indanyl) methyl acetate, 2-pentylcyclopentan-1-one, (+−)-1-(2,5-dimethyl-2,3-dihydro-1H-inden-2-yl)ethanone, 4-(1,1-dimethylpropyl)-1-cyclohexanone, 4-(2,6,6-trimethylcyclohexen-1-yl)but-3-en-2-one; 4-(2,6,6-trimethylcyclohex-2-en-1-yl)but-3-en-2-one, phenethyl alcohol, diethyl 1,4-cyclohexanedicarboxylate, (+)-(R)-3,7-dimethyl-6-octenal, 3,5,6-trimethyl-3-cyclohexene-1-carbaldehyde (A)+2,4,6-trimethyl-3-cyclohexene-1-carbaldehyde (B), 3,7-dimethylocta-2,6-dienal, 3-(4-methyl-3-pentenyl)-3-cyclohexene-1-carbaldehyde (A)+4-(4-methyl-3-pentenyl)-3-cyclohexene-1-carbaldehyde, 3-methyl-4-(2,6,6-trimethylcyclohex-2-en-1-yl)but-3-en-2-one; 1-(2,6,6-trimethylcyclohex-2-en-1-yl)pent-1-en-3-one, (4<I>Z</I>,8<I>E</I>)-13-oxabicyclo[10.1.0]trideca-4,8-diene, (4E,8E)-4,8-cyclododecadien-1-one (A)+(4E,8Z)-4,8-cyclododecadien-1-one (B)+(4Z,8E)-4,8-cyclododecadien-1-one (C), (1<I>R</I>,4<I>Z</I>,8<I>E</I>,12<I>R</I>)-13-oxabicyclo[10.1.0]trideca-4,8-diene, (4<I>Z</I>,8<I>E</I>)-13-oxabicyclo[10.1.0]trideca-4,8-diene, 2,2,7,7-tetramethyltricyclo[6.2.1.0~1,6~]undecan-6-ol, (2,5-dimethyl-1,3-dihydroinden-2-yl)methanol, 8,8-dimethyl-2,3,4,6,7,8~{a}-hexahydro-1~{H}-naphthalene-2-carbaldehyde; 8,8-dimethyl-2,3,5,6,7,8~{a}-hexahydro-1~{H}-naphthalene-2-carbaldehyde; 8,8-dimethyl-2,3,4,5,6,7-hexahydro-1~{H}-naphthalene-2-carbaldehyde; 2,2-dimethyl-octahydro-1~{H}-2,4~{a}-methanonapthalen-8-one, (+)-(1S,2S,3S,5R)-2,6,6-trimethylspiro[bicyclo[3.1.1]heptane-3,1'-cyclohexen]-2'-en-4'-one, 1-(3,3-dimethylcyclohexen-1-yl)pent-4-en-1-one; 1-(5,5-dimethylcyclohexen-1-yl)pent-4-en-1-one, (5RS,6RS)-2,6,10,10-tetramethyl-1-oxaspiro[4.5]decan-6-OL, (2,2,2-trichloro-1-phenylethyl) acetate, patchouli oil, (1~{S},3~{S},6~{R},7~{R},8~{S})-2,2,6,8-tetramethyltricyclo[5.3.1.0^{3,8}]undecan-3-ol, (4S,4aS,8aR)-4,8a-dimethyl-1,2,3,4,5,6,7-octahydronaphthalen-4a-ol, and combinations thereof.

In one aspect, the at least one olfactory receptor is an indole/skatole olfactory receptor. In one aspect, the indole/skatole olfactory receptor is selected from the group consisting of: the OR52N2 olfactory receptor, the OR11G2 olfactory receptor, the OR5AC2 olfactory receptor, the OR4C15 olfactory receptor, the OR8S1 olfactory receptor, the OR11H6 olfactory receptor, the OR11H4 olfactory receptor, the Olfr665 olfactory receptor, the Olfr740 olfactory receptor, the Olfr743 olfactory receptor, the Olfr746 olfactory receptor, the Olfr738 olfactory receptor, the Olfr739 olfactory receptor, the Olfr741 olfactory receptor, the Olfr742 olfactory receptor, the Olfr744 olfactory receptor, the Olfr748 olfactory receptor and the Olfr749 olfactory receptor.

In one aspect, the at least one compound that inhibits the indole/skatole olfactory receptor is selected from the group consisting of: benzyl formate, (+−)-1-phenylethyl acetate, (+−)-(3E)-4-(2,6,6-trimethyl-2-cyclohexen-1-yl)-3-buten-2-one, (+−)-perhydro-5,5,8A-trimethyl-2-trans-naphthalenone, 3-phenyl-1-propanol, [cis-4-(2-propanyl)cyclohexyl]methanol, 2-methyl-2-indanmethanol, (2-methyl-2-indanyl) methyl acetate, (+−)-5-ethyl-2-methyl-2-indanmethanol, (2,5-dimethyl-1,3-dihydroinden-2-yl)methanol, 5-methyl-2-indanmethanol, (+−)-1-(2,5-dimethyl-2,3-dihydro-1H-inden-2-yl)ethanone, 4-(1,1-dimethylpropyl)-1-cyclohexanone, (+−)-2-methoxymethyl-2,5-dimethylindan, 2,5,6-trimethyl-2-indanmethanol, (+−)-(2,4,5-trimethyl-2,3-dihydro-1H-inden-2-yl)methanol, (+−)-2-ethyl-5-methyl-2-indanmethanol, (+−)-2,4-dimethyl-2-indanmethanol, (+−)-2,4,6-trimethyl-2-indanmethanol, (+−)(2,7-dimethyl-1,2,3,4-tetrahydro-2-napthhalenyl)methanol, (+−)-(2,6-dimethyl-1,2,3,4-tetrahydro-2-naphthalenyl)methanol, (+−)-(5-methoxy-2-methyl-2,3-dihydro-1H-inden-2-YL)methanol, 2,2-dimethyl-3-phenyl-1-propanol alcohol, 1-(3,3-dimethylcyclohexen-1-yl)pent-4-en-1-one; 1-(5,5-dimethylcyclohexen-1-yl)pent-4-en-1-one, (+−)-1,2,6-trimethyl-2-indanmethanol, (+−)-2,4-dimethyl-4,4a,5,9b-tetrahydroindeno[1,2-d][1,3]dioxine (ISOMER A)+(+−)-2,4-dimethyl-4,4a,5,9b-tetrahydroindeno[1,2-d][1,3]dioxine (ISOMER B) (A+B), 8,8-dimethyl-2,3,4,6,7,8~{a}-hexahydro-1~{H}-naphthalene-2-carbaldehyde; 8,8-dimethyl-2,3,5,6,7,8~{a}-hexahydro-1~{H}-naphthalene-2-carbaldehyde; 8,8-dimethyl-2,3,4,5,6,7-hexahydro-1~{H}-naphthalene-2-carbaldehyde; 2,2-dimethyl-octahydro-1~{H}-2,4~{a}-methanonaphthalen-8-one, 4-t-butylcyclohexanone, 1-(2,2-dimethyl-6-methylidenecyclohexyl)pent-1-en-3-one; 3-methyl-4-(2,6,6-trimethylcyclohex-2-en-1-yl)but-3-en-2-one; 1-(2,6,6-trimethylcyclohexen-1-yl)pent-1-en-3-one; 1-(2,6,6-trimethylcyclohex-2-en-1-yl)pent-1-en-3-one, 2,2-dimethyl-4-phenyl-1,3-dioxolane, (4E,8E)-4,8-cyclododecadien-1-one (A)+(4E,8Z)-4,8-cyclododecadien-1-one (B)+(4Z,8E)-4,8-cyclododecadien-1-one (C), (+−)-2-((methoxymethoxy)methyl)-2,5-dimethyl-2,3-dihydro-1H-indene, 3-(4-hydroxy-4-methylpentyl)cyclohex-3-ene-1-carbaldehyde; 4-(4-hydroxy-4-methylpentyl)cyclohex-3-ene-1-carbaldehyde, amyl phenylacetate, 4-(2,6,6- trimethylcyclohexen-1-yl)but-3-en-2-one; 4-(2,6,6-trimethylcyclohex-2-en-1-yl)but-3-en-2-one, 1,1,2,3,3-pentamethyl-2,5,6,7-tetrahydroinden-4-one, 3-phenylbutanal, 2,4-dimethyl-4-phenyloxolane, 1-(5,5-dimethylcyclohexen-1-yl)pent-4-en-1-one, [1R-(1R*,4R*,6R*,10S*)]-4,12,12-trimethyl-9-methylene-5-oxatricyclo [8.2.0.0$^{4,6}$]dodecane, 2-methyl-3-(4-methylphenyl)propanal, 3-methyl-5-phenylpentanal, isopropyl quinolone, (+−)-(2E)-1-(2,6,6-trimethyl-2-cyclohexen-1-yl)-2-buten-1-one, 4-(2,6,6-trimethylcyclohexen-1-yl)but-3-en-2-one; 4-(2,6,6-trimethylcyclohex-2-en-1-yl)but-3-en-2-one, 4,5,6,7,8,9,10,11,12,13-decahydrocyclododeca[d][1,3]oxazole, and combinations thereof.

In one aspect, the perfuming composition comprises a malodor receptor antagonist system comprising at least one ingredient selected from the group of Table 1 and a non-functional perfume accord.

In one aspect, the perfuming composition comprises:
(i) from about 2 wt % to about 85 wt %, of a malodor receptor antagonist system comprising at least one ingredient selected from the group of Table 1;
(ii) from about 15 wt % to 98 wt % of a functional perfume accord comprising at least 2 perfuming ingredient(s) provided that any ingredient listed in Table 1 is excluded, the accord having a tonality preferably selected from floral, citrus and jasmine; and
(iii) optionally a non-functional perfume accord.

In one aspect, the perfuming composition is incorporated into a consumer product.

DETAILED DESCRIPTION

Figure 1:
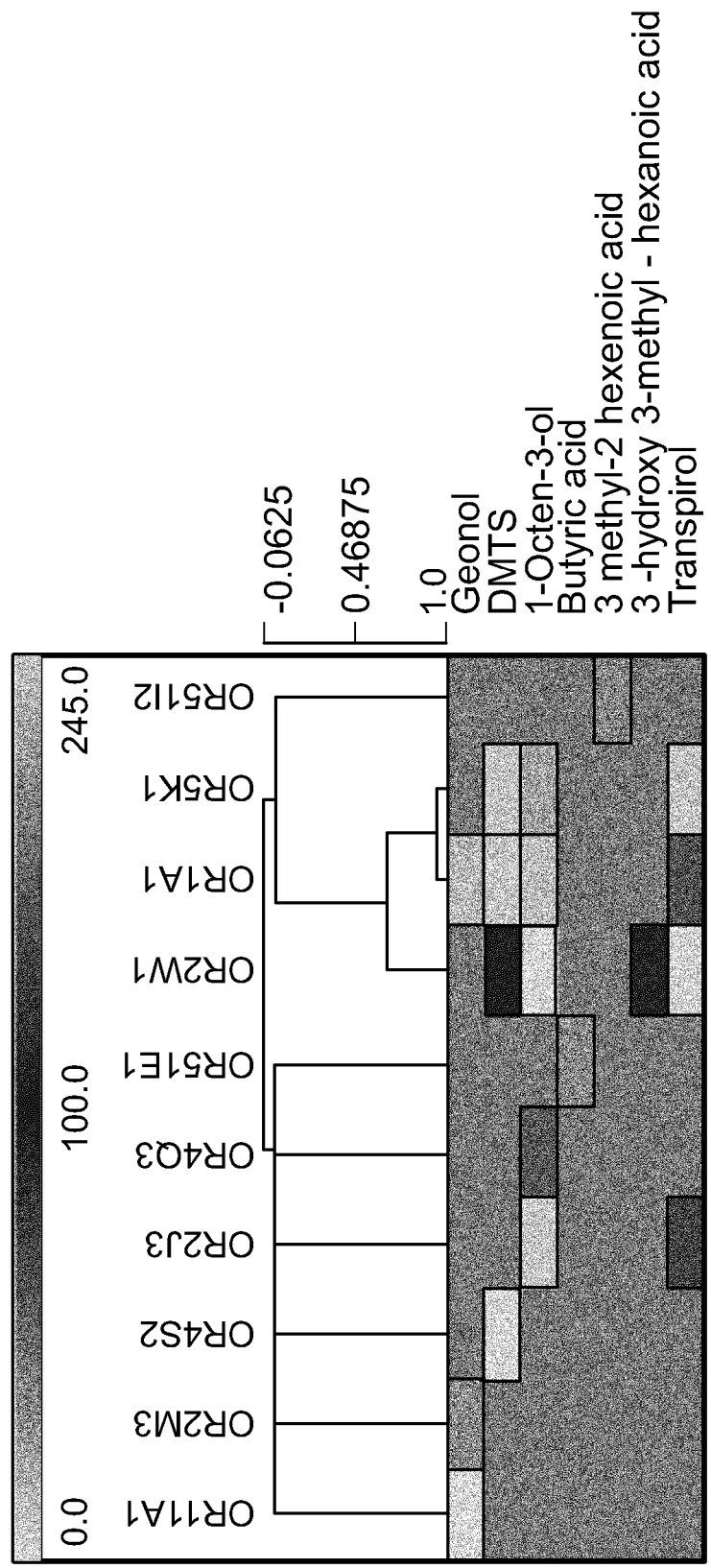
FIG. 1 depicts certain malodor targets and olfactory receptors according to some aspects presented herein.

In the following description, reference is made to specific aspects which may be practiced, which is shown by way of illustration. These aspects are described in detail to enable those skilled in the art to practice the invention described herein, and it is to be understood that other aspects may be utilized and that logical changes may be made without departing from the scope of the aspects presented herein. The following description of example aspects is, therefore, not to be taken in a limited sense, and the scope of the various aspects presented herein is defined by the appended claims.

The Abstract is provided to comply with 37 C.F.R. § 1.72(b) to allow the reader to quickly ascertain the nature and gist of the technical disclosure. The Abstract is submitted with the understanding that it will not be used to interpret or limit the scope or meaning of the claims.

Some aspects presented herein provide a method to inhibit, reduce, or suppress the perception of a malodor in a subject, comprising contacting the subject with at least one compound in an amount sufficient to inhibit, reduce, suppress the subject's perception of the malodor. In some aspects, the malodor is selected from the group consisting of: latrine malodor, laundry malodor, moldy malodor, and sweat malodor.

Non-limiting examples of kitchen malodor include any type of malodor present in a residential or commercial kitchen including, but not limited to: kitchen garbage odors that may result from the disposal of raw or cooked meat, fish, vegetables, fruit and/or dairy products; odors experienced during food preparation, especially odors generated from raw fish, raw garlic and raw onions; cooking odors, especially odors produced when cooking meat, fish, onion and/or garlic; the odor of cooking oil used for frying foods; burnt odors that may originate from the over-cooking or burning of foods; odors originating from the kitchen sink drain; odors originating from in-sink disposal units; and, odors originating from a refrigerator.

Non-limiting examples of bathroom or latrine malodor include any malodor type of malodor present in a residential or public bathroom/restroom including, but not limited to: odors present immediately after the use of the toilet; lingering toilet odors; stale urine odor; and, moldy or musty odors that often originate in damp areas of the bathroom such as around the bath or shower.

Non-limiting examples of tobacco odor include the odor generated during smoking of cigarettes, cigars or tobacco pipes, or the stale smoke odor that lingers after use of tobacco products in a room, or the odor originating from an ash tray that comprises debris from cigarettes, cigars or tobacco pipes.

Non-limiting examples of pet odor include any type of odor associated with a domestic pet, especially a cat or a dog, and includes, but is not limited to: fecal odors from litter boxes; urine odors from litter boxes; lingering urine odors; wet-dog odor; and, pet-bed odor.

Non-limiting examples of body malodor include any type of odor produced by the human body including, but not limited to: axillary (armpit) odor, scalp odor, foot odor and vaginal odor. "Body malodor" may also mean an odor that originates on the human body and is transferred to another substrate such as a textile; this may include, for example, the odor of worn socks, or the odor of worn sportswear.

Non-limiting examples of laundry malodor include soils such as those found on mechanics' clothes; food handlers, especially butchers' and kitchen workers' clothes; sewer workers' clothes; bar tenders' clothes; fire fighters' clothes; farm clothes; athletic clothing; factory workers' clothes; heavy machinery operators' clothes, mold, odors found in laundry machines, and the like.

Without intending to be limited to any particular theory, residential, body, or laundry malodors are typically due to various malodor targets such as indole, skatole, dimethyl trisulfide (DMTS), dimethyl disulfide (DMDS), p-cresol, and methanethiol (found in feces malodor); piperidine and morpholine (found in urine malodor); 1-octen-3-ol, geonol, butyric acid, nonene-1-ol, and borneol (found in laundry or mold malodors), pyridine and triethyl amine (found in kitchen and garbage malodors); and short chain fatty acids, such as 3-methyl-3-hydroxyhexanoic acid, 3-methyl-hexanoic acid, 3-2-methyl-2-hexenoic acid, 3-methyl-3-hydroxyhexanoic acid, 3-methyl-2-hexenoic acid, or 3-methyl-3-sulphanylhexanol (transpirol) (found in axilla malodors). As used herein, "malodor target" is meant to designate a molecular component of fecal malodor, sweat malodor, or moldy malodor, or laundry malodor.

In some aspects, the malodor target is butyric acid in the latrine malodor described in Lin et al, Environ. Sci. Technol., 2013, 47 (14), pp 7876-7882.

In some aspects, the malodor target is butyric acid in the latrine malodor described in Chappuis et al, Environ. Sci. Technol., 2015, 49 (10), pp 6134-6140.

In some aspects, the malodor target is butyric acid, according to the latrine malodor described in Yasuhara, Chemosphere, 1980, 9 (9), pp 587-592.

In some aspects, the malodor target is butyric acid according to the body malodor described in Gabbanini et al, Skin Res. & Technol, 2009, 15 (4), pp 503-510.

In some aspects, the malodor target is butyric acid according to the body malodor described in Gallager et al, B. J. Dermatol., 2008, 159 (4), pp 780-791.

In some aspects, the malodor target is butyric acid according to the laundry malodor described in McQueen et al, J. Textile Inst., 2008, 99 (6), pp 515-523.

In some aspects, the malodor target is butyric acid according to the malodor described in Susya et al, Atmospheric Environment, 2011, 45 (6), pp 1236-1241.

In some aspects, the malodor target is butyric acid according to the oral malodor described in Van den Velds et al, J. Dental Res., 2009, 88 (3), pp 285-289.

In some aspects, the malodor target is selected from the malodor targets disclosed in Munk et al, J. Surf. Deterg. 4 (2001) 385-394.

In some aspects, the malodor target is selected from the malodor targets disclosed in Chung et al, Fibers Polym. 13 (2012) 740-747.

In some aspects, the malodor target is selected from the malodor targets disclosed in Takeuchi et al, Flav. Fragr. J. 27 (2012) 89-94.

In some aspects, the malodor target is selected from the malodor targets disclosed in Nagoh et al, Tenside Surf. Det. 42 (2005) 7-12.

In some aspects, the malodor target is selected from the malodor targets disclosed in Stapleton et al, Lett. Appl. Microbiol. 56 (2013) 299-306.

In some aspects, the malodor target is selected from the malodor targets disclosed in Stapleton et al, J. Chromatography. A 1295 (2013) 147-151.

In some aspects, the malodor contains at least one malodor target selected from the group consisting of: indole/skatole, DMTS, butyric acid, 1-octen-3-ol, geonol, nonene-1-ol, and borneol.

In some aspects, the malodor target may be butyric acid. Alternatively, the malodor target may be 1-octen-3-ol. Alternatively, the malodor target may be geonol. Alternatively, the malodor target may be nonene-1-ol. Alternatively, the malodor target may be borneol. Alternatively, the malodor target may be indole/skatole. Alternatively, the malodor target may be DMTS.

Without intending to be limited to any particular theory, the at least one compound inhibits, reduces, or suppresses the subject's perception of the malodor by inhibiting at least one olfactory receptor responsible for the subject's perception of the malodor. In some aspects, the at least one compound is an antagonist of the at least one olfactory receptor.

As used herein, the term "olfactory receptor responsible for the subject's perception of the malodor" refers to an olfactory receptor that is activated by a malodor target.

As used herein, the term "butyric acid olfactory receptor" refers to an olfactory receptor that is activated by the malodor target butyric acid.

Non-limiting examples of butyric acid olfactory receptors suitable for inhibition by compounds of the present disclosure include: Olfr558 and OR51E1.

As used herein, the terms "geonol olfactory receptor," or refer to an olfactory receptor that is activated by the malodor target geonol. In some aspects, geonol is (+−)-perhydro-4alpha,8Abeta-dimethyl-4Anaphthalenol.

Non-limiting examples of geonol olfactory receptors suitable for inhibition by compounds of the present disclosure include: OR11A1, OR2M3, OR1A1, OR2W1, OR1A1, OR2J3, OR4Q3, and OR5K1.

As used herein, the terms "geosmin," or "geonol," refer to (4S,4aS,8aR)-4,8a-dimethyl-1,2,3,4,5,6,7-octahydronaphthalen-4a-ol.

As used herein, the term "1-octen-3-ol olfactory receptor" refers to an olfactory receptor that is activated by the malodor target 1-octen-3-ol.

Non-limiting examples of 1-octen-3-ol olfactory receptors suitable for inhibition by compounds of the present disclosure include: OR2W1, OR1A1, OR2J3, OR4Q3, and OR5K1.

As used herein, the term "DMTS" refers to an olfactory receptor that is activated by the malodor target DMTS.

Non-limiting examples of DMTS olfactory receptors suitable for inhibition by compounds of the present disclosure include: OR4S2, OR52N5, OR2L13, OR2AJ1, OR4C15, OR5AC2, OR8H3, OR11G2, OR52N2, OR5T1, OR2W1, OR1A1, Olfr1193, Olfr1093, Olfr1097, Olfr166, Olfr169, Olfr738, Olfr742, Olfr207, Olfr665, Olfr669, Olfr1211, Olfr263 and Olfr173.

As used herein, the term "indole/skatole" refers to an olfactory receptor that is activated by the malodor targets indole and/or skatole.

Non-limiting examples of indole/skatole olfactory receptors suitable for inhibition by compounds of the present disclosure include: OR52N2, OR11G2, OR5AC2, OR4C15, the OR8S1, OR11H6, OR11H4, Olfr665, Olfr738, Olfr739, Olfr740, Olfr741, Olfr742, Olfr743, Olfr744, Olfr746, Olfr748 and Olfr749.

Other examples of olfactory receptors suitable for inhibition by compounds of the present invention include orthologs of the human olfactory receptors described herein. Other examples of olfactory receptors suitable for inhibition by compounds of the present invention include Olfr263, Olfr403, Olfr137, Olfr735, Olfr173, Olfr96, Olfr164, Olfr558, Olfr1193, and Olfr641. Such receptors may have from between 70 and 90% amino acid identity with their corresponding human olfactory receptor ortholog.

As used herein, the terms "antagonists," "inhibitor," "blockers," "suppressors," "counteractants" and "modulators" of olfactory receptors are used interchangeably to refer to inhibitory, blocking, suppressing, or modulating molecules identified using in vivo, ex vivo and in vitro assays for olfactory transduction, e.g., ligands, antagonists, and their homologs and mimetics. Inhibitors are compounds that, e.g., bind to, partially or totally block stimulation, decrease, suppress, prevent, delay activation, inactivate, desensitize, or down regulate olfactory transduction, e.g., antagonists. Activators are compounds that, e.g., bind to, stimulate, increase, open activate, facilitate, enhance activation, sensitize, or up regulate olfactory transduction, e.g., agonists. Modulators include compounds that, e.g., alter the interaction of a receptor with: extracellular proteins that bind activators or inhibitor (e.g., odorant-binding proteins, ebnerin and other members of the hydrophobic carrier family); G proteins; kinases (e.g., homologs of rhodopsin kinase and beta adrenergic receptor kinases that are involved in deactivation and desensitization of a receptor); and arrestins, which also deactivate and desensitize receptors.

The ability of compounds of the present disclosure to inhibit or antagonize a butyric acid olfactory receptor may be determined by any suitable method readily selected by one of ordinary skill in the art, such as, for example, via an ex vivo cultured neuron assay, or via an in vitro assay using a cell line that expresses a butyric acid olfactory receptor.

Such assays for inhibitors and activators include, e.g., expressing OR family members in cells or cell membranes, applying putative modulator compounds, in the presence or absence of malodor molecules, e.g. butyric acid, and then determining the functional effects on olfactory transduction, as described in the Examples below. Samples or assays comprising OR family members that are treated with a potential inhibitor are compared to control samples without the inhibitor to examine the extent of inhibition. Control samples (untreated with inhibitors, but treated with the malodor) are assigned a relative maximal OR activity value of 100%. Inhibition of an OR is achieved when the normalized OR activity value relative to the control is about 80%, optionally 50% or 25-0%. Alternatively, in some aspects, inhibition of an OR is achieved if the $IC_{50}$ value of the antagonist compound is equal to or less than 1500 µM. Alternatively, in some aspects, inhibition of an OR is achieved if the $IC_{50}$ value of the antagonist compound is equal to or less than 200 µM. Alternatively, in some aspects, inhibition of an OR is achieved if the $IC_{50}$ value of the antagonist compound is equal to or less than 20 µM.

As used herein, the term "olfactory receptor", or "OR" refers to one or more members of a family of G protein-coupled receptors ($GPCR^5$) that are expressed in olfactory cells. Olfactory receptor cells can also be identified on the basis of morphology or by the expression of proteins specifically expressed in olfactory cells. OR family members may have the ability to act as receptors for odorants and induce an olfactory transduction cascade.

Compounds According to Some Aspects of the Present Disclosure

Figure 2:
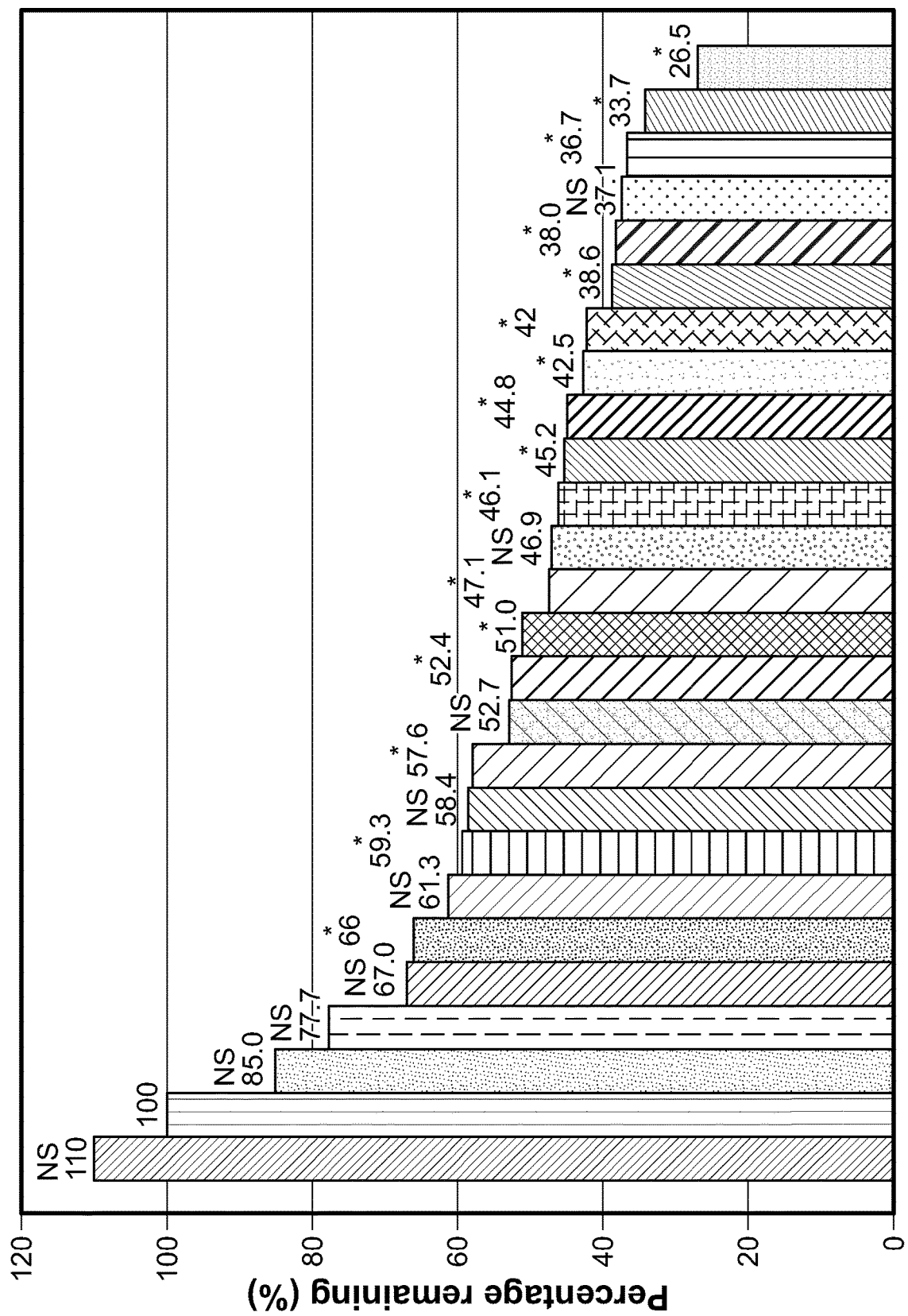
FIG. 2 shows the ability of compounds according to some aspects of the present disclosure to reduce the perceived intensity of geonol in human sensory panel tests. Many of these compounds are shown to inhibit the activity of a geonol olfactory receptor. NS, the % geonol perception remaining is not statistically different compared to geonol alone at isointense concentrations; Asterisk (*), the % geonol perception remaining is statistically different compared to geonol alone at isointense concentrations.

Referring to FIG. 2, and Example 1, the following compounds were shown to be antagonists of the geonol olfactory receptor: [1R-(1R*,4R*,6R*,10S*)]-4,12,12-trimethyl-9-methylene-5-oxatricyclo[8.2.0.0$^{4,6}$]dodecane, 1-(2,6,6-trimethyl-1-cyclohex-3-enyl)but-2-en-1-one, 2-tertbutyl phenol, 5-Methyl-2-(propan-2-yl)phenol, nona-2,6-dienal, 1,1-diethoxy-3,7-dimethylocta-2,6-diene, 3-(4-hydroxy-4-methylpentyl)cyclohex-3-ene-1-carbaldehyde; 4-(4-hydroxy-4-methylpentyl)cyclohex-3-ene-1-carbaldehyde, 1,4,8-trimethyl-13-oxabicyclo[10.1.0]trideca-4,8-diene; 1,5,8-trimethyl-13-oxabicyclo[10.1.0]trideca-4,8-diene, 3-(4-tert-butylphenyl)propanal, (4R,4aS,6R)-4,4a-dimethyl-6-prop-1-en-2-yl-3,4,5,6,7,8-hexahydronaphthalen-2-one, geranyl acetate, 1-(3,3-dimethylcyclohexen-1-yl)pent-4-en-1-one; 1-(5,5-dimethylcyclohexen-1-yl)pent-4-en-1-one, 1-(3,3-dimethylcyclohexen-1-yl)pent-4-en-1-one; 1-(5,5-dimethylcyclohexen-1-yl)pent-4-en-1-one, 2-ethoxy-5-prop-1-enylphenol, 8,9-epoxy-2,6,6,8-tetramethyl-tricyclo[5.3.1.0 (1,5)]undecane, nonylenic aldehyde, isobutylquinoline, cyclopentadec-4-en-1-one, (−)-(R)-3,7-dimethyl-6-octenenitrile, 2-methyl-5-propan-2-ylphenol, isopropyl quinolone, 5-hexyl-2-methylpyridine, (2,5-dimethyl-1,3-dihydroinden-2-yl)methanol, 2-pentylcyclopentan-1-one, 4-(2,6,6-trimethylcyclohexen-1-yl)but-3-en-2-one; 4-(2,6,6-trimethylcyclohex-2-en-1-yl)but-3-en-2-one, 3-methyl-4-(2,6,6-trimethylcyclohex-2-en-1-yl)but-3-en-2-one; 1-(2,6,6-trimethylcyclohex-2-en-1-yl)pent-1-en-3-one, 2,4-dimethylcyclohex-3-enecarbaldehyde, phenylethylol, 3,7-dimethylocta-2,6-dienal, (2,2,2-trichloro-1-phenylethyl) acetate, 4-(2,6,6-trimethylcyclohexen-1-yl)but-3-en-2-one, phenyl ethyl acetate, 7-hydroxy-3,7-dimethyloctanal, methyl citral, 6,10-dimethylundeca-5,9-dien-2-one, and 2-ethoxy-5-prop-1-enylphenol.

Referring to Example 2, the following compounds were shown to be antagonists of the 1-octen-3-ol olfactory receptor: isobutylquinoline, 2-tertbutyl phenol, [1R-(1R*,4R*, 6R*,10S*)]-4,12,12-trimethyl-9-methylene-5-oxatricyclo [8.2.0.0$^{4,6}$]dodecane, (4-methyl-4-phenylpentan-2-yl) acetate, (+−)-3-methylcyclopentadecanone, 1-(4,8-dimethyl-12-methylidenecyclododeca-4,8-dien-1-yl) ethanone; 1-(2,6,10-trimethylcyclododeca-1,5,9-trien-1-yl) ethanone; 1-(2,6,10-trimethylcyclododeca-2,5,9-trien-1-yl) ethanone, cyclopentadec-4-en-1-one, cyclododecanone, 2,4-dimethylcyclohex-3-enecarbaldehyde, 1,4-dioxacyclohexadecane-5,16-dione, pentanol, oxacyclohexadecan-2-one, 1,1,2,3,3-pentamethyl-2,5,6,7-tetrahydroinden-4-one, (+−)-perhydro-5,5,8A-trimethyl-2-trans-naphthalenone, 2,3,3-trimethyl-2H-inden-1-one, 4-(4, 8-dimethylnona-3,7-dienyl)pyridine, 4-[(1~{R},3~{R}, 6~{R})-2,2,3,6-tetramethylcyclohexyl]but-3-en-2-one; 4-[(1~{S},3~{S},6~{R})-2,2,3,6-tetramethylcyclohexyl] but-3-en-2-one, (+)-(1R,7R)-10,10-dimethyl-tricyclo [7.1.1.0(2,7)]undec-2-en-4-one, (9*E*)-cycloheptadec-9-en-1-one, 8,8-dimethyl-2,3,4,6,7,8~{a}-hexahydro-1~{H}-naphthalene-2-carbaldehyde; 8,8-dimethyl-2,3,5,6,7,8~{a}-hexahydro-1~{H}-naphthalene-2-carbaldehyde; 8,8-dimethyl-2,3,4,5,6,7-hexahydro-1~{H}-naphthalene-2-carbaldehyde; 2,2-dimethyl-octahydro-1~{H}-2,4~{a}-methanonapthalen-8-one, 2,4~{a},8,8-tetramethyl-1~{a},2,4,5,6,7-hexahydro-1~{H}-cycloprop[j]naphthalen-3-one; 2,6,6,8-tetramethyltricyclo[5.3.1.0^{1,5}]undecan-9-one, and methyl citral.

In some aspects, antagonists of the geonol olfactory receptor may also be antagonists of the 1-octen-3-ol olfactory receptor. Alternatively, antagonists of the geonol olfactory receptor may inhibit, reduce, or suppress a subject's perception of the 1-octen-3-ol malodor target.

Referring to Example 3, the following compounds were shown to be antagonists of the butyric acid olfactory receptor: (2~{R})-2,4,10,10-tetramethylspiro[5.5]undec-3-en-11-one; (5~{S})-3,5,10,10-tetramethylspiro[5.5]undec-3-en-11-one, (+−)-3-methylcyclopentadecanone, (3~{R})-3-methylcyclopentadec-5-en-1-one, (−)-(3R)-3-methyl-1-cyclopentadecanone, methoxycyclododecane, 1-(4,8-dimethyl-12-methylidenecyclododeca-4,8-dien-1-yl)ethanone; 1-(2,6,10-trimethylcyclododeca-1,5,9-trien-1-yl)ethanone; 1-(2,6,10-trimethylcyclododeca-2,5,9-trien-1-yl)ethanone, 1-(2,6,6-trimethylcyclohexen-1-yl)hepta-1,6-dien-3-one; 1-(2,6,6-trimethylcyclohex-2-en-1-yl)hepta-1,6-dien-3-one, (+−)-(2E)-1-(2,6,6-trimethyl-2-cyclohexen-1-yl)-2-buten-1-one, (2E)-1-(2,6,6-trimethyl-1-cyclohexen-1-yl)-2-buten-1-one, 1-(2,6,6-trimethyl-1-cyclohex-3-enyl)but-2-en-1-one, [1R-(1R*,4R*,6R*,10S*)]-4,12,12-trimethyl-9-methylene-5-oxatricyclo[8.2.0.0$^{4,6}$]dodecane, (4-methyl-4-phenylpentan-2-yl) acetate, and (ethoxymethoxy)cyclododecane.

Antagonists for the Butyric Acid Olfactory Receptor

In some aspects, the compounds of the present disclosure have an $IC_{50}$ for the butyric acid olfactory receptor from 6 to 200 μM. In some aspects, the compounds of the present disclosure have an $IC_{50}$ for the butyric acid olfactory receptor from 8 to 200 μM. In some aspects, the compounds of the present disclosure have an $IC_{50}$ for the butyric acid olfactory receptor from 10 to 200 μM. In some aspects, the compounds of the present disclosure have an $IC_{50}$ for the butyric acid olfactory receptor from 20 to 200 μM. In some aspects, the compounds of the present disclosure have an $IC_{50}$ for the butyric acid olfactory receptor from 30 to 200 μM. In some aspects, the compounds of the present disclosure have an $IC_{50}$ for the butyric acid olfactory receptor from 40 to 200 μM. In some aspects, the compounds of the present disclosure have an $IC_{50}$ for the butyric acid olfactory receptor from 50 to 200 μM. In some aspects, the compounds of the present disclosure have an $IC_{50}$ for the butyric acid olfactory receptor from 60 to 200 μM. In some aspects, the compounds of the present disclosure have an $IC_{50}$ for the butyric acid olfactory receptor from 70 to 200 μM. In some aspects, the compounds of the present disclosure have an $IC_{50}$ for the butyric acid olfactory receptor from 80 to 200 μM. In some aspects, the compounds of the present disclosure have an $IC_{50}$ for the butyric acid olfactory receptor from 90 to 200 μM. In some aspects, the compounds of the present disclosure have an $IC_{50}$ for the butyric acid olfactory receptor from 100 to 200 μM. In some aspects, the compounds of the present disclosure have an $IC_{50}$ for the butyric acid olfactory receptor from 120 to 200 μM. In some aspects, the compounds of the present disclosure have an $IC_{50}$ for the butyric acid olfactory receptor from 140 to 200 μM. In some aspects, the compounds of the present disclosure have an $IC_{50}$ for the butyric acid olfactory receptor from 160 to 200 μM. In some aspects, the compounds of the present disclosure have an $IC_{50}$ for the butyric acid olfactory receptor from 180 to 200 μM.

In some aspects, the compounds of the present disclosure have an $IC_{50}$ for the butyric acid olfactory receptor from 4 to 180 μM. In some aspects, the compounds of the present disclosure have an $IC_{50}$ for the butyric acid olfactory receptor from 4 to 160 μM. In some aspects, the compounds of the present disclosure have an $IC_{50}$ for the butyric acid olfactory receptor from 4 to 140 μM. In some aspects, the compounds of the present disclosure have an $IC_{50}$ for the butyric acid olfactory receptor from 4 to 120 μM. In some aspects, the compounds of the present disclosure have an $IC_{50}$ for the butyric acid olfactory receptor from 4 to 100 μM. In some aspects, the compounds of the present disclosure have an $IC_{50}$ for the butyric acid olfactory receptor from 4 to 90 μM. In some aspects, the compounds of the present disclosure have an $IC_{50}$ for the butyric acid olfactory receptor from 4 to 80 μM. In some aspects, the compounds of the present disclosure have an $IC_{50}$ for the butyric acid olfactory receptor from 4 to 70 μM. In some aspects, the compounds of the present disclosure have an $IC_{50}$ for the butyric acid olfactory receptor from 4 to 60 μM. In some aspects, the compounds of the present disclosure have an $IC_{50}$ for the butyric acid olfactory receptor from 4 to 50 μM. In some aspects, the compounds of the present disclosure have an $IC_{50}$ for the butyric acid olfactory receptor from 4 to 40 μM. In some aspects, the compounds of the present disclosure have an $IC_{50}$ for the butyric acid olfactory receptor from 4 to 30 μM. In some aspects, the compounds of the present disclosure have an $IC_{50}$ for the butyric acid olfactory receptor from 4 to 20 μM. In some aspects, the compounds of the present disclosure have an $IC_{50}$ for the butyric acid olfactory receptor from 4 to 10 μM. In some aspects, the compounds of the present disclosure have an $IC_{50}$ for the butyric acid olfactory receptor from 4 to 9 μM. In some aspects, the compounds of the present disclosure have an $IC_{50}$ for the butyric acid olfactory receptor from 4 to 8 μM. In some aspects, the compounds of the present disclosure have an $IC_{50}$ for the butyric acid olfactory receptor from 4 to 7 μM. In some aspects, the compounds of the present disclosure have an $IC_{50}$ for the butyric acid olfactory receptor from 4 to 6 μM. In some aspects, the compounds of the present disclosure have an $IC_{50}$ for the butyric acid olfactory receptor from 4 to 5 μM.

In some aspects, the compounds of the present disclosure have an $IC_{50}$ for the butyric acid olfactory receptor of 4, or 5, or 6, or 7, or 8, or 9, or 10, or 20, or 30, or 40, or 50, or 60, or 70, or 80, or 90, or 100, or 120, or 140, or 160, or 180, or 200 μM.

In some aspects, the at least one compound that inhibits the butyric acid olfactory receptor is selected from the group consisting of: (1RS,6RS,11RS)-2,2,9,11-tetramethylspiro[5.5]undec-8-en-1-yl acetate, (+−)-2,2,7,11-tetramethylspiro[5.5]undec-8-en-1-yl-acetate, (+−)-2,3,7,7-tetramethylspiro[4.5]dec-2-en-6-yl acetate, (+−)-2,3,7,7-tetramethylspiro[4.5]dec-6-yl acetate, 1,5,10,10-tetramethylspiro[5.5]undec-3-en-11-yl acetate, 2,3,9,9-tetramethylspiro[4.5]decan-10-yl)acetate, (5,10,10-trimethylspiro[5.5]undec-2-en-11-yl) formate, (3,5,10,10-tetramethylspiro[5.5]undec-2-en-11-yl) acetate, (2,3,9,9-tetramethylspiro[4.5]dec-2-en-10-yl)acetate, (9,9-dimethylspiro[4.5]dec-2-en-10-yl)acetate, 10-methoxy-9,9-dimethylspiro[4.5]dec-2-ene, 4,10,10,11-tetramethylspiro[5.5]undec-2-en-11-ol, 5,10,10,11-tetramethylspiro[5.5]undec-3-en-11-ol, a mixture of 4,10,10,11-tetramethylspiro[5.5]undec-2-en-11-ol and 5,10,10,11-tetramethylspiro[5.5]undec-3-en-11-ol, 2,4,8-trimethylspiro

[5.5]undec-3-en-11-ol, 2,9,11-trimethylspiro[5.5]undec-9-en-5-ol, a mixture of 2,4,8-trimethylspiro[5.5]undec-3-en-11-ol and 2,9,11-trimethylspiro[5.5]undec-9-en-5-ol, 3-methyl-5-propan-2-ylspiro[5.5]undec-2-en-11-ol, 11-methylspiro[5.5]undecan-5-ol, 3,10,10-trimethylspiro[5.5]undec-3-en-11-ol, 4,10,10-trimethylspiro[5.5]undec-3-en-11-ol, a mixture of 3,10,10-trimethylspiro[5.5]undec-3-en-11-ol and 4,10,10-trimethylspiro[5.5]undec-3-en-11-ol [2,2-dimethyl-1-(2,4,6-trimethylcyclohex-3-en-1-yl)propyl] acetate, [2,2-dimethyl-1-(2,4,6-trimethylcyclohexyl)propyl] acetate, (1RS)-2,2-dimethyl-1-[(1SR,2SR)-2-methylcyclohexyl]propyl acetate, 9,9-dimethylspiro[4.5]dec-2-en-10-ol, 2,3,9,9-tetramethylspiro[4.5]decan-10-ol, (2,2,3,3,9,9-hexamethylspiro[4.5]decan-10-yl)acetate, 9-methoxy-8,8-dimethylspiro[4.4]non-2-ene, (8,8-dimethylspiro[4.4]non-2-en-9-yl) acetate, 2,3,8,8-tetramethylspiro[4.4]non-2-en-9-one, 2,3,9,9-tetramethylspiro[4.5]dec-2-en-10-ol, 4-methoxy-3,3-dimethylspiro[4.4]nonane, (4,9,9-trimethylspiro[4.5]dec-2-en-10-yl) acetate, 2,4,9,9-tetramethylspiro[4.5]dec-2-en-10-ol, (2,3,9,9-tetramethylspiro[4.5]dec-2-en-10-yl) formate, (2,4,9,9-tetramethylspiro[4.5]dec-2-en-10-yl) acetate, (+−)-2,3-dimethylspiro[4.5]dec-2-en-6-yl acetate, (4~{S},5~{R},6~{S},11~{S})-4,11-dimethylspiro[5.5]undecan-5-ol, 9,9-dimethylspiro[4.5]dec-2-en-10-one, 2,3,9,9-tetramethylspiro[4.5]dec-2-en-10-one, 2,4,9,9-tetramethylspiro[4.5]dec-2-en-10-one, 1,1',1',5-tetramethyl-2'-methylidenespiro[6-oxabicyclo[3.1.0]hexane-3,3'-cyclohexane],4,9,9-trimethylspiro[4.5]dec-2-en-10-one, 2,2-dimethyl-6,6-bis(2-methylprop-2-enyl)cyclohexan-1-one, 2,2-dimethyl-5,5-bis(2-methylprop-2-enyl)cyclopentan-1-one, 2-but-3-en-2-yl-6,6-dimethyl-2-prop-2-enylcyclohexan-1-one, 2,2-bis(2-methyl-2-propen-1-yl) cyclohexanone, a mixture of 2-but-3-en-2-yl-6,6-dimethyl-2-prop-2-enylcyclohexan-1-one and 2,2-bis(2-methyl-2-propen-1-yl)cyclohexanone, 2,2-dimethyl-1-(2-methylcyclohexyl)propan-1-ol, 2,2-dimethyl-1-(3-methylcyclohexyl)propan-1-ol, a mixture of 2,2-dimethyl-1-(2-methylcyclohexyl)propan-1-ol and 2,2-dimethyl-1-(3-methylcyclohexyl)propan-1-ol, 2,2-dimethyl-6,6-bis(2-methylprop-2-enyl)cyclohexan-1-ol, 1-methoxy-2,6-dimethyl-1-prop-2-enylcyclohexane, methyl 1-(3-methylbut-2-enyl)cyclohex-2-ene-1-carboxylate, methyl 1-(3-methylbut-2-enyl)cyclohex-3-ene-1-carboxylate, a mixture of methyl 1-(3-methylbut-2-enyl)cyclohex-2-ene-1-carboxylate and methyl 1-(3-methylbut-2-enyl)cyclohex-3-ene-1-carboxylate, 2,2-dimethyl-5,5-bis(2-methylprop-2-enyl)cyclopentan-1-ol, 1-(2,6-dimethylcyclohex-3-en-1-yl)-2,2-dimethylpropan-1-ol, 1-(2-methyl-4-tricyclo[5.2.1.0$^{1,5}$] decanyl)ethyl acetate, 1-(2,4-dimethyl-4-tricyclo[5.2.1.0$^{1,5}$] decanyl) acetate, 1-((1R,3S,3aS,6S)-1,2,3-trimethyloctahydro-3a,6-methanoinden-1-yl)ethan-1-one, 1-(2,4-dimethyl-4-tricyclo[5.2.1.0^{1,5}]decanyl)ethanone, 2,3,4-trimethyltricyclo[5.2.1.0^{1,5}]decane-4-carbaldehyde, (2,3,4-trimethyl-4-tricyclo[5.2.1.0^{1,5}]decanyl) methyl acetate, 1-((3aS,6S)-2,3-dimethyloctahydro-3a,6-methanoinden-1-yl)ethan-1-one oxime, 1,3-dimethyloctahydro-3a,6-methanoindene-1-carbaldehyde oxime, ~{N}-[1-[(1~{R},7~{R})-2,3,4-trimethyl-4-tricyclo [5.2.1.0$^{1,5}$]decanyl]ethylidene]hydroxylamine, (+−)-1-(2,4-dimethyltricyclo[5.2.1.0$^{1,5}$]dec-4-yl)ethanone, (+−)-1-(2,4-dimethyltricyclo[5.2.1.0~1.5~]dec-4-yl) ethyl acetate, 1-[(1RS,2RS,4SR,7RS)-2,3,4-trimethyltricyclo[5.2.1.0~] dec-4-yl) ethanone, (E/Z)-1-[(1RS,7RS)-2,3-dimethyltricyclo[5.2.1.0$^{1,5}$]dec-4-yl) ethanone oxime, (E/Z)-1-[(1S,7S)-2,3,4-trimethyltricyclo[5.2.1.0~1.5~]dec-4-yl) ethanone oxime, (E/Z)-1-((3aS,6S)-1,2,3-trimethyloctahydro-3a,6-methanoinden-1-yl)ethanone oxime, (+−)-1-(3-methyloctahydro-3a,6-methanoinden-1-yl)ethyl acetate, and combinations thereof.

In some aspects, an antagonist of the butyric acid olfactory receptor is a compound having the structure:

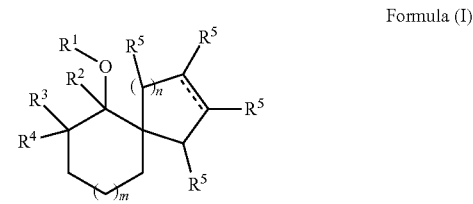

Formula (I)

in a form of any one of the stereoisomers or as a mixture thereof
wherein the index m represents 0 or 1;
wherein the index n represents 1 or 2;
wherein the dotted lines represent a single or a double bond;
wherein $R^1$ represents a hydrogen atom, a methyl group or a $R^6C(=O)$ group
wherein $R^6$ represents a hydrogen atom or a methyl, ethyl, propyl or isopropyl group;
wherein $R^2$, $R^3$ and $R^4$ represent, independently from each other, a hydrogen atom or a methyl group;
wherein each $R^5$ represent, independently from each other, a hydrogen atom or a $C_{1-3}$ alkyl or alkenyl group; and
wherein the compound of Formula (I) is an antagonist of a butyric acid olfactory receptor.

For the sake of clarity, by the expression "any one of its stereoisomers", or the similar, it is meant the normal meaning understood by a person skilled in the art, i.e. that the invention compounds can be a pure or be in the form of a mixture of enantiomers or diastereoisomers.

For the sake of clarity, by the expression "wherein the dotted line represents a carbon-carbon single or a carbon-carbon double bond", or the similar, it is meant the normal meaning understood by a person skilled in the art, i.e. that the whole bonding (solid and dotted line) between the carbon atoms connected by said dotted line is a carbon-carbon single or double bond.

In some aspects, $R^2$ may be a hydrogen atom.
In some aspects, $R^3$ may be a methyl group.
In some aspects, $R^4$ may be a methyl group.
In some aspects, the index m may be 1.
In some aspects, the index n may be 1.
In some aspects, the dotted line may represent a double bond.
In some aspects, $R^1$ may represent a hydrogen atom or a $R^6C(=O)$ group wherein $R^6$ represents a hydrogen atom or a methyl group.
In some aspects, $R^1$ may represent a $R^6C(=O)$ group wherein $R^6$ represents a hydrogen atom or a methyl group.
In some aspects, $R^1$ may represent a $CH_3C(=O)$.
In some aspects; each $R^5$ may represent, independently from each other, a hydrogen atom or a $C_{1-3}$ alkyl group.
In some aspects; each $R^5$ may represent, independently from each other, a hydrogen atom or a methyl or ethyl group.
In some aspects; each $R^5$ may represent, independently from each other, a hydrogen atom or a methyl group.
In some aspects; one or two $R^5$ may represent a methyl group and the other a hydrogen atom.

In some aspects, an antagonist of the butyric acid olfactory receptor is a compound having the structure:

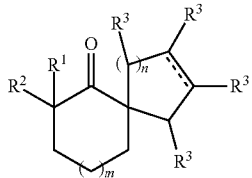

Formula (II)

in a form of any one of the stereoisomers or as a mixture thereof
wherein the index m represents 0 or 1;
wherein the index n represents 1 or 2;
wherein the dotted lines represent a single or a double bond;
wherein $R^1$, and $R^2$ represent, independently from each other, a hydrogen atom or a methyl group;
wherein each $R^3$ represent, independently from each other, a hydrogen atom or a $C_{1-3}$ alkyl or alkenyl group; and
wherein the compound of Formula (II) is an antagonist of a butyric acid olfactory receptor.

In some aspects, an antagonist of the butyric acid olfactory receptor is a compound having the structure:

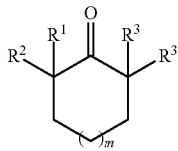

Formula (III)

in a form of any one of the stereoisomers or as a mixture thereof
wherein the index m represents 0 or 1;
wherein $R^1$, and $R^2$ represent, independently from each other, a hydrogen atom or a methyl group;
wherein each $R^3$ represent, independently from each other, a hydrogen atom or a $C_{1-4}$ alkyl or alkenyl group; and
wherein the compound of Formula (III) is an antagonist of a butyric acid olfactory receptor.

In some aspects, an antagonist of the butyric acid olfactory receptor is a compound having the structure:

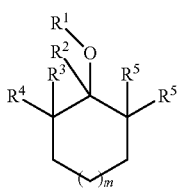

Formula (IV)

in a form of any one of the stereoisomers or as a mixture thereof
wherein the index m represents 0 or 1;
wherein $R^1$ represents a hydrogen atom, a methyl group or a $R^6C(=O)$ group wherein $R^6$ represents a hydrogen atom or a methyl, ethyl, propyl or isopropyl group;
wherein $R^2$, $R^3$ and $R^4$ represent, independently from each other, a hydrogen atom, a methyl group, a $C_{1-4}$ alkyl or alkenyl group;
wherein each $R^5$ represent, independently from each other, a hydrogen atom or a $C_{1-4}$ alkyl or alkenyl group; and
wherein the compound of Formula (IV) is an antagonist of a butyric acid olfactory receptor.

In some aspects, the compound of Formula (I) is selected from the compounds disclosed in U.S. Pat. No. 7,256,170 B2.

In some aspects, the compound of Formula (I) is selected from the group consisting of: (1RS,6RS,11RS)-2,2,9,11-tetramethylspiro[5.5]undec-8-en-1-yl acetate, (+−)-2,2,7,11-tetramethylspiro[5.5]undec-8-en-1-yl-acetate, (+−)-2,3,7,7-tetramethylspiro[4.5]dec-2-en-6-yl acetate, (+−)-2,3,7,7-tetramethylspiro[4.5]dec-6-yl acetate, 1,5,10,10-tetramethylspiro[5.5]undec-3-en-11-ylacetate, (5,10,10-trimethylspiro[5.5]undec-2-en-11-yl) formate, (3,5,10,10-tetramethylspiro[5.5]undec-2-en-11-yl) acetate, (2,3,9,9-tetramethylspiro[4.5]dec-2-en-10-yl)acetate, (9,9-dimethylspiro[4.5]dec-2-en-10-yl)acetate, 10-methoxy-9,9-dimethylspiro[4.5]dec-2-ene, 4,10,10,11-tetramethylspiro[5.5]undec-2-en-11-ol, 5,10,10,11-tetramethylspiro[5.5]undec-3-en-11-ol, a mixture of 4,10,10,11-tetramethylspiro[5.5]undec-2-en-11-ol and 5,10,10,11-tetramethylspiro[5.5]undec-3-en-11-ol, 2,4,8-trimethylspiro[5.5]undec-3-en-11-ol, 2,9,11-trimethylspiro[5.5]undec-9-en-5-ol, a mixture of 2,4,8-trimethylspiro[5.5]undec-3-en-11-ol and 2,9,11-trimethylspiro[5.5]undec-9-en-5-ol, 3-methyl-5-propan-2-yl-spiro[5.5]undec-2-en-11-ol, 11-methylspiro[5.5]undecan-5-ol, 3,10,10-trimethylspiro[5.5]undec-3-en-11-ol, 4,10,10-trimethylspiro[5.5]undec-3-en-11-ol, a mixture of 3,10,10-trimethylspiro[5.5]undec-3-en-11-ol and 4,10,10-trimethylspiro[5.5]undec-3-en-11-ol, [2,2-dimethyl-1-(2,4,6-trimethylcyclohex-3-en-1-yl)propyl] acetate, [2,2-dimethyl-1-(2,4,6-trimethylcyclohexyl)propyl] acetate, (1RS)-2,2-dimethyl-1-[(1SR,2SR)-2-methylcyclohexyl] propyl acetate, 9,9-dimethylspiro[4.5]dec-2-en-10-ol, 2,3,9,9-tetramethylspiro[4.5]decan-10-ol, (2,2,3,3,9,9-hexamethylspiro[4.5]decan-10-yl) acetate, 9-methoxy-8,8-dimethylspiro[4.4]non-2-ene, (8,8-dimethylspiro[4.4]non-2-en-9-yl) acetate, 2,3,8,8-tetramethylspiro[4.4]non-2-en-9-one, 2,3,9,9-tetramethylspiro[4.5]dec-2-en-10-ol, 4-methoxy-3,3-dimethylspiro[4.4]nonane, (4,9,9-trimethylspiro[4.5]dec-2-en-10-yl) acetate, 2,4,9,9-tetramethylspiro[4.5]dec-2-en-10-ol, (2,3,9,9-tetramethylspiro[4.5]dec-2-en-10-yl) formate, (2,4,9,9-tetramethylspiro[4.5]dec-2-en-10-yl) acetate, (+−)-2,3-dimethylspiro[4.5]dec-2-en-6-yl acetate, and (4~{S},5~{R},6~{S},11~{S})-4,11-dimethylspiro[5.5]undecan-5-ol.

In some aspects, the compound of Formula (I) is selected from the group consisting of: (+−)-2,3,7,7-tetramethylspiro[4.5]dec-2-en-6-yl acetate, (+−)-2,3,7,7-tetramethylspiro[4.5]dec-6-yl acetate, (9,9-dimethylspiro[4.5]dec-2-en-10-yl) acetate, and 10-methoxy-9,9-dimethylspiro[4.5]dec-2-ene.

In some aspects, the compound of Formula (II) is selected from the group consisting of: 9,9-dimethylspiro [4.5]dec-2-en-10-one, 2,3,9,9-tetramethylspiro [4.5]dec-2-en-10-one, 2,4,9,9-tetramethylspiro [4.5]dec-2-en-10-one, 1,1',1',5-tetramethyl-2'-methylidenespiro[6-oxabicyclo[3.1.0]hexane-3,3'-cyclohexane], and 4,9,9-trimethylspiro[4.5]dec-2-en-10-one.

In some aspects, the compound of Formula (III) is selected from the group consisting of: 2,2-dimethyl-6,6-bis(2-methylprop-2-enyl)cyclohexan-1-one, 2,2-dimethyl-5,5-bis(2-methylprop-2-enyl)cyclopentan-1-one, 2-but-3-en-2-yl-6,6-dimethyl-2-prop-2-enylcyclohexan-1-one, a mixture of 2,2-dimethyl-5,5-bis(2-methylprop-2-enyl)cyclopentan-1-one and 2-but-3-en-2-yl-6,6-dimethyl-2-prop-2-enylcyclohexan-1-one, and 2,2-bis(2-methyl-2-propen-1-yl)cyclohexanone.

In some aspects, the compound of Formula (IV) is selected from the group consisting of: 2,2-dimethyl-1-(2-methylcyclohexyl)propan-1-ol, 2,2-dimethyl-1-(3-methylcyclohexyl)propan-1-ol, a mixture of 2,2-dimethyl-1-(2-methylcyclohexyl)propan-1-ol and 2,2-dimethyl-1-(3-methylcyclohexyl)propan-1-ol, 2,2-dimethyl-6,6-bis(2-methylprop-2-enyl)cyclohexan-1-ol, 1-methoxy-2,6-dimethyl-1-prop-2-enylcyclohexane, methyl 1-(3-methylbut-2-enyl)cyclohex-2-ene-1-carboxylate, methyl 1-(3-methylbut-2-enyl)cyclohex-3-ene-1-carboxylate, a mixture of methyl 1-(3-methylbut-2-enyl)cyclohex-2-ene-1-carboxylate and methyl 1-(3-methylbut-2-enyl)cyclohex-3-ene-1-carboxylate, and 2,2-dimethyl-5,5-bis(2-methylprop-2-enyl)cyclopentan-1-ol.

In some aspects, the compound of Formula (I) has the structure:

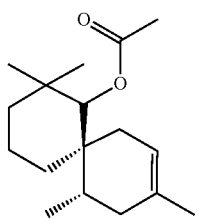

In some aspects, the compound of Formula (I) has the structure:

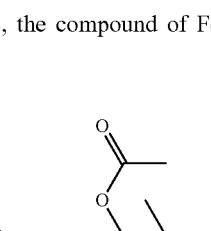

In some aspects, the compound of Formula (I) has the structure:

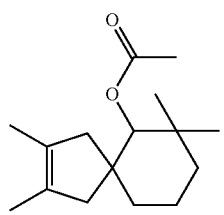

In some aspects, the compound of Formula (I) has the structure:

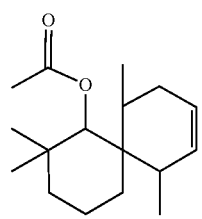 [SMILES: CC(=O)OC1C(C)(C)CCCC12C(C)C=CCC2C]

In some aspects, the compound of Formula (I) has the structure:

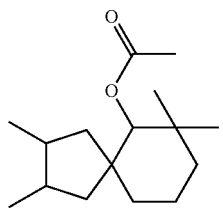

In some aspects, the compound of Formula (I) has the structure:

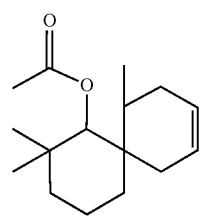 [SMILES: CC(=O)OC1C(C)(C)CCCC12CC=CCC2C]

In some aspects, the compound of Formula (I) has the structure:

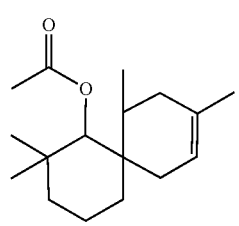

In some aspects, the compound of Formula (I) has the structure:

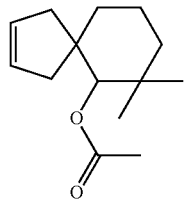 [SMILES: CC(=O)OC1C(C)(C)CCCC12CC=CC2]

In some aspects, the compound of Formula (I) has the structure:

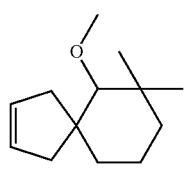

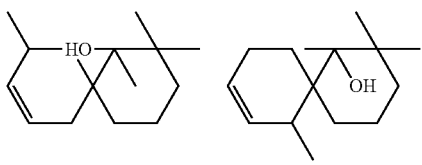

In some aspects, the compound of Formula (I) has the structure:

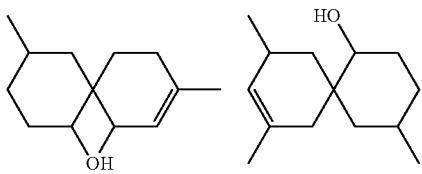

In some aspects, the compound of Formula (I) has the structure:

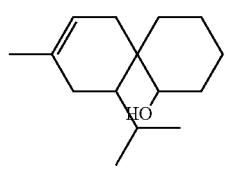 [SMILES: CC1=CCC2(CCCCC2O)C(C(C)C)C1]

In some aspects, the compound of Formula (I) has the structure:

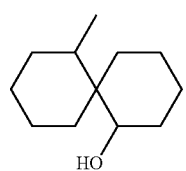

In some aspects, the compound of Formula (I) has the structure:

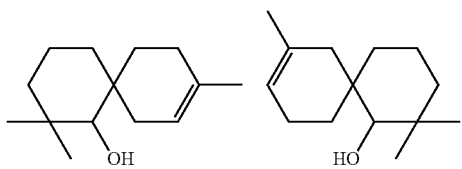

In some aspects, the compound of Formula (I) has the structure:

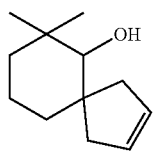

In some aspects, the compound of Formula (I) has the structure:

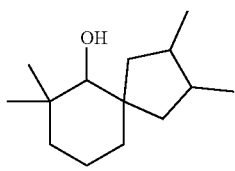

In some aspects, the compound of Formula (I) has the structure:

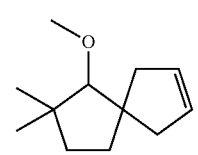

In some aspects, the compound of Formula (I) has the structure:

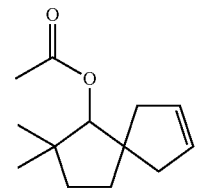

In some aspects, the compound of Formula (I) has the structure:

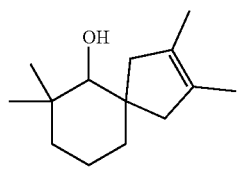

In some aspects, the compound of Formula (I) has the structure:

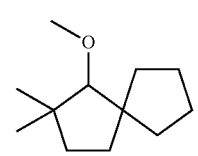

In some aspects, the compound of Formula (I) has the structure:

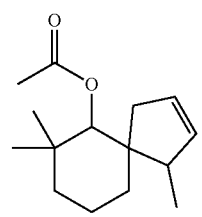 [SMILES: CC(=O)OC1C(C)(C)CCCC12CC=CC2C]

In some aspects, the compound of Formula (I) has the structure:

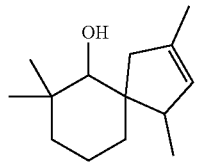

In some aspects, the compound of Formula (I) has the structure:

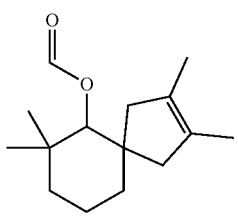

In some aspects, the compound of Formula (I) has the structure:

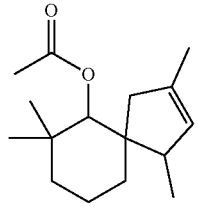 [SMILES: CC(=O)OC1C(C)(C)CCCC12CC(C)=CC2C]

In some aspects, the compound of Formula (I) has the structure:

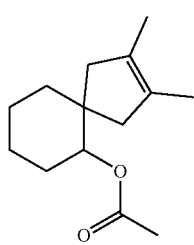 [SMILES: CC(=O)OC1CCCCC12CC(C)=C(C)C2]

In some aspects, the compound of Formula (I) has the structure:

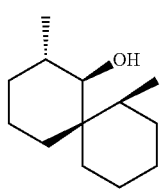

In some aspects, the compound of Formula (II) has the structure:

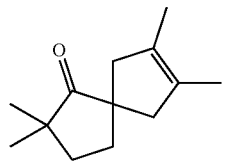

In some aspects, the compound of Formula (II) has the structure:

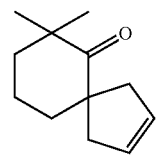

In some aspects, the compound of Formula (II) has the structure:

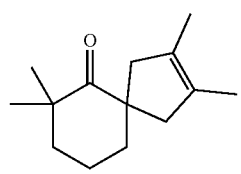

In some aspects, the compound of Formula (II) has the structure:

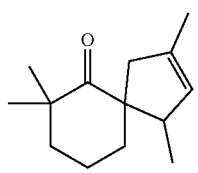

In some aspects, the compound of Formula (II) has the structure:

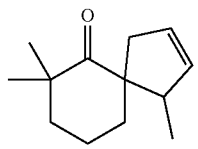

In some aspects, the compound of Formula (III) has the structure:

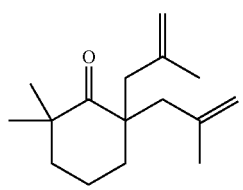 [SMILES: C=C(C)CC1(CC(=C)C)CCCC(C)(C)C1=O]

In some aspects, the compound of Formula (III) has the structure:

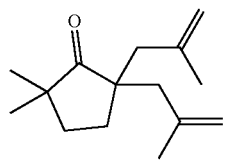 [SMILES: C=C(C)CC1(CC(=C)C)CCC(C)(C)C1=O]

In some aspects, the compound of Formula (III) has the structure:

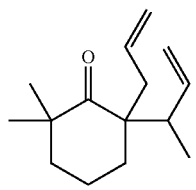 [SMILES: C=CCC1(C(C)C=C)CCCC(C)(C)C1=O]

In some aspects, the compound of Formula (III) has the structure:

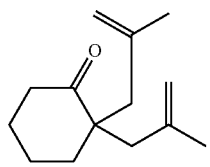

In some aspects, the compound of Formula (IV) has the structure:

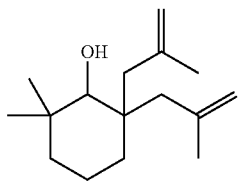 [SMILES: C=C(C)CC1(CC(=C)C)CCCC(C)(C)C1O]

In some aspects, the compound of Formula (IV) has the structure:

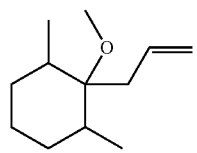

In some aspects, the following compound is an inhibitor of the at least one butyric acid olfactory receptor:

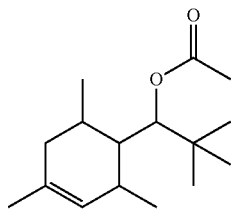 [SMILES: CC(=O)OC(C1C(C)C=C(C)CC1C)C(C)(C)C]

[2,2-dimethyl-1-(2,4,6-trimethylcyclohex-3-en-1-yl)propyl] acetate.

In some aspects, the following compound is an inhibitor of the at least one butyric acid olfactory receptor:

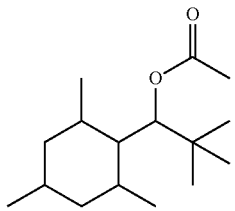 [SMILES: CC(=O)OC(C1C(C)CC(C)CC1C)C(C)(C)C]

[2,2-dimethyl-1-(2,4,6-trimethylcyclohexyl)propyl] acetate.

In some aspects, the following compound is an inhibitor of the at least one butyric acid olfactory receptor:

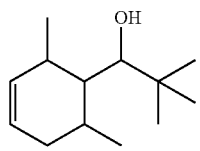

1-(2,6-dimethylcyclohex-3-en-1-yl)-2,2-dimethylpropan-1-ol.

In some aspects, the following compound is an inhibitor of the at least one butyric acid olfactory receptor:

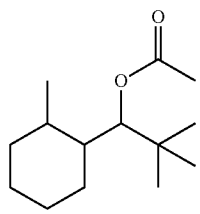 [SMILES: CC(=O)OC(C1CCCCC1C)C(C)(C)C]

(1RS)-2,2-dimethyl-1-[(1SR,2SR)-2-methylcyclohexyl]propyl acetate.

In some aspects, the following compound is an inhibitor of the at least one butyric acid olfactory receptor:

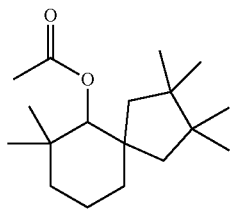

(2,2,3,3,9,9-hexamethylspiro[4.5]decan-10-yl) acetate.

In some aspects, the following compound is an inhibitor of the at least one butyric acid olfactory receptor:

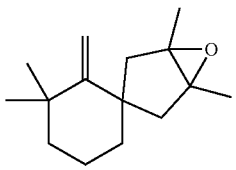

1,1',1',5-tetramethyl-2'-methylidenespiro [6-oxabicyclo[3.1.0]hexane-3,3'-cyclohexane].

In some aspects, the following compound is an inhibitor of the at least one butyric acid olfactory receptor:

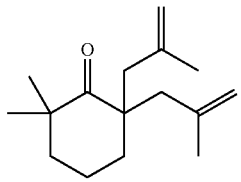 [SMILES: C=C(C)CC1(CC(=C)C)CCCC(C)(C)C1=O]

2,2-dimethyl-6,6-bis(2-methylprop-2-enyl)cyclohexan-1-one.

In some aspects, the following compound is an inhibitor of the at least one butyric acid olfactory receptor:

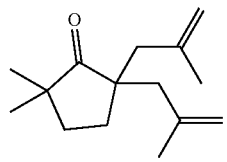 [SMILES: C=C(C)CC1(CC(=C)C)CCC(C)(C)C1=O]

2,2-dimethyl-5,5-bis(2-methylprop-2-enyl)cyclopentan-1-one.

In some aspects, the following compound is an inhibitor of the at least one butyric acid olfactory receptor:

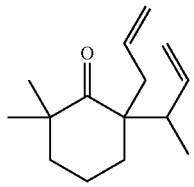 [SMILES: C=CCC1(C(C)C=C)CCCC(C)(C)C1=O]

2-but-3-en-2-yl-6,6-dimethyl-2-prop-2-enylcyclohexan-1-one.

In some aspects, the following compound is an inhibitor of the at least one butyric acid olfactory receptor:

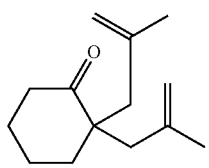

2,2-bis(2-methyl-2-propen-1-yl)cyclohexanone.

In some aspects, the following compound is an inhibitor of the at least one butyric acid olfactory receptor:

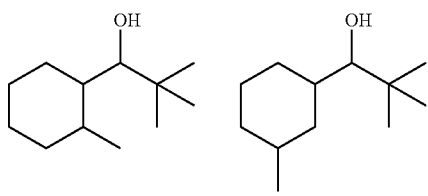

2,2-dimethyl-1-(2-methylcyclohexyl)propan-1-ol, 2,2-dimethyl-1-(3-methylcyclohexyl)propan-1-ol, or mixtures thereof.

In some aspects, the following compound is an inhibitor of the at least one butyric acid olfactory receptor:

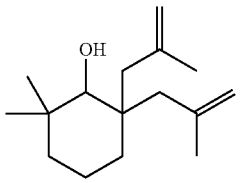 [SMILES: C=C(C)CC1(CC(=C)C)CCCC(C)(C)C1O]

2,2-dimethyl-6,6-bis(2-methylprop-2-enyl)cyclohexan-1-ol.

In some aspects, the following compound is an inhibitor of the at least one butyric acid olfactory receptor:

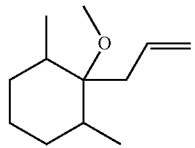

1-methoxy-2,6-dimethyl-1-prop-2-enylcyclohexane.

In some aspects, the following compound is an inhibitor of the at least one butyric acid olfactory receptor:

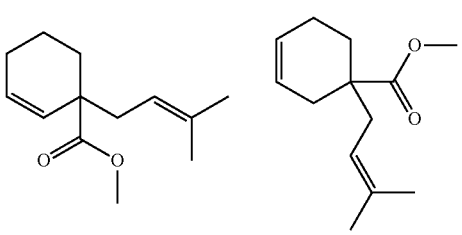

methyl 1-(3-methylbut-2-enyl)cyclohex-2-ene-1-carboxylate, methyl 1-(3-methylbut-2-enyl)cyclohex-3-ene-1-carboxylate, or mixtures thereof.

In some aspects, the following compound is an inhibitor of the at least one butyric acid olfactory receptor:

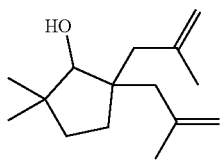 [SMILES: C=C(C)CC1(CC(=C)C)CCC(C)(C)C1O]

2,2-dimethyl-5,5-bis(2-methylprop-2-enyl)cyclopentan-1-ol.

In some aspects, the antagonist of the butyric acid receptor is a compound selected from the group consisting of: 1-(2-methyl-4-tricyclo[5.2.1.0$^{1,5}$]decanyl)ethyl acetate, 1-(2,4-dimethyl-4-tricyclo[5.2.1.0$^{1,5}$]decanyl)ethyl acetate, 1-((1R,3S,3aS,6S)-1,2,3-trimethyloctahydro-3a,6-methanoinden-1-yl)ethan-1-one, 1-(2,4-dimethyl-4-tricyclo[5.2.1.0^{1,5}]decanyl)ethanone, 2,3,4-trimethyltricyclo[5.2.1.0^{1,5}]decane-4-carbaldehyde, (2,3,4-trimethyl-4-tricyclo[5.2.1.0^{1,5}]decanyl)methyl acetate, 1-((3aS,6S)-2,3-dimethyloctahydro-3a,6-methanoinden-1-yl)ethan-1-one oxime, 1,3-dimethyloctahydro-3a,6-methanoindene-1-carbaldehyde oxime, ~{N}-[1-[(1~{R},7~{R})-2,3,4-trimethyl-4-tricyclo[5.2.1.0$^{1,5}$]decanyl]ethylidene]hydroxylamine, (+−)-1-(2,4-dimethyltricyclo[5.2.1.0$^{1,5}$]dec-4-yl) ethanone, (+−)-1-(2,4-dimethyltricyclo[5.2.1.0~1.5~]dec-4-yl) ethyl acetate, 1-[(1RS,2RS,4SR,7RS)-2,3,4-trimethyltricyclo[5.2.1.0~]dec-4-yl) ethanone, (E/Z)-1-[(1RS,7RS)-2,3-dimethyltricyclo[5.2.1.0$^{1.5}$]dec-4-yl) ethanone oxime, (E/Z)-1-[(1S,7S)-2,3,4-trimethyltricyclo[5.2.1.0~1.5~]dec-4-yl) ethanone oxime, (E/Z)-1-((3aS, 6S)-1,2,3-trimethyloctahydro-3a,6-methanoinden-1-yl) ethanone oxime, (+−)-1-(3-methyloctahydro-3a,6-methanoinden-1-yl)ethyl acetate, and mixtures thereof.

In some aspects, the antagonist of the at least one butyric acid receptor is a compound having structure:

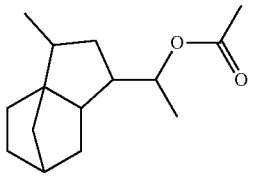 [SMILES: CC(=O)OC(C)C1CC(C)C23CCC(CC12)C3]

In some aspects, the antagonist of the at least one butyric acid receptor is a compound having structure:

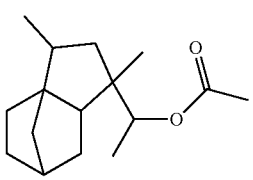 [SMILES: CC(=O)OC(C)C1(C)CC(C)C23CCC(CC12)C3]

In some aspects, the antagonist of the at least one butyric acid receptor is a compound having structure:

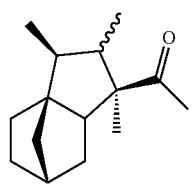 [SMILES: CC(=O)[C@]1(C)C(C)[C@H](C)[C@@]23CC[C@@H](CC12)C3]

In some aspects, the antagonist of the at least one butyric acid receptor is a compound having structure:

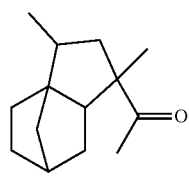

In some aspects, the antagonist of the at least one butyric acid receptor is a compound having structure:

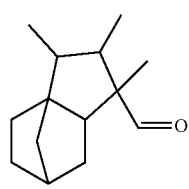

In some aspects, the antagonist of the at least one butyric acid receptor is a compound having structure:

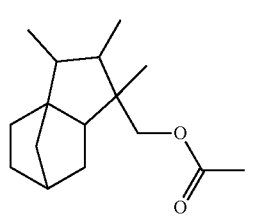 [SMILES: CC(=O)OCC1(C)C(C)C(C)C23CCC(CC12)C3]

In some aspects, the antagonist of the at least one butyric acid receptor is a compound having structure:

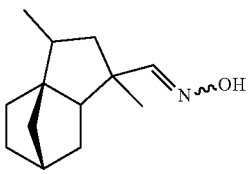

In some aspects, the antagonist of the at least one butyric acid receptor is a compound having structure:

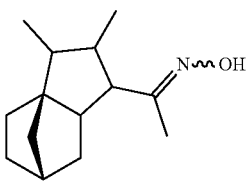 [SMILES: CC(=NO)C1C(C)C(C)[C@@]23CC[C@@H](CC12)C3]

In some aspects, the antagonist of the at least one butyric acid receptor is a compound having structure:

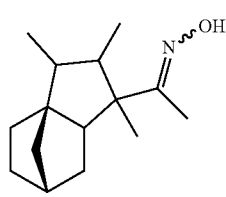 [SMILES: CC(=NO)C1(C)C(C)C(C)[C@@]23CC[C@@H](CC12)C3]

In some aspects, the antagonist of the at least one butyric acid receptor is a compound having structure:

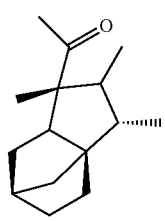 [SMILES: CC(=O)[C@]1(C)C(C)[C@H](C)[C@@]23CC[C@@H](CC12)C3]

In some aspects, the antagonist of the at least one butyric acid receptor is a compound having structure:

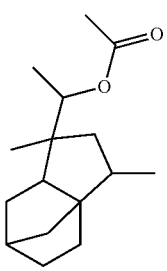 [SMILES: CC(=O)OC(C)C1(C)CC(C)C23CCC(CC12)C3]

In some aspects, the antagonist of the at least one butyric acid receptor is a compound having structure:

In some aspects, the antagonist of the at least one butyric acid receptor is a compound having structure:

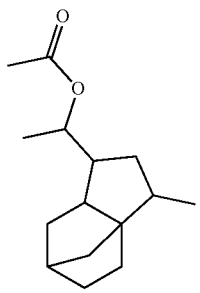 [SMILES: CC(=O)OC(C)C1CC(C)C23CCC(CC12)C3]

In some aspects, the antagonist of the at least one butyric acid receptor is a compound having structure:

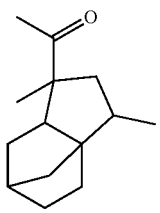

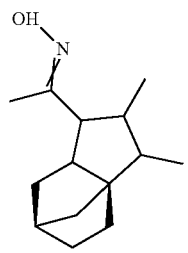 [SMILES: CC(=NO)C1C(C)C(C)[C@@]23CC[C@@H](CC12)C3]

Antagonists for the Geonol Olfactory Receptor

In some aspects, the compounds of the present disclosure have an $IC_{50}$ for the geonol olfactory receptor from 6 to 200 µM. In some aspects, the compounds of the present disclosure have an $IC_{50}$ for the geonol olfactory receptor from 8 to 200 µM. In some aspects, the compounds of the present disclosure have an $IC_{50}$ for the geonol olfactory receptor from 10 to 200 µM. In some aspects, the compounds of the present disclosure have an $IC_{50}$ for the geonol olfactory receptor from 20 to 200 µM. In some aspects, the compounds of the present disclosure have an $IC_{50}$ for the geonol olfactory receptor from 30 to 200 µM. In some aspects, the compounds of the present disclosure have an $IC_{50}$ for the geonol olfactory receptor from 40 to 200 µM. In some aspects, the compounds of the present disclosure have an $IC_{50}$ for the geonol olfactory receptor from 50 to 200 µM. In some aspects, the compounds of the present disclosure have an $IC_{50}$ for the geonol olfactory receptor from 60 to 200 µM. In some aspects, the compounds of the present disclosure have an $IC_{50}$ for the geonol olfactory receptor from 70 to 200 µM. In some aspects, the compounds of the present disclosure have an $IC_{50}$ for the geonol olfactory receptor from 80 to 200 µM. In some aspects, the compounds of the present disclosure have an $IC_{50}$ for the geonol olfactory receptor from 90 to 200 µM. In some aspects, the compounds of the present disclosure have an $IC_{50}$ for the geonol olfactory receptor from 100 to 200 µM. In some aspects, the compounds of the present disclosure have an $IC_{50}$ for the geonol olfactory receptor from 120 to 200 µM. In some aspects, the compounds of the present disclosure have an $IC_{50}$ for the geonol olfactory receptor from 140 to 200 µM. In some aspects, the compounds of the present disclosure have an $IC_{50}$ for the geonol olfactory receptor from 160 to 200 µM. In some aspects, the compounds of the present disclosure have an $IC_{50}$ for the geonol olfactory receptor from 180 to 200 µM.

In some aspects, the compounds of the present disclosure have an $IC_{50}$ for the geonol olfactory receptor from 4 to 180 µM. In some aspects, the compounds of the present disclosure have an $IC_{50}$ for the geonol olfactory receptor from 4 to 160 µM. In some aspects, the compounds of the present disclosure have an $IC_{50}$ for the geonol olfactory receptor from 4 to 140 µM. In some aspects, the compounds of the present disclosure have an $IC_{50}$ for the geonol olfactory receptor from 4 to 120 µM. In some aspects, the compounds of the present disclosure have an $IC_{50}$ for the geonol olfactory receptor from 4 to 100 µM. In some aspects, the compounds of the present disclosure have an $IC_{50}$ for the geonol olfactory receptor from 4 to 90 µM. In some aspects, the compounds of the present disclosure have an $IC_{50}$ for the geonol olfactory receptor from 4 to 80 µM. In some aspects, the compounds of the present disclosure have an $IC_{50}$ for the geonol olfactory receptor from 4 to 70 µM. In some aspects, the compounds of the present disclosure have an $IC_{50}$ for the geonol olfactory receptor from 4 to 60 µM. In some aspects, the compounds of the present disclosure have an $IC_{50}$ for the geonol olfactory receptor from 4 to 50 µM. In some aspects, the compounds of the present disclosure have an $IC_{50}$ for the geonol olfactory receptor from 4 to 40 µM. In some aspects, the compounds of the present disclosure have an $IC_{50}$ for the geonol olfactory receptor from 4 to 30 µM. In some aspects, the compounds of the present disclosure have an $IC_{50}$ for the geonol olfactory receptor from 4 to 20 µM. In some aspects, the compounds of the present disclosure have an $IC_{50}$ for the geonol olfactory receptor from 4 to 10 µM. In some aspects, the compounds of the present disclosure have an $IC_{50}$ for the geonol olfactory receptor from 4 to 9 µM. In some aspects, the compounds of the present disclosure have an $IC_{50}$ for the geonol olfactory receptor from 4 to 8 µM. In some aspects, the compounds of the present disclosure have an $IC_{50}$ for the geonol olfactory receptor from 4 to 7 µM. In some aspects, the compounds of the present disclosure have an $IC_{50}$ for the geonol olfactory receptor from 4 to 6 µM. In some aspects, the compounds of the present disclosure have an $IC_{50}$ for the geonol olfactory receptor from 4 to 5 µM.

In some aspects, the compounds of the present disclosure have an $IC_{50}$ for the geonol olfactory receptor of 4, or 5, or 6, or 7, or 8, or 9, or 10, or 20, or 30, or 40, or 50, or 60, or 70, or 80, or 90, or 100, or 120, or 140, or 160, or 180, or 200 µM.

In some aspects, the at least one compound that inhibits the geonol olfactory receptor is selected from the group consisting of: [1R-(1R*,4R*,6R*,10S*)]-4,12,12-trimethyl-9-methylene-5-oxatricyclo[8.2.0.0$^{4,6}$]dodecane, 1-(2,6,6-trimethyl-1-cyclohex-3-enyl)but-2-en-1-one, 2-tertbutyl phenol, 5-Methyl-2-(propan-2-yl)phenol, nona-2,6-dienal, 1,1-diethoxy-3,7-dimethylocta-2,6-diene, 3-(4-hydroxy-4-methylpentyl)cyclohex-3-ene-1-carbaldehyde; 4-(4-hydroxy-4-methylpentyl)cyclohex-3-ene-1-carbaldehyde, 1,4,8-trimethyl-13-oxabicyclo[10.1.0]trideca-4,8-diene; 1,5,8-trimethyl-13-oxabicyclo[10.1.0]trideca-4,8-diene, 3-(4-tert-butylphenyl)propanal, (4R,4aS,6R)-4,4a-dimethyl-6-prop-1-en-2-yl-3,4,5,6,7,8-hexahydronaphthalen-2-one, geranyl acetate, 1-(3,3-dimethylcyclohexen-1-yl)pent-4-en-1-one; 1-(5,5-dimethylcyclohexen-1-yl)pent-4-en-1-one, 1-(3,3-dimethylcyclohexen-1-yl)pent-4-en-1-one; 1-(5,5-dimethylcyclohexen-1-yl)pent-4-en-1-one, 2-ethoxy-5-prop-1-enylphenol, 2,6,6,8-tetramethyl-9-oxatetracyclo[5.4.1.0^{1,5}.0^{8,10}]dodecane, nonylenic aldehyde, isobutylquinoline, cyclopentadec-4-en-1-one, (−)-(R)-3,7-dimethyl-6-octenenitrile, 2-methyl-5-propan-2-ylphenol, isopropyl quinolone, 5-hexyl-2-methylpyridine, (2,5-dimethyl-1,3-dihydroinden-2-yl)methanol, 2-pentylcyclopentan-1-one, 4-(2,6,6-trimethylcyclohexen-1-yl)but-3-en-2-one; 4-(2,6,6-trimethylcyclohex-2-en-1-yl)but-3-en-2-one; 3-methyl-4-(2,6,6-trimethylcyclohex-2-en-1-yl)but-3-en-2-one; 1-(2,6,6-trimethylcyclohex-2-en-1-yl)pent-1-en-3-one, 2,4-dimethylcyclohex-3-enecarbaldehyde, phenylethylol, 3,7-dimethylocta-2,6-dienal, (2,2,2-trichloro-1-phenylethyl) acetate, 4-(2,6,6-trimethylcyclohexen-1-yl)but-3-en-2-one, phenyl ethyl acetate, 7-hydroxy-3,7-dimethyloctanal, methyl citral, 6,10-dimethylundeca-5,9-dien-2-one, 2-ethoxy-5-prop-1-enylphenol, and combinations thereof.

Antagonists for the 1-Octen-3-ol Olfactory Receptor

In some aspects, the compounds of the present disclosure have an $IC_{50}$ for the 1-octen-3-ol olfactory receptor from 6 to 200 µM. In some aspects, the compounds of the present disclosure have an $IC_{50}$ for the 1-octen-3-ol olfactory receptor from 8 to 200 µM. In some aspects, the compounds of the present disclosure have an $IC_{50}$ for the 1-octen-3-ol olfactory receptor from 10 to 200 µM. In some aspects, the compounds of the present disclosure have an $IC_{50}$ for the 1-octen-3-ol olfactory receptor from 20 to 200 µM. In some aspects, the compounds of the present disclosure have an $IC_{50}$ for the 1-octen-3-ol olfactory receptor from 30 to 200 µM. In some aspects, the compounds of the present disclosure have an $IC_{50}$ for the 1-octen-3-ol olfactory receptor from 40 to 200 µM. In some aspects, the compounds of the present disclosure have an $IC_{50}$ for the 1-octen-3-ol olfactory receptor from 50 to 200 µM. In some aspects, the compounds of the present disclosure have an $IC_{50}$ for the 1-octen-3-ol olfactory receptor from 60 to 200 µM. In some aspects, the compounds of the present disclosure have an $IC_{50}$ for the 1-octen-3-ol olfactory receptor from 70 to 200 µM. In some aspects, the compounds of the present disclosure have an $IC_{50}$ for the 1-octen-3-ol olfactory receptor from 80 to 200 µM. In some aspects, the compounds of the present disclosure have an $IC_{50}$ for the 1-octen-3-ol olfactory receptor from 90 to 200 µM. In some aspects, the compounds of the present disclosure have an $IC_{50}$ for the 1-octen-3-ol olfactory receptor from 100 to 200 µM. In some aspects, the compounds of the present disclosure have an $IC_{50}$ for the 1-octen-3-ol olfactory receptor from 120 to 200 µM. In some aspects, the compounds of the present disclosure have an $IC_{50}$ for the 1-octen-3-ol olfactory receptor from 140 to 200 µM. In some aspects, the compounds of the present disclosure have an $IC_{50}$ for the 1-octen-3-ol olfactory receptor from 160 to 200 µM. In some aspects, the compounds of the present disclosure have an $IC_{50}$ for the 1-octen-3-ol olfactory receptor from 180 to 200 µM.

In some aspects, the compounds of the present disclosure have an $IC_{50}$ for the 1-octen-3-ol olfactory receptor from 4 to 180 µM. In some aspects, the compounds of the present disclosure have an $IC_{50}$ for the 1-octen-3-ol olfactory receptor from 4 to 160 µM. In some aspects, the compounds of the present disclosure have an $IC_{50}$ for the 1-octen-3-ol olfactory receptor from 4 to 140 µM. In some aspects, the compounds of the present disclosure have an $IC_{50}$ for the 1-octen-3-ol olfactory receptor from 4 to 120 µM. In some aspects, the compounds of the present disclosure have an $IC_{50}$ for the 1-octen-3-ol olfactory receptor from 4 to 100 µM. In some aspects, the compounds of the present disclosure have an $IC_{50}$ for the 1-octen-3-ol olfactory receptor from 4 to 90 µM. In some aspects, the compounds of the present disclosure have an $IC_{50}$ for the 1-octen-3-ol olfactory receptor from 4 to 80 µM. In some aspects, the compounds of the present disclosure have an $IC_{50}$ for the 1-octen-3-ol olfactory receptor from 4 to 70 µM. In some aspects, the compounds of the present disclosure have an $IC_{50}$ for the 1-octen-3-ol olfactory receptor from 4 to 60 µM. In some aspects, the compounds of the present disclosure have an $IC_{50}$ for the 1-octen-3-ol olfactory receptor from 4 to 50 µM. In some aspects, the compounds of the present disclosure have an $IC_{50}$ for the 1-octen-3-ol olfactory receptor from 4 to 40 µM. In some aspects, the compounds of the present disclosure have an $IC_{50}$ for the 1-octen-3-ol olfactory receptor from 4 to 30 µM. In some aspects, the compounds of the present disclosure have an $IC_{50}$ for the 1-octen-3-ol olfactory receptor from 4 to 20 µM. In some aspects, the compounds of the present disclosure have an $IC_{50}$ for the 1-octen-3-ol olfactory receptor from 4 to 10 µM. In some aspects, the compounds of the present disclosure have an $IC_{50}$ for the 1-octen-3-ol olfactory receptor from 4 to 9 µM. In some aspects, the compounds of the present disclosure have an $IC_{50}$ for the 1-octen-3-ol olfactory receptor from 4 to 8 µM. In some aspects, the compounds of the present disclosure have an $IC_{50}$ for the 1-octen-3-ol olfactory receptor from 4 to 7 µM. In some aspects, the compounds of the present disclosure have an $IC_{50}$ for the 1-octen-3-ol olfactory receptor from 4 to 6 µM. In some aspects, the compounds of the present disclosure have an $IC_{50}$ for the 1-octen-3-ol olfactory receptor from 4 to 5 µM.

In some aspects, the compounds of the present disclosure have an $IC_{50}$ for the 1-octen-3-ol of 4, or 5, or 6, or 7, or 8, or 9, or 10, or 20, or 30, or 40, or 50, or 60, or 70, or 80, or 90, or 100, or 120, or 140, or 160, or 180, or 200 µM.

In some aspects, the at least one compound that inhibits the 1-octen-3-ol olfactory receptor is selected from the group consisting of: isobutylquinoline, 2-tertbutyl phenol, [1R-(1R*,4R*,6R*,10S*)]-4,12,12-trimethyl-9-methylene-5-oxatricyclo[8.2.0.0^{4,6}]dodecane, (4-methyl-4-phenylpentan-2-yl)acetate, (+−)-3-methylcyclopentadecanone, 1-(4,8-dimethyl-12-methylidenecyclododeca-4,8-dien-1-yl) ethanone; 1-(2,6,10-trimethylcyclododeca-1,5,9-trien-1-yl) ethanone; 1-(2,6,10-trimethylcyclododeca-2,5,9-trien-1-yl) ethanone, cyclopentadec-4-en-1-one, cyclododecanone, 2,4-dimethylcyclohex-3-enecarbaldehyde, 1,4-dioxacyclohexadecane-5,16-dione, pentanol, oxacyclohexadecan-2-one, 1,1,2,3,3-pentamethyl-2,5,6,7-tetrahydroinden-4-one, (+−)-perhydro-5,5,8A-trimethyl-2-trans-naphthalenone, 2,3,3-trimethyl-2H-inden-1-one, 4-(4,8-dimethylnona-3,7-dienyl)pyridine, 4-[(1~{R},3~{R},6~{R})-2,2,3,6-tetramethylcyclohexyl]but-3-en-2-one; 4-[(1~{S},3~{S},6~{R})-2,2,3,6-tetramethylcyclohexyl]but-3-en-2-one, (+)-(1R,7R)-10,10-dimethyl-tricyclo[7.1.1.0(2,7)]undec-2-en-4-one, (9<I>E</I>)-cycloheptadec-9-en-1-one, 8,8-dimethyl-2,3,4,6,7,8~{a}-hexahydro-1~{H}-naphthalene-2-carbaldehyde; 8,8-dimethyl-2,3,5,6,7,8~{a}-hexahydro-1~{H}-naphthalene-2-carbaldehyde; 8,8-dimethyl-2,3,4,5,6,7-hexahydro-1~{H}-naphthalene-2-carbaldehyde; 2,2-dimethyl-octahydro-1~{H}-2,4~{a}-methanonapthalen-8-one, 2,4~{a},8,8-tetramethyl-1~{a},2,4,5,6,7-hexahydro-1~{H}-cycloprop[j]naphthalen-3-one; 2,6,6,8-tetramethyltricyclo[5.3.1.0^{1,5}]undecan-9-one, methyl citral, and combinations thereof.

Antagonists for the DMTS Olfactory Receptor

In some aspects, the compounds of the present disclosure have an $IC_{50}$ for the DMTS olfactory receptor from 6 to 200 µM. In some aspects, the compounds of the present disclosure have an $IC_{50}$ for the DMTS olfactory receptor from 8 to 200 µM. In some aspects, the compounds of the present disclosure have an $IC_{50}$ for the DMTS olfactory receptor from 10 to 200 µM. In some aspects, the compounds of the present disclosure have an $IC_{50}$ for the DMTS olfactory receptor from 20 to 200 µM. In some aspects, the compounds of the present disclosure have an $IC_{50}$ for the DMTS olfactory receptor from 30 to 200 µM. In some aspects, the compounds of the present disclosure have an $IC_{50}$ for the DMTS olfactory receptor from 40 to 200 µM. In some aspects, the compounds of the present disclosure have an $IC_{50}$ for the DMTS olfactory receptor from 50 to 200 µM. In some aspects, the compounds of the present disclosure have an $IC_{50}$ for the DMTS olfactory receptor from 60 to 200 µM. In some aspects, the compounds of the present disclosure have an $IC_{50}$ for the DMTS olfactory receptor from 70 to 200 µM. In some aspects, the compounds of the present disclosure have an $IC_{50}$ for the DMTS olfactory receptor from 80 to 200 µM. In some aspects, the compounds of the present disclosure have an $IC_{50}$ for the DMTS olfactory receptor from 90 to 200 µM. In some aspects, the compounds of the present disclosure have an $IC_{50}$ for the DMTS olfactory receptor from 100 to 200 µM. In some aspects, the compounds of the present disclosure have an $IC_{50}$ for the DMTS olfactory receptor from 120 to 200 µM. In some aspects, the compounds of the present disclosure have an $IC_{50}$ for the DMTS olfactory receptor from 140 to 200 µM. In some aspects, the compounds of the present disclosure have an $IC_{50}$ for the DMTS olfactory receptor from 160 to 200 µM. In some aspects, the compounds of the present disclosure have an $IC_{50}$ for the DMTS olfactory receptor from 180 to 200 µM.

In some aspects, the compounds of the present disclosure have an $IC_{50}$ for the DMTS olfactory receptor from 4 to 180 µM. In some aspects, the compounds of the present disclosure have an $IC_{50}$ for the DMTS olfactory receptor from 4 to 160 µM. In some aspects, the compounds of the present disclosure have an $IC_{50}$ for the DMTS olfactory receptor from 4 to 140 µM. In some aspects, the compounds of the present disclosure have an $IC_{50}$ for the DMTS olfactory receptor from 4 to 120 µM. In some aspects, the compounds of the present disclosure have an $IC_{50}$ for the DMTS olfactory receptor from 4 to 100 µM. In some aspects, the compounds of the present disclosure have an $IC_{50}$ for the DMTS olfactory receptor from 4 to 90 µM. In some aspects, the compounds of the present disclosure have an $IC_{50}$ for the DMTS olfactory receptor from 4 to 80 µM. In some aspects, the compounds of the present disclosure have an $IC_{50}$ for the DMTS olfactory receptor from 4 to 70 µM. In some aspects, the compounds of the present disclosure have an $IC_{50}$ for the DMTS olfactory receptor from 4 to 60 µM. In some aspects, the compounds of the present disclosure have an $IC_{50}$ for the DMTS olfactory receptor from 4 to 50 µM. In some aspects, the compounds of the present disclosure have an $IC_{50}$ for the DMTS olfactory receptor from 4 to 40 µM. In some aspects, the compounds of the present disclosure have an $IC_{50}$ for the DMTS olfactory receptor from 4 to 30 µM. In some aspects, the compounds of the present disclosure have an $IC_{50}$ for the DMTS olfactory receptor from 4 to 20 µM. In some aspects, the compounds of the present disclosure have an $IC_{50}$ for the DMTS olfactory receptor from 4 to 10 µM. In some aspects, the compounds of the present disclosure have an $IC_{50}$ for the DMTS olfactory receptor from 4 to 9 µM. In some aspects, the compounds of the present disclosure have an $IC_{50}$ for the DMTS olfactory receptor from 4 to 8 µM. In some aspects, the compounds of the present disclosure have an $IC_{50}$ for the DMTS olfactory receptor from 4 to 7 µM. In some aspects, the compounds of the present disclosure have an $IC_{50}$ for the DMTS olfactory receptor from 4 to 6 µM. In some aspects, the compounds of the present disclosure have an $IC_{50}$ for the DMTS olfactory receptor from 4 to 5 µM.

In some aspects, the compounds of the present disclosure have an $IC_{50}$ for the 1-octen-3-ol of 4, or 5, or 6, or 7, or 8, or 9, or 10, or 20, or 30, or 40, or 50, or 60, or 70, or 80, or 90, or 100, or 120, or 140, or 160, or 180, or 200 µM.

In some aspects, the at least one compound that inhibits the DMTS olfactory receptor is selected from the group consisting of: (+−)-(3E)-4-(2,6,6-trimethyl-2-cyclohexen-1-yl)-3-buten-2-one, (+−)-3,6,8,8-tetramethyloctahydro-1H-3a,7-methanoazulen-6-ol, nona-2,6-dienal, (+−)-perhydro-5,5,8A-trimethyl-2-trans-naphthalenone, (1RS,2SR,5RS,7RS,8SR)-5-methyltricyclo[6.2.1.0~2,7~]undecan-4-one (A)+(1RS,2SR,5SR,7RS,8SR)-5-methyltricyclo[6.2.1.0~2,7~]undecan-4-one (B), ethyl 2,6,6-trimethyl-1,3-cyclohexadiene-1-carboxylate, 1,4,8-trimethyl-13-oxabicyclo[10.1.0]trideca-4,8-diene; 1,5,8-trimethyl-13-oxabicyclo[10.1.0]trideca-4,8-diene, ethyl 4,6,6-trimethyl-1,3-cyclohexadiene-1-carboxylate, (2-methyl-2-indanyl)methyl acetate, 2-pentylcyclopentan-1-one, (+−)-1-(2,5-dimethyl-2,3-dihydro-1H-inden-2-yl)ethanone, 4-(1,1-dimethylpropyl)-1-cyclohexanone, 4-(2,6,6-trimethylcyclohexen-1-yl)but-3-en-2-one; 4-(2,6,6-trimethylcyclohex-2-en-1-yl)but-3-en-2-one, phenethyl alcohol, diethyl 1,4-cyclohexanedicarboxylate, (+)-(R)-3,7-dimethyl-6-octenal, 3,5,6-trimethyl-3-cyclohexene-1-carbaldehyde (A)+2,4,6-trimethyl-3-cyclohexene-1-carbaldehyde (B), 3,7-dimethyl-octa-2,6-dienal, 3-(4-methyl-3-pentenyl)-3-cyclohexene-1-carbaldehyde (A)+4-(4-methyl-3-pentenyl)-3-cyclohexene-1-carbaldehyde, 3-methyl-4-(2,6,6-trimethylcyclohex-2-en-1-yl)but-3-en-2-one; 1-(2,6,6-trimethylcyclohex-2-en-1-yl)pent-1-en-3-one, (4<I>Z</I>,8<I>E</I>)-13-oxabicyclo[10.1.0]trideca-4,8-diene, (4E,8E)-4,8-cyclododecadien-1-one (A)+(4E,8Z)-4,8-cyclododecadien-1-one (B)+(4Z,8E)-4,8-cyclododecadien-1-one (C), (1<I>R</I>,4<I>Z</I>,8<I>E</I>,12<I>R</I>)-13-oxabicyclo[10.1.0]trideca-4,8-diene; (4<I>Z</I>,8<I>E</I>)-13-oxabicyclo[10.1.0]trideca-4,8-diene, 2,2,7,7-tetramethyltricyclo[6.2.1.0~1,6~]undecan-6-ol, (2,5-dimethyl-1,3-dihydroinden-2-yl)methanol, 8,8-dimethyl-2,3,4,6,7,8~{a}-hexahydro-1~{H}-naphthalene-2-carbaldehyde; 8,8-dimethyl-2,3,5,6,7,8~{a}-hexahydro-1~{H}-naphthalene-2-carbaldehyde; 8,8-dimethyl-2,3,4,5,6,7-hexahydro-1~{H}-naphthalene-2-carbaldehyde; 2,2-dimethyl-octahydro-1~{H}-2,4~{a}-methanonaphthalen-8-one, (+)-(1S,2S,3S,5R)-2,6,6-trimethylspiro[bicyclo[3.1.1]heptane-3,1'-cyclohexane]-2'-en-4'-one, 1-(3,3-dimethylcyclohexen-1-yl)pent-4-en-1-one; 1-(5,5-dimethylcyclohexen-1-yl)pent-4-en-1-one, (5RS,6RS)-2,6,10,10-tetramethyl-1-oxaspiro[4.5]decan-6-OL (2,2,2-trichloro-1-phenylethyl) acetate, patchouli oil, (1~{S},3~{S},6~{R},7~{R},8~{S})-2,2,6,8-tetramethyltricyclo[5.3.1.0^{3,8}]undecan-3-ol, (4S,4aS,8aR)-4,8a-dimethyl-1,2,3,4,5,6,7-octahydronaphthalen-4a-ol, and combinations thereof.

Antagonists for the Indole/Skatole Olfactory Receptor

In some aspects, the compounds of the present disclosure have an $IC_{50}$ for the Indole/skatole olfactory receptor from 6 to 200 µM. In some aspects, the compounds of the present disclosure have an $IC_{50}$ for the Indole/skatole olfactory receptor from 8 to 200 µM. In some aspects, the compounds of the present disclosure have an $IC_{50}$ for the Indole/skatole olfactory receptor from 10 to 200 µM. In some aspects, the compounds of the present disclosure have an IC$_{50}$ for the Indole/skatole olfactory receptor from 20 to 200 µM. In some aspects, the compounds of the present disclosure have an IC$_{50}$ for the Indole/skatole olfactory receptor from 30 to 200 µM. In some aspects, the compounds of the present disclosure have an IC$_{50}$ for the Indole/skatole olfactory receptor from 40 to 200 µM. In some aspects, the compounds of the present disclosure have an IC$_{50}$ for the Indole/skatole olfactory receptor from 50 to 200 µM. In some aspects, the compounds of the present disclosure have an IC$_{50}$ for the Indole/skatole olfactory receptor from 60 to 200 µM. In some aspects, the compounds of the present disclosure have an IC$_{50}$ for the Indole/skatole olfactory receptor from 70 to 200 µM. In some aspects, the compounds of the present disclosure have an IC$_{50}$ for the Indole/skatole olfactory receptor from 80 to 200 µM. In some aspects, the compounds of the present disclosure have an IC$_{50}$ for the Indole/skatole olfactory receptor from 90 to 200 µM. In some aspects, the compounds of the present disclosure have an IC$_{50}$ for the Indole/skatole olfactory receptor from 100 to 200 µM. In some aspects, the compounds of the present disclosure have an IC$_{50}$ for the Indole/skatole olfactory receptor from 120 to 200 µM. In some aspects, the compounds of the present disclosure have an IC$_{50}$ for the Indole/skatole olfactory receptor from 140 to 200 µM. In some aspects, the compounds of the present disclosure have an IC$_{50}$ for the Indole/skatole olfactory receptor from 160 to 200 µM. In some aspects, the compounds of the present disclosure have an IC$_{50}$ for the Indole/skatole olfactory receptor from 180 to 200 µM.

In some aspects, the compounds of the present disclosure have an IC$_{50}$ for the Indole/skatole olfactory receptor from 4 to 180 µM. In some aspects, the compounds of the present disclosure have an IC$_{50}$ for the Indole/skatole olfactory receptor from 4 to 160 µM. In some aspects, the compounds of the present disclosure have an IC$_{50}$ for the Indole/skatole olfactory receptor from 4 to 140 µM. In some aspects, the compounds of the present disclosure have an IC$_{50}$ for the Indole/skatole olfactory receptor from 4 to 120 µM. In some aspects, the compounds of the present disclosure have an IC$_{50}$ for the Indole/skatole olfactory receptor from 4 to 100 µM. In some aspects, the compounds of the present disclosure have an IC$_{50}$ for the Indole/skatole olfactory receptor from 4 to 90 µM. In some aspects, the compounds of the present disclosure have an IC$_{50}$ for the Indole/skatole olfactory receptor from 4 to 80 µM. In some aspects, the compounds of the present disclosure have an IC$_{50}$ for the Indole/skatole olfactory receptor from 4 to 70 µM. In some aspects, the compounds of the present disclosure have an IC$_{50}$ for the Indole/skatole olfactory receptor from 4 to 60 µM. In some aspects, the compounds of the present disclosure have an IC$_{50}$ for the Indole/skatole olfactory receptor from 4 to 50 µM. In some aspects, the compounds of the present disclosure have an IC$_{50}$ for the Indole/skatole olfactory receptor from 4 to 40 µM. In some aspects, the compounds of the present disclosure have an IC$_{50}$ for the Indole/skatole olfactory receptor from 4 to 30 µM. In some aspects, the compounds of the present disclosure have an IC$_{50}$ for the Indole/skatole olfactory receptor from 4 to 20 µM. In some aspects, the compounds of the present disclosure have an IC$_{50}$ for the Indole/skatole olfactory receptor from 4 to 10 µM. In some aspects, the compounds of the present disclosure have an IC$_{50}$ for the Indole/skatole olfactory receptor from 4 to 9 µM. In some aspects, the compounds of the present disclosure have an IC$_{50}$ for the Indole/skatole olfactory receptor from 4 to 8 µM. In some aspects, the compounds of the present disclosure have an IC$_{50}$ for the Indole/skatole olfactory receptor from 4 to 7 µM. In some aspects, the compounds of the present disclosure have an IC$_{50}$ for the Indole/skatole olfactory receptor from 4 to 6 µM. In some aspects, the compounds of the present disclosure have an IC$_{50}$ for the Indole/skatole olfactory receptor from 4 to 5 µM.

In some aspects, the compounds of the present disclosure have an IC$_{50}$ for the 1-octen-3-ol of 4, or 5, or 6, or 7, or 8, or 9, or 10, or 20, or 30, or 40, or 50, or 60, or 70, or 80, or 90, or 100, or 120, or 140, or 160, or 180, or 200 µM.

In some aspects, the at least one compound that inhibits the indole/skatole olfactory receptor is selected from the group consisting of: benzyl formate, (+−)-1-phenylethyl acetate, (+−)-(3E)-4-(2,6,6-trimethyl-2-cyclohexen-1-yl)-3-buten-2-one, (+−)-perhydro-5,5,8A-trimethyl-2-trans-naphthalenone, 3-phenyl-1-propanol, [cis-4-(2-propanyl)cyclohexyl]methanol, 2-methyl-2-indanmethanol, (2-methyl-2-indanyl)methyl acetate, (+−)-5-ethyl-2-methyl-2-indanmethanol, (2,5-dimethyl-1,3-dihydroinden-2-yl)methanol, 5-methyl-2-indanmethanol, (+−)-1-(2,5-dimethyl-2,3-dihydro-1H-inden-2-yl)ethanone, 4-(1,1-dimethylpropyl)-1-cyclohexanone, (+−)-2-methoxymethyl-2,5-dimethylindan,2,5,6-trimethyl-2-indanmethanol, (+−)-(2,4,5-trimethyl-2,3-dihydro-1H-inden-2-yl)methanol, (+−)-2-ethyl-5-methyl-2-indanmethanol, (+−)-2,4-dimethyl-2-indanmethanol, (+−)-2,4,6-trimethyl-2-indanmethanol, (+−)(2,7-dimethyl-1,2,3,4-tetrahydro-2-napththalenyl) methanol, (+−)-(2,6-dimethyl-1,2,3,4-tetrahydro-2-naphthalenyl)methanol, (+−)-(5-methoxy-2-methyl-2,3-dihydro-1H-inden-2-YL)methanol, 2,2-dimethyl-3-phenyl-1-propanol alcohol, 1-(3,3-dimethylcyclohexen-1-yl)pent-4-en-1-one; 1-(5,5-dimethylcyclohexen-1-yl)pent-4-en-1-one, (+−)-1,2,6-trimethyl-2-indanmethanol, (+−)-2,4-dimethyl-4,4a,5,9b-tetrahydroindeno[1,2-d][1,3]dioxine (ISOMER A)+ (+−)-2,4-dimethyl-4,4a,5,9b-tetrahydroindeno[1,2-d][1,3] dioxine (ISOMER B) (A+B), 8,8-dimethyl-2,3,4,6,7,8~{a}-hexahydro-1~{H}-naphthalene-2-carbaldehyde; 8,8-dimethyl-2,3,5,6,7,8~{a}-hexahydro-1~{H}-naphthalene-2-carbaldehyde; 8,8-dimethyl-2,3,4,5,6,7-hexahydro-1~{H}-naphthalene-2-carbaldehyde; 2,2-dimethyl-octahydro-1~{H}-2,4~{a}-methanonapthalen-8-one, 4-t-butylcyclohexanone, 1-(2,2-dimethyl-6-methylidenecyclohexyl)pent-1-en-3-one; 3-methyl-4-(2,6,6-trimethylcyclohex-2-en-1-yl)but-3-en-2-one; 1-(2,6,6-trimethylcyclohexen-1-yl)pent-1-en-3-one; 1-(2,6,6-trimethylcyclohex-2-en-1-yl)pent-1-en-3-one, 2,2-dimethyl-4-phenyl-1,3-dioxolane, (4E,8E)-4,8-cyclododecadien-1-one (A)+(4E,8Z)-4,8-cyclododecadien-1-one (B)+(4Z,8E)-4,8-cyclododecadien-1-one (C), (+−)-2-((methoxymethoxy)methyl)-2,5-dimethyl-2,3-dihydro-1H-indene, 3-(4-hydroxy-4-methylpentyl)cyclohex-3-ene-1-carbaldehyde; 4-(4-hydroxy-4-methylpentyl)cyclohex-3-ene-1-carbaldehyde, amyl phenylacetate, 4-(2,6,6-trimethylcyclohexen-1-yl)but-3-en-2-one; 4-(2,6,6-trimethylcyclohex-2-en-1-yl)but-3-en-2-one, 1,1,2,3,3-pentamethyl-2,5,6,7-tetrahydroinden-4-one, 3-phenylbutanal, 2,4-dimethyl-4-phenyloxolane, 1-(5,5-dimethylcyclohexen-1-yl)pent-4-en-1-one, [1R-(1R*,4R*,6R*,10S*)]-4,12,12-trimethyl-9-methylene-5-oxatricyclo[8.2.0.0$^{4,6}$]dodecane, 2-methyl-3-(4-methylphenyl)propanal, 3-methyl-5-phenylpentanal, isopropyl quinolone, (+−)-(2E)-1-(2,6,6-trimethyl-2-cyclohexen-1-yl)-2-buten-1-one, 4-(2,6,6-trimethylcyclohexen-1-yl)but-3-en-2-one; 4-(2,6,6-trimethylcyclohex-2-en-1-yl)but-3-en-2-one, 4,5,6,7,8,9,10,11,12,13-decahydrocyclododeca[d][1,3]oxazole, and combinations thereof.

In some aspects, the at least one compound may be modified to prolong, modify, increase, or ehnance the olfactive and/or malodor counteractant benefit provided by the at least one compound. One example of the modification may be to generate a precursor, or profragrance molecule using the at least one compound, wherein the profragrance may release the at least one compound by a chemical reaction during or after application (using $O_2$, light, enzymes, water (pH) or temperature as the release trigger).

In some aspects, the profragrance does not provide any olfactive and/or malodor counteractant benefits.

Examples of methods used to generate a prorarance are described in International Patent Application Publication No. WO2013/139766.

In some aspects, the profragrance may be a β-thio carbonyl profragrance derivative including, but not limited to: 3-(dodecylthio)-1-(2,6,6-trimethylcyclohex-3-en-1-yl)butan-1-one (derived from δ-damascone, also known and referred to herein as Haloscent® D, trademark and origin: Firmenich SA) or 3-(dodecylthio)-1-(2,6,6-trimethylcyclohex-2-en-1-yl)butan-1-one (derived from α-damascone) or 4-(dodecylthio)-4-(2,6,6-trimethylcyclohex-2-en-1-yl)butan-2-one (derived from ionone, also known and referred to herein as Haloscent® I, trademark and origin: Firmenich SA), or mixtures thereof.

Another example of a β-thio carbonyl profragrance derivative of formula (I) suitable for use in the present disclosure include the β-thio carbonyl profragrance derivatives disclosed in International Patent Application Publication No. WO2013/032885.

Methods According to Some Aspects of the Present Disclosure

Some aspects presented herein provide a method to inhibit, reduce, or suppress the perception of a malodor in a subject, comprising contacting the subject with at least one compound selected from the group consisting of: (1RS,6RS,11RS)-2,2,9,11-tetramethylspiro[5.5]undec-8-en-1-yl acetate, (+−)-2,2,7,11-tetramethylspiro[5.5]undec-8-en-1-yl-acetate, (+−)-2,3,7,7-tetramethylspiro[4.5]dec-2-en-6-yl acetate, (+−)-2,3,7,7-tetramethylspiro[4.5]dec-6-yl acetate, 1,5,10,10-tetramethylspiro[5.5]undec-3-en-11-yl acetate, 2,3,9,9-tetramethylspiro[4.5]decan-10-yl)acetate, (5,10,10-trimethylspiro[5.5]undec-2-en-11-yl) formate, (3,5,10,10-tetramethylspiro[5.5]undec-2-en-11-yl) acetate, (2,3,9,9-tetramethylspiro[4.5]dec-2-en-10-yl)acetate, (9,9-dimethylspiro[4.5]dec-2-en-10-yl)acetate, 10-methoxy-9,9-dimethylspiro[4.5]dec-2-ene, 4,10,10,11-tetramethylspiro[5.5]undec-2-en-11-ol, 5,10,10,11-tetramethylspiro[5.5]undec-3-en-11-ol, a mixture of 4,10,10,11-tetramethylspiro[5.5]undec-2-en-11-ol and 5,10,10,11-tetramethylspiro[5.5]undec-3-en-11-ol, 2,4,8-trimethylspiro[5.5]undec-3-en-11-ol, 2,9,11-trimethylspiro[5.5]undec-9-en-5-ol, a mixture of 2,4,8-trimethylspiro[5.5]undec-3-en-11-ol and 2,9,11-trimethylspiro[5.5]undec-9-en-5-ol, 3-methyl-5-propan-2-ylspiro[5.5]undec-2-en-11-ol, 11-methylspiro[5.5]undecan-5-ol, 3,10,10-trimethylspiro[5.5]undec-3-en-11-ol, 4,10,10-trimethylspiro[5.5]undec-3-en-11-ol, a mixture of 3,10,10-trimethylspiro[5.5]undec-3-en-11-ol and 4,10,10-trimethylspiro[5.5]undec-3-en-11-ol [2,2-dimethyl-1-(2,4,6-trimethylcyclohex-3-en-1-yl)propyl] acetate, [2,2-dimethyl-1-(2,4,6-trimethylcyclohexyl)propyl] acetate, (1RS)-2,2-dimethyl-1-[(1SR,2SR)-2-methylcyclohexyl]propyl acetate, 9,9-dimethylspiro[4.5]dec-2-en-10-ol, 2,3,9,9-tetramethylspiro[4.5]decan-10-ol, (2,2,3,3,9,9-hexamethylspiro[4.5]decan-10-yl) acetate, 9-methoxy-8,8-dimethylspiro[4.4]non-2-ene, (8,8-dimethylspiro[4.4]non-2-en-9-yl) acetate, 2,3,8,8-tetramethylspiro[4.4]non-2-en-9-one, 2,3,9,9-tetramethylspiro[4.5]dec-2-en-10-ol, 4-methoxy-3,3-dimethylspiro[4.4]nonane, (4,9,9-trimethylspiro[4.5]dec-2-en-10-yl) acetate, 2,4,9,9-tetramethylspiro[4.5]dec-2-en-10-ol, (2,3,9,9-tetramethylspiro[4.5]dec-2-en-10-yl) formate, (2,4,9,9-tetramethylspiro[4.5]dec-2-en-10-yl) acetate, (+−)-2,3-dimethylspiro[4.5]dec-2-en-6-yl acetate, (4~{S},5~{R},6~{S},11~{S})-4,11-dimethylspiro[5.5]undecan-5-ol, 9,9-dimethylspiro[4.5]dec-2-en-10-one, 2,3,9,9-tetramethylspiro[4.5]dec-2-en-10-one, 2,4,9,9-tetramethylspiro[4.5]dec-2-en-10-one, 1,1',1',5-tetramethyl-2'-methylidenespiro[6-oxabicyclo[3.1.0]hexane-3,3'-cyclohexane], 4,9,9-trimethylspiro[4.5]dec-2-en-10-one, 2,2-dimethyl-6,6-bis(2-methylprop-2-enyl)cyclohexan-1-one, 2,2-dimethyl-5,5-bis(2-methylprop-2-enyl)cyclopentan-1-one, 2-but-3-en-2-yl-6,6-dimethyl-2-prop-2-enylcyclohexan-1-one, 2,2-bis(2-methyl-2-propen-1-yl)cyclohexanone, a mixture of 2-but-3-en-2-yl-6,6-dimethyl-2-prop-2-enylcyclohexan-1-one and 2,2-bis(2-methyl-2-propen-1-yl)cyclohexanone, 2,2-dimethyl-1-(2-methylcyclohexyl)propan-1-ol, 2,2-dimethyl-1-(3-methylcyclohexyl)propan-1-ol, a mixture of 2,2-dimethyl-1-(2-methylcyclohexyl)propan-1-ol and 2,2-dimethyl-1-(3-methylcyclohexyl)propan-1-ol, 2,2-dimethyl-6,6-bis(2-methylprop-2-enyl)cyclohexan-1-ol, 1-methoxy-2,6-dimethyl-1-prop-2-enylcyclohexane, methyl 1-(3-methylbut-2-enyl)cyclohex-2-ene-1-carboxylate, methyl 1-(3-methylbut-2-enyl)cyclohex-3-ene-1-carboxylate, a mixture of methyl 1-(3-methylbut-2-enyl)cyclohex-2-ene-1-carboxylate and methyl 1-(3-methylbut-2-enyl)cyclohex-3-ene-1-carboxylate, 2,2-dimethyl-5,5-bis(2-methylprop-2-enyl)cyclopentan-1-ol, 1-(2,6-dimethylcyclohex-3-en-1-yl)-2,2-dimethylpropan-1-ol, 1-(2-methyl-4-tricyclo[5.2.1.0$^{1,5}$]decanyl)ethyl acetate, 1-(2,4-dimethyl-4-tricyclo[5.2.1.0$^{1,5}$]decanyl)ethyl acetate, 1-((1R,3S,3aS,6S)-1,2,3-trimethyloctahydro-3a,6-methanoinden-1-yl)ethan-1-one, 1-(2,4-dimethyl-4-tricyclo[5.2.1.0ˆ{1,5}]decanyl)ethanone, 2,3,4-trimethyltricyclo[5.2.1.0ˆ{1,5}]decane-4-carbaldehyde, (2,3,4-trimethyl-4-tricyclo[5.2.1.0ˆ{1,5}]decanyl)methyl acetate, 1-((3aS,6S)-2,3-dimethyloctahydro-3a,6-methanoinden-1-yl)ethan-1-one oxime, 1,3-dimethyloctahydro-3a,6-methanoindene-1-carbaldehyde oxime, ~{N}-[1-[(1~{R},7~{R})-2,3,4-trimethyl-4-tricyclo[5.2.1.0$^{1,5}$]decanyl]ethylidene]hydroxylamine, (+−)-1-(2,4-dimethyltricyclo[5.2.1.0$^{1,5}$]dec-4-yl)ethanone, (+−)-1-(2,4-dimethyltricyclo[5.2.1.0~1.5~]dec-4-yl) ethyl acetate, 1-[(1RS,2RS,4SR,7RS)-2,3,4-trimethyltricyclo[5.2.1.0~]dec-4-yl) ethanone, (E/Z)-1-[(1RS,7RS)-2,3-dimethyltricyclo[5.2.1.0$^{1.5}$]dec-4-yl) ethanone oxime, (E/Z)-1-[(1S,7S)-2,3,4-trimethyltricyclo[5.2.1.0~1.5~]dec-4-yl) ethanone oxime, (E/Z)-1-((3aS,6S)-1,2,3-trimethyloctahydro-3a,6-methanoinden-1-yl)ethanone oxime, (+−)-1-(3-methyloctahydro-3a,6-methanoinden-1-yl)ethyl acetate, [1R-(1R*,4R*,6R*,10S*)]-4,12,12-trimethyl-9-methylene-5-oxatricyclo[8.2.0.0$^{4,6}$]dodecane, 1-2,6,6-trimethyl-3-cyclohexen-1-yl-2-buten-1-one, 2-tertbutyl phenol, 5-Methyl-2-(propan-2-yl)phenol, nona-2,6-dienal, 1,1-diethoxy-3,7-dimethylocta-2,6-diene, 3-(4-hydroxy-4-methylpentyl)cyclohex-3-ene-1-carbaldehyde; 4-(4-hydroxy-4-methylpentyl)cyclohex-3-ene-1-carbaldehyde, 1,4,8-trimethyl-13-oxabicyclo[10.1.0]trideca-4,8-diene; 1,5,8-trimethyl-13-oxabicyclo[10.1.0]trideca-4,8-diene, 3-(4-tert-butylphenyl)propanal, (4R,4aS,6R)-4,4a-dimethyl-6-prop-1-en-2-yl-3,4,5,6,7,8-hexahydronaphthalen-2-one, geranyl acetate, 1-(3,3-dimethylcyclohexen-1-yl)pent-4-en-1-one; 1-(5,5-dimethylcyclohexen-1-yl)pent-4-en-1-one, 1-(3,3-dimethylcyclohexen-1-yl)pent-4-en-1-one; 1-(5,5-dimethylcyclohexen-1-yl)pent-4-en-1-one, 2-ethoxy-5-prop-1- enylphenol, 2,6,6,8-tetramethyl-9-oxatetracyclo[5.4.1.0^{1,5}.0^{8,10}]dodecane, nonylenic aldehyde, isobutylquinoline, cyclopentadec-4-en-1-one, (−)-(R)-3,7-dimethyl-6-octenenitrile, 2-methyl-5-propan-2-ylphenol, isopropyl quinolone, 5-hexyl-2-methylpyridine, (2,5-dimethyl-1,3-dihydroinden-2-yl)methanol, 2-pentylcyclopentan-1-one, 4-(2,6,6-trimethylcyclohexen-1-yl)but-3-en-2-one; 4-(2,6,6-trimethylcyclohex-2-en-1-yl)but-3-en-2-one, 3-methyl-4-(2,6,6-trimethylcyclohex-2-en-1-yl)but-3-en-2-one; 1-(2,6,6-trimethylcyclohex-2-en-1-yl)pent-1-en-3-one, 2,4-dimethylcyclohex-3-enecarbaldehyde, phenylethylol, 3,7-dimethylocta-2,6-dienal, (2,2,2-trichloro-1-phenylethyl) acetate, 4-(2,6,6-trimethylcyclohexen-1-yl)but-3-en-2-one, phenyl ethyl acetate, 7-hydroxy-3,7-dimethyloctanal, methyl citral, 6,10-dimethylundeca-5,9-dien-2-one, 2-ethoxy-5-prop-1-enylphenol, (4-methyl-4-phenylpentan-2-yl) acetate, (+−)-3-methylcyclopentadecanone, 1-(4,8-dimethyl-12-methylidenecyclododeca-4,8-dien-1-yl)ethanone; 1-(2,6,10-trimethylcyclododeca-1,5,9-trien-1-yl) ethanone; 1-(2,6,10-trimethylcyclododeca-2,5,9-trien-1-yl) ethanone, cyclododecanone, (Z)-3,4,5,6,6-pentamethylhept-3-en-2-one, 1,4-dioxacyclohexadecane-5,16-dione, pentanol, oxacyclohexadecan-2-one, 1,1,2,3,3-pentamethyl-2,5,6,7-tetrahydroinden-4-one, (+−)-perhydro-5,5,8,8A-trimethyl-2-trans-naphthalenone, 2,3,3-trimethyl-2H-inden-1-one, 4-(4,8-dimethylnona-3,7-dienyl)pyridine, 4-[(1~{R},3~{R},6~{R})-2,2,3,6-tetramethylcyclohexyl]but-3-en-2-one; 4-[(1~{S},3~{S},6~{R})-2,2,3,6-tetramethylcyclohexyl]but-3-en-2-one, (+)-(1R,7R)-10,10-dimethyl-tricyclo[7.1.1.0(2,7)]undec-2-en-4-one, (9<I>E</I>)-cycloheptadec-9-en-1-one, 8,8-dimethyl-2,3,4,6,7,8~{a}-hexahydro-1~{H}-naphthalene-2-carbaldehyde; 8,8-dimethyl-2,3,5,6,7,8~{a}-hexahydro-1~{H}-naphthalene-2-carbaldehyde; 8,8-dimethyl-2,3,4,5,6,7-hexahydro-1~{H}-naphthalene-2-carbaldehyde; 2,2-dimethyl-octahydro-1~{H}-2,4-~{a}-methanonaphthalen-8-one, 2,4~{a},8,8-tetramethyl-1~{a},2,4,5,6,7-hexahydro-1~{H}-cycloprop[j]naphthalen-3-one; 2,6,6,8-tetramethyltricyclo[5.3.1.0$^{1,5}$]undecan-9-one, (+−)-(3E)-4-(2,6,6-trimethyl-2-cyclohexen-1-yl)-3-buten-2-one, (+−)-3,6,8,8-tetramethyloctahydro-1H-3a,7-methanoazulen-6-ol, (1RS,2SR,5RS,7RS,8SR)-5-methyltricyclo[6.2.1.0~2,7~] undecan-4-one (A)+(1RS,2SR,5SR,7RS,8SR)-5-methyltricyclo[6.2.1.0~2,7~]undecan-4-one (B), ethyl 2,6,6-trimethyl-1,3-cyclohexadiene-1-carboxylate, ethyl 4,6,6-trimethyl-1,3-cyclohexadiene-1-carboxylate, (2-methyl-2-indanyl)methyl acetate, 2-pentylcyclopentan-1-one, (+−)-1-(2,5-dimethyl-2,3-dihydro-1H-inden-2-yl)ethanone, 4-(1,1-dimethylpropyl)-1-cyclohexanone, phenethyl alcohol, diethyl 1,4-cyclohexanedicarboxylate, (+)-(R)-3,7-dimethyl-6-octenal, 3,5,6-trimethyl-3-cyclohexene-1-carbaldehyde (A)+2,4,6-trimethyl-3-cyclohexene-1-carbaldehyde (B), 3,7-dimethylocta-2,6-dienal, 3-(4-methyl-3-pentenyl)-3-cyclohexene-1-carbaldehyde (A)+4-(4-methyl-3-pentenyl)-3-cyclohexene-1-carbaldehyde, (4<I>Z</I>,8<I>E</I></I>)-13-oxabicyclo[10.1.0]trideca-4,8-diene, (4E,8E)-4,8-cyclododecadien-1-one (A)+(4E,8Z)-4,8-cyclododecadien-1-one (B)+(4Z,8E)-4,8-cyclododecadien-1-one (C), 13-oxabicyclo[10.1.0]trideca-4,8-diene 2,2,7,7-tetramethyltricyclo[6.2.1.0~1,6~]undecan-6-ol, (+)-(1S,2S,3S,5R)-2,6,6-trimethylspiro[bicyclo[3.1.1]heptane-3,1'-cyclohexane]-2'-en-4'-one, (5RS,6RS)-2,6,10,10-tetramethyl-1-oxaspiro[4.5]decan-6-ol, (2,2,2-trichloro-1-phenylethyl) acetate, patchouli oil, (1~{S},3~{S},6~{R},7~{R},8~{S})-2,2,6,8-tetramethyltricyclo[5.3.1.0$^{3,8}$]undecan-3-ol, (4S,4aS,8aR)-4,8a-dimethyl-1,2,3,4,5,6,7-octahydronaphthalen-4a-ol, benzyl formate, (+−)-1-phenylethyl acetate, 3-phenyl-1-propanol, [cis-4-(2-propanyl)cyclohexyl]methanol, 2-methyl-2-indanmethanol, (2-methyl-2-indanyl)methyl acetate, (+−)-5-ethyl-2-methyl-2-indanmethanol, 5-methyl-2-indanmethanol, (+−)-2-methoxymethyl-2,5-dimethylindan, 2,5,6-trimethyl-2-indanmethanol, (+−)-(2,4,5-trimethyl-2,3-dihydro-1H-inden-2-yl)methanol, (+−)-2-ethyl-5-methyl-2-indanmethanol, (+−)-2,4-dimethyl-2-indanmethanol, (+−)-2,4,6-trimethyl-2-indanmethanol, (+−)(2,7-dimethyl-1,2,3,4-tetrahydro-2-naphthalenyl)methanol, (+−)-(2,6-dimethyl-1,2,3,4-tetrahydro-2-naphthalenyl)methanol, (+−)-(5-methoxy-2-methyl-2,3-dihydro-1H-inden-2-YL)methanol, 2,2-dimethyl-3-phenyl-1-propanol alcohol, (+−)-1,2,6-trimethyl-2-indanmethanol, (+−)-2,4-dimethyl-4,4a,5,9b-tetrahydroindeno[1,2-d][1,3]dioxine (ISOMER A)+(+−)-2,4-dimethyl-4,4a,5,9b-tetrahydroindeno[1,2-d][1,3]dioxine (ISOMER B) (A+B), 4-t-butylcyclohexanone, 1-(2,2-dimethyl-6-methylidenecyclohexyl)pent-1-en-3-one; 3-methyl-4-(2,6,6-trimethylcyclohex-2-en-1-yl)but-3-en-2-one; 1-(2,6,6-trimethylcyclohexen-1-yl)pent-1-en-3-one; 1-(2,6,6-trimethylcyclohex-2-en-1-yl)pent-1-en-3-one, 2,2-dimethyl-4-phenyl-1,3-dioxolane, (+−)-2-((methoxymethyl)methyl)-2,5-dimethyl-2,3-dihydro-1H-indene, amyl phenylacetate, 3-phenylbutanal, 2,4-dimethyl-4-phenyloxolane, 1-(5,5-dimethylcyclohexen-1-yl)pent-4-en-1-one, 2-methyl-3-(4-methylphenyl)propanal, 3-methyl-5-phenylpentanal, (+−)-(2E)-1-(2,6,6-trimethyl-2-cyclohexen-1-yl)-2-buten-1-one, 4-(2,6,6-trimethylcyclohexen-1-yl)but-3-en-2-one; 4-(2,6,6-trimethylcyclohex-2-en-1-yl)but-3-en-2-one, 4,5,6,7,8,9,10,11,12,13-decahydrocyclododeca[d][1,3]oxazole, and combinations thereof, wherein the at least one compound is contacted in an amount sufficient to inhibit, reduce, or suppress the subject's perception of the malodor.

In some aspects, the subject is contacted by treating a surface with, or dispensing at least partly in the air, the at least one compound.

In some aspects, the amount sufficient to reduce, prevent, or inhibit the subject's perception of malodor is from 10 to 100 ppm.

In some aspects, the amount sufficient to reduce, prevent, or inhibit the subject's perception of malodor is from 20 to 100 ppm. In some aspects, the amount sufficient to reduce, prevent, or inhibit the subject's perception of malodor is from 30 to 100 ppm. In some aspects, the amount sufficient to reduce, prevent, or inhibit the subject's perception of malodor is from 40 to 100 ppm. In some aspects, the amount sufficient to reduce, prevent, or inhibit the subject's perception of malodor is from 50 to 100 ppm. In some aspects, the amount sufficient to reduce, prevent, or inhibit the subject's perception of malodor is from 60 to 100 ppm. In some aspects, the amount sufficient to reduce, prevent, or inhibit the subject's perception of malodor is from 70 to 100 ppm. In some aspects, the amount sufficient to reduce, prevent, or inhibit the subject's perception of malodor is from 80 to 100 ppm. In some aspects, the amount sufficient to reduce, prevent, or inhibit the subject's perception of malodor is from 90 to 100 ppm.

In some aspects, the amount sufficient to reduce, prevent, or inhibit the subject's perception of malodor is from 10 to 90 ppm. In some aspects, the amount sufficient to reduce, prevent, or inhibit the subject's perception of malodor is from 10 to 80 ppm. In some aspects, the amount sufficient to reduce, prevent, or inhibit the subject's perception of malodor is from 10 to 70 ppm. In some aspects, the amount sufficient to reduce, prevent, or inhibit the subject's perception of malodor is from 10 to 60 ppm. In some aspects, the amount sufficient to reduce, prevent, or inhibit the subject's perception of malodor is from 10 to 50 ppm. In some aspects, the amount sufficient to reduce, prevent, or inhibit the subject's perception of malodor is from 10 to 40 ppm. In some aspects, the amount sufficient to reduce, prevent, or inhibit the subject's perception of malodor is from 10 to 30 ppm. In some aspects, the amount sufficient to reduce, prevent, or inhibit the subject's perception of malodor is from 10 to 20 ppm.

In some aspects, the contacting inhibits at least one olfactory receptor in the subject.

In some aspects, the at least one olfactory receptor is a butyric acid olfactory receptor.

In some aspects, the at least one olfactory receptor is a geonol olfactory receptor.

In some aspects, the at least one olfactory receptor is a 1-octen-3-ol olfactory receptor.

In some aspects, the at least one olfactory receptor is an indole/skatole olfactory receptor.

In some aspects, the at least one olfactory receptor is a DMTS olfactory receptor.

In some aspects, the amount of the at least one compound that is effective to inhibit the activity of malodor olfactory receptors is calculated using an $IC_{50}$ value, as determined using a receptor-based assay. In some aspects, the amount of the at least one compound that is effective to inhibit the activity of malodor olfactory receptors ranges from 10 to 100 ppm in solution.

Some aspects presented herein provides a method to inhibit, reduce, or suppress the perception of a malodor in a subject, comprising contacting the subject with at least one compound selected from the group consisting of: (1RS,6RS,11RS)-2,2,9,11-tetramethylspiro[5.5]undec-8-en-1-yl acetate, (+−)-2,2,7,11-tetramethylspiro[5.5]undec-8-en-1-yl-acetate, (+−)-2,3,7,7-tetramethylspiro[4.5]dec-2-en-6-yl acetate, (+−)-2,3,7,7-tetramethylspiro[4.5]dec-6-yl acetate, 1,5,10,10-tetramethylspiro[5.5]undec-3-en-11-yl acetate, 2,3,9,9-tetramethylspiro[4.5]decan-10-yl)acetate, (5,10,10-trimethylspiro[5.5]undec-2-en-11-yl) formate, (3,5,10,10-tetramethylspiro[5.5]undec-2-en-11-yl) acetate, (2,3,9,9-tetramethylspiro[4.5]dec-2-en-10-yl)acetate, (9,9-dimethylspiro[4.5]dec-2-en-10-yl)acetate, 10-methoxy-9,9-dimethylspiro[4.5]dec-2-ene, 4,10,10,11-tetramethylspiro[5.5]undec-2-en-11-ol, 5,10,10,11-tetramethylspiro[5.5]undec-3-en-11-ol, a mixture of 4,10,10,11-tetramethylspiro[5.5]undec-2-en-11-ol and 5,10,10,11-tetramethylspiro[5.5]undec-3-en-11-ol, 2,4,8-trimethylspiro[5.5]undec-3-en-11-ol, 2,9,11-trimethylspiro[5.5]undec-9-en-5-ol, a mixture of 2,4,8-trimethylspiro[5.5]undec-3-en-11-ol and 2,9,11-trimethylspiro[5.5]undec-9-en-5-ol, 3-methyl-5-propan-2-ylspiro[5.5]undec-2-en-11-ol, 11-methylspiro[5.5]undecan-5-ol, 3,10,10-trimethylspiro[5.5]undec-3-en-11-ol, 4,10,10-trimethylspiro[5.5]undec-3-en-11-ol, a mixture of 3,10,10-trimethylspiro[5.5]undec-3-en-11-ol and 4,10,10-trimethylspiro[5.5]undec-3-en-11-ol [2,2-dimethyl-1-(2,4,6-trimethylcyclohex-3-en-1-yl)propyl] acetate, [2,2-dimethyl-1-(2,4,6-trimethylcyclohexyl)propyl] acetate, (1RS)-2,2-dimethyl-1-[(1SR,2SR)-2-methylcyclohexyl]propyl acetate, 9,9-dimethylspiro[4.5]dec-2-en-10-ol, 2,3,9,9-tetramethylspiro[4.5]decan-10-ol, (2,2,3,3,9,9-hexamethylspiro[4.5]decan-10-yl) acetate, 9-methoxy-8,8-dimethylspiro[4.4]non-2-ene, (8,8-dimethylspiro[4.4]non-2-en-9-yl) acetate, 2,3,8,8-tetramethylspiro[4.4]non-2-en-9-one, 2,3,9,9-tetramethylspiro[4.5]dec-2-en-10-ol, 4-methoxy-3,3-dimethylspiro[4.4]nonane, (4,9,9-trimethylspiro[4.5]dec-2-en-10-yl) acetate, 2,4,9,9-tetramethylspiro[4.5]dec-2-en-10-ol, (2,3,9,9-tetramethylspiro[4.5]dec-2-en-10-yl) formate, (2,4,9,9-tetramethylspiro[4.5]dec-2-en-10-yl) acetate, (+−)-2,3-dimethylspiro[4.5]dec-2-en-6-yl acetate, (4~{S},5~{R},6~{S},11~{S})-4,11-dimethylspiro[5.5]undecan-5-ol, 9,9-dimethylspiro[4.5]dec-2-en-10-one, 2,3,9,9-tetramethylspiro[4.5]dec-2-en-10-one, 2,4,9,9-tetramethylspiro[4.5]dec-2-en-10-one, 1,1',1',5-tetramethyl-2'-methylidenespiro[6-oxabicyclo[3.1.0]hexane-3,3'-cyclohexane], 4,9,9-trimethylspiro[4.5]dec-2-en-10-one, 2,2-dimethyl-6,6-bis(2-methylprop-2-enyl)cyclohexan-1-one, 2,2-dimethyl-5,5-bis(2-methylprop-2-enyl)cyclopentan-1-one, 2-but-3-en-2-yl-6,6-dimethyl-2-prop-2-enylcyclohexan-1-one, 2,2-bis(2-methyl-2-propen-1-yl)cyclohexanone, a mixture of 2-but-3-en-2-yl-6,6-dimethyl-2-prop-2-enylcyclohexan-1-one and 2,2-bis(2-methyl-2-propen-1-yl)cyclohexanone, 2,2-dimethyl-1-(2-methylcyclohexyl)propan-1-ol, 2,2-dimethyl-1-(3-methylcyclohexyl)propan-1-ol, a mixture of 2,2-dimethyl-1-(2-methylcyclohexyl)propan-1-ol and 2,2-dimethyl-1-(3-methylcyclohexyl)propan-1-ol, 2,2-dimethyl-6,6-bis(2-methylprop-2-enyl)cyclohexan-1-ol, 1-methoxy-2,6-dimethyl-1-prop-2-enylcyclohexane, methyl 1-(3-methylbut-2-enyl)cyclohex-2-ene-1-carboxylate, methyl 1-(3-methylbut-2-enyl)cyclohex-3-ene-1-carboxylate, a mixture of methyl 1-(3-methylbut-2-enyl)cyclohex-2-ene-1-carboxylate and methyl 1-(3-methylbut-2-enyl)cyclohex-3-ene-1-carboxylate, 2,2-dimethyl-5,5-bis(2-methylprop-2-enyl)cyclopentan-1-ol, 1-(2,6-dimethylcyclohex-3-en-1-yl)-2,2-dimethylpropan-1-ol, 1-(2-methyl-4-tricyclo[5.2.1.0$^{1,5}$]decanyl)ethyl acetate, 1-(2,4-dimethyl-4-tricyclo[5.2.1.0$^{1,5}$]decanyl)ethyl acetate, 1-((1R,3S,3aS,6S)-1,2,3-trimethyloctahydro-3a,6-methanoinden-1-yl)ethan-1-one, 1-(2,4-dimethyl-4-tricyclo[5.2.1.0^{1,5}]decanyl)ethanone, 2,3,4-trimethyltricyclo[5.2.1.0^{1,5}]decane-4-carbaldehyde, (2,3,4-trimethyl-4-tricyclo[5.2.1.0^{1,5}]decanyl) methyl acetate, 1-((3aS,6S)-2,3-dimethyloctahydro-3a,6-methanoinden-1-yl)ethan-1-one oxime, 1,3-dimethyloctahydro-3a,6-methanoindene-1-carbaldehyde oxime, ~{N}-[1-[(1~{R},7~{R})-2,3,4-trimethyl-4-tricyclo[5.2.1.0$^{1,5}$]decanyl]ethylidene]hydroxylamine, (+−)-1-(2,4-dimethyltricyclo[5.2.1.0$^{1,5}$]dec-4-yl) ethanone, (+−)-1-(2,4-dimethyltricyclo[5.2.1.0~1.5~]-dec-4-yl) ethyl acetate, 1-[(1RS,2RS,4SR,7RS)-2,3,4-trimethyltricyclo[5.2.1.0$^{1.}$~]dec-4-yl) ethanone, (E/Z)-1-[(1RS,7RS)-2,3-dimethyltricyclo[5.2.1.0$^{1.5}$]dec-4-yl) ethanone oxime, (E/Z)-1-[(1S,7S)-2,3,4-trimethyltricyclo[5.2.1.0~1.5~]dec-4-yl) ethanone oxime, (E/Z)-1-((3aS,6S)-1,2,3-trimethyloctahydro-3a,6-methanoinden-1-yl)ethanone oxime, (+−)-1-(3-methyloctahydro-3a,6-methanoinden-1-yl)ethyl acetate, [1R-(1R*,4R*,6R*,10S*)]-4,12,12-trimethyl-9-methylene-5-oxatricyclo[8.2.0.0$^{4,6}$]dodecane, 1-2,6,6-trimethyl-3-cyclohexen-1-yl-2-buten-1-one, 2-tertbutyl phenol, 5-Methyl-2-(propan-2-yl)phenol, nona-2,6-dienal, 1,1-diethoxy-3,7-dimethylocta-2,6-diene, 3-(4-hydroxy-4-methylpentyl)cyclohex-3-ene-1-carbaldehyde; 4-(4-hydroxy-4-methylpentyl)cyclohex-3-ene-1-carbaldehyde, 1,4,8-trimethyl-13-oxabicyclo[10.1.0]trideca-4,8-diene; 1,5,8-trimethyl-13-oxabicyclo[10.1.0]trideca-4,8-diene, 3-(4-tert-butylphenyl)propanal, (4R,4aS,6R)-4,4a-dimethyl-6-prop-1-en-2-yl-3,4,5,6,7,8-hexahydronaphthalen-2-one, geranyl acetate, 1-(3,3-dimethylcyclohexen-1-yl)pent-4-en-1-one; 1-(5,5-dimethylcyclohexen-1-yl)pent-4-en-1-one, 1-(3,3-dimethylcyclohexen-1-yl)pent-4-en-1-one; 1-(5,5-dimethylcyclohexen-1-yl)pent-4-en-1-one, 2-ethoxy-5-prop-1-enylphenol, 2,6,6,8-tetramethyl-9-oxatetracyclo[5.4.1.0^{1,5}].0^{8,10}]dodecane, nonylenic aldehyde, isobutylquinoline, cyclopentadec-4-en-1-one, (−)-(R)-3,7- dimethyl-6-octenenitrile, 2-methyl-5-propan-2-ylphenol, isopropyl quinolone, 5-hexyl-2-methylpyridine, (2,5-dimethyl-1,3-dihydroinden-2-yl)methanol, 2-pentylcyclopentan-1-one, 4-(2,6,6-trimethylcyclohexen-1-yl)but-3-en-2-one; 4-(2,6,6-trimethylcyclohex-2-en-1-yl)but-3-en-2-one, 3-methyl-4-(2,6,6-trimethylcyclohex-2-en-1-yl)but-3-en-2-one; 1-(2,6,6-trimethylcyclohex-2-en-1-yl)pent-1-en-3-one, 2,4-dimethylcyclohex-3-enecarbaldehyde, phenylethylol, 3,7-dimethylocta-2,6-dienal, (2,2,2-trichloro-1-phenylethyl) acetate, 4-(2,6,6-trimethylcyclohexen-1-yl)but-3-en-2-one, phenyl ethyl acetate, 7-hydroxy-3,7-dimethyloctanal, methyl citral, 6,10-dimethylundeca-5,9-dien-2-one, 2-ethoxy-5-prop-1-enylphenol, (4-methyl-4-phenylpentan-2-yl) acetate, (+−)-3-methylcyclopentadecanone, 1-(4,8-dimethyl-12-methylidenecyclododeca-4,8-dien-1-yl)ethanone; 1-(2,6,10-trimethylcyclododeca-1,5,9-trien-1-yl) ethanone; 1-(2,6,10-trimethylcyclododeca-2,5,9-trien-1-yl) ethanone, cyclododecanone, (Z)-3,4,5,6,6-pentamethylhept-3-en-2-one, 1,4-dioxacyclohexadecane-5,16-dione, pentanol, oxacyclohexadecan-2-one, 1,1,2,3,3-pentamethyl-2,5,6,7-tetrahydroinden-4-one, (+−)-perhydro-5,5,8A-trimethyl-2-trans-naphthalenone, 2,3,3-trimethyl-2H-inden-1-one, 4-(4,8-dimethylnona-3,7-dienyl)pyridine, 4-[(1~{R}, 3~{R},6~{R})-2,2,3,6-tetramethylcyclohexyl]but-3-en-2-one; 4-[(1~{S},3~{S},6~{R})-2,2,3,6-tetramethylcyclohexyl]but-3-en-2-one, (+)-(1R,7R)-10,10-dimethyl-tricyclo[7.1.1.0(2,7)]undec-2-en-4-one, (9<I>E</I>)-cycloheptadec-9-en-1-one, 8,8-dimethyl-2,3,4,6,7,8~{a}-hexahydro-1~{H}-naphthalene-2-carbaldehyde; 8,8-dimethyl-2,3,5,6,7,8~{a}-hexahydro-1~{H}-naphthalene-2-carbaldehyde; 8,8-dimethyl-2,3,4,5,6,7-hexahydro-1~{H}-naphthalene-2-carbaldehyde; 2,2-dimethyl-octahydro-1~{H}-2,4~{a}-methanonapthalen-8-one, 2,4~{a},8,8-tetramethyl-1~{a},2,4,5,6,7-hexahydro-1~{H}-cyclopropa[ ]naphthalen-3-one; 2,6,6,8-tetramethyl-tricyclo[5.3.1.01$^{1.5}$]undecan-9-one, (+−)-(3E)-4-(2,6,6-trimethyl-2-cyclohexen-1-yl)-3-buten-2-one, (+−)-3,6,8,8-tetramethyloctahydro-1H-3a,7-methanoazulen-6-ol, (1RS, 2SR,5RS,7RS,8SR)-5-methyltricyclo[6.2.1.0~2,7~] undecan-4-one (A)+(1RS,2SR,5SR,7RS,8SR)-5-methyltricyclo[6.2.1.0~2,7~]undecan-4-one (B), ethyl2,6,6-trimethyl-1,3-cyclohexadiene-1-carboxylate, ethyl 4,6,6-trimethyl-1,3-cyclohexadiene-1-carboxylate, (2-methyl-2-indanyl)methyl acetate, 2-pentylcyclopentan-1-one, (+−)-1-(2,5-dimethyl-2,3-dihydro-1H-inden-2-yl)ethanone, 4-(1,1-dimethylpropyl)-1-cyclohexanone, phenethyl alcohol, diethyl 1,4-cyclohexanedicarboxylate, (+)-(R)-3,7-dimethyl-6-octenal, 3,5,6-trimethyl-3-cyclohexene-1-carbaldehyde (A)+2,4,6-trimethyl-3-cyclohexene-1-carbaldehyde (B), 3,7-dimethylocta-2,6-dienal, 3-(4-methyl-3-pentenyl)-3-cyclohexene-1-carbaldehyde (A)+4-(4-methyl-3-pentenyl)-3-cyclohexene-1-carbaldehyde, (4<I>Z</I>,8<I>E</I>)-13-oxabicyclo[10.1.0]trideca-4,8-diene, (4E,8E)-4,8-cyclododecadien-1-one (A)+(4E,8Z)-4,8-cyclododecadien-1-one (B)+(4Z,8E)-4,8-cyclododecadien-1-one (C), 13-oxabicyclo[10.1.0]trideca-4,8-diene 2,2,7,7-tetramethyltricyclo[6.2.1.0~1,6~]undecan-6-ol, (+)-(1S,2S, 3S,5R)-2,6,6-trimethylspiro [bicyclo [3.1.1]heptane-3,1'-cyclohexane]-2'-en-4'-one, (5RS,6RS)-2,6,10,10-tetramethyl-1-oxaspiro[4.5]decan-6-ol, (2,2,2-trichloro-1-phenylethyl) acetate, patchouli oil, (1~{S},3~{S},6~{R}, 7~{R},8~{S})-2,2,6,8-tetramethyltricyclo[5.3.1.0$^{3,8}$] undecan-3-ol, (4S,4aS,8aR)-4,8a-dimethyl-1,2,3,4,5,6,7-octahydronaphthalen-4a-ol, benzyl formate, (+−)-1-phenylethyl acetate, 3-phenyl-1-propanol, [cis-4-(2-propanyl)cyclohexyl]methanol, 2-methyl-2-indanmethanol, (2-methyl-2-indanyl)methyl acetate, (+−)-5-ethyl-2-methyl-2-indanmethanol, 5-methyl-2-indanmethanol, (+−)-2-methoxymethyl-2,5-dimethylindan, 2,5,6-trimethyl-2-indanmethanol, (+−)-(2,4,5-trimethyl-2,3-dihydro-1H-inden-2-yl)methanol, (+−)-2-ethyl-5-methyl-2-indanmethanol, (+−)-2,4-dimethyl-2-indanmethanol, (+−)-2,4,6-trimethyl-2-indanmethanol, (+−)(2,7-dimethyl-1,2,3,4-tetrahydro-2-napththalenyl)methanol, (+−)-(2,6-dimethyl-1,2,3,4-tetrahydro-2-naphthalenyl)methanol, (+−)-(5-methoxy-2-methyl-2,3-dihydro-1H-inden-2-YL)methanol, 2,2-dimethyl-3-phenyl-1-propanol alcohol, (+−)-1,2,6-trimethyl-2-indanmethanol, (+−)-2,4-dimethyl-4,4a,5,9b-tetrahydroindeno[1,2-d][1,3]dioxine (ISOMER A)+(+−)-2, 4-dimethyl-4,4a,5,9b-tetrahydroindeno[1,2-d][1,3]dioxine (ISOMER B) (A+B), 4-t-butylcyclohexanone, 1-(2,2-dimethyl-6-methylidenecyclohexyl)pent-1-en-3-one; 3-methyl-4-(2,6,6-trimethylcyclohex-2-en-1-yl)but-3-en-2-one; 1-(2, 6,6-trimethylcyclohexen-1-yl)pent-1-en-3-one; 1-(2,6,6-trimethylcyclohex-2-en-1-yl)pent-1-en-3-one, 2,2-dimethyl-4-phenyl-1,3-dioxolane, (+−)-2-((methoxymethyl)methyl)-2,5-dimethyl-2,3-dihydro-1H-indene, amyl phenylacetate, 3-phenylbutanal, 2,4-dimethyl-4-phenyloxolane, 1-(5,5-dimethylcyclohexen-1-yl)pent-4-en-1-one, 2-methyl-3-(4-methylphenyl)propanal, 3-methyl-5-phenylpentanal, (+−)-(2E)-1-(2,6,6-trimethyl-2-cyclohexen-1-yl)-2-buten-1-one, 4-(2,6,6-trimethylcyclohexen-1-yl)but-3-en-2-one; 4-(2,6,6-trimethylcyclohex-2-en-1-yl)but-3-en-2-one, 4,5,6,7,8,9,10, 11,12,13-decahydrocyclododeca[d][1,3]oxazole, and combinations thereof, wherein the at least one olfactory receptor is selected from the group consisting of: a butyric acid olfactory receptor, a geonol olfactory receptor, a 1-octen-3-ol olfactory receptor, and indole/skatole olfactory receptor, and a DMTS olfactory receptor, and wherein the at least one compound is contacted in an amount sufficient to inhibit the at least one olfactory receptor.

In some aspects, the at least one olfactory receptor is selected from the group consisting of: OR2W1, OR1A1, OR2J3, OR4Q3, OR5K1, OR11A1, OR2M3, OR51E1, OR4S2, OR51I2, OR2H1, OR2W3, OR8G1, and corresponding mouse orthologs Olfr263, Olfr403, Olfr735, Olfr96 Olfr1193, Olfr641, Olfr137, Olfr173, Olfr164, and Olfr558, as well as mouse OR[5] Olfr1487, Olfr339, Olfr1126, Olfr93, Olfr398, Olfr120, Olfr1364, Olfr937, Olfr1322, and Olfr46.

In some aspects, the inhibition of the at least one olfactory receptor inhibits, reduces, suppresses, the perception of a malodor in a subject.

In some aspects, the malodor is selected from the group consisting of: latrine malodor, laundry malodor, moldy malodor, and sweat malodor.

In some aspects, the at least one olfactory receptor is a butyric acid olfactory receptor. In some aspects, the butyric acid olfactory receptor is selected from the group consisting of: the OR51E1 olfactory receptor and the Olfr558 olfactory receptor.

In some aspects, the at least one compound that inhibits the butyric acid olfactory receptor is selected from the group consisting of: (1RS,6RS,11RS)-2,2,9,11-tetramethylspiro [5.5]undec-8-en-1-yl acetate, (+−)-2,2,7,11-tetramethylspiro [5.5]undec-8-en-1-yl-acetate, (+−)-2,3,7,7-tetramethylspiro [4.5]dec-2-en-6-yl acetate, (+−)-2,3,7,7-tetramethylspiro [4.5]dec-6-yl acetate, 1,5,10,10-tetramethylspiro[5.5]undec-3-en-11-yl acetate, 2,3,9,9-tetramethylspiro[4.5]decan-10-yl)acetate, (5,10,10-trimethylspiro[5.5]undec-2-en-11-yl) formate, (3,5,10,10-tetramethylspiro[5.5]undec-2-en-11-yl)

acetate, (2,3,9,9-tetramethylspiro[4.5]dec-2-en-10-yl)acetate, (9,9-dimethylspiro[4.5]dec-2-en-10-yl)acetate, 10-methoxy-9,9-dimethylspiro[4.5]dec-2-ene, 4,10,10,11-tetramethylspiro[5.5]undec-2-en-11-ol, 5,10,10,11-tetramethylspiro[5.5]undec-3-en-11-ol, a mixture of 4,10,10,11-tetramethylspiro[5.5]undec-2-en-11-ol and 5,10,10,11-tetramethylspiro[5.5]undec-3-en-11-ol, 2,4,8-trimethylspiro[5.5]undec-3-en-11-ol, 2,9,11-trimethylspiro[5.5]undec-9-en-5-ol, a mixture of 2,4,8-trimethylspiro[5.5]undec-3-en-11-ol and 2,9,11-trimethylspiro[5.5]undec-9-en-5-ol, 3-methyl-5-propan-2-ylspiro[5.5]undec-2-en-11-ol, 11-methylspiro[5.5]undecan-5-ol, 3,10,10-trimethylspiro[5.5]undec-3-en-11-ol, 4,10,10-trimethylspiro[5.5]undec-3-en-11-ol, a mixture of 3,10,10-trimethylspiro[5.5]undec-3-en-11-ol and 4,10,10-trimethylspiro[5.5]undec-3-en-11-ol [2,2-dimethyl-1-(2,4,6-trimethylcyclohex-3-en-1-yl)propyl] acetate, [2,2-dimethyl-1-(2,4,6-trimethylcyclohexyl)propyl] acetate, (1RS)-2,2-dimethyl-1-[(1SR,2SR)-2-methylcyclohexyl]propyl acetate, 9,9-dimethylspiro[4.5]dec-2-en-10-ol, 2,3,9,9-tetramethylspiro[4.5]decan-10-ol, (2,2,3,3,9,9-hexamethylspiro[4.5]decan-10-yl)acetate, 9-methoxy-8,8-dimethylspiro[4.4]non-2-ene, (8,8-dimethylspiro[4.4]non-2-en-9-yl) acetate, 2,3,8,8-tetramethylspiro[4.4]non-2-en-9-one, 2,3,9,9-tetramethylspiro[4.5]dec-2-en-10-ol, 4-methoxy-3,3-dimethylspiro[4.4]nonane, (4,9,9-trimethylspiro[4.5]dec-2-en-10-yl) acetate, 2,4,9,9-tetramethylspiro[4.5]dec-2-en-10-ol, (2,3,9,9-tetramethylspiro[4.5]dec-2-en-10-yl) formate, (2,4,9,9-tetramethylspiro[4.5]dec-2-en-10-yl) acetate, (+−)-2,3-dimethylspiro[4.5]dec-2-en-6-yl acetate, (4~{S},5~{R},6~{S},11~{S})-4,11-dimethylspiro[5.5]undecan-5-ol, 9,9-dimethylspiro[4.5]dec-2-en-10-one, 2,3,9,9-tetramethylspiro[4.5]dec-2-en-10-one, 2,4,9,9-tetramethylspiro[4.5]dec-2-en-10-one, 1,1',1',5-tetramethyl-2'-methylidenespiro[6-oxabicyclo[3.1.0]hexane-3,3'-cyclohexane],4,9,9-trimethylspiro[4.5]dec-2-en-10-one, 2,2-dimethyl-6,6-bis(2-methylprop-2-enyl)cyclohexan-1-one, 2,2-dimethyl-5,5-bis(2-methylprop-2-enyl)cyclopentan-1-one, 2-but-3-en-2-yl-6,6-dimethyl-2-prop-2-enylcyclohexan-1-one, 2,2-bis(2-methyl-2-propen-1-yl)cyclohexanone, a mixture of 2-but-3-en-2-yl-6,6-dimethyl-2-prop-2-enylcyclohexan-1-one and 2,2-bis(2-methyl-2-propen-1-yl)cyclohexanone, 2,2-dimethyl-1-(2-methylcyclohexyl)propan-1-ol, 2,2-dimethyl-1-(3-methylcyclohexyl)propan-1-ol, a mixture of 2,2-dimethyl-1-(2-methylcyclohexyl)propan-1-ol and 2,2-dimethyl-1-(3-methylcyclohexyl)propan-1-ol, 2,2-dimethyl-6,6-bis(2-methylprop-2-enyl)cyclohexan-1-ol, 1-methoxy-2,6-dimethyl-1-prop-2-enylcyclohexane, methyl 1-(3-methylbut-2-enyl)cyclohex-2-ene-1-carboxylate, methyl 1-(3-methylbut-2-enyl)cyclohex-3-ene-1-carboxylate, a mixture of methyl 1-(3-methylbut-2-enyl)cyclohex-2-ene-1-carboxylate and methyl 1-(3-methylbut-2-enyl)cyclohex-3-ene-1-carboxylate, 2,2-dimethyl-5,5-bis(2-methylprop-2-enyl)cyclopentan-1-ol, 1-(2,6-dimethylcyclohex-3-en-1-yl)-2,2-dimethylpropan-1-ol, 1-(2-methyl-4-tricyclo[5.2.1.0$^{1,5}$] decanyl)ethyl acetate, 1-(2,4-dimethyl-4-tricyclo[5.2.1.0$^{1,5}$] decanyl) acetate, 1-((1R,3S,3aS,6S)-1,2,3-trimethyloctahydro-3a,6-methanoinden-1-yl)ethan-1-one, 1-(2,4-dimethyl-4-tricyclo[5.2.1.0ˆ{1,5}]decanyl)ethanone, 2,3,4-trimethyltricyclo[5.2.1.0ˆ{1,5}]decane-4-carbaldehyde, (2,3,4-trimethyl-4-tricyclo[5.2.1.0ˆ{1,5}]decanyl) methyl acetate, 1-((3aS,6S)-2,3-dimethyloctahydro-3a,6-methanoinden-1-yl)ethan-1-one oxime, 1,3-dimethyloctahydro-3a,6-methanoindene-1-carbaldehyde oxime, ~{N}-[1-[(1~{R},7~{R})-2,3,4-trimethyl-4-tricyclo [5.2.1.0$^{1,5}$]decanyl]ethylidene]hydroxylamine, (+−)-1-(2,4-dimethyltricyclo[5.2.1.0$^{1,5}$]dec-4-yl)ethanone, (+−)-1-(2,4-dimethyltricyclo[5.2.1.0~1.5~]dec-4-yl) ethyl acetate, 1-[(1RS,2RS,4SR,7RS)-2,3,4-trimethyltricyclo[5.2.1.0$^{1.}$~] dec-4-yl) ethanone, (E/Z)-1-[(1RS,7RS)-2,3-dimethyltricyclo[5.2.1.0-]dec-4-yl) ethanone oxime, (E/Z)-1-[(1S,7S)-2, 3,4-trimethyltricyclo[5.2.1.0~1.5~]dec-4-yl) ethanone oxime, (E/Z)-1-((3aS,6S)-1,2,3-trimethyloctahydro-3a,6-methanoinden-1-yl)ethanone oxime, (+−)-1-(3-methyloctahydro-3a,6-methanoinden-1-yl)ethyl acetate, and combinations thereof.

In some aspects, the at least one olfactory receptor is a geonol olfactory receptor. In some aspects, the geonol olfactory receptor is selected from the group consisting of: the OR11A1 olfactory receptor, the OR2M3 olfactory receptor, the OR1A1 olfactory receptor, the OR2W1 olfactory receptor, the OR1A1 olfactory receptor, the OR2J3 olfactory receptor, the OR4Q3 olfactory receptor, and the OR5K1 olfactory receptor.

In some aspects, the at least one compound that inhibits the geonol olfactory receptor is selected from the group consisting of: [1R-(1R*,4R*,6R*,10S*)]-4,12,12-trimethyl-9-methylene-5-oxatricyclo[8.2.0.0$^{4,6}$]dodecane, 1-(2,6,6-trimethyl-1-cyclohex-3-enyl)but-2-en-1-one, 2-tertbutyl phenol, 5-Methyl-2-(propan-2-yl)phenol, nona-2,6-dienal, 1,1-diethoxy-3,7-dimethylocta-2,6-diene, 3-(4-hydroxy-4-methylpentyl)cyclohex-3-ene-1-carbaldehyde; 4-(4-hydroxy-4-methylpentyl)cyclohex-3-ene-1-carbaldehyde, 1,4,8-trimethyl-13-oxabicyclo[10.1.0]trideca-4,8-diene; 1,5,8-trimethyl-13-oxabicyclo[10.1.0]trideca-4,8-diene, 3-(4-tert-butylphenyl)propanal, (4R,4aS,6R)-4,4a-dimethyl-6-prop-1-en-2-yl-3,4,5,6,7,8-hexahydronaphthalen-2-one, geranyl acetate, 1-(3,3-dimethylcyclohexen-1-yl)pent-4-en-1-one; 1-(5,5-dimethylcyclohexen-1-yl)pent-4-en-1-one, 1-(3,3-dimethylcyclohexen-1-yl)pent-4-en-1-one; 1-(5,5-dimethylcyclohexen-1-yl)pent-4-en-1-one, 2-ethoxy-5-prop-1-enylphenol, 2,6,6,8-tetramethyl-9-oxatetracyclo[5.4.1.0ˆ{1,5}0.ˆ{8,10}]dodecane, nonylenic aldehyde, isobutylquinoline, cyclopentadec-4-en-1-one, (−)-(R)-3,7-dimethyl-6-octenenitrile, 2-methyl-5-propan-2-ylphenol, isopropyl quinolone, 5-hexyl-2-methylpyridine, (2,5-dimethyl-1,3-dihydroinden-2-yl)methanol, 2-pentylcyclopentan-1-one, 4-(2,6,6-trimethylcyclohexen-1-yl)but-3-en-2-one; 4-(2,6,6-trimethylcyclohex-2-en-1-yl)but-3-en-2-one, 3-methyl-4-(2,6,6-trimethylcyclohex-2-en-1-yl)but-3-en-2-one; 1-(2,6,6-trimethylcyclohex-2-en-1-yl)pent-1-en-3-one, 2,4-dimethylcyclohex-3-enecarbaldehyde, phenylethylol, 3,7-dimethylocta-2,6-dienal, (2,2,2-trichloro-1-phenylethyl) acetate, 4-(2,6,6-trimethylcyclohexen-1-yl)but-3-en-2-one, phenyl ethyl acetate, 7-hydroxy-3,7-dimethyloctanal, methyl citral, 6,10-dimethylundeca-5,9-dien-2-one, 2-ethoxy-5-prop-1-enylphenol, and combinations thereof.

In some aspects, the effective amount of the 1-(2,6,6-trimethyl-1-cyclohex-3-enyl)but-2-en-1-one is from 0.02 to 0.2% w/v.

In some aspects, the effective amount of the 4-(2,6,6-trimethylcyclohexen-1-yl)but-3-en-2-one; 4-(2,6,6-trimethylcyclohex-2-en-1-yl)but-3-en-2-one is from 0.02 to 0.2% w/v.

In some aspects, the effective amount of the 1-(3,3-dimethylcyclohexen-1-yl)pent-4-en-1-one; 1-(5,5-dimethylcyclohexen-1-yl)pent-4-en-1-one is 0.03% w/v.

In some aspects, the effective amount of the isobutylquinoline is from 1 to 10% w/v.

In some aspects, the effective amount of the methyl citral is 1% w/v.

In some aspects, the effective amount of the 1,1-diethoxy-3,7-dimethylocta-2,6-diene is from 0.005 to 0.03% w/v.

In some aspects, the effective amount of the phenylethyl acetate is 0.3% w/v.

In some aspects, the effective amount of the 2-tertbutyl phenol is 0.5% w/v.

In some aspects, the effective amount of the 2,4-dimethylcyclohex-3-enecarbaldehyde is 0.2% w/v.

In some aspects, the effective amount of the 6,10-dimethylundeca-5,9-dien-2-one is 5% w/v.

In some aspects, the effective amount of the 4-(2,6,6-trimethylcyclohexen-1-yl)but-3-en-2-one is 5% w/v.

In some aspects, the effective amount of the 3,7-dimethylocta-2,6-dienal is from 0.002 to 0.15% w/v.

In some aspects, the effective amount of the 7-hydroxy-3,7-dimethyloctanal is from 20 to 100% w/v.

In some aspects, the effective amount of the 3-methyl-4-(2,6,6-trimethylcyclohex-2-en-1-yl)but-3-en-2-one; 1-(2,6,6-trimethylcyclohex-2-en-1-yl)pent-1-en-3-one is from 0.1 to 1% w/v.

In some aspects, the effective amount of the (2,5-dimethyl-1,3-dihydroinden-2-yl)methanol is 15% w/v.

In some aspects, the effective amount of the 2-methyl-5-propan-2-ylphenol is 2% w/v.

In some aspects, the effective amount of the 2-ethoxy-5-prop-1-enylphenol is from 0.5 to 5% w/v.

In some aspects, the at least one olfactory receptor is a 1-octen-3-ol olfactory receptor. In some aspects, the 1-octen-3-ol olfactory receptor is selected from the group consisting of: the OR2W1 olfactory receptor, the OR1A1 olfactory receptor, the OR2J3 olfactory receptor, the OR4Q3 olfactory receptor, and the OR5K1 olfactory receptor.

In some aspects, the at least one compound that inhibits the 1-octen-3-ol olfactory receptor is selected from the group consisting of: isobutylquinoline, 2-tertbutyl phenol, [1R-(1R*,4R*,6R*,10S*)]-4,12,12-trimethyl-9-methylene-5-oxatricyclo[8.2.0.04'6]dodecane, (4-methyl-4-phenylpentan-2-yl)acetate, (+−)-3-methylcyclopentadecanone, 1-(4,8-dimethyl-12-methylidenecyclododeca-4,8-dien-1-yl)ethanone; 1-(2,6,10-trimethylcyclododeca-1,5,9-trien-1-yl)ethanone; 1-(2,6,10-trimethylcyclododeca-2,5,9-trien-1-yl)ethanone, cyclopentadec-4-en-1-one, cyclododecanone, 2,4-dimethylcyclohex-3-enecarbaldehyde, 1,4-dioxacyclohexadecane-5,16-dione, pentanol, oxacyclohexadecan-2-one, 1,1,2,3,3-pentamethyl-2,5,6,7-tetrahydroinden-4-one, (+−)-perhydro-5,5,8A-trimethyl-2-trans-naphthalenone, 2,3,3-trimethyl-2H-inden-1-one, 4-(4,8-dimethylnona-3,7-dienyl)pyridine, 4-[(1~{R},3~{R},6~{R})-2,2,3,6-tetramethylcyclohexyl]but-3-en-2-one; 4-[(1~{S},3~{S},6~{R})-2,2,3,6-tetramethylcyclohexyl]but-3-en-2-one, (+)-(1R,7R)-10,10-dimethyl-tricyclo[7.1.1.0(2,7)]undec-2-en-4-one, (9<I>E</I>)-cycloheptadec-9-en-1-one, 8,8-dimethyl-2,3,4,6,7,8~{a}-hexahydro-1~{H}-naphthalene-2-carbaldehyde; 8,8-dimethyl-2,3,5,6,7,8~{a}-hexahydro-1~{H}-naphthalene-2-carbaldehyde; 8,8-dimethyl-2,3,4,5,6,7-hexahydro-1~{H}-naphthalene-2-carbaldehyde; 2,2-dimethyl-octahydro-1~{H}-2,4~{a}-methanonapthalen-8-one, 2,4~{a},8,8-tetramethyl-1~{a},2,4,5,6,7-hexahydro-1~{H}-cyclopropa[ ]naphthalen-3-one; 2,6,6,8-tetramethyltricyclo[5.3.1.0^{1,5}]undecan-9-one, methyl citral, and combinations thereof.

In some aspects, the effective amount of the (2,2,2-trichloro-1-phenylethyl) acetate is 10% w/v.

In some aspects, the effective amount of the 1,4-dioxacyclohexadecane-5,16-dione is 50% w/v.

In some aspects, the effective amount of the oxacyclohexadecan-2-one is 50% w/v.

In some aspects, the effective amount of the methyl citral is 1% w/v.

In some aspects, the effective amount of the cyclopentadec-4-en-1-one is from 0.5 to 5% w/v.

In some aspects, the effective amount of the 2,4-dimethylcyclohex-3-enecarbaldehyde is 0.5% w/v.

In some aspects, the effective amount of the crops rhubarb is 1% w/v.

In some aspects, the effective amount of the 1,1-diethoxy-3,7-dimethylocta-2,6-diene is from 0.005 to 0.03% w/v.

In some aspects, the effective amount of the 2,3,3-trimethyl-2H-inden-1-one is from 0.07 to 0.7% w/v.

In some aspects, the effective amount of the 2,4~{a},8,8-tetramethyl-1~{a},2,4,5,6,7-hexahydro-1~{H}-cyclopropa[j]naphthalen-3-one; 2,6,6,8-tetramethyltricyclo[5.3.1.0^{1,5}]undecan-9-one is from 2 to 20% w/v.

In some aspects, the at least one olfactory receptor is a DMTS olfactory receptor. In one aspect, the DMTS olfactory receptor is selected from the group consisting of: the OR4S2 olfactory receptor, the OR52N5 olfactory receptor, the OR2L13 olfactory receptor, the OR2AJ1 olfactory receptor, the OR4C15 olfactory receptor, the OR5AC2 olfactory receptor, the OR8H3 olfactory receptor, the OR11G2 olfactory receptor, the OR52N2 olfactory receptor, the OR5T1 olfactory receptor, the OR2W1 olfactory receptor, the OR1A1 olfactory receptor, the OR5K1 olfactory receptor, the Olfr1193 olfactory receptor, the Olfr1093 olfactory receptor, the Olfr1097 olfactory receptor, the Olfr166 olfactory receptor, the Olfr169 olfactory receptor, the Olfr738 olfactory receptor, the Olfr173 olfactory receptor, the Olfr263 olfactory receptor, the Olfr403 olfactory receptor, the Olfr742 olfactory receptor, the Olfr207 olfactory receptor, the Olfr665 olfactory receptor, the Olfr669 olfactory receptor, and the Olfr1211 olfactory receptor.

In some aspects, the at least one compound that inhibits the DMTS olfactory receptor is selected from the group consisting of: (+−)-(3E)-4-(2,6,6-trimethyl-2-cyclohexen-1-yl)-3-buten-2-one, (+−)-3,6,8,8-tetramethyloctahydro-1H-3a,7-methanoazulen-6-ol, nona-2,6-dienal, (+−)-perhydro-5,5,8A-trimethyl-2-trans-naphthalenone, (1RS,2SR,5RS,7RS,8SR)-5-methyltricyclo[6.2.1.0~2,7~]undecan-4-one (A)+(1RS,2SR,5SR,7RS,8SR)-5-methyltricyclo[6.2.1.0~2,7~]undecan-4-one (B), ethyl 2,6,6-trimethyl-1,3-cyclohexadiene-1-carboxylate, 1,4,8-trimethyl-13-oxabicyclo[10.1.0]trideca-4,8-diene; 1,5,8-trimethyl-13-oxabicyclo[10.1.0]trideca-4,8-diene, ethyl 4,6,6-trimethyl-1,3-cyclohexadiene-1-carboxylate, (2-methyl-2-indanyl)methyl acetate, 2-pentylcyclopentan-1-one, (+−)-1-(2,5-dimethyl-2,3-dihydro-1H-inden-2-yl)ethanone, 4-(1,1-dimethylpropyl)-1-cyclohexanone, 4-(2,6,6-trimethylcyclohexen-1-yl)but-3-en-2-one; 4-(2,6,6-trimethylcyclohex-2-en-1-yl)but-3-en-2-one, phenethyl alcohol, diethyl 1,4-cyclohexanedicarboxylate, (+)-(R)-3,7-dimethyl-6-octenal, 3,5,6-trimethyl-3-cyclohexene-1-carbaldehyde (A)+2,4,6-trimethyl-3-cyclohexene-1-carbaldehyde (B), 3,7-dimethyl-octa-2,6-dienal, 3-(4-methyl-3-pentenyl)-3-cyclohexene-1-carbaldehyde (A)+4-(4-methyl-3-pentenyl)-3-cyclohexene-1-carbaldehyde, 3-methyl-4-(2,6,6-trimethylcyclohex-2-en-1-yl)but-3-en-2-one; 1-(2,6,6-trimethylcyclohex-2-en-1-yl)pent-1-en-3-one, (4<I>Z</I>,8<I>E</I>)-13-oxabicyclo[10.1.0]trideca-4,8-diene, (4E,8E)-4,8-cyclododecadien-1-one (A)+(4E,8Z)-4,8-cyclododecadien-1-one (B)+(4Z,8E)-4,8-cyclododecadien-1-one (C), (1<I>R</I>,4<I>Z</I>,8<I>E</I>,12<I>R</I>)-13-oxabicyclo[10.1.0]trideca-4,8-diene; (4<I>Z</I>,8<I>E</I>)-13-oxabicyclo[10.1.0]trideca-4,8-diene, 2,2,7,7-tetramethyltricyclo[6.2.1.0~1,6~]undecan-6-ol, (2,5-dimethyl-1,3-dihydroinden-2-yl)methanol, 8,8-dimethyl-2,3,4,6,7,8~{a}-hexahydro-1~{H}-naphthalene-2-carbaldehyde; 8,8-dimethyl-2,3,5,6,7,8~{a}- hexahydro-1~{H}-naphthalene-2-carbaldehyde; 8,8-dimethyl-2,3,4,5,6,7-hexahydro-1~{H}-naphthalene-2-carbaldehyde; 2,2-dimethyl-octahydro-1~{H}-2,4~{a}-methanonaphthalen-8-one, (+)-(1S,2S,3S,5R)-2,6,6-trimethylspiro[bicyclo[3.1.1]heptane-3,1'-cyclohexane]-2'-en-4'-one, 1-(3,3-dimethylcyclohexen-1-yl)pent-4-en-1-one; 1-(5,5-dimethylcyclohexen-1-yl)pent-4-en-1-one, (5RS,6RS)-2,6,10,10-tetramethyl-1-oxaspiro[4.5~]decan-6-OL, (2,2,2-trichloro-1-phenylethyl) acetate, patchouli oil, (1~{S},3~{S},6~{R},7~{R},8~{S})-2,2,6,8-tetramethyltricyclo[5.3.1.0ˆ{3,8}]undecan-3-ol, (4S,4aS,8aR)-4,8a-dimethyl-1,2,3,4,5,6,7-octahydronaphthalen-4a-ol, and combinations thereof.

In some aspects, the at least one olfactory receptor is an indole/skatole olfactory receptor. In one aspect, the indole/skatole olfactory receptor is selected from the group consisting of: the OR52N2 olfactory receptor, the OR11G2 olfactory receptor, the OR5AC2 olfactory receptor, the OR4C15 olfactory receptor, the OR8S1 olfactory receptor, the OR11H6 olfactory receptor, the OR11H4 olfactory receptor, the Olfr665 olfactory receptor, the Olfr740 olfactory receptor, the Olfr743 olfactory receptor, and the Olfr746 olfactory receptor, the Olfr738 olfactory receptor, the Olfr739 olfactory receptor, the Olfr741 olfactory receptor, the Olfr742 olfactory receptor, the Olfr744 olfactory receptor, the Olfr748 olfactory receptor and the Olfr749 olfactory receptor.

In some aspects, the at least one compound that inhibits the indole/skatol olfactory receptor is selected from the group consisting of: benzyl formate, (+−)-1-phenylethyl acetate, (+−)-(3E)-4-(2,6,6-trimethyl-2-cyclohexen-1-yl)-3-buten-2-one, (+−)-perhydro-5,5,8A-trimethyl-2-trans-naphthalenone, 3-phenyl-1-propanol, [cis-4-(2-propanyl)cyclohexyl]methanol, 2-methyl-2-indanmethanol, (2-methyl-2-indanyl)methyl acetate, (+−)-5-ethyl-2-methyl-2-indanmethanol, (2,5-dimethyl-1,3-dihydroinden-2-yl) methanol, 5-methyl-2-indanmethanol, (+−)-1-(2,5-dimethyl-2,3-dihydro-1H-inden-2-yl)ethanone, 4-(1,1-dimethylpropyl)-1-cyclohexanone, (+−)-2-methoxymethyl-2,5-dimethylindan, 2,5,6-trimethyl-2-indanmethanol, (+−)-(2,4,5-trimethyl-2,3-dihydro-1H-inden-2-yl)methanol, (+−)-2-ethyl-5-methyl-2-indanmethanol, (+−)-2,4-dimethyl-2-indanmethanol, (+−)-2,4,6-trimethyl-2-indanmethanol, (+−)(2,7-dimethyl-1,2,3,4-tetrahydro-2-naphthalenyl) methanol, (+−)-(2,6-dimethyl-1,2,3,4-tetrahydro-2-naphthalenyl)methanol, (+−)-(5-methoxy-2-methyl-2,3-dihydro-1H-inden-2-YL)methanol, 2,2-dimethyl-3-phenyl-1-propanol alcohol, 1-(3,3-dimethylcyclohexen-1-yl)pent-4-en-1-one; 1-(5,5-dimethylcyclohexen-1-yl)pent-4-en-1-one, (+−)-1,2,6-trimethyl-2-indanmethanol, (+−)-2,4-dimethyl-4,4a,5,9b-tetrahydroindeno[1,2-d][1,3]dioxine (ISOMER A)+(+−)-2,4-dimethyl-4,4a,5,9b-tetrahydroindeno[1,2-d][1,3] dioxine (ISOMER B) (A+B), 8,8-dimethyl-2,3,4,6,7,8~{a}-hexahydro-1~{H}-naphthalene-2-carbaldehyde; 8,8-dimethyl-2,3,5,6,7,8~{a}-hexahydro-1~{H}-naphthalene-2-carbaldehyde; 8,8-dimethyl-2,3,4,5,6,7-hexahydro-1~{H}-naphthalene-2-carbaldehyde; 2,2-dimethyl-octahydro-1~{H}-2,4~{a}-methanonaphthalen-8-one, 4-t-butylcyclohexanone, 1-(2,2-dimethyl-6-methylidenecyclohexyl)pent-1-en-3-one; 3-methyl-4-(2,6,6-trimethylcyclohex-2-en-1-yl)but-3-en-2-one; 1-(2,6,6-trimethylcyclohexen-1-yl)pent-1-en-3-one; 1-(2,6,6-trimethylcyclohex-2-en-1-yl)pent-1-en-3-one, 2,2-dimethyl-4-phenyl-1,3-dioxolane, (4E,8E)-4,8-cyclododecadien-1-one (A)+(4E,8Z)-4,8-cyclododecadien-1-one (B)+(4Z,8E)-4,8-cyclododecadien-1-one (C), (+−)-2-((methoxymethyl)methyl)-2,5-dimethyl-2,3-dihydro-1H-indene, 3-(4-hydroxy-4-methylpentyl)cyclohex-3-ene-1-carbaldehyde; 4-(4-hydroxy-4-methylpentyl)cyclohex-3-ene-1-carbaldehyde, amyl phenylacetate, 4-(2,6,6-trimethylcyclohexen-1-yl)but-3-en-2-one; 4-(2,6,6-trimethylcyclohex-2-en-1-yl)but-3-en-2-one, 1,1,2,3,3-pentamethyl-2,5,6,7-tetrahydroinden-4-one, 3-phenylbutanal, 2,4-dimethyl-4-phenyloxalane, 1-(5,5-dimethylcyclohexen-1-yl)pent-4-en-1-one, [1R-(1R*,4R*,6R*,10S*)]-4,12,12-trimethyl-9-methylene-5-oxatricyclo[8.2.0.0$^{4,6}$]dodecane, 2-methyl-3-(4-methylphenyl) propanal, 3-methyl-5-phenylpentanal, isopropyl quinolone, (+−)-(2E)-1-(2,6,6-trimethyl-2-cyclohexen-1-yl)-2-buten-1-one, 4-(2,6,6-trimethylcyclohexen-1-yl)but-3-en-2-one; 4-(2,6,6-trimethylcyclohex-2-en-1-yl)but-3-en-2-one, 4,5,6,7,8,9,10,11,12,13-decahydrocyclododeca[d][1,3]oxazole, and combinations thereof.

In some aspects, the term "contacting" refers to administering to a subject, a composition comprising the at least one compound as described herein, wherein the administering results in dosing the subject with an effective amount of the at least one compound. Administration may be via any method readily selected by one of ordinary skill in the art. Methods include, but are not limited to, topical administration, inhalation, and the like. Accordingly the present disclosure contemplates formulating a composition comprising the at least one compound as described herein with a suitable carrier to facilitate administering a composition comprising the at least one compound as described herein to the subject.

Alternatively, in some aspects, the term "contacting" refers to dispensing or dispersing a composition comprising the at least one compound as described herein into a volume in need thereof, wherein the dispensing or dispersing results in dosing the subject with an effective amount of the at least one compound. Dispersion or dispensing of the at least one compound as described herein may be achieved by any method readily selected by one of ordinary skill in the art. Examples include, but are not limited to, a spray, a nebulizer, evaporation of a solution containing the at least one compound as described herein, and the like.

Accordingly the present disclosure contemplates formulating a composition comprising the at least one compound as described herein with a suitable carrier to facilitate treating a surface or volume with a composition comprising the at least one compound as described herein to the subject.

In some aspects, the term "contacting" refers to contacting a surface of a malodor source with a composition comprising the at least one compound as described herein, wherein the contacting results in an effective amount of the at least one compound being deposited on the surface. A composition comprising the at least one compound as described herein may be contacted on a surface by any method readily selected by one of ordinary skill in the art. Examples include, but are not limited to, a spray, a wipe, a solution, and the like.

Products and Formulations According to Some Aspects Presented Herein

In some aspects, the present disclosure provides a perfumed consumer product comprising the at least one compound in an amount sufficient to reduce, prevent, or inhibit the subject's perception of malodor. In some aspects, the perfumed consumer product is selected from the group consisting of: air care products, home care products and laundry care products.

In some aspects, the perfumed consumer product comprising an effective amount of the at least one compound comprises a formulation selected from the group consisting of: aerosol and/or water-based air freshener spray, wick/reed air freshener, liquid electrical (plug-in) air freshener, a solid support air freshener, gel-based air freshener, membrane-containing air freshener, bleaching, cleaning, washing detergent powder, liquid all-purpose cleaner, specialty cleaner and liquid detergent.

It is understood by a person skilled in the art that the at least one compound, as defined herein, may be added into composition described herein in neat form, or in a solvent. Alternatively, the at least one compound may first be modified, for example by entrapped with an entrapment material such as for example polymers, capsules, microcapsules, nanocapsules, liposomes, precursors, film formers, absorbents such as for example by using carbon or zeolites, cyclic oligosaccharides and mixtures thereof. Alternatively, the at least one compound may be chemically bound to substrates which are adapted to release the compounds upon application of an exogenous stimulus such as light, enzymes, or the like.

Accordingly, some aspects presented herein provide a composition comprising:
   a. the at least one compound;
   b. at least one ingredient selected from the group consisting of a perfumery carrier and a perfumery base; and
   c. optionally at least one perfumery adjuvant.

As used herein, the term "perfumery carrier" refers to a material which is practically neutral from a perfumery point of view, i.e. which does not significantly alter the organoleptic properties of perfuming ingredients. The perfumery carrier may be a liquid or a solid.

Non-limiting examples of liquid perfumery carriers include an emulsifying system, i.e. a solvent and a surfactant system, or a solvent commonly used in perfumery. A detailed description of the nature and type of solvents commonly used in perfumery cannot be exhaustive. However, non-limiting examples solvents include dipropyleneglycol, diethyl phthalate, isopropyl myristate, benzyl benzoate, 2-(2-ethoxyethoxy)-1-ethanol or ethyl citrate. For the compositions which comprise both a perfumery carrier and a perfumery base, other suitable perfumery carriers than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company).

Non-limiting examples of solid perfumery carriers include absorbing gums or polymers, or yet encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloide: Stabilisatoren, Dickungs-und Geliermittel in Lebensmitteln, Band 2 der Schriftenreihe Lebensmittelchemie, Lebensmittelqualitat, Behr's Verlag GmbH & Co., Hamburg, 1996. The encapsulation is a well-known process to a person skilled in the art, and may be performed, for instance, using techniques such as spray-drying, agglomeration or yet extrusion; or consists of a coating encapsulation, including coacervation and complex coacervation technique.

As used herein, the term "perfumery base" refers a composition comprising at least one perfuming co-ingredient. A perfuming co-ingredient does not include the at least one compound. As used herein, the term "perfuming co-ingredient" refers to compound, which is used in a perfuming preparation or a composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of his general knowledge and according to intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulphurous heterocyclic compounds and essential oils, and the perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that the co-ingredients may also be compounds known to release in a controlled manner various types of perfuming compounds.

As used herein, the term "perfumery adjuvant" refers to an ingredient capable of imparting additional added benefit such as a color, a particular light resistance, chemical stability, etc. A detailed description of the nature and type of adjuvant commonly used in perfuming bases cannot be exhaustive, but it has to be mentioned that the ingredients are well known to a person skilled in the art.

As used herein, the term perfume or perfume oil or perfume accord are used to designate a mixture of perfuming ingredients.

In some aspects, the perfuming composition comprises a malodor receptor antagonist system comprising at least one ingredient selected from the group of Table 1 and a non-functional perfume accord.

In some aspects, the perfuming composition comprises:
   (i) from about 2 wt % to about 85 wt %, of a malodor receptor antagonist system comprising at least one ingredient selected from the group of Table 1;
   (ii) from about 15 wt % to 98 wt % of a functional perfume accord comprising at least 2 perfuming ingredient(s) provided that any ingredient listed in Table 1 is excluded, the accord having a tonality preferably selected from floral, citrus and jasmine; and
   (iii) optionally a non-functional perfume accord.

Without intending to be limited to any particular theory, the association of a malodor receptor antagonist system comprising at least one ingredient selected from the group of Table 1 with a functional perfume accord consisting of perfuming ingredients performing against a malodor, improves the effect of the functional perfume accord in limiting, decreasing or eliminating the perception of the malodor.

As used herein, the terms malodor receptor antagonist, malodor antagonist system or malodor antagonist ingredient, also referred to as group I is meant to designate one or several compounds that each have the capacity to block at least one olfactory receptor that responds to a malodor target, identified by measuring activity of olfactory neurons or isolated receptors in cultured cell lines whose responses are driven by receptors as described under the examples below.

As used herein, the term functional perfume accord (referred to as group II) is meant to designate a mixture of at least two perfuming ingredients, referred as functional perfuming ingredients which have been established through e.g. sensory measurement as performing against at least one element of a malodor.

As used herein, the term non-functional perfume accord (referred to as group III) is meant to be a mixture of at least one, alternatively, at least two perfuming ingredients, referred to as non-functional perfuming ingredients that are not performing as a malodor counteractant, i.e. perfuming ingredients that are not part of group I or group II.

Moreover, by "perfuming ingredient" it is meant here a compound, which can be used in a perfuming preparation or a composition to impart at least an hedonic effect. In other words such an ingredient, to be considered as being a perfuming one, must be recognized by a person skilled in the art of perfumery as being able to impart or modify in a positive or pleasant way the odor of a composition, and not just as having an odor.

The nature and type of the perfuming ingredients do not warrant a more detailed description here, which in any case would not be exhaustive, the skilled person being able to select them on the basis of their general knowledge and according to intended use or application and the desired organoleptic effect. In general terms, these perfuming ingredients belong to chemical classes as varied as alcohols, lactones, aldehydes, ketones, esters, ethers, acetates, nitriles, terpenoids, nitrogenous or sulphurous heterocyclic compounds and essential oils, and the perfuming co-ingredients can be of natural or synthetic origin.

In particular one may cite perfuming ingredients which are commonly used in perfume formulations, such as:
  Aldehydic ingredients: decanal, dodecanal, 2-methyl-undecanal, 10-undecenal, octanal and/or nonenal;
  Aromatic-herbal ingredients: eucalyptus oil, camphor, eucalyptol, menthol and/or alpha-pinene;
  Balsamic ingredients: coumarine, ethylvanillin and/or vanillin;
  Citrus ingredients: dihydromyrcenol, 3,7-dimethylocta-2,6-dienal, orange oil, linalyl acetate, (−)-(R)-3,7-dimethyl-6-octenenitrile, orange terpenes, limonene, 1-P-menthen-8-yl acetate and/or 1,4(8)-P-menthadiene;
  Floral ingredients: Methyl dihydrojasmonate, linalool, Citronellol, phenylethanol, 3-(4-tert-butylphenyl)-2-methylpropanal, hexylcinnamic aldehyde, benzyl acetate, benzyl salicylate, tetrahydro-2-isobutyl-4-methyl-4(2H)-pyranol, beta ionone, methyl 2-(methylamino)benzoate, (E)-3-methyl-4-(2,6,6-trimethyl-2-cyclohexen-1-yl)-3-buten-2-one, hexyl salicylate, 3,7-dimethyl-1,6-nonadien-3-ol, 3-(4-isopropylphenyl)-2-methylpropanal, verdyl acetate, geraniol, P-menth-1-en-8-ol, 4-(1,1-dimethylethyl)-1-cyclohexyle acetate, 1,1-dimethyl-2-phenylethyl acetate, 4-cyclohexyl-2-methyl-2-butanol, amyl salicylate, high cis methyl dihydrojasmonate, 3-methyl-5-phenyl-1-pentanol, verdyl proprionate, geranyl acetate, tetrahydro linalool, cis-7-P-menthanol, Propyl (S)-2-(1,1-dimethylpropoxy)propanoate, 2-methoxynaphthalene, 2,2,2-trichloro-1-phenylethyl acetate, 4/3-(4-hydroxy-4-methylpentyl)-3-cyclohexene-1-carbaldehyde, amylcinnamic aldehyde, 4-phenyl-2-butanone, isononyle acetate, 4-(1,1-diméthyléthyl)-1-cyclohexyl acetate, verdyl isobutyrate and/or mixture of methyl-ionones isomers;
  Fruity ingredients: gamma undecalactone, 4-decanolide, ethyl 2-methyl-pentanoate, hexyl acetate, ethyl 2-methylbutanoate, gamma nonalactone, allyl heptanoate, 2-phenoxyethyl isobutyrate, ethyl 2-methyl-1,3-dioxolane-2-acetate and/or diethyl 1,4-cyclohexane dicarboxylate;
  Green ingredients: 2,4-Dimethyl-3-cyclohexene-1-carbaldehyde, 2-tert-butyl-1-cyclohexyl acetate, (+−)-1-phenylethyl acetate, allyl (2-methylbutoxy)acetate, 4-methyl-3-decen-5-ol, diphenyl ether, (Z)-3-hexen-1-ol and/or 1-(5,5-dimethyl-1-cyclohexen-1-yl)-4-penten-1-one;
  Musk ingredients: 1,4-dioxa-5,17-cycloheptadecanedione, pentadecenolide, 3-Methyl-5-cyclopentadecen-1-one, 1,3,4,6,7,8-hexahydro-4,6,6,7,8,8-hexamethylcyclopenta-g-2-benzopyrane, (1S,1'R)-2-[1-(3',3'-dimethyl-1'-cyclohexyl)ethoxy]-2-methylpropyl propanoate, pentadecanolide and/or (1S,1'R)-[1-(3',3'-Dimethyl-1'-cyclohexyl)ethoxycarbonyl]methylpropanoate;
  Woody ingredients: 1-(octahydro-2,3,8,8-tetramethyl-2-naphtalenyl)-1-ethanone, patchouli oil, terpenes fractions of patchouli oil, (1'R,E)-2-ethyl-4-(2',2',3'-trimethyl-3'-cyclopenten-1'-yl)-2-buten-1-ol, 2-ethyl-4-(2,2,3-trimethyl-3-cyclopenten-1-yl)-2-buten-1-ol, Methyl cedryl ketone, 5-(2,2,3-trimethyl-3-cyclopentenyl)-3-methylpentan-2-ol, 1-(2,3,8,8-tetramethyl-1,2,3,4,6,7,8,8a-octahydronaphthalen-2-yl)ethan-1-one and/or isobornyl acetate;
  Other ingredients (e.g. amber, powdery spicy or watery): dodecahydro-3a,6,6,9a-tetramethyl-naphtho[2,1-b] furan and any of its stereoisomers, heliotropin, anisic aldehyde, eugenol, cinnamic aldehyde, clove oil, 3-(1,3-benzodioxol-5-yl)-2-methylpropanal and/or 3-(3-isopropyl-1-phenyl)butanal.

Perfuming ingredients may not be limited to the above mentioned, and many other of these ingredients are in any case listed in reference texts such as the book by S. Arctander, Perfume and Flavor Chemicals, 1969, Montclair, N.J., USA, or its more recent versions, or in other works of a similar nature, as well as in the patent literature in the field of perfumery. It is also understood that co-ingredients may also be compounds known to release in a controlled manner various types of perfuming compounds.

TABLE 1

Malodor receptor antagonists - Group I
CHEMICAL NAME (1RS,6RS,11RS)-2,2,9,11-TETRAMETHYLSPIRO[5.5]UNDEC-8-EN-1-YL ACETATE
BENZYL ACETATE
2-PHENYLETHYL ACETATE
(1R,2R)-1,7,7-TRIMETHYL-BICYCLO[2.2.1]HEPT-2-YL ACETATE
3-(4-METHYL-3-PENTENYL)-3-CYCLOHEXENE-1-CARBALDEHYDE (A) + 4-(4-METHYL-3-PENTENYL)-3-CYCLOHEXENE-1-CARBALDEHYDE
7-PROPYL-2H,4H-1,5-BENZODIOXEPIN-3-ONE
ALLYL (3-METHYLBUTOXY)ACETATE (A) + (+−)-ALLYL (2-METHYLBUTOXY)ACETATE (B)
(ETHOXYMETHOXY)CYCLODODECANE
(+−)-(1E)-1-(2,6,6-TRIMETHYL-2-CYCLOHEXEN-1-YL)-1,6-HEPTADIEN-3-ONE (A) + (1E)-1-(2,6,6-TRIMETHYL-1-CYCLOHEXEN-1-YL)-1,6-HEPTADIEN-3-ONE(B)
3,5-DIETHYL-5,6-DIMETHYL-2-CYCLOHEXEN-1-ONE (A) + 3,5-DIETHYL-2,5-DIMETHYL-2-CYCLOHEXEN-1-ONE (B)
3-(4-TERT-BUTYLPHENYL)PROPANAL
3ARS,5ASR,9ASR,9BSR)-3A,6,6,9A-TETRAMETHYLDODECAHYDRONAPHTHO[2,1-B]FURAN
7-ISOPROPYL-2H,4H-1,5-BENZODIOXEPIN-3-ONE
(4E,8E)-4,8-CYCLODODECADIEN-1-ONE (A) + (4E,8Z)-4,8-CYCLODODECADIEN-1-ONE (B) + (4Z,8E)-4,8-

TABLE 1-continued

Malodor receptor antagonists - Group I
CHEMICAL NAME

CYCLODODECADIEN-1-ONE (C)
(+)-(R)-3,7-DIMETHYL-6-OCTENAL
(+−)-1,3-DIMETHYL-3-PHENYLBUTYL ACETATE
1,2,3,4,5,6,7,8-OCTAHYDRO-8,8-DIMETHYL-2-
NAPHTHALENECARBALDEHYDE (A) + (B,C,D) +
OCTAHYDRO-5,5-DIMETHYL-2-
NAPHTHALENECARBALDEHYDE
(+−)-CIS-2-PENTYL-1-CYCLOPENTANOL
(+−)-3-(4-ISOPROPYLPHENYL)-2-METHYLPROPANAL
ETHYL 2,6,6-TRIMETHYL-1,3-CYCLOHEXADIENE-1-
CARBOXYLATE
(+−)-(2E)-1-(2,6,6-TRIMETHYL-2-CYCLOHEXEN-1-YL)-2-
BUTEN-1-ONE
(2E)-1-(2,6,6-TRIMETHYL-1-CYCLOHEXEN-1-YL)-2-BUTEN-
1-ONE
(2E)-1-[(1RS,2SR)-2,6,6-TRIMETHYL-3-CYCLOHEXEN-1-
YL]-2-BUTEN-1-ONE
(+−)-2-PENTYLCYCLOPENTANONE
(+−)-3,7-DIMETHYL-1-OCTEN-3-OL
1-(5,5-DIMETHYL-1-CYCLOHEXEN-1-YL)-4-PENTEN-1-ONE
BENZYL FORMATE
2-PHENYLETHYL FORMATE
DIETHYL 1,4-CYCLOHEXANEDICARBOXYLATE
3-(2,2-DIMETHYLPROPYL)PYRIDINE
(1RS,2SR,8RS)-2-(8-ISOPROPYL-6-METHYL-
BICYCLO[2.2.2]OCT-5-EN-2-YL)-1,3-DIOXOLANE
3-(3,3-DIMETHYL-2,3-DIHYDRO-1H-INDEN-5-
YL)PROPANAL (A) + 3-(1,1-DIMETHYL-2,3-DIHYDRO-1H-
INDEN-4-YL)PROPANAL (B) + 3-(1,1-DIMETHYL-2,3-
DIHYDRO-1H-INDEN-5-YL)PROPANAL(C)
3,5,6-TRIMETHYL-3-CYCLOHEXENE-1-CARBALDEHYDE (A) +
2,4,6-TRIMETHYL-3-CYCLOHEXENE-1-CARBALDEHYDE (B)
2-ISOBUTYLQUINOLINE
6(8)-ISOPROPYLQUINOLINE
(+−)-2,5-DIMETHYL-2-INDANMETHANOL
(+−)-2,6-DIMETHYL-5-HEPTENAL
(2RS,5SR)-5-METHYL-2-(2-PROPANYL)CYCLOHEXANONE
(A) + (2RS,5RS)-5-METHYL-2-(2-
PROPANYL)CYCLOHEXANONE (B)
(−)-(3R)-3-METHYL-1-CYCLOPENTADECANONE
4,12,12-TRIMETHYL-9-METHYLENE-5-
OXATRICYCLO[8.2.0.0(4,6)]DODECANE
(4-METHYL-4-PHENYLPENTAN-2-YL) ACETATE
(−)-(1R,9S)-4,11,11-TRIMETHYL-8-
METHYLENEBICYCLO[7.2.0]UNDEC-4-ENE
4-(1,1-DIMETHYLPROPYL)CYCLOHEXANOL
2-PHENYLETHANOL
(1RS,2SR,5RS,7RS,8SR)-5-
METHYLTRICYCLO[6.2.1.0~2,7~]UNDECAN-4-ONE (A) +
(1RS,2SR,5SR,7RS,8SR)-5-
METHYLTRICYCLO[6.2.1.0~2,7~]UNDECAN-4-ONE (B)
(+−)-2,2,2-TRICHLORO-1-PHENYLETHYL ACETATE
ETHYL 4,6,6-TRIMETHYL-1,3-CYCLOHEXADIENE-1-
CARBOXYLATE
(+−)-(6RS,10RS)-2,2,8,10-
TETRAMETHYLSPIRO[5.5]UNDEC-8-EN-1-ONE (A) + (+−)-
(6RS,10SR)-2,2,8,10-TETRAMETHYLSPIRO[5.5]UNDEC-8-
EN-1-ONE (B) + (6RS,7RS)-2,2,7,9-
TETRAMETHYLSPIRO[5.5]UNDEC-8-EN-1-ONE (C) +
(6RS,7SR)-2,2,7,9-TETRAMETHYLSPIRO[5.5]UNDEC-8-EN-
1-ONE (D)
(5RS,6RS)-2,6,10,10-TETRAMETHYL-1-
OXASPIRO[4.5]DECAN-6-OL
(4Z)-4-DODECENAL
2,2,7,7-TETRAMETHYLTRICYCLO[6.2.1.0~1,6~]UNDECAN-
6-OL
1-(2,6,10-TRIMETHYL)-1-(2,5,9-CYCLODODECATRIEN-1-
YL)-1-ETHANONE + 1-(2,6,10-TRIMETHYL)-1-(1,5,9-
CYCLODODECATRIEN-1-YL)-1-ETHANONE + 1-(6,10-
DIMETHYL, 2-METHYLENE)-1-(2,5,9-
CYCLODODECATRIEN-1-YL)-1-ETHANONE
(+)-(1S,2S,3S,5R)-2,6,6-
TRIMETHYLSPIRO[BICYCLO[3.1.1]HEPTANE-3,1'-
CYCLOHEXANE]-2'-EN-4'-ONE
3-PHENYL-1-PROPANOL
2,2-DIMETHYL-3-PHENYL-1-PROPANOL
(+−)-3,6,8,8-TETRAMETHYLOCTAHYDRO-1H-3A,7-
METHANOAZULEN-6-OL
(+−)-(4Z,8E)-1,5,8-TRIMETHYL-13-
OXABICYCLO[10.1.0]TRIDECA-4,8-DIENE (A) + (+−)-
(4Z,8E)-1,4,8-TRIMETHYL-13-
OXABICYCLO[10.1.0]TRIDECA-4,8-DIENE (B)
(+−)-PERHYDRO-4ALPHA,8ABETA-DIMETHYL-4A-
NAPHTHALENOL
(+−)-2,2-DIMETHYL-4-PHENYL-1,3-DIOXOLANE
(+−)-2,4-DIMETHYL-4,4A,5,9B-TETRAHYDROINDENO[1,2-
D][1,3]DIOXINE (ISOMER A) + (+−)-2,4-DIMETHYL-
4,4A,5,9B-TETRAHYDROINDENO[1,2-D][1,3]DIOXINE
(ISOMER B) (A + B)
(−)-(3R,6S,8S)-2,2,6,8-
TETRAMETHYLTRICYCLO[5.3.1.0~3,8~]UNDECAN-3-OL
PATCHOULI OIL
2-PHENYLETHYL 2-HYDROXYBENZOATE
4-TERT BUTYLPHENOL
(1RS,2RS)-2-(2-METHYL-2-PROPANYL)CYCLOHEXYL
ACETATE (A) + (1RS,2SR)-2-(2-METHYL-2-
PROPANYL)CYCLOHEXYL ACETATE (B)
(+−)-1-PHENYLETHYL ACETATE
(4RS,6SR)-3,5,5-TRIETHYL-2,4,6-TRIMETHYL-2-
CYCLOHEXEN-1-ONE (A) + (4RS,6RS)-3,5,5-TRIETHYL-
2,4,6-TRIMETHYL-2-CYCLOHEXEN-1-ONE (B)
8,9-EPOXYCEDRANE
CYCLODODECANONE
(Z)-4-CYCLOPENTADECEN-1-ONE
(+−)-3-(3-ISOPROPYL-1-PHENYL)BUTANAL
(+−)-TETRAHYDRO-2-ISOBUTYL-4-METHYL-4(2H)-
PYRANOL
2-(1-METHYLPROPYL)-1-CYCLOHEXANONE
4-(4,8-DIMETHYL-3,7-NONADIEN-1-YL)PYRIDINE
[CIS-4-(2-PROPANYL)CYCLOHEXYL]METHANOL
(+)-(3R,5Z)-3-METHYL-5-CYCLOPENTADECEN-1-ONE
(+−)-3-METHYLCYCLOPENTADECANONE
(+)-(4R,4AS,6R)-4,4A-DIMETHYL-6-(1-PROPEN-2-YL)-
4,4A,5,6,7,8-HEXAHYDRO-2(3H)-NAPHTHALENONE
METHOXYCYCLODODECANE
4-(2-METHYL-2-PROPANYL)CYCLOHEXANONE
(2E,6Z)-2,6-NONADIENAL
3-(6,6-DIMETHYL-BICYCLO[3.1.1]HEPT-2-EN-2-
YL)PROPANAL
CEDRAN-8-YL ACETATE
(+−)-2,4-DIMETHYL-4-PHENYLTETRAHYDROFURAN
(+−)-2,3,3-TRIMETHYL-1-INDANONE
2-TERT-BUTYLPHENOL
7-(2-METHYL-2-PROPANYL)-2H-1,5-BENZODIOXEPIN-
3(4H)-ONE
(+)-(1R,7R)-10,10-DIMETHYL-
TRICYCLO[7.1.1.0(2,7)]UNDEC-2-EN-4-ONE
(+−)-2-TERT-BUTYL-1-CYCLOHEXANONE
(1S,4S,9S,10R,13R)-5,5,9,13-TETRAMETHYL-14,16-
DIOXATETRACYCLO[11.2.1.0~1,10~.0~4,9~]HEXADECANE
(A) + (1R,4S,9S,10R,13S)-5,5,9,13-TETRAMETHYL-14,16-
DIOXATETRACYCLO[11.2.1.0~1,10~.0~4,9~]HEXADECANE (B)
(−)-(R)-3,7-DIMETHYL-6-OCTENENITRILE
(+−)-(3E)-4-(2,6,6-TRIMETHYL-2-CYCLOHEXEN-1-YL)-3-
BUTEN-2-ONE (A) + (3E)-4-(2,6,6-TRIMETHYL-1-
CYCLOHEXEN-1-YL)-3-BUTEN-2-ONE (B);
(1RS,2RS)-2,4-DIMETHYL-3-CYCLOHEXENE-1-
CARBALDEHYDE (A) + (1RS,2SR)-2,4-DIMETHYL-3-
CYCLOHEXENE-1-CARBALDEHYDE (B)
(E)-3,7-DIMETHYL-2,6-OCTADIENAL (A) + (Z)-3,7-
DIMETHYL-2,6-OCTADIENAL (B)
(3E)-4-(2,6,6-TRIMETHYL-1-CYCLOHEXEN-1-YL)-3-BUTEN-
2-ONE
4,7,11,11-TETRAMETHYL-
TRICYCLO[5.4.0.0(1,3)]UNDECAN-5-ONE (A) + 2,6,6,8-
TETRAMETHYL-TRICYCLO[5.3.1.0(1,5)]UNDECAN-9-ONE
(B)
(+−)-(3E)-3-METHYL-4-(2,6,6-TRIMETHYL-2-CYCLOHEXEN-
1-YL)-3-BUTEN-2-ONE (A) + (+−)-1-(2,6,6-
TRIMETHYL-2-CYCLOHEXEN-1-YL)-1-PENTEN-3-ONE (B)
(+−)-(E)-3-METHYL-4-(2,6,6-TRIMETHYL-2-CYCLOHEXEN-
1-YL)-3-BUTEN-2-ONE (A) + (E)-1-(2,6,6-TRIMETHYL-2-
CYCLOHEXEN-1-YL)-1-PENTEN-3-ONE (B) + (+−)-(E)-1-
(2,2-DIMETHYL-6-METHYLENE-1-CYCLOHEXYL)-1-

TABLE 1-continued

Malodor receptor antagonists - Group I
CHEMICAL NAME

PENTEN-3-ONE (C) + (E)-1-(2,6,6-TRIMETHYL-1-
CYCLOHEXEN-1-YL)-1-PENTEN-3-ONE (D)
(+−)-(3E)-4-(2,6,6-TRIMETHYL-2-CYCLOHEXEN-1-YL)-3-
BUTEN-2-ONE
4-(1,1-DIMETHYLPROPYL)-1-CYCLOHEXANONE
(4$Z$,8$E$)-13-OXABICYCLO[10.1.0]TRIDECA-
4,8-DIENE
(1$R$,4$Z$,8$E$,12$R$)-13-
OXABICYCLO[10.1.0]TRIDECA-4,8-
DIENE; (4$Z$,8$E$)-13-
OXABICYCLO[10.1.0]TRIDECA-4,8-DIENE
(2$E$)-1,1-DIETHOXY-3,7-DIMETHYLOCTA-2,6-
DIENE
3-(4-HYDROXY-4-METHYLPENTYL)CYCLOHEX-3-ENE-1-
CARBALDEHYDE; 4-(4-HYDROXY-4-
METHYLPENTYL)CYCLOHEX-3-ENE-1-CARBALDEHYDE
GERANYL ACETATE
2-ETHOXY-5-PROP-1-ENYLPHENOL
($E$)-NON-2-ENAL
2-METHYL-5-PROPAN-2-YLPHENOL
5-HEXYL-2-METHYLPYRIDINE
2-PHENYLETHANOL
PHENYL ETHYL ACETATE
7-HYDROXY-3,7-DIMETHYLOCTANAL
CYCLODODECANONE
1$L'\{2\}$,2$L'\{2\}$,3$L'\{2\}$-
TRINOBELACYCLOPROPANE; ($E$)-3,4,5,6,6-
PENTAMETHYLHEPT-3-EN-2-ONE; ($E$)-3,4,5,6,6-
PENTAMETHYLHEPT-4-EN-2-ONE; 3,5,6,6-TETRAMETHYL-
4-METHYLIDENEHEPTAN-2-ONE
1,4-DIOXACYCLOHEXADECANE-5,16-DIONE
PENTAN-1-OL
OXACYCLOHEXADECAN-2-ONE
1,1,2,3,3-PENTAMETHYL-2,5,6,7-TETRAHYDROINDEN-4-
ONE
(4A$S$,8A$R$)-5,5,8A-TRIMETHYL-
3,4,4A,6,7,8-HEXAHYDRO-1$H$-NAPHTHALEN-2-
ONE
4-[(3E)-4,8-DIMETHYLNONA-3,7-DIENYL]PYRIDINE
($E$)-4-[(1$R$,3$R$,6$R$)-2,2,3,6-
TETRAMETHYLCYCLOHEXYL]BUT-3-EN-2-ONE; ($E$)-
4-[(1$S$,3$S$,6$R$)-2,2,3,6-
TETRAMETHYLCYCLOHEXYL]BUT-3-EN-2-ONE
METHYL CITRAL
(9$E$)-CYCLOHEPTADEC-9-EN-1-ONE
2,2-DIMETHYL-3-PHENYLPROPAN-1-OL
(2$E$)-3,7-DIMETHYLOCTA-2,6-DIENAL
2,2-DIMETHYL-4-PHENYL-1,3-DIOXOLANE
3-PHENYL-1-PROPANOL
2-METHYL-2-INDANMETHANOL
BENZYL FORMATE
(2-METHYL-2-INDANYL)METHYL ACETATE
(+−)-5-ETHYL-2-METHYL-2-INDANMETHANOL
5-METHYL-2-INDANMETHANOL
(+−)-1-(2,5-DIMETHYL-2,3-DIHYDRO-1H-INDEN-2-
YL)ETHANONE
(+−)-2-METHOXYMETHYL-2,5-DIMETHYLINDAN
2,5,6-TRIMETHYL-2-INDANMETHANOL
(+−)-(2,4,5-TRIMETHYL-2,3-DIHYDRO-1H-INDEN-2-
YL)METHANOL
(+−)-2-ETHYK-5-METHYL-2-INDANMETHANOL
(+−)-2,4-DIMETHYL-2-INDANMETHANOL
(+−)-2,4,6-TRIMETHYL-2-INDANMETHANOL
(+−)-(2,7-DIMETHYL-1,2,3,4-TETRAHYDRO-2-
NAPTHTHALENYL)METHANOL
(+−)-(2,6-DIMETHYL-1,2,3,4-TETRAHYDRO-2-
NAPHTHALENYL)METHANOL
(+−)-(5-METHOXY-2-METHYL-2,3-DIHYDRO-1H-INDEN-2-
YL)METHANOL
(+−)-1,2,6-TRINETHYL-2-INDANMETHANOL
4-T-BUTYLCYCLOHEXANONE (+−)-2-
((METHOXYMETHOXY)METHYL)-2,5-DIMETHYL-2,3-
DIHYDRO-1H-INDENE
(+−)-(4E,8E)-13-OXABICYCLO[10.1.0]TRIDECA-4,8-DIENE
(A) + (+−)-(4E,8Z)-13-OXABICYCLO[10.1.0]TRIDECA-4,8-
DIENE (B) + (+−)-(4Z,8E)-13-
OXABICYCLO[10.1.0]TRIDECA-4,8-DIENE (C)

MESO-(1R,2S,4R)-4-METHYL-
TRICYCLO[5.2.1.0(2,6)]DECANE-4-METHANOL
(+−)-3-(3-METHYL-5-INDANYL)PROPANAL (A) + (+−)-3-(1-
METHYL-5-INDANYL)PROPANAL (B)
2-METHYL-2-INDANMETHANOL
(+−)-5-ETHYL-2-METHYL-2-INDANMETHANOL
(+−)-5-ISOPROPYL-2-METHYL-2-INDANMETHANOL
(2-METHYL-2-INDANYL)METHYL ACETATE
(+−)-5-METHYL-2-INDANMETHANOL
(+−)-(2,5-DIMETHYL-2-INDANYL)METHYL ACETATE
1-(2,5-DIMETHYL-2-INDANYL)-1-ETHANONE
1-(2,5-DIMETHYL-2-INDANYL)-1-ETHANOL
2-(2,5-DIMETHYL-2-INDANYL)-2-PROPANOL
2-METHOXYMETHYL-2,5-DIMETHYLINDAN
(+−)-PERHYDRO-2,5-DIMETHYL-CIS-2-INDENEMETHANOL
(+−)-2-ETHYL-5-METHYL-2-INDANMETHANOL
2,5,6-TRIMETHYL-2-INDANMETHANOL
(+−)-2,4-DIMETHYL-2-INDANMETHANOL
(+−)-1,2,5-TRIMETHYL-2-INDANMETHANOL
(+−)-1,2,6-TRIMETHYL-2-INDANMETHANOL
(+−)-(2,4,5-TRIMETHYL-2,3-DIHYDRO-1H-INDEN-2-
YL)METHANOL
(+−)-2,3,4,5,6,7-HEXAHYDRO-2,5-DIMETHYL-2(1H)-
INDENEMETHANOL
(+−)-5-TERT-BUTYL-2-METHYL-2-INDANMETHANOL
(+−)-(2,7-DIMETHYL-1,2,3,4-TETRAHYDRO-2-
NAPTHTHALENYL)METHANOL
(+−)-(2,6-DIMETHYL-1,2,3,4-TETRAHYDRO-2-
NAPHTHALENYL)METHANOL
(+−)-(5-METHOXY-2-METHYL-2,3-DIHYDRO-1H-INDEN-2-
YL)METHANOL
2,4,6-TRIMETHYL-2-INDANMETHANOL
(+−)-3-(3-ETHYL-2,3-DIHYDRO-1H-INDEN-4-YL)PROPANAL
(A) AND/OR (+−)-3-(3-ETHYL-2,3-DIHYDRO-1H-INDEN-5-
YL)PROPANAL (B) AND/OR (+−)-3-(1-ETHYL-2,3-DIHYDRO-
1H-INDEN-5-YL)PROPANAL (C) AND/OR (+−)-3-(1-ETHYL-
2,3-DIHYDRO-1H-INDEN-4-YL)PROPANAL (D)
(4ARS,9BRS)-4A,8-DIMETHYL-4,4A,5,9B-
TETRAHYDROINDENO[1,2-D][1,3]DIOXIN
(+−)-2-((METHOXYMETHOXY)METHYL)-2,5-DIMETHYL-
2,3-DIHYDRO-1H-INDENE
(−)-(R)-2,5-DIMETHYL-2-INDANMETHANOL
(4ARS,8ASR)-5,5,8A-TRIMETHYLOCTAHYDRO-2(1H)-
NAPHTHALENONE
5-METHYL-2-(PROPAN-2-YL)PHENOL
(+−)-1-(2,4-DIMETHYLTRICYCLO[5.2.1.01.5]DEC-4-YL)
ETHANONE
(+−)-1-(2,4-DIMETHYLTRICYCLO[5.2.1.0~1.5~]DEC-4-YL)
ETHYL ACETATE
1-[(1RS,2RS,4SR,7RS)-2,3,4-
TRIMETHYLTRICYCLO[5.2.1.01.~]DEC-4-YL) ETHANONE
(E/Z)-1-[(1RS,7RS)-2,3-
DIMETHYLTRICYCLO[5.2.1.0~1.5~]DEC-4-YL) ETHANONE
OXIME
(E/Z)-1-[(1S,7S)-2,3,4-
TRIMETHYLTRICYCLO[5.2.1.0~1.5~]DEC-4-YL) ETHANONE
OXIME
(E/Z)-1-((3AS,6S)-1,2,3-TRIMETHYLOCTAHYDRO-3A,6-
METHANOINDEN-1-YL)ETHANONE OXIME
(+−)-1-(3-METHYLOCTAHYDRO-3A,6-METHANOINDEN-1-
YL)ETHYL ACETATE
(+−)-2,3,7,7-TETRAMETHYLSPIRO[4.5]DEC-6-YL ACETATE
(5,10,10-TRIMETHYLSPIRO[5.5]UNDEC-2-EN-11-YL)
FORMATE
(3,5,10,10-TETRAMETHYLSPIRO[5.5]UNDEC-2-EN-11-YL)
ACETATE
(9,9-DIMETHYLSPIRO[4.5]DEC-2-EN-10-YL) ACETATE
10-METHOXY-9,9-DIMETHYLSPIRO[4.5]DEC-2-ENE
4,10,10,11-TETRAMETHYLSPIRO[5.5]UNDEC-2-EN-11-OL;
5,10,10,11-TETRAMETHYLSPIRO[5.5]UNDEC-3-EN-11-OL
2,4,8-TRIMETHYLSPIRO[5.5]UNDEC-3-EN-11-OL;
2,9,11-TRIMETHYLSPIRO[5.5]UNDEC-9-EN-5-OL
3-METHYL-5-PROPAN-2-YLSPIRO[5.5]UNDEC-2-EN-11-
OL, 11-METHYLSPIRO[5.5]UNDECAN-5-OL
3,10,10-TRIMETHYLSPIRO[5.5]UNDEC-3-EN-11-OL;
4,10,10-TRIMETHYLSPIRO[5.5]UNDEC-3-EN-11-OL
[2,2-DIMETHYL-1-(2,4,6-TRIMETHYLCYCLOHEX-3-EN-1-

TABLE 1-continued

Malodor receptor antagonists - Group I
CHEMICAL NAME

YL)PROPYL] ACETATE
[2,2-DIMETHYL-1-(2,4,6-TRIMETHYLCYCLOHEXYL)PROPYL] ACETATE
(1RS)-2,2-DIMETHYL-1-[(1SR,2SR)-2-METHYLCYCLOHEXYL]PROPYL ACETATE

TABLE 2

Functional perfuming ingredients - Group II
CHEMICAL NAME (2E)-2-METHYL-3-PHENYL-2-PROPENAL
(+−)-(E)-1-(2,2-DIMETHYL-6-METHYLENE-1-CYCLOHEXYL)-2-BUTEN-1-ONE
(+−)-(E)-TRANS-ALPHA-IRONE (A) + (+−)-(E)-CIS-ALPHA-IRONE (B) + (+−)-(E)-BETA-IRONE (C)
(+−)-(E)-4-(2,5,6,6-TETRAMETHYL-1-CYCLOHEXEN-1-YL)-3-BUTEN-2-ONE
(1E)-1-(2,6,6-TRIMETHYL-1-CYCLOHEXEN-1-YL)-1-PENTEN-3-ONE
(+−)-(E)-3-METHYL-4-(2,6,6-TRIMETHYL-2-CYCLOHEXEN-1-YL)-3-BUTEN-2-ONE
UNDECANAL
(E)-3-PHENYL-2-PROPENAL
ALDEHYDE SUPRA
(1S,1'R)-2-[1-(3',3'-DIMETHYL-1'-CYCLOHEXYL)ETHOXY]-2-METHYLPROPYL 2-PROPENOATE
ETHYL BUTANOATE
7-METHYL-2H-1,5-BENZODIOXEPIN-3(4H)-ONE
CEDARWOOD OIL VIRGINIA
(+−)-3,7-DIMETHYL-6-OCTEN-1-OL
2-CHROMENONE
(2E)-2-DODECENAL
METHYL (1RS,2SR)-2,6,6-TRIMETHYL-3-CYCLOHEXENE-1-CARBOXYLATE (A) + METHYL (1RS,2RS)-2,6,6-TRIMETHYL-3-CYCLOHEXENE-1-CARBOXYLATE (B)
3,7-DIMETHYL-2,6-NONADIENENITRILE (A) + 3,7-DIMETHYL-3,6-NONADIENENITRILE (B)
(+−)-2-METHYL-3-[4-(2-METHYL-2-PROPANYL)PHENYL]PROPANAL
(+−)-1-(2,2,3,6-TETRAMETHYL-CYCLOHEXYL)-3-HEXANOL
(+)-(3S)-3-[(1R)-4-METHYL-3-CYCLOHEXEN-1-YL]BUTANAL (A) + (+)-(3R)-3-[(1R)-4-METHYL-3-CYCLOHEXEN-1-YL]BUTANAL
3,6,7-TRIMETHYL-2,6-OCTADIENAL
(+−)-3ENDO-METHOXY-7,7-DIMETHYL-10-METHYLENE-BICYCLO[4.3.1]DECANE (A) + (+−)-3EXO-METHOXY-7,7-DIMETHYL-10-METHYLENE-BICYCLO[4.3.1]DECANE (B)
3-(4,4-DIMETHYL-1-CYCLOHEXEN-1-YL)PROPANAL
ALPHA.-TERPINEOL + .GAMMA.-TERPINEOL MIXTURE WITH OTHER TERPENES
2-METHYL-3-HEXANONE OXIME
(2Z,6Z)-2,6-NONADIENENITRILE (A) + (2E,6Z)-2,6-NONADIENENITRILE (B)
DECANAL
DODECANAL
OCTANAL
NONANAL
(2E)-2-BENZYLIDENEOCTANAL
(+−)-5-HEPTYLDIHYDRO-2(3H)-FURANONE
BERGAMOT
BERGAMOT FUROCOUMARIN-FREE
(+−)-(1-ETHOXYETHOXY)CYCLODODECANE
LAVANDIN GROSSO ARR
LAVANDIN GROSSO SYNTH
METHYL 2-NONYNOATE
1-METHOXY-4-METHYLBENZENE
1-METHYL-4-(2-PROPANYLIDENE)CYCLOHEXENE TABLE 2-continued Functional perfuming ingredients - Group II
CHEMICAL NAME (+−)-(E)-4-METHYL-3-DECEN-5-OL
1,3-UNDECADIEN-5-YNE
YLANG
YLANG EXTRA Group I:

Ingredient(s) from Table 1 are comprised between 2 and 85 wt % of the composition used according to the present disclosure. According to one aspect, the composition used according to the present disclosure comprises a malodor antagonist system as defined above in an amount comprised between 6 and 70 wt %. According to another aspect, the composition used according to the present disclosure comprises a malodor antagonist system as defined above in an amount comprised between 8 and 60 wt %. According to another aspect, the composition used according to the present disclosure comprises a malodor antagonist system as defined above in an amount comprised between 8 and 46 wt %.

According to a particular aspect of the present disclosure, the malodor receptor antagonist system (group I) from the composition used according to the present disclosure comprises at least 3 ingredients selected from Table 1. According to another aspect, at least 4, alternatively, at least 5, alternatively, at least 6, or alternatively, at least 8 ingredients selected from Table 1 are part of the malodor receptor antagonist system.

Group II:

Group II in the present disclosure is a functional perfume accord as defined above. In some aspects, the group II functional perfume accord is present in amounts ranging from 15 to 98 wt % of the composition used according to the present disclosure. According to one aspect, it is present in amounts ranging from 30-94 wt %. According to another aspect, it is present in amounts ranging from 40-92 wt % of the composition. According to another aspect, it is present in amounts ranging from 29-92 wt % of the composition.

According to a particular aspect, group II consists of one or more ingredients from the group of Table 2.

Group III:

According to a particular aspect, the composition used according to the present disclosure comprise a nonfunctional perfume accord as defined above. The nonfunctional perfume accord consists of perfuming ingredients as defined above which are neither part of group II nor part of group I. If present in the composition according to the present disclosure, a non-functional perfume accord can typically be comprised in amounts ranging from 0.5 to 70 wt %, alternatively, from 0.5 to 50 wt % of the composition as defined in any of the above aspects presented herein.

Group IV—Delivery System:

According to a particular aspect, compositions as defined above can be used in combination with a delivery system. The use of a delivery system allows achieving optimal gas-phase concentrations of active ingredients in the composition. Suitable delivery systems for the purpose of the present disclosure include but are not limited to:

Passive plating supports comprising one or more of the following porous or non-porous substrates in loose powder or compacted form chosen from the following non-limiting examples: cellulose (paper/cardboard), vermiculite, other industrial absorbents, perlite, calcium carbonate, pumice, other minerals, wood, sawdust, ground corn cob, ground rice hull, rice hull ash, other agricultural by-products, biochars, starches, modified starches;

Spray-dried moisture-activated encapsulation systems wherein compositions according to the present disclosure are encapsulated by a spray drying process within a matrix containing but not limited to one or more of the following: maltodextrin, octenyl succinated starch (modified starch);

Core-shell encapsulation systems, such as mechanically activated microcapsules with an impermeable shell (for example, polyurea, polyurethane, and others) and composition according to the present disclosure in the core;

Liquid mixtures containing surfactants;

Polymeric materials.

Use of a composition as defined in any of the above aspects, wherein the composition further comprises encapsulating materials such as polymers to form microcapsules or microparticles, or materials to form liquid delivery system for the composition such as an emulsion, a microemulsion, a miniemulsion, a gel, a microgel, an anhydrous gel or a dispersion is therefore also an object of the present disclosure.

According to a particular aspect, the composition as defined in any of the above aspects is absorbed on a porous or non-porous substrate in loose powder or compacted form, the substrate being selected from cellulose (paper/cardboard), vermiculite, other industrial absorbents, perlite, calcium carbonate, pumice, wood, sawdust, ground corn cob, ground rice hull, rice hull ash, biochars, starches, modified starches and mixtures thereof.

A second object of the present disclosure consists of a malodor receptor antagonist system consisting of at least 3, alternatively, at least 4 ingredients selected from the group of Table 1.

Another object of the present disclosure is a malodor counteracting composition comprising:
a) from about 2 to about 85 wt % of an active amount a malodor receptor antagonist system comprising at least one, alternatively, at least 3 ingredients selected from Table 1;
b) from about 15 to about 98 wt % of a functional perfume accord comprising at least two ingredients selected from the group consisting of ingredients selected from Table 2; and
c) optionally a non-functional perfume accord comprising at least two perfuming ingredients.

According to a particular aspect, the composition comprises from about 6 to about 70 wt % of group I. According to another aspect it comprises from about 8 to about 60 wt % of group I.

In some aspects, the composition further comprises at least one other MOC compound. As used herein, the term "other MOC compounds" refers to a material which is already known for a MOC activity and is commonly used in the industry for such use. The at least one other MOC compound can be included to further boost, or complement, the MOC activity of the at least one compound.

Non-limiting examples of the at least one other MOC compound include antimicrobial agents, malodor absorbers, chemical neutralisers e.g. acid-base reagents, thiol traps, odor blockers, cross-adaptation agents e.g. as disclosed in U.S. Pat. No. 5,538,719 incorporated herein by reference, malodor complexation agents e.g. various cyclodextrins.

Examples of antimicrobial agents include, but are not limited to, metal salts such as zinc citrate, zinc oxide, zinc pyrethiones, and octopirox; organic acids, such as sorbic acid, benzoic acid, and their salts; parabens, such as methyl paraben, propyl paraben, butyl paraben, ethyl paraben, isopropyl paraben, isobutyl paraben, benzyl paraben, and their salts; alcohols, such as benzyl alcohol, phenyl ethyl alcohol; boric acid; 2,4,4'-trichloro-2-hydroxy-diphenyl ether; phenolic compounds, such as phenol, 2-methyl phenol, 4-ethyl phenol; essential oils such as rosemary, thyme, lavender, eugenol, geranium, tea tree, clove, lemon grass, peppermint, or their active components such as anethole, thymol, eucalyptol, farnesol, menthol, limonene, methyl salicylate, salicylic acid, terpineol, nerolidol, geraniol, and mixtures thereof.

Examples of malodor absorbers include, but are not limited to molecular sieves, such as zeolites, silicas, aluminosilcates, and cyclodextrins; and organic absorbents, such as for example, activated charcoal, dried citrus pulp, cherry pit extract, corncob, and mixtures thereof.

In some aspects, compositions described herein may comprise one, or more than of the at least one compounds as described herein. Without intending to be limited to any particular theory, a composition comprising more than one of the at least one compound described herein may enable a person skilled in the art to prepare MOC compositions possessing an activity fine-tuned toward the targeted malodor or source of malodor.

For the sake of clarity, it is also understood that any mixture resulting directly from a chemical synthesis, e.g. a reaction medium without an adequate purification, in which the at least one compound would be involved as a starting, intermediate or end-product could not be considered as a MOC composition according to the present disclosure as far as the mixture does not provide the at least one compound in a suitable form. Thus, unpurified reaction mixtures are generally excluded from the present disclosure unless otherwise specified.

Furthermore, the at least one compound may also be used in any consumer product for which it may be useful to have a MOC activity at least. Consequently, another object of the present disclosure is represented by a MOC consumer product comprising, as an active ingredient, at least one composition, as defined above. It is understood that the MOC consumer product, by its nature can also be a perfuming one.

As used herein, the term "MOC, and optionally perfuming, consumer product" or similar, refers to a consumer product which is expected to deliver at least a MOC effect, and optionally also a pleasant perfuming effect, to the surface to which it is applied (e.g. skin, hair, textile, or home surface, but also air). In other words, a consumer product according to the present disclosure is a perfumed consumer product which comprises the functional formulation, as well as optionally additional benefit agents, corresponding to the desired consumer product, e.g. a detergent or an air freshener, and an effective amount of at least one invention's compound.

The nature and type of the constituents of the MOC consumer product do not warrant a more detailed description here, which in any case would not be exhaustive, the skilled person being able to select them on the basis of his general knowledge and according to the nature and the desired effect of the product.

Non-limiting examples of suitable perfuming consumer product include:
a perfume, such as a fine perfume, an Eau de Toilette, a cologne or an after-shave lotion;
a fabric care product, such as a liquid detergent, a powder detergent, detergent tablets, a detergent bar, a detergent paste, a detergent pouch, a liquid fabric softener, fabric softener sheets, a fabric scent booster, a laundry pre-treatment, a fabric refresher, an ironing water, a laundry bleach, a carpet powder or a carpet cleaner;

a hair care product, such as a shampoo, a hair conditioner, a hair cream, a hair oil, a hair styling product (such as a spray, mousse or gel), a hair coloration product or a hair permanent wave product;

a skin care product, such as a face cream, a face lotion, a shaving product (such as a foam, cream, gel or oil), a body and/or hand product (such as a lotion, cream, gel or oil), a skin firming product, a depilatory, a talcum powder, a foot care cream or lotion, baby wipes, cleansing wipes, moisturizer wipes, a sun-protection product (such as a spray, lotion, cream or oil), an after-sun lotion, or a self-tanning product;

a body deodorant or antiperspirant product, such as a body deodorant spray, a roll-on deodorant, a deodorant stick, a deodorant cream, an antiperspirant spray, an antiperspirant stick, a roll-on antiperspirant liquid, an antiperspirant stick, or an antiperspirant cream;

a skin-cleansing product, such as a soap bar, a shower gel, a liquid hand soap, a bath foam or an intimate wash product;

an air freshening product, such as an air freshener spray, a gel air freshener, a liquid-wick air freshener, a solid air freshener comprising a porous substrate (such as a paper or card blotter, a porous ceramic, or a porous plastic), a liquid or gel air freshener comprising a permeable membrane, an electrically operated air freshener, and a dual purpose air freshener/disinfectant spray; and/or a surface care product, such as an all-purpose cleaner, a furniture polish, a wood floor cleaner, a window cleaner, a hand dishwashing product (such as a liquid, gel or paste), a machine dishwashing product (such as a powder, liquid, gel, tablet or sachet), a toilet bowl cleaning liquid, an in-cistern toilet cleaner, a toilet rim block, or a toilet rim liquid; a pet-litter.

Some of the above-mentioned MOC consumer products may represent an aggressive medium for the at least one compound, thus it may be necessary to protect the latter from premature decomposition, for example by encapsulation or by chemically bounding it to another chemical which is suitable to release the invention's ingredient upon a suitable external stimulus, such as an enzyme, light, heat or a change of pH.

In some aspects, the composition as defined in any of the above aspect may be absorbed on a porous or non-porous substrate in loose powder or compacted form, the substrate being selected from cellulose (paper/cardboard), vermiculite, other industrial absorbents, perlite, calcium carbonate, pumice, wood, sawdust, ground corn cob, ground rice hull, rice hull ash, biochars, starches, modified starches and mixtures thereof.

Accordingly, in some aspects, the present disclosure provides a perfumed consumer product comprising an effective amount of the at least one compound. In some aspects, the perfumed consumer product is selected from the group consisting of: air care products, home care products and laundry care products.

In some aspects, the perfumed consumer product comprising an effective amount of the at least one compound comprises a formulation selected from the group consisting of: aerosol and/or water-based air freshener spray, wick/reed air freshener, liquid electrical (plug-in) air freshener, a solid support air freshener, gel-based air freshener, membrane-containing air freshener, bleaching, cleaning, washing detergent powder, liquid all-purpose cleaner, specialty cleaner and liquid detergent.

It should be appreciated by those skilled in the art that the conception and the specific aspects disclosed might be readily utilized as a basis for modifying or formulating other formulations for carrying the same purposes of the present invention. It should also be realized by those skilled in the art that such equivalent formulations do not depart from the spirit and scope of the disclosure as set forth herein.

The proportions in which the at least one compound can be incorporated into the various aforementioned products or compositions vary within a wide range of values. These values are dependent on the nature of MOC consumer product and on the desired organoleptic effect as well as the nature of the co-ingredients in a given composition when the at least one compound is mixed with other ingredients, solvents or additives commonly used in the art.

In general, for example, in the case of perfuming compositions, typical concentrations are in the order of 0.001% to 5% by weight, or even more, of the at least one compound, based on the weight of the composition into which they are incorporated. Concentrations lower than these, such as in the order of 0.01% to 100% by weight, can be used when the compositions described herein are incorporated into MOC consumer products, the percentage being relative to the weight of the consumer product.

In particular, the concentration of MOC composition according to the aspects described herein, used in the various aforementioned consumer products varies within a various wide range of values depending on the nature of the consumer product. For instance, a MOC composition according some aspects described herein can be used in a perfume product at a concentration of 0.01% to 50% by weight, alternatively at a concentration of 0.2% to 40% by weight, alternatively at a concentration of 0.5% to 25% by weight. For instance, a MOC composition according to some aspects described herein can be used in a fabric care product at a concentration of 0.01% to 20% by weight, alternatively at a concentration of 0.05% to 10% by weight, alternatively at a concentration of 0.1% to 5% by weight. Yet for instance, a MOC composition according to some aspects described herein can be used in a hair care product at a concentration of 0.01% to 10% by weight, alternatively at a concentration of 0.05% to 5% by weight, alternatively at a concentration of 0.1% to 3% by weight. For instance, a MOC composition according to some aspects described herein can be used in a skin care product at a concentration of 0.01% to 10% by weight, alternatively at a concentration of 0.05% to 5% by weight, most preferably at a concentration of 0.1% to 2.5% by weight. For instance, a MOC composition according to some aspects described herein can be used in a body deodorant or antiperspirant product at a concentration of 0.01% to 10% by weight, alternatively at a concentration of 0.05% to 7% by weight, alternatively at a concentration of 0.1% to 5% by weight. Yet for instance, a MOC composition according to some aspects described herein can be used in a skin cleansing product at a concentration of 0.01% to 5% by weight, alternatively at a concentration of 0.05% to 3% by weight, alternatively at a concentration of 0.1% to 2.5% by weight. For instance, a MOC composition according to some aspects described herein can be used in an air freshening product at a concentration of 0.01% to 100% by weight. For instance, a MOC composition according to some aspects described herein can be used in a surface care product at a concentration of 0.001% to 10% by weight, alternatively at a concentration of 0.01% to 5% by weight, alternatively at a concentration of 0.1% to 2% by weight. Yet, for instance, a MOC composition according to some aspects described herein can be used in a pet-litter product at a concentration of 0.001% to 1% by weight, alternatively at a concentration of 0.005% to 0.5% by weight, alternatively at a concentration of 0.01% to 0.3% by weight.

The present invention is best illustrated but is not limited to the following examples.

EXAMPLES

Example 1: Identification of Geonol Olfactory Receptor Inhibitors

Cell-Based Screening:

Cell lines expressing either the OR11A1, or the OR2M3 olfactory receptor were used as antagonist screening platforms to identify compounds that have the property to decrease the geonol induced receptor activity. Each cell line was screened with a volatile compound library for their inhibitory properties and potential geonol smell inhibition. First, individual binary mixtures of geonol with each one of the test compounds were presented to the cells.

Single point monitoring of the geonol induced cell activity in the presence or absence of a test compound allowed for the identification of compounds with a putative suppression or inhibitory effect. These hits were further confirmed in an inhibitory dose-response curve assay to evaluate the potency of activity inhibition as a measure of the $IC_{50}$ (the inhibitor concentration at which the receptor activity is inhibited by the half-maximal inhibition efficacy level of a given test compound).

A dose-dependent decrease of receptor activity was recorded with increasing concentrations of test compounds in the presence of a single activating concentration of geonol ($EC_{80}$) and corresponding dose-response inhibition curves were obtained. The compounds listed in Table 2 are examples of compounds that decreased the geonol induced activity of at least one olfactory receptor.

Sensory Evaluation:

Five 16 oz glass jars containing either REF (geonol only), geonol only control, antagonist only, mixture of geonol and isointense antagonist, or mixture of geonol and low intensity antagonist were presented to the panelists (last four samples were randomized across panelists). The panelists were asked to familiarize themselves with the earthy/moss odor quality from the REF jar first, then rate the pleasantness, earthy/moss odor intensity and overall odor intensity of the next four samples on a 0-10 linear scale. The inter-stimulus interval between the samples was two minutes to avoid adaptation. The results are superimposed in FIG. 4, wherein the figure shows the percentage of geonol malodor (earthy/moss odor) remaining in binary iso-intense mixtures of geonol and 25 different antagonists to REF sample.

A one-way Analysis of Variance (ANOVA) with Duncan mean comparison at 95% confidence level was done to compare the average earthy/moss odor intensity among geonol only sample, antagonist only sample, and mixtures of Geonol reference/antagonist at two different ratios. The results from the cell-based screening and the sensory evaluation are shown in Table 3 and FIG. 2.

*means that the earthy/moss odor of the mixture of isointense geonol and antagonist was significantly lower than geonol only sample at 95% confidence level. NS means that no significant difference of earthy/moss odor intensity was found between, between the iso-intense mixture and geonol only sample at 95% confidence NT indicates that the antagonist was not tested in human sensory tests.

TABLE 3

Geonol Olfactory Receptor Antagonists

| Compound | $IC_{50}$ | % Inhibition | % Remaining in human sensory tests |
|---|---|---|---|
| 2-tertbutyl phenol | 88 | 100 | 46* |
| thymol | 107 | 100 | 53 |
| nona-2,6-dienal | 156 | 80 | 67 |
| 1,1-diethoxy-3,7-dimethylocta-2,6-diene | 371 | 55 | 51* |
| [1R-(1R*,4R*,6R*,10S*)]-4,12,12-trimethyl-9-methylene-5-oxatricyclo[8.2.0.0^{4,6}]dodecane | 1233 | 50 | NT |
| 3-(4-hydroxy-4-methylpentyl)cyclohex-3-ene-1-carbaldehyde; 4-(4-hydroxy-4-methylpentyl)cyclohex-3-ene-1-carbaldehyde | 217 | 60 | NT |
| 1,4,8-trimethyl-13-oxabicyclo[10.1.0]trideca-4,8-diene; 1,5,8-trimethyl-13-oxabicyclo[10.1.0]trideca-4,8-diene | 81 | 50 | 85 |
| 3-(4-tert-butylphenyl)propanal | 316 | 50 | NT |
| (4R,4aS,6R)-4,4a-dimethyl-6-prop-1-en-2-yl-3,4,5,6,7,8-hexahydronaphthalen-2-one | 486 | 50 | NT |
| 6,10-dimethylundeca-5,9-dien-2-one | 133 | 50 | 45* |
| 1-(3,3-dimethylcyclohexen-1-yl)pent-4-en-1-one; 1-(5,5-dimethylcyclohexen-1-yl)pent-4-en-1-one | 111 | 45 | 58* |
| 1-(3,3-dimethylcyclohexen-1-yl)pent-4-en-1-one; 1-(5,5-dimethylcyclohexen-1-yl)pent-4-en-1-one | 148 | 45 | NT |
| 2-ethoxy-5-prop-1-enylphenol | 111 | 33 | 34* |
| 1-(2,6,6-trimethyl-1-cyclohex-3-enyl)but-2-en-1-one | 301 | 10 | 66* |
| 2-ethoxy-5-prop-1-enylphenol, 8,9-epoxy-2,6,6,8-tetramethyl-tricyclo[5.3.1.0(1,5)]undecane | 301 | 30 | NT |
| 1-(4,8-dimethyl-12-methylidenecyclododeca-4,8-dien-1-yl)ethanone; 1-(2,6,10-trimethylcyclododeca-1,5,9-trien-1-yl)ethanone; 1-(2,6,10-trimethylcyclododeca-2,5,9-trien-1-yl)ethanone | 301 | 20 | NT |
| nonylenic aldehyde | 151 | 30 | NT |
| isobutylquinoline | 109 | 45 | 52* |
| cyclopentadec-4-en-1-one | 61 | 45 | 47 |
| (−)-(R)-3,7-dimethyl-6-octenenitrile | 300 | 10 | NT |
| 2-methyl-5-propan-2-ylphenol | 215 | | 27** |
| isopropyl quinoline | 400 | | 110 |
| 5-hexyl-2-methylpyridine 10% Citr | 555 | | 37 |
| (2,5-dimethyl-1,3-dihydroinden-2-yl)methanol | | | 37* |
| 2-pentylcyclopentan-1-one | | | 78 |
| 4-(2,6,6-trimethylcyclohexen-1-yl)but-3-en-2-one; 4-(2,6,6-trimethylcyclohex-2-en-1-yl)but-3-en-2-one | | | 59* |
| 3-methyl-4-(2,6,6-trimethylcyclohex-2-en-1-yl)but-3-en-2-one; 1-(2,6,6-trimethylcyclohex-2-en-1-yl)pent-1-en-3-one | | | 38* |
| 2,4-dimethylcyclohex-3-enecarbaldehyde | | | 45* |
| phenylethylol | | | 58 |

TABLE 3-continued

Geonol Olfactory Receptor Antagonists

| Compound | IC$_{50}$ | % Inhibition | % Remaining in human sensory tests |
|---|---|---|---|
| 3,7-dimethylocta-2,6-dienal | | | 42* |
| (2,2,2-trichloro-1-phenylethyl) acetate crist | | | 61 |
| 4-(2,6,6-trimethylcyclohexen-1-yl)but-3-en-2-one | | | 43* |
| phenyl ethyl acetate | | | 47* |
| 7-hydroxy-3,7-dimethyloctanal | | | 39* |

Example 2: Identification of 1-octen-3-ol Olfactory Receptor Inhibitors

Cell lines expressing either the OR2W1 or the OR1A1 olfactory receptor was used as an antagonist screening platform to identify compounds that have the property to decrease the 1-octen-3-ol induced receptor activity. Each cell line was screened with a volatile compound library for their inhibitory properties and potential 1-octen-3-ol smell inhibition. First, individual binary mixtures of 1-octen-3-ol with each one of the test compounds were presented to the cells.

Single concentration monitoring of the 1-octen-3-ol induced cell activity in the presence or absence of a test compound allowed for the identification of compounds with a putative suppression or inhibitory effect. These hits were further confirmed in an inhibitory dose-response curve assay to evaluate the potency of activity inhibition as a measure of the IC$_{50}$ (the inhibitor concentration at which the receptor activity is inhibited by the half-maximal inhibition efficacy level of a given test compound) and % maximum inhibition (normalized to baseline agonist activity).

A dose-dependent decrease of receptor activity was recorded with increasing concentrations of test compounds in the presence of a single activating concentration of 1-octen-3-ol (EC$_{80}$) and corresponding dose-response inhibition curves were obtained. The compounds listed in Table 4 are examples of compounds that decreased the 1-octen-3-ol induced activity of at least one receptor.

TABLE 4

1-octen-3-ol Olfactory Receptor Antagonists

| Compound | IC$_{50}$ (µM) | % Inhibition |
|---|---|---|
| Clycododecanone | 8.79 | 118.47 |
| 2,4-dimethylcyclohex-3-enecarbaldehyde | 18.76 | 107.99 |
| 1,4-dioxacyclohexadecane-5,16-dione | 24.25 | 116.54 |
| [1R-(1R*,4R*,6R*,10S*)]-4,12,12-trimethyl-9-methylene-5-oxatricyclo[8.2.0.0$^{4,6}$]dodecane | 25.11 | 123.63 |
| Pentanol, 1- | 28.32 | 94.31 |
| OXACYCLOHEXADECAN-2-ONE | 32.15 | 111.31 |
| tert-butylphenol, 2- | 36.95 | 100.34 |
| (+−)-3-methylcyclopentadecanone | 43.96342 | 113.50 |
| 1,1,2,3,3-pentamethyl-2,5,6,7-tetrahydroinden-4-one | 51.185156 | 118.44 |
| (4-methyl-4-phenylpentan-2-yl) acetate | 61.70 | 98.90 |
| (+−)-perhydro-5,5,8A-trimethyl-2-trans-naphthalenone | 63.22 | 102.97 |
| 2,3,3-trimethyl-2H-inden-1-one | 75.60 | 128.39 |

TABLE 4-continued

1-octen-3-ol Olfactory Receptor Antagonists

| Compound | IC$_{50}$ (µM) | % Inhibition |
|---|---|---|
| 1-(4,8-dimethyl-12-methylidenecyclododeca-4,8-dien-1-yl)ethanone; 1-(2,6,10-trimethylcyclododeca-1,5,9-trien-1-yl)ethanone; 1-(2,6,10-trimethylcyclododeca-2,5,9-trien-1-yl)ethanone | 82.36 | 113.23 |
| 4-(4,8-dimethylnona-3,7-dienyl)pyridine | 134.31 | 111.87 |
| Cyclopentadec-4-en-1-one | 155.72 | 90.98 |
| 4-[(1~{R},3~{R},6~{R})-2,2,3,6-tetramethylcyclohexyl]but-3-en-2-one; 4-[(1~{S},3~{S},6~{R})-2,2,3,6-tetramethylcyclohexyl]but-3-en-2-one | 186.12 | 90.82 |
| (+)-(1R,7R)-10,10-dimethyl-tricyclo[7.1.1.0(2,7)]undec-2-en-4-one 90 DIPG | 193.99 | 128.51 |
| (9<I>E</I>)-cycloheptadec-9-en-1-one | 210.10 | 97.22 |
| 1,4,8-trimethyl-13-oxabicyclo[10.1.0]trideca-4,8-diene; 1,5,8-trimethyl-13-oxabicyclo[10.1.0]trideca-4,8-diene | 266.47 | 70.92 |
| 8,8-dimethyl-2,3,4,5,6,7,8~{a}-hexahydro-1~{H}-naphthalene-2-carbaldehyde; 8,8-dimethyl-2,3,5,6,7,8~{a}-hexahydro-1~{H}-naphthalene-2-carbaldehyde; 8,8-dimethyl-2,3,4,5,6,7-hexahydro-1~{H}-naphthalene-2-carbaldehyde; 2,2-dimethyl-octahydro-1~{H}-2,4~{a}-methanonapthalen-8-one | 1641.48 | 83.15 |
| 2,4~{a},8,8-tetramethyl-1~{a},2,4,5,6,7-hexahydro-1~{H}-cyclopropa[j]naphthalen-3-one; 2,6,6,8-tetramethyltricyclo[5.3.1.0^{1,5}]undecan-9-one | 2362.92 | 109.43 |
| Isobutylquinoline | >600 | 30.14 |

Example 3: Identification of Butyric Acid Olfactory Receptor Inhibitors

A cell line expressing the OR51E1 olfactory receptor was used as an antagonist screening platform to identify compounds that have the property to decrease the butyric acid induced receptor activity. The stable cell line was screened with a volatile compound library for their inhibitory properties and potential butyric acid smell inhibition. First, individual binary mixtures of butyric acid with each one of the test compounds were presented to the cells.

Single concentration monitoring of the butyric acid induced cell activity in the presence or absence of a test compound allowed for the identification of compounds with a putative suppression or inhibitory effect. These hits were further confirmed in an inhibitory dose-response curve assay to evaluate the potency of activity inhibition as a measure of the IC$_{50}$ (the inhibitor concentration at which the receptor activity is inhibited by the half-maximal inhibition efficacy level of a given test compound) and % maximum inhibition (normalized to baseline agonist activity).

A dose-dependent decrease of receptor activity was recorded with increasing concentrations of test compounds in the presence of a single activating concentration of butyric acid (EC$_{80}$) and corresponding dose-response inhibition curves were obtained. The compounds listed in Table 5 are examples of compounds that decreased the butyric acid induced activity of at least one receptor.

TABLE 5

Butyric Acid Olfactory Receptor Antagonists

| Name | IC$_{50}$ (μM) |
| --- | --- |
| [(5~{S},6~{S},11~{R})-3,5,10,10-tetramethylspiro[5.5]undec-2-en-11-yl] acetate | 37.7 |
| (2~{R})-2,4,10,10-tetramethylspiro[5.5]undec-3-en-11-one; (5~{S})-3,5,10,10-tetramethylspiro[5.5]undec-3-en-11-one | |
| (+−)-3-methylcyclopentadecanone | 159.4 |
| (3~{R})-3-methylcyclopentadec-5-en-1-one | 53.7 |
| (−)-(3R)-3-methyl-1-cyclopentadecanone | 27.3 |
| Methoxycyclododecane | 84.1 |
| 1-(4,8-dimethyl-12-methylidenecyclododeca-4,8-dien-1-yl)ethanone; 1-(2,6,10-trimethylcyclododeca-1,5,9-trien-1-yl)ethanone; 1-(2,6,10-trimethylcyclododeca-2,5,9-trien-1-yl)ethanone | 100.9 |
| 1-(2,6,6-trimethylcyclohexen-1-yl)hepta-1,6-dien-3-one; 1-(2,6,6-trimethylcyclohex-2-en-1-yl)hepta-1,6-dien-3-one | 100 |
| (+−)-(2E)-1-(2,6,6-trimethyl-2-cyclohexen-1-yl)-2-buten-1-one | 50.5 |
| (2E)-1-(2,6,6-trimethyl-1-cyclohexen-1-yl)-2-buten-1-one | 184.4 |
| 1-(2,6,6-trimethyl-1-cyclohex-3-enyl)but-2-en-1-one | 210.5 |
| [1R-(1R*,4R*,6R*,10S*)]-4,12,12-trimethyl-9-methylene-5-oxatricyclo[8.2.0.0$^{4,6}$]dodecane | 97 |
| (4-methyl-4-phenylpentan-2-yl) acetate | 59.2 |
| (ethoxymethoxy)cyclododecane | 69.2 |

Example 4: Compositions According to Some Aspects Presented Herein

The following tables represent compositions according to the present disclosure.

TABLE 6

Composition Floral E

| INGREDIENTS | PARTS 1000 |
| --- | --- |
| ALDEHYDE C 11 UNDECYLIC | 15 |
| (+−)-3,7-DIMETHYL-6-OCTEN-1-OL | 200 |
| HEXYLCINNAMIC ALDEHYDE | 150 |
| 3-METHYL-4-(2,6,6-TRIMETHYLCYCLOHEX-2-EN-1-YL)BUT-3-EN-2-ONE; 1-(2,6,6-TRIMETHYLCYCLOHEX-2-EN-1-YL)PENT-1-EN-3-ONE | 70 |
| (+−)-2-METHYL-3-[4-(2-METHYL-2-PROPANYL)PHENYL]PROPANAL | 120 |
| (2,5-DIMETHYL-1,3-DIHYDROINDEN-2-YL)METHANOL ® | 100 |
| PHENYLETHYL ACETATE | 240 |
| 4-(2,6,6-TRIMETHYLCYCLOHEXEN-1-YL)BUT-3-EN-2-ONE; 4-(2,6,6-TRIMETHYLCYCLOHEX-2-EN-1-YL)BUT-3-EN-2-ONE | 80 |
| 2,4-DIMETHYLCYCLOHEX-3-ENECARBALDEHYDE | 25 |

TABLE 7

Composition Floral P

| INGREDIENTS | PARTS 1000 |
| --- | --- |
| ALDEHYDE C 11 UNDECYLIC | 15 |
| (+−)-3,7-DIMETHYL-6-OCTEN-1-OL | 180 |

TABLE 7-continued

Composition Floral P

| INGREDIENTS | PARTS 1000 |
| --- | --- |
| (+−)-(2E)-1-(2,6,6-TRIMETHYL-2-CYCLOHEXEN-1-YL)-2-BUTEN-1-ONE | 20 |
| 2-PENTYLCYCLOPENTAN-1-ONE | 20 |
| HEXYLCINNAMIC ALDEHYDE | 120 |
| 3-METHYL-4-(2,6,6-TRIMETHYLCYCLOHEX-2-EN-1-YL)BUT-3-EN-2-ONE; 1-(2,6,6-TRIMETHYLCYCLOHEX-2-EN-1-YL)PENT-1-EN-3-ONE | 70 |
| (+−)-2-METHYL-3-[4-(2-METHYL-2-PROPANYL)PHENYL]PROPANAL | 120 |
| (2,5-DIMETHYL-1,3-DIHYDROINDEN-2-YL)METHANOL ® | 100 |
| PHENYLETHYL ACETATE | 200 |
| (2,2,2-TRICHLORO-1-PHENYLETHYL) ACETATE | 50 |
| 4-(2,6,6-TRIMETHYLCYCLOHEXEN-1-YL)BUT-3-EN-2-ONE; 4-(2,6,6-TRIMETHYLCYCLOHEX-2-EN-1-YL)BUT-3-EN-2-ONE | 80 |
| 2,4-DIMETHYLCYCLOHEX-3-ENECARBALDEHYDE | 25 |

TABLE 8

Composition Floral RD

| INGREDIENTS | PARTS 1000 |
| --- | --- |
| ALDEHYDE C 11 UNDECYLIC | 15 |
| (+−)-3,7-DIMETHYL-6-OCTEN-1-OL | 180 |
| (+−)-(2E)-1-(2,6,6-TRIMETHYL-2-CYCLOHEXEN-1-YL)-2-BUTEN-1-ONE | 20 |
| 2-PENTYLCYCLOPENTAN-1-ONE | 20 |
| (+−)-3,7-DIMETHYL-1-OCTEN-3-OL | 130 |
| HEXYLCINNAMIC ALDEHYDE | 120 |
| 3-METHYL-4-(2,6,6-TRIMETHYLCYCLOHEX-2-EN-1-YL)BUT-3-EN-2-ONE; 1-(2,6,6-TRIMETHYLCYCLOHEX-2-EN-1-YL)PENT-1-EN-3-ONE | 90 |
| (2,5-DIMETHYL-1,3-DIHYDROINDEN-2-YL)METHANOL ® | 40 |
| PHENYLETHYL ALCOHOL | 220 |
| (2,2,2-TRICHLORO-1-PHENYLETHYL) ACETATE | 50 |
| 4-(2,6,6-TRIMETHYLCYCLOHEXEN-1-YL)BUT-3-EN-2-ONE; 4-(2,6,6-TRIMETHYLCYCLOHEX-2-EN-1-YL)BUT-3-EN-2-ONE | 90 |
| 2,4-DIMETHYLCYCLOHEX-3-ENECARBALDEHYDE | 25 |

TABLE 9

Composition Citrus B

| INGREDIENTS | PARTS 1000 |
| --- | --- |
| ALDEHYDE C8 | 30 |
| ALDEHYDE C9 | 30 |
| ALDEHYDE C10 | 50 |
| ALDEHYDE C11 UNDECYLIC | 10 |
| 3,7-DIMETHYLOCTA-2,6-DIENAL | 170 |
| (+−)-3,7-DIMETHYL-6-OCTEN-1-OL | 80 |
| (−)-(R)-3,7-DIMETHYL-6-OCTENENITRILE | 120 |
| (+−)-(3E)-3-METHYL-4-(2,6,6-TRIMETHYL-2-CYCLOHEXEN-1-YL)-3-BUTEN-2-ONE (A) + (+−)-(1E)-1-(2,6,6-TRIMETHYL-2-CYCLOHEXEN-1-YL)-1-PENTEN-3-ONE (B | 100 |

TABLE 9-continued

Composition Citrus B

| INGREDIENTS | PARTS 1000 |
|---|---|
| (2,5-DIMETHYL-1,3-DIHYDROINDEN-2-YL)METHANOL ® | 80 |
| TERPINOLENE | 190 |
| 4-(2,6,6-TRIMETHYLCYCLOHEXEN-1-YL)BUT-3-EN-2-ONE; 4-(2,6,6-TRIMETHYLCYCLOHEX-2-EN-1-YL)BUT-3-EN-2-ONE | 100 |
| 2,4-DIMETHYLCYCLOHEX-3-ENECARBALDEHYDE | 40 |

TABLE 10

Composition Citrus H

| INGREDIENTS | PARTS 1000 |
|---|---|
| ALDEHYDE C8 | 35 |
| ALDEHYDE C9 | 30 |
| ALDEHYDE C10 | 55 |
| ALLYL AMYL GLYCOLATE | 3 |
| BHT | 40 |
| 3ARS,5ASR,9ASR,9BSR)-3A,6,6,9A-TETRAMETHYLDODECAHYDRONAPHTHO[2,1-B]FURAN | 2 |
| 3,7-DIMETHYLOCTA-2,6-DIENAL | 170 |
| (+)-(R)-3,7-DIMETHYL-6-OCTENAL | 90 |
| (−)-(R)-3,7-DIMETHYL-6-OCTENENITRILE | 100 |
| (+−)-3-(4-ISOPROPYLPHENYL)-2-METHYLPROPANAL | 90 |
| 1-(2,6,6-TRIMETHYL-1-CYCLOHEX-3-ENYL)BUT-2-EN-1-ONE | 15 |
| (+−)-3,7-DIMETHYL-1-OCTEN-3-OL | 100 |
| (+−)-(3E)-3-METHYL-4-(2,6,6-TRIMETHYL-2-CYCLOHEXEN-1-YL)-3-BUTEN-2-ONE (A) + (+−)-(1E)-1-(2,6,6-TRIMETHYL-2-CYCLOHEXEN-1-YL)-1-PENTEN-3-ONE (B) | 45 |
| (2,5-DIMETHYL-1,3-DIHYDROINDEN-2-YL)METHANOL ® | 40 |
| TERPINOLENE | 100 |
| 4-(2,6,6-TRIMETHYLCYCLOHEXEN-1-YL)BUT-3-EN-2-ONE; 4-(2,6,6-TRIMETHYLCYCLOHEX-2-EN-1-YL)BUT-3-EN-2-ONE | 45 |
| 2,4-DIMETHYLCYCLOHEX-3-ENECARBALDEHYDE | 40 |

TABLE 11

Composition Jasmin E

| INGREDIENTS | PARTS 1000 |
|---|---|
| AMYL CINNAMIC ALDEHYDE | 75 |
| BENZYL ACETATE | 250 |
| BENZYL PHENYLACETATE | 60 |
| CIS JASMONE | 30 |
| DECALACTONE CP | 25 |
| (+−)-3,7-DIMETHYL-1-OCTEN-3-OL | 90 |
| ETHYL 2 METHYLBUTYRATE @ 10% DIPG | 2 |
| ETHYL PRALINE | 7 |
| EUGENOL | 20 |
| ISOEUGENOL EXTRA NAT US | 4 |
| 3-METHYL-4-(2,6,6-TRIMETHYLCYCLOHEX-2-EN-1-YL)BUT-3-EN-2-ONE; 1-(2,6,6-TRIMETHYLCYCLOHEX-2-EN-1-YL)PENT-1-EN-3-ONE | 100 |
| (2,5-DIMETHYL-1,3-DIHYDROINDEN-2-YL)METHANOL | 50 |
| LINALYL ACETATE AR | 55 |
| METHYL ANTHRANILATE DIST | 2 |
| METHYL BENZOATE | 3 |
| PARATOLYL ALDEHYDE | 8 |

TABLE 11-continued

Composition Jasmin E

| INGREDIENTS | PARTS 1000 |
|---|---|
| PHENYLACETALDEHYDE | 4 |
| (2,2,2-TRICHLORO-1-PHENYLETHYL) ACETATE CRIST | 50 |
| 4-(2,6,6-TRIMETHYLCYCLOHEXEN-1-YL)BUT-3-EN-2-ONE; 4-(2,6,6-TRIMETHYLCYCLOHEX-2-EN-1-YL)BUT-3-EN-2-ONE | 150 |
| 2,4-DIMETHYLCYCLOHEX-3-ENECARBALDEHYDE | 15 |

TABLE 12

Composition Floral V

| INGREDIENTS | PARTS 1000 |
|---|---|
| ALDEHYDE C 11 UNDECYLIC | 17 |
| BHT | 20 |
| (+−)-3,7-DIMETHYL-6-OCTEN-1-OL | 190 |
| (+−)-(2E)-1-(2,6,6-TRIMETHYL-2-CYCLOHEXEN-1-YL)-2-BUTEN-1-ONE | 21 |
| 2-PENTYLCYCLOPENTAN-1-ONE | 21 |
| DIYDROLINALOL | 110 |
| HEXYLCINNAMIC ALDEHYDE | 100 |
| 3-METHYL-4-(2,6,6-TRIMETHYLCYCLOHEX-2-EN-1-YL)BUT-3-EN-2-ONE; 1-(2,6,6-TRIMETHYLCYCLOHEX-2-EN-1-YL)PENT-1-EN-3-ONE | 95 |
| (2,5-DIMETHYL-1,3-DIHYDROINDEN-2-YL)METHANOL | 40 |
| PHENYLETHYL ALCOHOL | 232 |
| (2,2,2-TRICHLORO-1-PHENYLETHYL) ACETATE | 52 |
| 4-(2,6,6-TRIMETHYLCYCLOHEXEN-1-YL)BUT-3-EN-2-ONE; 4-(2,6,6-TRIMETHYLCYCLOHEX-2-EN-1-YL)BUT-3-EN-2-ONE | 94 |
| 2,4-DIMETHYLCYCLOHEX-3-ENECARBALDEHYDE | 8 |

TABLE 13

Composition Citrus B2

| INGREDIENTS | PARTS 1000 |
|---|---|
| 3,7-DIMETHYLOCTA-2,6-DIENAL | 180 |
| (+−)-3,7-DIMETHYL-1-OCTEN-3-OL | 120 |
| (+)-(R)-3,7-DIMETHYL-6-OCTENAL | 100 |
| (−)-(R)-3,7-DIMETHYL-6-OCTENENITRILE | 100 |
| (+−)-3-(4-ISOPROPYLPHENYL)-2-METHYLPROPANAL | 100 |
| ALDEHYDE C 10 | 55 |
| TERPINOLENE | 50 |
| 3-METHYL-4-(2,6,6-TRIMETHYLCYCLOHEX-2-EN-1-YL)BUT-3-EN-2-ONE; 1-(2,6,6-TRIMETHYLCYCLOHEX-2-EN-1-YL)PENT-1-EN-3-ONE | 45 |
| 4-(2,6,6-TRIMETHYLCYCLOHEXEN-1-YL)BUT-3-EN-2-ONE; 4-(2,6,6-TRIMETHYLCYCLOHEX-2-EN-1-YL)BUT-3-EN-2-ONE | 45 |
| BHT | 40 |
| (2,5-DIMETHYL-1,3-DIHYDROINDEN-2-YL)METHANOL | 40 |
| 2,4-DIMETHYLCYCLOHEX-3-ENECARBALDEHYDE | 40 |
| ALDEHYDEC8 | 35 |
| ALDEHYDEC9 | 30 |
| 1-(2,6,6-TRIMETHYL-1-CYCLOHEX-3-ENYL)BUT-2-EN-1-ONE | 15 |

TABLE 13-continued

Composition Citrus B2

| INGREDIENTS | PARTS 1000 |
|---|---|
| ALLYL AMYL GLYCOLATE A | 3 |
| 3ARS,5ASR,9ASR,9BSR)-3A,6,6,9A-TETRAMETHYLDODECAHYDRONAPHTHO[2,1-B]FURAN | 2 |

TABLE 14

Composition Jasmine E

| INGREDIENT | AMOUNT (PARTS BY WEIGHT) |
|---|---|
| BENZYL ACETATE A | 1250 |
| 4-(2,6,6-TRIMETHYLCYCLOHEXEN-1-YL)BUT-3-EN-2-ONE; 4-(2,6,6-TRIMETHYLCYCLOHEX-2-EN-1YL)BUT-3-EN-2-ONE B | 750 |
| 3-METHYL-4-(2,6,6-TRIMETHYLCYCLOHEX-2-EN-1-YL)BUT-3-EN-2-ONE; 1-(2,6,6-TRIMETHYLCYCLOHEX-2-EN-1-YL)PENT-1-EN-3-ONE B | 500 |
| (+−)-3,7-DIMETHYL-1-OCTE-3-OL A | 450 |
| AMYLCINNAMIC ALDEHYDE R | 375 |
| BENZYL PHENYLACETATE A | 300 |
| LINALYL ACETATE AR | 275 |
| (2,5-DIMETHYL-1,3-DIHYDROINDEN-2-YL)METHANOL | 250 |
| (2,2,2-TRICHLORO-1-PHENYLETHYL) ACETATE A | 250 |
| CIS JASMONE | 150 |
| DECALACTONE CP | 125 |
| EUGENOL F | 100 |
| 2,4-DIMETHYLCYCLOHEX-3-ENECARBALDEHYDE | 75 |
| PARATOLYL ALDEHYDE | 40 |
| ETHYL PRALINE | 35 |
| PHENYLACETALDEHYDE | 20 |
| ISOEUGENOL EXTRA NAT US | 20 |
| METHYL BENZOATE | 15 |
| METHYL ANTHRANILATE DIST | 10 |
| DIPROPYLENE GLYCOL | 9 |
| ETHYL 2 METHYLBUTYRATE | 1 |

TABLE 15

Composition Floral D

| MOLECULE NAME | PARTS |
|---|---|
| UNDECANAL | 15 |
| (E)-2-PENTYL-3-PHENYL-2-PROPENAL | 150 |
| (+−)-3,7-DIMETHYL-6-OCTEN-1-OL | 200 |
| (+−)-(3E)-3-METHYL-4-(2,6,6-TRIMETHYL-2-CYCLOHEXEN-1-YL)-3-BUTEN-2-ONE (A) + (+−)-(1E)-1-(2,6,6-TRIMETHYL-2-CYCLOHEXEN-1-YL)-1-PENTEN-3-ONE(B) | 70 |
| (+−)-2-METHYL-3-[4-(2-METHYL-2-PROPANYL)PHENYL]PROPANAL | 120 |
| (+−)-2,5-DIMETHYL-2-INDANMETHANOL | 100 |
| 2-PHENYLETHANOL | 240 |
| (+−)-(3E)-4-(2,6,6-TRIMETHYL-2-CYCLOHEXEN-1-YL)-3-BUTEN-2-ONE (A) + (3E)-4-(2,6,6-TRIMETHYL-1-CYCLOHEXEN-1-YL)-3-BUTEN-2-ONE (B); | 80 |
| (1RS,2RS)-2,4-DIMETHYL-3-CYCLOHEXENE-1-CARBALDEHYDE (A) + (1RS,2SR)-2,4-DIMETHYL-3-CYCLOHEXENE-1-CARBALDEHYDE (B) | 25 |

Example 5: Sensory Measurement of Residual Malodor Score for Individual Malodor Receptor Antagonist Systems, Individual Functional Perfuming Ingredients and for Compositions According to the Present Disclosure Malodor receptor antagonist systems and compositions were evaluated at a gas phase concentration of 3.4 microg/l air. The sensory method to evaluate compositions required the use of specially designed air dilution olfactometers to achieve well controlled and stable gas phase concentrations of the compositions and of the malodor to the group of test subjects.

The 30 subjects first evaluated the malodor reconstitution alone and then rated the 3 attributes "Freshness", "Pleasantness" and "malodor" (the malodor character) on a 0 to 10 scale. The next evaluation was performed 30 seconds later to avoid odor adaptation; the malodor reconstitution was injected together with the test composition in the olfactometer. Ratings for the same descriptors recorded.

Figure 3:
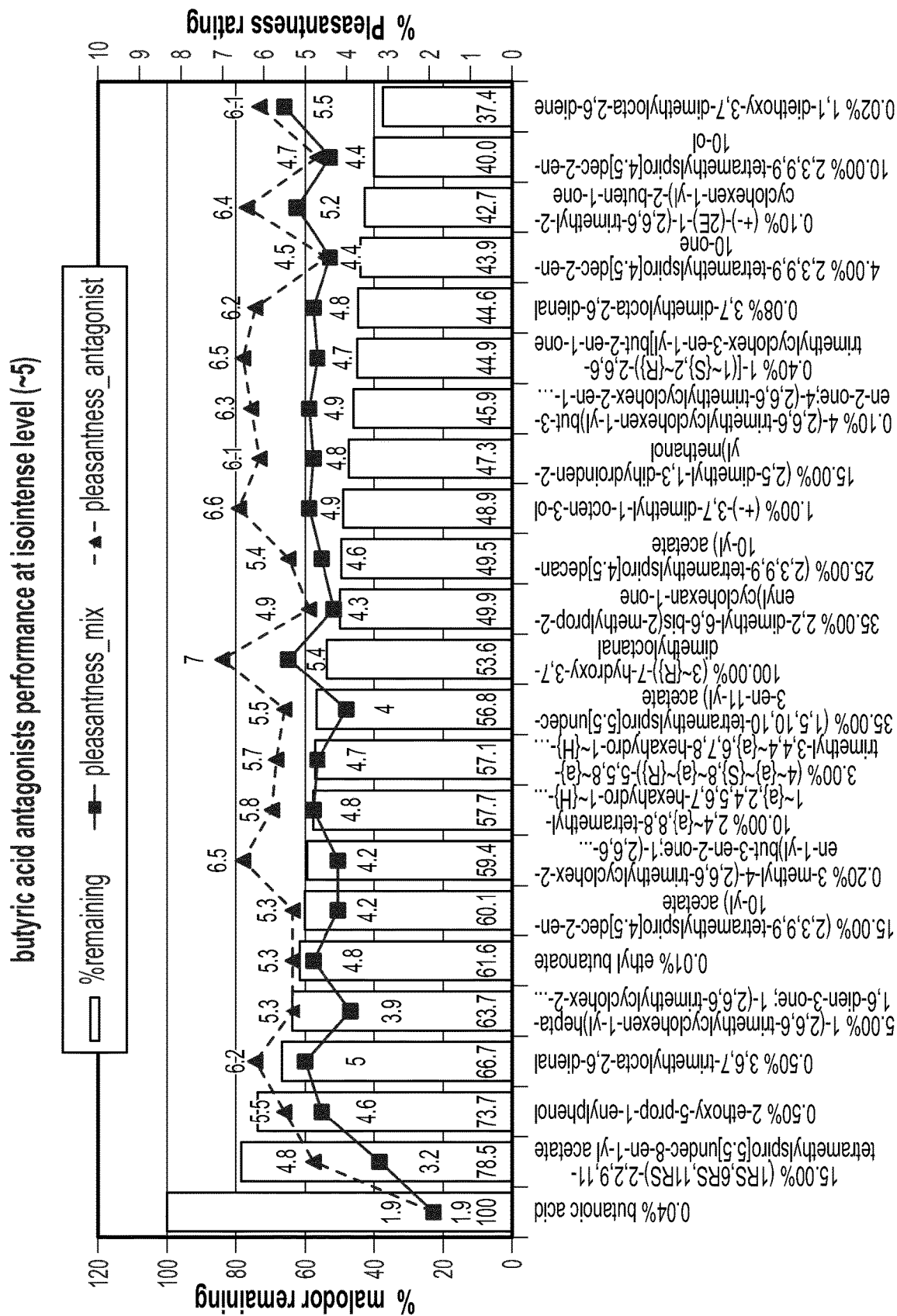
FIG. 3 shows the ability of compounds according to some aspects of the present disclosure to reduce the perceived intensity of butyric acid in human sensory panel tests (grey bars). The pleasantness of the compounds delivered alone (triangles, dashed-line) and in a mixture with butyric acid at isointense concentrations (squares, solid line). Many of these compounds are shown to inhibit the activity of a butyric acid olfactory receptor. All compounds showed a statistically significant reduction in malodor compared to butyric acid at 0.04% (isointense).
Figure 4:
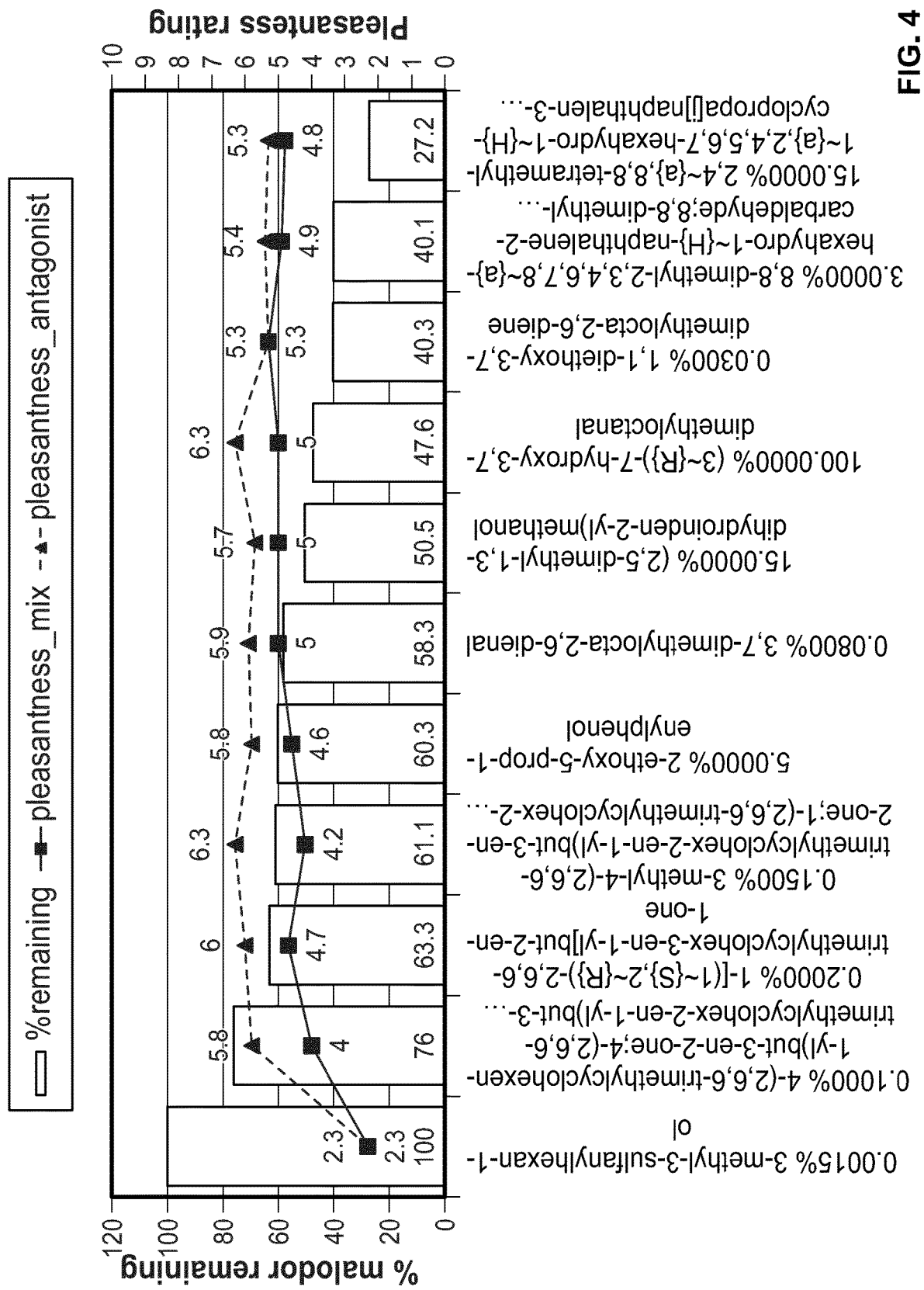
FIG. 4 shows the ability of compounds according to some aspects of the present disclosure to reduce the perceived intensity of transpirol in human sensory panel tests (grey bars). The pleasantness of the compounds delivered alone (triangles, dashed-line) and in a mixture with transpirol at isointense concentrations (squares, solid line). Many of these compounds are shown to inhibit the activity of a transpirol olfactory receptor. All compounds showed a statistically significant reduction in malodor compared to transpirol at 0.0015% (isointense).
Figure 5:
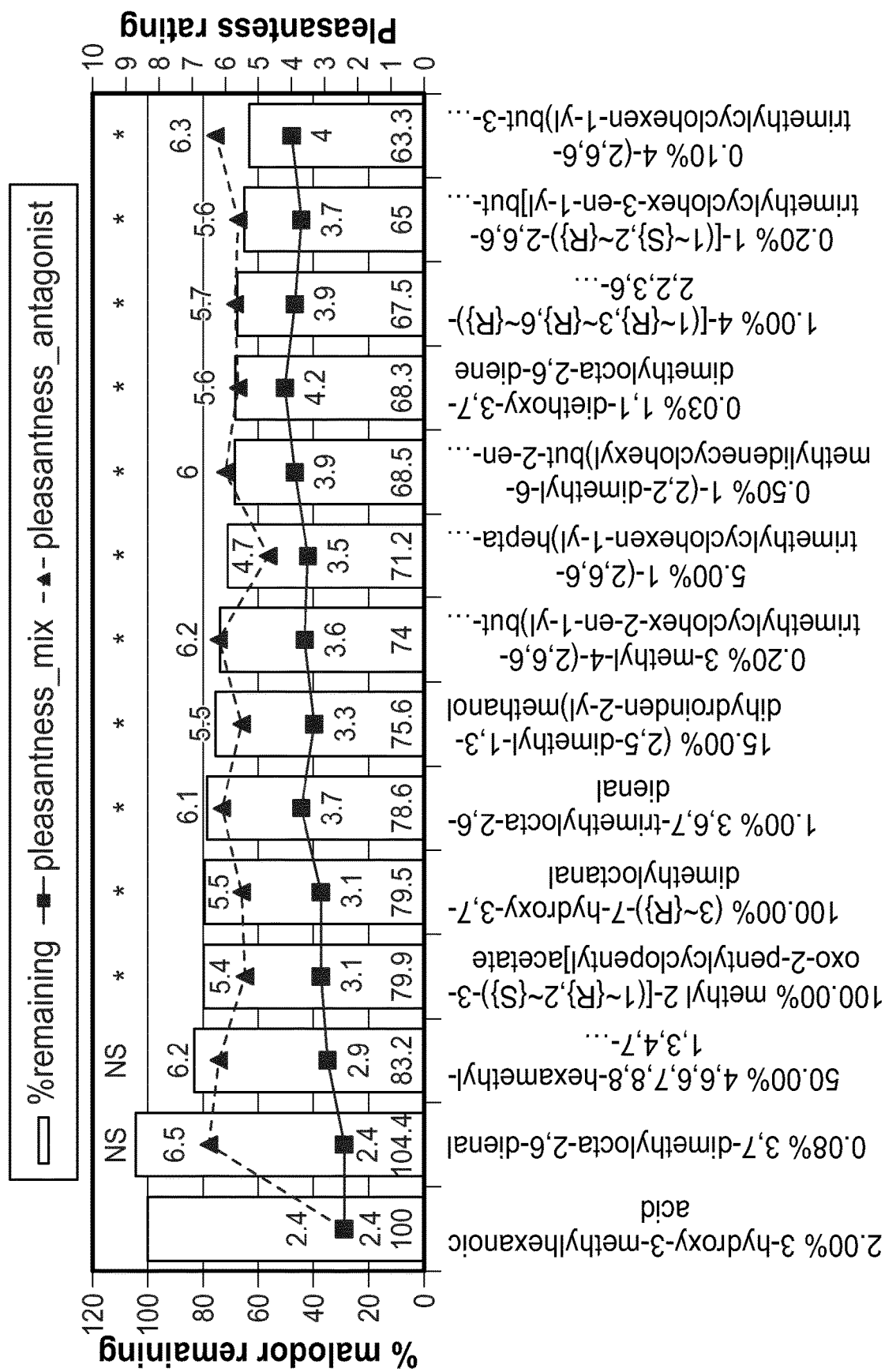
FIG. 5 shows the ability of compounds according to some aspects of the present disclosure to reduce the perceived intensity of HMHA in human sensory panel tests (grey bars). The pleasantness of the compounds delivered alone (triangles, dashed-line) and in a mixture with HMHA at isointense concentrations (squares, solid line). Many of these compounds are shown to inhibit the activity of an HMHA olfactory receptor. NS indicates no statistically significant reduction in malodor compared to HMHA at 2% (isointense). * (asterisk) compounds showed a statistically significant reduction in malodor compared to HMHA at 2% (isointense).
Figure 6:
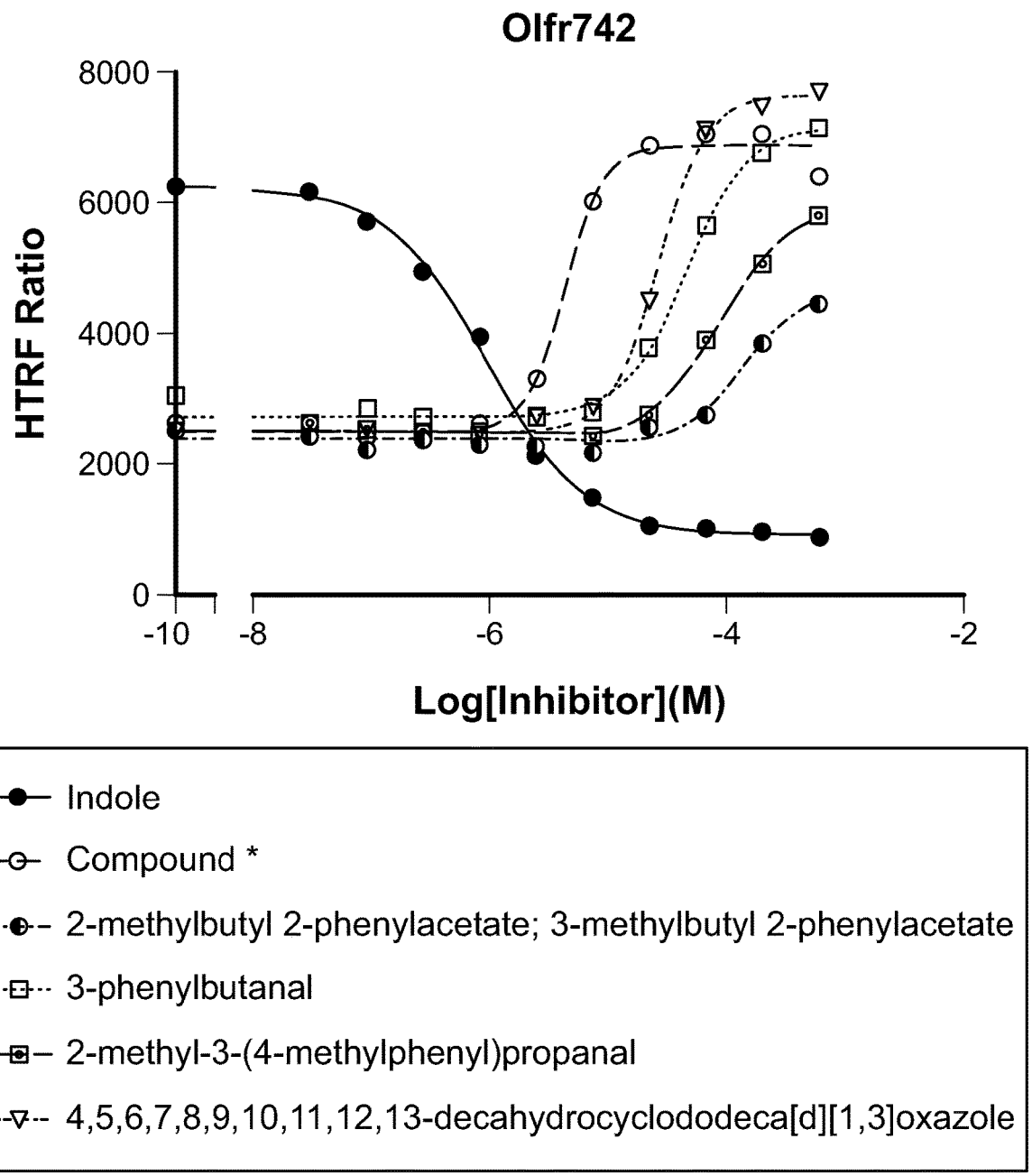
FIG. 6 shows the potency of various antagonists as inhibitors of the indole/skatole acid olfactory receptor Olfr742 under highly stringent screening conditions.
Figure 7:
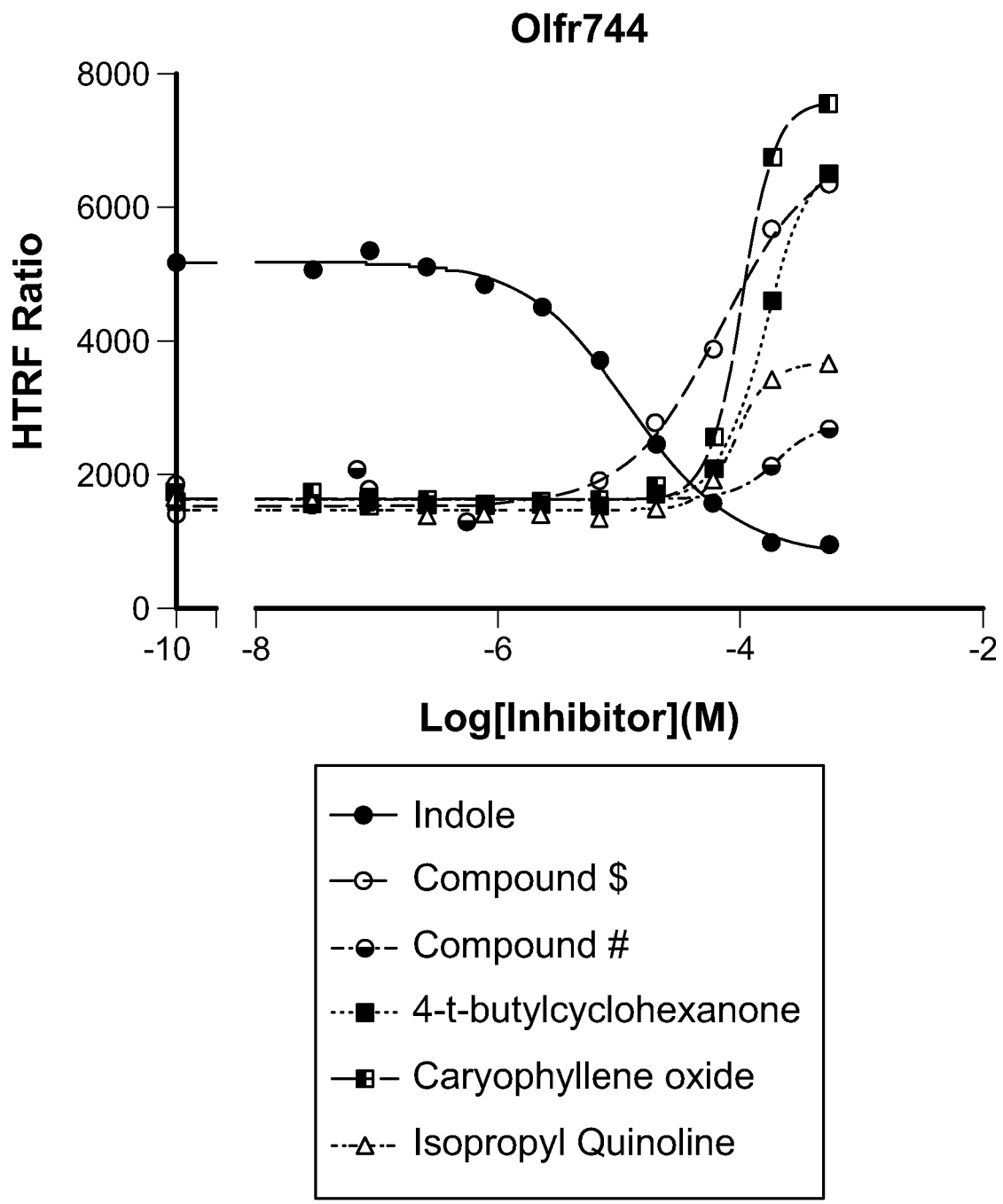
FIG. 7 shows the potency of various antagonists as inhibitors of the indole/skatole acid olfactory receptor Olfr744 under highly stringent screening conditions.
Figure 8:
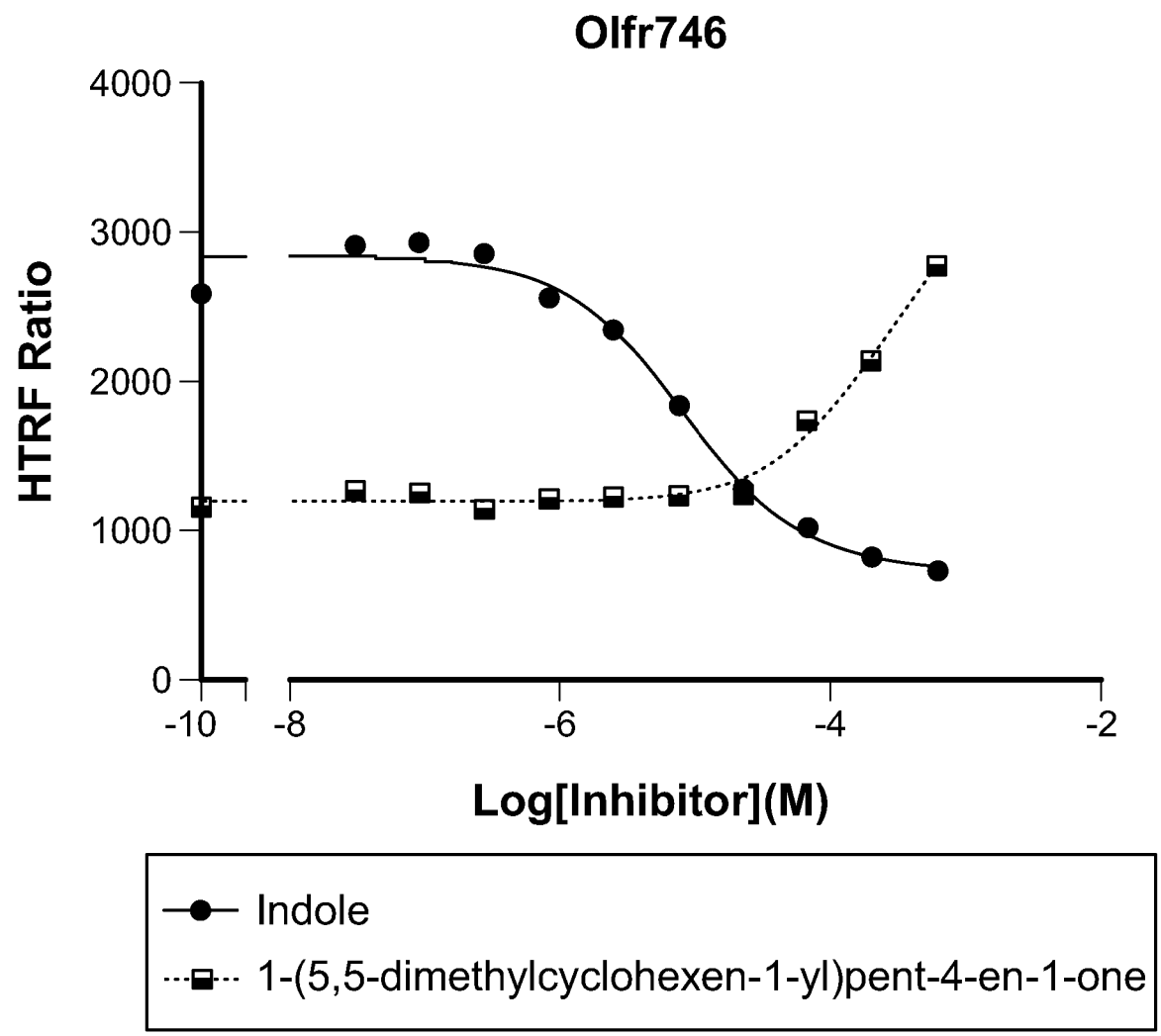
FIG. 8 shows the potency of various antagonists as inhibitors of the indole/skatole acid olfactory receptor Olfr749 under highly stringent screening conditions.
Figure 9:
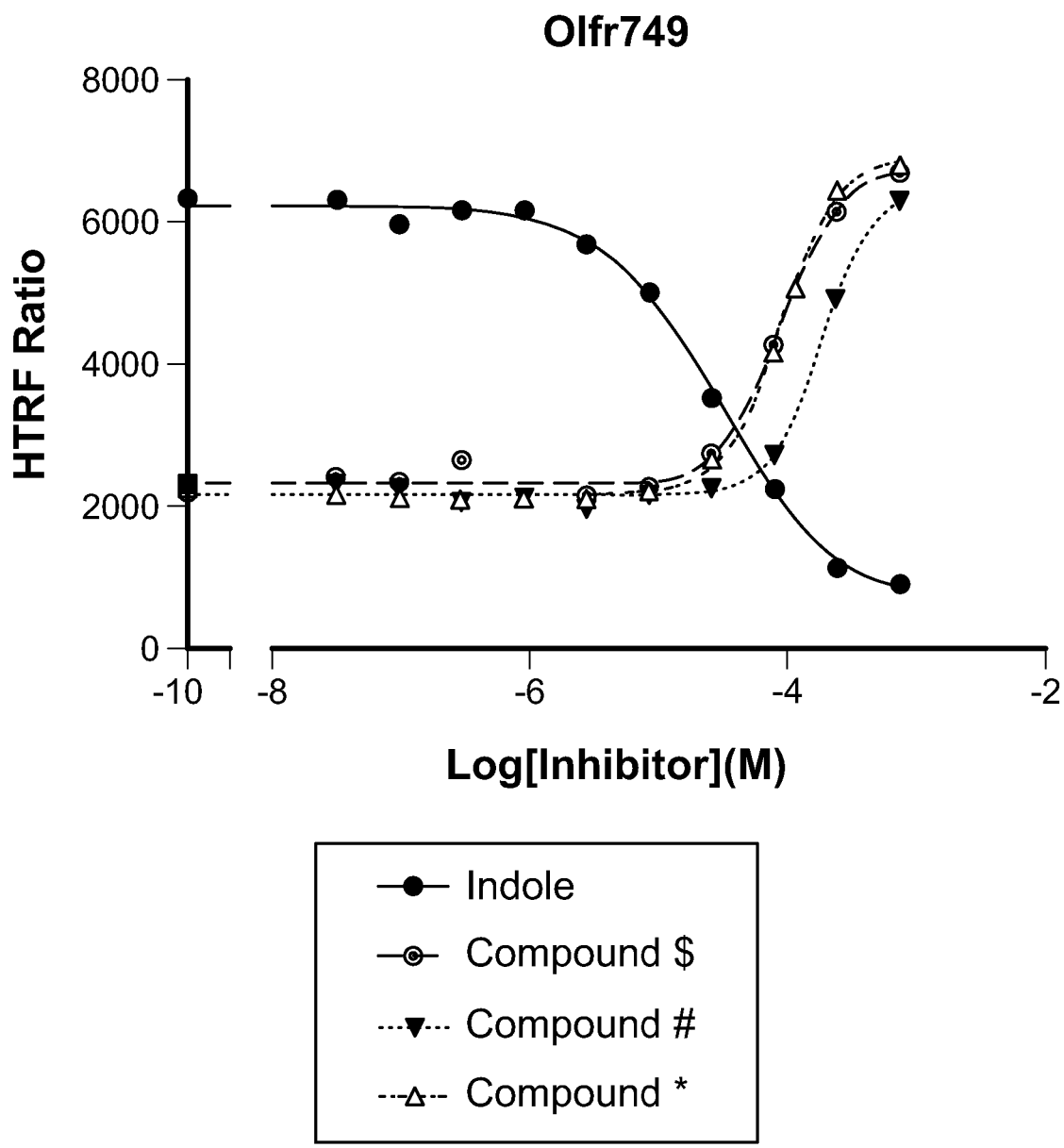
FIG. 9 shows the potency of various antagonists as inhibitors of the indole/skatole acid olfactory receptor Olfr746 under highly stringent screening conditions.

The results are shown in Tables 16 and 17, and FIGS. 3 to 5.

The model malodor reconstitution for fecal malodor will be fecal reonstitution made of indole, methyl mercaptan, p-cresol and butyric acid. The gas phase concentration of the fecal malodor reconstitution and of its ingredients will correspond to the headspace analytical results from a toilet gas phase sampling (Charles J F Chappuis, Yvan Niclass, Christine Vuilleumier, and Christian Starkenmann Quantitative Headspace Analysis of Selected Odorants from Latrines in Africa and India Environ. Sci. Technol. 2015, 49, 6134?6140).

The results will be expressed as the averaged rates for the three descriptors for the particular malodor reconstitution alone and the particular malodor reconstitution in combination with the tested composition.

TABLE 16

Human sensory performance of test compounds delivered with and without medium intensity (0.1%) geonol. The column heading for significance of difference in pleasantness rating is abbreviated Pl.

| Medium Dilution/Low Dilution | IUPAC Name | Test Compound Only | | Medium Dilution Test Compound + Geonol | | Low Dilution Test Compound + Geonol | |
|---|---|---|---|---|---|---|---|
| | | Pl. | % Earthy/Moss Odor | Pl. | % Earthy/Moss Odor Remaining | Pl. | % Earthy/Moss Odor Remaining |
| 1.5%/0.3% | [(1~{S},2~{R})-2-~{tert}-butylcyclohexyl] acetate | * | 15.30% * | * | 49.50% * | * | 66.80% * |

TABLE 16-continued

Human sensory performance of test compounds delivered with and without medium intensity (0.1%) geonol.
The column heading for significance of difference in pleasantness rating is abbreviated Pl.

| Medium Dilution/Low Dilution | IUPAC Name | Test Compound Only | | | Medium Dilution Test Compound + Geonol | | | Low Dilution Test Compound + Geonol | | |
|---|---|---|---|---|---|---|---|---|---|---|
| | | Pl. | % Earthy/Moss Odor | | Pl. | % Earthy/Moss Odor Remaining | | Pl. | % Earthy/Moss Odor Remaining | |
| 0.15%/0.02% | 3,7-dimethylocta-2,6-dienal | * | 27.60% | * | * | 58.00% | * | * | 76.40% | * |
| 0.03%/0.005% | 1,1-diethoxy-3,7-dimethylocta-2,6-diene | * | 25.00% | * | * | 63.30% | * | * | 64.00% | * |
| 50%/5% | oxacyclohexadecan-2-one | * | 18.70% | * | * | 55.10% | * | * | 60.80% | * |
| 100%/20% | (3~{R})-7-hydroxy-3,7-dimethyloctanal | * | 30.30% | * | * | 57.20% | * | NS | 68.20% | * |
| 5%/0.5% | 2-ethoxy-5-prop-1-enylphenol | * | 27.10% | * | * | 51.70% | * | NS | 70.60% | * |
| 1.0%/0.1% | 3-methyl-4-(2,6,6-trimethylcyclohex-2-en-1-yl)but-3-en-2-one; 1-(2,6,6-trimethylcyclohex-2-en-1-yl)pent-1-en-3-one | * | 29.40% | * | * | 56.20% | * | NS | 75.80% | * |
| 0.2%/0.02% | 4-(2,6,6-trimethylcyclohexen-1-yl)but-3-en-2-one; 4-(2,6,6-trimethylcyclohex-2-en-1-yl)but-3-en-2-one | * | 27.10% | * | * | 70.30% | * | * | 73.40% | * |
| 2%/0.2% | 2-methyl-5-propan-2-ylphenol | NS | 40.10% | * | NS | 56.00% | * | NS | 77.30% | NS |
| 5%/1% | 6,10-dimethylundeca-5,9-dien-2-one | * | 52.80% | * | * | 74.00% | * | NS | 105.30% | NS |
| 2%/0.5% | 4-(2,6,6-trimethylcyclohexen-1-yl)butan-2-one | NS | 30.30% | * | * | 62.30% | * | NS | 74.80% | * |
| 40%/4% | 3-acetyloxynonyl acetate; (3-pentyloxan-4-yl) acetate | * | 26.20% | * | * | 62.50% | * | NS | 81.10% | NS |
| 15%/0.75% | (2,5-dimethyl-1,3-dihydroinden-2-yl)methanol | * | 41.70% | * | * | 63.10% | * | NS | 86.90% | NS |
| 1%/0.2% | 3,6,7-trimethylocta-2,6-dienal | * | 26.90% | * | * | 64.90% | * | NS | 99.10% | NS |
| 5%/0.8% | 4-(2,6,6-trimethylcyclohexen-1-yl)but-3-en-2-one | * | 41.80% | * | NS | 66.40% | * | NS | 91.20% | NS |
| 0.5%/0.05% | 2-{tert}-butylphenol | NS | 41.30% | * | NS | 68.40% | * | NS | 88.00% | * |
| 40%/0.5% | 2-ethyl-4-[(1~{S})-2,2,3-trimethylcyclopent-3-en-1-yl]but-2-en-1-ol | NS | 34.90% | * | NS | 64.30% | * | NS | 85.20% | NS |
| 0.2%/0.02% | 1-[(1~{S},2~{R})-2,6,6-trimethylcyclohex-3-en-1-yl]but-2-en-1-one | * | 31.80% | * | NS | 78.20% | * | NS | 90.40% | NS |
| 0.03%/0.003% | 1-(3,3-dimethylcyclohexen-1-yl)pent-4-en-1-one; 1-(5,5-dimethylcyclohexen-1-yl)pent-4-en-1-one | * | 34.50% | * | NS | 72.30% | * | NS | 85.80% | NS |
| 10%/1% | 2-(2-methylpropyl)quinoline | NS | 37.80% | * | NS | 71.70% | * | NS | 79.60% | * |
| 0.3%/0.02% | 2-phenylethyl acetate | NS | 35.30% | * | NS | 65.80% | * | NS | 97.10% | NS |
| 0.7%/0.07% | 2-(1-ethoxyethoxy)ethylbenzene; 2-[1-(2-phenylethoxy)ethoxy]ethylbenzene | NS | 36.60% | * | NS | 62.40% | * | NS | 91.20% | NS |
| 100%/10% | 3-(4-hydroxy-4-methylpentyl)cyclohex-3-ene-1-carbaldehyde; 4-(4-hydroxy-4-methylpentyl)cyclohex-3-ene-1-carbaldehyde | * | 15.40% | * | NS | 78.70% | * | NS | 85.70% | NS |
| 100%/2% | 1-(2,3,8,8-tetramethyl-1,3,4,6,7,8~{a}-hexahydronaphthalen-2-yl)ethanone; 1-(2,3,8,8-tetramethyl-1,3,5,6,7,8~{a}-hexahydronaphthalen-2-yl)ethanone; 1-(2,3,8,8-tetramethyl-1,3,4,5,6,7-hexahydronaphthalen-2-yl)ethanone | * | 34.30% | * | NS | 74.80% | * | * | 77.40% | * |
| 1.5%/0.3% | (2-methyl-1-phenylpropan-2-yl) acetate | * | 34.00% | * | * | 72.10% | * | NS | 89.10% | NS |
| 0.2%/0.02% | (1~{S},2~{R})-2,4-dimethylcyclohex-3-ene-1-carbaldehyde | * | 48.10% | * | * | 71.50% | * | * | 80.60% | NS |

TABLE 16-continued

Human sensory performance of test compounds delivered with and without medium intensity (0.1%) geonol.
The column heading for significance of difference in pleasantness rating is abbreviated Pl.

| Medium Dilution/Low Dilution | IUPAC Name | Pl. | Test Compound Only % Earthy/Moss Odor | Pl. | Medium Dilution Test Compound + Geonol % Earthy/Moss Odor Remaining | | Pl. | Low Dilution Test Compound + Geonol % Earthy/Moss Odor Remaining | |
|---|---|---|---|---|---|---|---|---|---|
| 50%/7% | 5-hexyl-2-methylpyridine | NS | 46.40% | * | NS | 66.30% | * | NS | 88.20% | NS |
| 7%/0.7% | 2-phenylethanol | NS | 47.50% | * | NS | 78.20% | NS | NS | 98.80% | NS |
| 3%/0.5% | 5-methyl-2-propan-2-ylphenol | NS | 54.70% | * | NS | 78.60% | NS | NS | 91.00% | NS |
| 0.5%/0.05% | 1$l^{2},2$l^{2},3$l^{2}-trinobelacyclopropane; 3,4,5,6,6-pentamethylhept-3-en-2-one; 3,4,5,6,6-pentamethylhept-4-en-2-one; 3,5,6,6-tetramethyl-4-en-2-one; 3,5,6,6-tetramethyl-4-methylideneheptan-2-one | * | 52.60% | * | NS | 86.30% | NS | NS | 102.70% | NS |
| 3%/0.5% | (4~{a}~{S},8~{a}~{R})-5,5,8~{a}-trimethyl-3,4,4~{a},6,7,8-hexahydro-1~{H}-naphthalen-2-one | * | 45.20% | * | NS | 87.20% | NS | NS | 81.20% | NS |
| 40%/2% | 1,4,8-trimethyl-13-oxabicyclo[10.1.0]trideca-4,8-diene; 1,5,8-trimethyl-13-oxabicyclo[10.1.0]trideca-4,8-diene | * | 43.30% | * | * | 91.50% | NS | NS | 92.00% | NS |
| 0.04%/0.004% | 2-pentylcyclopentan-1-one | * | 40.90% | * | * | 86.80% | NS | NS | 101.60% | NS |
| 5%/0.4% | cyclopentadec-4-en-1-one | * | 49.90% | * | * | 82.10% | NS | NS | 93.40% | NS |
| 0.05%/0.005% | 6-propan-2-ylquinoline; 8-propan-2-ylquinoline | *u. | 54.70% | * | *u. | 104.70% | NS | *u. | 99.60% | NS |
| 30%/3% | 3-methyl-5-phenylpentan-1-ol | * | 11.30% | * | NS | 80.70% | NS | NS | 87.10% | NS |
| 0.005%/0.0001% | nona-2,6-dienal | NS | 65.40% | * | NS | 88.60% | NS | NS | 83.70% | NS |
| 100%/5% | (4R,4aS,6R)-4,4a-dimethyl-6-prop-1-en-2-yl-3,4,5,6,7,8-hexahydronaphthalen-2-one | NS | 70.60% | * | NS | 99.70% | NS | NS | 103.90% | NS |
| 2%/0.04% | (1~{S},3~{S},6~{R},7~{R},8~{S})-2,2,6,8-tetramethyltricyclo[5.3.1.0^{3,8}]undecan-3-ol | NS | 94.10% | NS | NS | 129.80% | *more | NS | 104.60% | NS |
| 1%/0.2% | ethyl deca-2,4,7-trienoate | *u. | 62.20% | * | *u. | 78.10% | NS | *u. | 86.20% | NS |
| 10%/0.4% | (2,2,2-trichloro-1-phenylethyl) acetate | * | 38.60% | * | * | 61.30% | NS | * | 95.80% | NS |

* denotes significant difference from 0.15 geonol at the 95% confidence level.
NS denotes no significant difference.
*u- denotes significantly less pleasant than 0.1% geonol at 95% confidence level

TABLE 17

Human sensory performance of test compounds delivered with and without medium intensity (0.15%) 1-octen-3-ol. The column heading for significance of difference in pleasantness rating is abbreviated Pl.

| Test Compound Name (Medium Dilution/Low Dilution) | IUPAC Name | Pl. | Test Compound Only % Mushroom/Earthy/Fungal Odor | Pl. | Medium Dilution Test Compound + 1-octen-3-ol % Mushroom/Earthy/Fungal Odor Remaining | Pl. | Low Dilution Test Compound + 1-octen-3-ol % Mushroom/Earthy/Fungal Odor Remaining |
|---|---|---|---|---|---|---|---|
| 20%/2% | 2,4~{a},8,8-tetramethyl-1~{a},2,4,5,6,7-hexahydro-1~{H}-cyclopropa[j]naphthalen-3-one; 2,6,6,8-tetramethyltricyclo[5.3.1.0^{1,5}]undecan-9-one | * | 36.90% | * | 53.50% | * | 72.10% * |
| 0.2%/0.02% | 3-methyl-4-(2,6,6-trimethylcyclohex-2-en-1-yl)but-3-en-2-one; 1-(2,6,6-trimethylcyclohex-2-en-1-yl)pent-1-en-3-one | * | 20.00% | * | 53.50% * | * | 75.80% * |
| 100%/20% | (3~{R})-7-hydroxy-3,7-dimethyloctanal | * | 20.70% | * | 56.50% * | * | 70.00% * |
| 3%/0.4% | 8,8-dimethyl-2,3,4,6,7,8~{a}-hexahydro-1~{H}-naphthalene-2-carb aldehyde; 8,8-dimethyl-2,3,5,6,7,8~{a}-hexahydro-1~{H}-naphthalene-2-carbaldehyde; 8,8-dimethyl-2,3,4,5,6,7-hexahydro-1~{H}-naphthalene-2-carbaldehyde; 2,2-dimethyl-octahydro-1~{H}-2,4~{a}-methanonapthalen-8-one | * | 39.80% | * | 59.30% * | * | 81.70% * |

TABLE 17-continued

Human sensory performance of test compounds delivered with and without medium intensity (0.15%) 1-octen-3-ol. The column heading for significance of difference in pleasantness rating is abbreviated Pl.

| Test Compound Name (Medium Dilution/ Low Dilution) | IUPAC Name | Pl. | Test Compound Only % Mushroom/ Earthy/Fungal Odor | Pl. | Medium Dilution Test Compound + 1-octen-3-ol % Mushroom/ Earthy/Fungal Odor Remaining | Pl. | Pl. | Low Dilution Test Compound + 1-octen-3-ol % Mushroom/ Earthy/Fungal Odor Remaining | Pl. |
|---|---|---|---|---|---|---|---|---|---|
| 100%/10% | 3-methylcyclopentadecan-1-one | * | 11.60% | * | 75.20% | * | * | 73.60% | * |
| 0.2%/0.02% | 1-[(1~{S},2~{R})-2,6,6-trimethylcyclohex-3-en-1-yl]but-2-en-1-one | * | 24.00% | * | 72.20% | * | * | 73.10% | * |
| 3%/0.5% | (4~{a}~{S},8~{a}~{R})-5,5,8~{a}-trimethyl-3,4,4~{a},6,7,8-hexahydro-1~{H}-naphthalen-2-one | * | 30.80% | * | 62.30% | * | * | 85.40% | NS |
| 1%/0.1% | 2-(2-methylpropyl)quinoline | * | 27.30% | * | 75.00% | * | NS | 88.20% | NS |
| 0.7%/0.07% | 1,1,2,3,3-pentamethyl-2,5,6,7-tetrahydroinden-4-one | *u. | 25.90% | * | 56.00% *u. | * | NS | 77.90% | * |
| 0.7%/0.07% | 2,3,3-trimethyl-2~{H}-inden-1-one | * | 16.50% | * | 57.90% | * | NS | 94.40% | NS |
| 0.08%/0.008% | 3,7-dimethylocta-2,6-dienal | * | 22.30% | * | 65.60% | * | NS | 93.10% | NS |
| 0.03%/0.005% | 1,1-diethoxy-3,7-dimethylocta-2,6-diene | * | 32.80% | NS | 67.60% | * | NS | 80.50% | * |
| 1%/0.2% | 3,6,7-trimethylocta-2,6-dienal | * | 16.40% | * | 68.40% | * | NS | 97.80% | NS |
| 10%/1% | 1-(4,8-dimethyl-12-methylidenecyclododeca-4,8-dien-1-yl)ethanone; 1-(2,6,10-trimethylcyclododeca-1,5,9-trien-1-yl)ethanone; 1-(2,6,10-trimethylcyclododeca-2,5,9-trien-1-yl)ethanone | * | 26.70% | * | 68.50% | * | NS | 88.90% | NS |
| 5%/0.5% | cyclopentadec-4-en-1-one | * | 25.80% | * | 71.20% | * | * | 80.00% | * |
| 0.5%/0.05% | 1$l^{2},2$l^{2},3$l^{2}-trinobelacyclopropane; 3,4,5,6,6-pentamethylhept-3-en-2-one; 3,4,5,6,6-pentamethylhept-4-en-2-one; 3,5,6,6-tetramethyl-4-methylideneheptan-2-one | * | 36.20% | * | 71.30% | * | NS | 83.90% | NS |
| 50%/5% | oxacyclohexadecan-2-one | * | 13.90% | NS | 72.10% | * | NS | 90.70% | NS |
| 0.1%/0.01% | 4-(2,6,6-trimethylcyclohexen-1-yl)but-3-en-2-one; 4-(2,6,6-trimethylcyclohex-2-en-1-yl)but-3-en-2-one | * | 20.30% | * | 73.90% | * | NS | 94.80% | NS |
| 0.5%/0.05% | 2-ethoxy-5-prop-1-enylphenol | * | 23.20% | NS | 79.20% | * | NS | 76.50% | * |
| 50%/2% | 1,4,8-trimethyl-13-oxabicyclo[10.1.0]trideca-4,8-diene; 1,5,8-trimethyl-13-oxabicyclo[10.1.0]trideca-4,8-diene | * | 30.20% | NS | 79.50% | * | NS | 93.80% | NS |
| 50%/5% | 1,4-dioxacyclohexadecane-5,16-dione | * | 14.90% | NS | 80.40% | * | NS | 89.10% | NS |
| 20%/5% | 4-(4,8-dimethylnona-3,7-dienyl)pyridine | NS | 44.40% | NS | 73.60% | * | NS | 89.70% | NS |
| 1%/0.1% | (4-methyl-4-phenylpentan-2-yl) acetate | NS | 52.70% | NS | 77.70% | * | NS | 90.30% | NS |
| 1%/0.2% | ethyl deca-2,4,7-trienoate | NS | 56.50% | NS | 95.50% | NS | NS | 94.50% | NS |
| 1%/0.1% | 4-[(1~{R},3~{R},6~{R})-2,2,3,6-tetramethylcyclohexyl]but-3-en-2-one; 4-[(1~{S},3~{S},6~{R})-2,2,3,6-tetramethylcyclohexyl]but-3-en-2-one | * | 19.90% | * | 83.30% | NS | NS | 103.70% | NS |
| 15%/0.75% | (2,5-dimethyl-1,3-dihydroinden-2-yl)methanol | * | 36.30% | NS | 88.10% | NS | NS | 101.10% | NS |
| 10%/0.4% | (2,2,2-trichloro-1-phenylethyl) acetate | * | 30.00% | NS | 84.60% | * | NS | 89.50% | NS |

* denotes significant difference from 0.15% 1-octen-3-ol at the 95% confidence level.
NS denotes no significant difference.
*u- denotes significantly less pleasant than 0.15% 1-octen-3-ol at 95% confidence level

Example 6: Malodor Reduction Efficacy Test of a Candle Comprising Fragrance Compositions According to the Present Disclosure The air freshener device used in this example is a candle; such devices deliver fragrance by two means. First, fragrances incorporated into the candle will evaporate slowly as it migrates through the wax and onto the surface of the candle. The second means, by far greater, is through the "melt pool". The melt pool is generated while the candle is lit and the flame melts portions of the candle forming a pool at the top. The warm mixture will be expected to deliver fragrance at a greater rate.

The fragrances candles will be prepared by mixing the fragrance compositions with the candle formula indicated in the table below. 100 grams of the wax mixture will be placed in a 3 in. tall, round, glass container with a 3 in. diameter and a wax-coated, felt wick (CD #6, clipped to a 0.5 in. height). For the test sample containing malodor only, a candle without fragrance will be prepared (Candle wax 4625A IGI at 88%).

| Ingredient | Level |
|---|---|
| Candle wax 4625A IGI | 82.5% |
| Microwax 5715A IGI | 2.0% |
| Triple press Stearic acid | 10.0% |
| Fragrance | 5.5% |
| | 100.0% |

Candle Formulation

| Ingredient | Level |
| --- | --- |
| Candle wax 4625A IGI | 88.5% |
| Microwax 5715A IGI | 2.0% |
| Triple press Stearic acid | 10.0% |
|  | 100.0% |

Control Formulation

The sensory cabins will be assessed by 15 untrained but experienced assessors. Data will be analyzed using one-way analysis of variance (ANOVA), followed by Fisher's least significant difference (LSD) method for multiple comparisons ($\alpha=0.05$). The number of assessors (N) and the LSD will be as follows: N=15, LSD=0.70.

Example 7: Malodor Reduction Efficacy Test of an Aerosol Air Fresheners Comprising Fragrance Compositions According to the Present Disclosure The air freshener device used in this example is an aerosol; such devices deliver fragrance into an environment by means of a pressurized aqueous fragrances solution.

The fragrances aerosols will be prepared by mixing fragrance compositions with the aerosol formula indicated in the table below.

| Ingredient | Level |
| --- | --- |
| Deionized Water | 69.25% |
| Sodium Borate | 0.07% |
| Sodium Molybdate | 0.34% |
| Span 80 | 0.25% |
| Dipropylene Glycol | 0.09% |
| Fragrance | 0.3% |
| A-60 Propellant | 29.7% |
|  | 100.0% |

Aerosol Formulation

The sensory cabins will be assessed by 15 untrained but experienced assessors. Data will be analyzed using one-way analysis of variance (ANOVA), followed by Fisher's least significant difference (LSD) method for multiple comparisons ($\alpha=0.05$). The number of assessors (N) and the LSD will be as follows: N=15, LSD=0.70.

Example 8: Malodor Reduction Efficacy Test of a Sachet-Type Freshener Comprising Fragrance Compositions According to the Present Disclosure The air freshener device used in this example is a sachet-type air freshener; such devices utilize a particulate substrate, infused with fragrance contained in a permeable pouch, the pouch being formed from paper, woven fabric or non-woven material.

The fragrances sachets will prepared by mixing the fragrance compositions with ground corn-cob particles (NaturEzorb®-100, origin: Aproa) at 20% loading by weight. 12 grams of the resulting mixtures will then be placed in a 2.5 inch×2.5 inch paper pouch. A sample comprising un-fragrances corn-cob will be prepared for the malodor only cabin.

The sensory cabins will be assessed by 15 untrained but experienced assessors. Data will be analyzed using one-way analysis of variance (ANOVA), followed by Fisher's least significant difference (LSD) method for multiple comparisons ($\alpha=0.05$). The number of assessors (N) and the LSD will be as follows: N=15, LSD=0.70.

Example 9: Malodor Reduction Efficacy Test of a Liquid-Type Freshener Comprising Fragrance Compositions According to the Present Disclosure The air freshener device used in this example is an electric-wick air freshener; such devices utilize a heating element to drive fragrance composition from a wick inserted into a reservoir with the fragrance.

The fragrance compositions will be mixed with equal parts by weight Augeo Clean Multi (Solvay). 20 grams of the resulting mixtures will then be placed in reservoirs with wicks (sintered plastic). The heater units used are designed to heat the wick to 70° C.

The sensory cabins will be assessed by 15 untrained but experienced assessors. Data will be analyzed using one-way analysis of variance (ANOVA), followed by Fisher's least significant difference (LSD) method for multiple comparisons ($\alpha=0.05$). The number of assessors (N) and the LSD will be as follows: N=15, LSD=0.70.

Example 10: Malodor Reduction Efficacy Test of a Bleach Powder Comprising Fragrance Compositions According to the Present Disclosure The malodor reduction of a fragrance composition described by the present disclosure will be measured in a bleach cleaning powder. The bleach cleaning powder is a bleach powder combined with spray-dried fragrance. Standard usage of this product is to apply the powder to the area to be treated and dissolved with water, followed by scrubbing to loosen all particles and then rinsed.

Fragrances bleach samples will be prepared by adding 0.15 grams of spray-dried powder (comprised of 50% w/w perfume, 50% w/w octenyl succinated modified starch) to 9.85 grams of Stable Bleaching Powder (Grade I, Gujarat Alkalies and Chemicals Limited, Gujarat, India).

The malodor reconstitution will be applied onto fine vermiculite (Specialty Vermiculite Corp, Enoree, S.C.) with a 70% loading by weight. 9 grams of the test composition will then presented to assessors in round aluminum tins. The aluminum tins have a 3 in. diameter with a 1 in. height. For the test sample with fragrance only, a tin with untreated vermiculite is used.

A 70% by weight latrine malodor loaded vermiculite was prepared by admixing 350 g of the latrine malodor with 150 g of vermiculite (Fine grade, Specialty Vermiculite Corp, Enoree, S.C.). The efficacy of the cellulose-based air fresheners comprising fragrance formulations according to the present disclosure will be assessed following the practices described in ASTM E 1593-06 "Method for Assessing the Efficacy of Air Care Products in Reducing Sensorialy Perceived Indoor Air Malodor Intensity". A booth labeled "Reference" containing only a malodor tin will be presented to assessors first to familiarize them with the malodor. Using a scale of 1 to 7 (1 signifying no odor, 4 moderate odor and 7 extremely strong malodor), assessors will be then to evaluate each sample in specified order and rate malodor intensity and total odor intensity.

The samples will be assessed by 19 untrained assessors. By "untrained assessors" we mean users of air fresheners who have not received formal olfactive training but who are used to participating in fragrances assessments and have experience in rating the odor attributes.

Using 60 ft³ evaluation rooms, the floors of the cabins will be wet with water and samples will be scrubbed onto the floors until dissolved. The malodor reconstitution will then be added. The environmental conditions during the test will be 72 F, 40% RH with 5 air changes per hour. A portable desk fan, set on low, will be placed at the floor of the cabin to circulate the air within. Booths will be labeled with a randomly generated 3 digit code. Sample presentation will be blind, balanced, randomized and sequential monadic. After 5 minutes from activation, assessors will be directed to open the smelling window to evaluate each sample and wait for 60 seconds before proceeding to answer a series of questions relating to the odor they perceived in the room. The assessors will be asked to rate the malodor strength and total odor intensity. Data will be analyzed using Analysis of Variance (ANOVA) and the difference between two means determined using the least significant difference ($\alpha=0.05$).

Example 11: C50 Values of Compounds Presented Herein for Various Olfactory Receptors The malodor reduction of fragrance composition described by the present disclosure will be measured in a bleach cleaning powder. The bleach cleaning powder is a bleach powder combined with spray-dried fragrance. Standard usage of this product is to apply the powder to the area to be treated and dissolved with water, followed by scrubbing to loosen all particles and then rinsed.

TABLE 18

Antagonists of geonol receptors Olfr339, Olfr1487, Olfr1A1, OR11A1, Olfr96.

| Ingredient | Inhibition(%) | $IC_{50}$ (µM) |
|---|---|---|
| 2-(3-phenylpropyl)pyridine | 196 | 40.964 |
| Galbanum essential oil | 157 | 84.679 |
| methyl 2-[(7-hydroxy-3,7-dimethyloct-1-enyl)amino]benzoate | 103 | 212.951 |
| 4-dodecylsulfanyl-4-(2,6,6-trimethylcyclohexen-1-yl)butan-2-one; 4-dodecylsulfanyl-4-(2,6,6-trimethylcyclohex-2-en-1-yl)butan-2-one | 101 | 70.070 |
| cypriol oil | 90 | 124.647 |
| methyl (10E)-12-oxo-10-dodecenoate | 86 | 109.040 |
| CLEARWOOD ® | 85 | 219.223 |
| [(1~{R},2~{S},4~{S})-1,7,7-trimethyl-2-bicyclo[2.2.1]heptanyl] acetate | 84 | 659.704 |
| (4-methyl-4-phenylpentan-2-yl) acetate | 84 | 627.458 |
| (1~{S},4~{R},9~{S},10~{R},13~{S})-5,5,9,13-tetramethyl-14,16-dioxatetracyclo[11.2.1.0^{1,10}.0^{4,9}]hexadecane; (1~{S},4~{S},9~{R},10~{R},13~{R})-5,5,9,13-tetramethyl-14,16-dioxatetracyclo[11.2.1.0^{1,10}.0^{4,9}]hexadecane | 83 | 184.774 |
| guaiacwood oil | 80 | 48.116 |
| (3~{a}~{R},5~{a}~{R},9~{a}~{S},9~{b}~{R})-3~{a},6,6,9~{a}-tetramethyl-2,4,5,5~{a},7,8,9,9~{b}-octahydro-1~{H}-benzo[e][1]benzofuran | 78 | 27.071 |
| 2,4~{a},8,8-tetramethyl-1~{a},2,4,5,6,7-hexahydro-1~{H}-cyclopropa[j]naphthalen-3-one; 2,6,6,8-tetramethyltricyclo[5.3.1.0^{1,5}]undecan-9-one | 78 | 47.959 |
| Fir balsam essential oil | 78 | 402.887 |
| Davana oil | 75 | 95.458 |
| 1,1,2,3,3-pentamethyl-2,5,6,7-tetrahydroinden-4-one | 71 | 267.625 |
| (4~{a}~{S},8~{a}~{R})-5,5,8~{a}-trimethyl-3,4,4~{a},6,7,8-hexahydro-1~{H}-naphthalen-2-one | 71 | 96.702 |
| (1~{S},3~{S},6~{R},7~{R},8~{S})-2,2,6,8-tetramethyltricyclo[5.3.1.0^{3,8}]undecan-3-ol | 68 | 34.893 |
| 1-(2,6,6-trimethylcyclohexen-1-yl)hepta-1,6-dien-3-one; 1-(2,6,6-trimethylcyclohex-2-en-1-yl)hepta-1,6-dien-3-one | 66 | 49.094 |
| 1$l^{2},2$l^{2},3$l^{2}-trinobelacyclopropane; 3,4,5,6,6-pentamethylhept-3-en-2-one; 3,4,5,6,6-pentamethylhept-4-en-2-one; 3,5,6,6-tetramethyl-4-methylideneheptan-2-one | 64 | 1000.000 |
| 1-(2,3,8,8-tetramethyl-1,3,4,6,7,8~{a}-hexahydronaphthalen-2-yl)ethanone; 1-(2,3,8,8-tetramethyl-1,3,5,6,7,8~{a}-hexahydronaphthalen-2-yl)ethanone; 1-(2,3,8,8-tetramethyl-1,3,4,5,6,7-hexahydronaphthalen-2-yl)ethanone | 64 | 65.144 |
| Calamus oil | 64 | 80.940 |
| 2-(1-propoxyethoxy)ethylbenzene | 61 | 190.412 |
| 4-(1-ethoxyethenyl)-3,3,5,5-tetramethylcyclohexan-1-one; 1-ethoxy-4-(1-ethoxyethenyl)-3,3,5,5-tetramethylcyclohexene | 61 | 156.518 |
| Miel de Provence | 58 | 18.018 |
| (E)-3-methyl-4-(2,6,6-trimethyl-1-cyclohex-2-enyl)but-3-en-2-one | 58 | 1115.858 |
| 3-methyl-4-(2,6,6-trimethylcyclohex-2-en-1-yl)but-3-en-2-one | 58 | 109.992 |
| [(1~{S},2~{R})-2-~{tert}-butylcyclohexyl] acetate | 56 | 164.321 |
| 4,6,6,7,8,8-hexamethyl-1,3,4,7-tetrahydrocyclopenta[g]isochromene | 56 | 894.367 |

TABLE 18-continued

Antagonists of geonol receptors Olfr339, Olfr1487, Olfr1A1, OR11A1, Olfr96.

| Ingredient | Inhibition(%) | IC$_{50}$ (µM) |
|---|---|---|
| (2-methyl-1-phenylpropan-2-yl) acetate | 54 | 385.955 |
| 2-(1-ethoxyethoxy)ethylbenzene; 2-[1-(2-phenylethoxy)ethoxy]ethylbenzene | 53 | 140.424 |
| 2-methylbutyl 2-phenylacetate; 3-methylbutyl 2-phenylacetate | 52 | 445.900 |
| DYNAMOME ® | 52 | 17.442 |
| 4-(2,6,6-trimethylcyclohexen-1-yl)but-3-en-2-one | 51 | 289.265 |
| 1-(2,2-dimethyl-6-methylidenecyclohexyl)pent-1-en-3-one; 3-methyl-4-(2,6,6-trimethylcyclohex-2-en-1-yl)but-3-en-2-one; 1-(2,6,6-trimethylcyclohexen-1-yl)pent-1-en-3-one; 1-(2,6,6-trimethylcyclohex-2-en-1-yl)pent-1-en-3-one | 49 | 135.811 |
| (2~{R},5~{S})-10-ethyl-2,6,6-trimethyl-1-oxaspiro[4.5]deca-3,9-diene | 47 | 127.325 |
| 1-indol-1-yl-3,7-dimethyloctane-1,7-diol | 46 | 201.009 |
| 2-methylpropyl 2-phenylacetate | 45 | 140.762 |
| 3,4'-dimethylspiro[oxirane-2,9'-tricyclo[6.2.1.0^{2,7}]undec-4-ene] | 45 | 281.423 |
| benzyl 3-methylbutanoate | 41 | 219.645 |
| dec-2-enal | 40 | 262.094 |
| 1-(5,5-dimethylcyclohexen-1-yl)pent-4-en-1-one | 40 | 219.685 |
| (5~{S},6~{R})-2,6,10,10-tetramethyl-1-oxaspiro[4.5]decan-6-ol | 40 | 172.532 |
| [(5~{S},6~{S},11~{R})-3,5,10,10-tetramethylspiro[5.5]undec-2-en-11-yl] acetate | 38 | 267.356 |
| 3-methyl-5-phenylpentan-1-ol | 37 | 1101.715 |
| 4-(2,6,6-trimethylcyclohexen-1-yl)butan-2-one | 36 | 117.579 |
| 4-methyl-1-phenylpentan-2-ol | 36 | 517.147 |
| 2,2-dimethyl-3-methylidenebicyclo[2.2.1]heptane | 36 | 218.700 |
| 2-ethyl-4-(2,2,3-trimethylcyclopent-3-en-1-yl)but-2-en-1-ol | 35 | 172.707 |
| 1-(2,6,6-trimethylcyclohexa-1,3-dien-1-yl)but-2-en-1-one | 35 | 129.443 |
| (1~{a}~{R},4~{a}~{S},7~{S},8~{a}~{R})-4,4,7-trimethyl-2,3,4~{a},5,6,8-hexahydro-1~{a}~{H}-naphtho[1,8~{a}-b]oxiren-7-ol; 4-[(1~{R},2~{R},6~{R})-1,3,3-trimethyl-7-oxabicyclo [4.1.0]heptan-2-yl]butan-2-one; 3,7,7-trimethyl-11-oxatricyclo [4.4.1.0^{1,6}]undecan-3-ol | 35 | 242.056 |
| [1-methyl-2-[[(1~{S},3~{S},5~{R})-1,2,2-trimethyl-3-bicyclo[3.1.0]hexanyl]methyl]cyclopropyl] methanol | 34 | 21.307 |
| oxacyclohexadecan-2-one | 34 | 290.791 |
| 1,4-dioxacyclohexadecane-5,16-dione | 33 | 135.748 |
| (2~{S})-2-methyl-4-[(1~{R})-2,2,3-trimethylcyclopent-3-en-1-yl]pent-4-en-1-ol | 33 | 36.632 |
| (1~{R},2~{S})-2-pentylcyclopentan-1-ol | 33 | 146.950 |
| 3-methyl-5-(2,2,3-trimethylcyclopent-3-en-1-yl)pent-4-en-2-ol | 33 | 76.004 |
| (2~{R})-2,4,10,10-tetramethylspiro[5.5]undec-3-en-11-one; (5~{S})-3,5,10,10-tetramethylspiro[5.5]undec-3-en-11-one | 33 | 64.062 |
| diethyl benzene-1,2-dicarboxylate | 32 | 1578.385 |
| 3-methyl-5-(2,2,3-trimethylcyclopent-3-en-1-yl)pentan-2-ol | 32 | 28.839 |
| 2-(3,8-dimethyl-1,2,3,3~{a},4,5,6,7-octahydroazulen-5-yl)propan-2-yl acetate;2-(3,8-dimethyl-1,2,3,4,5,6,7,8-octahydroazulen-5-yl)propan-2-yl acetate | 31 | 158.245 |
| 6-heptyloxan-2-one | 29 | 196.621 |
| 3-(5,5,6-trimethyl-2-bicyclo[2.2.1]heptanyl)cyclohexan-1-ol | 29 | 100.485 |
| ANIMALIS BM | 28 | 32.090 |
| (1~{S},2~{R},3~{R},5~{R})-2,6,6-trimethylspiro[bicyclo[3.1.1]heptane-3,4'-cyclohex-2-ene]-1'-one | 27 | 42.437 |
| 2-(3-methylbutoxy)ethylbenzene | 22 | 126.047 |
| 1,4-dioxacycloheptadecane-5,17-dione | 21 | 31.747 |
| 3-acetyloxynonyl acetate; (3-pentyloxan-4-yl) acetate | 20 | 295.320 |
| 2-ethyl-4-[1~{S})-2,2,3-trimethylcyclopent-3-en-1-yl]but-2-en-1-ol | 19 | 44.571 |
| myrrh resinoid | 19 | 213.416 |
| (1~{R},2~{S})-2-pentylcyclopentan-1-ol | 16 | 194.708 |

TABLE 19

Antagonists of 1-octen-3-ol receptors OR2W1, Olfr93, Olfr120, Olfr398.

| | Inhibition(%) | IC$_{50}$ (μM) |
|---|---|---|
| 2-[(8~{S},8~{a}~{S})-8,8~{a}-dimethyl-1,3,4,6,7,8-hexahydronaphthalen-2-ylidene]propyl acetate; [(1~{S},2~{S},5~{S},8~{R})-7,7-dimethyl-6-methylidene-2-tricyclo[6.2.1.0^{1,5}]undecanyl]methyl acetate | 353 | 58.114 |
| 2,5,5-trimethyl-1,3,4,4~{a},6,7-hexahydronaphthalen-2-ol; 2,5,5-trimethyl-3,4,4~{a},6,7,8-hexahydronaphthalen-2-ol; 2,5,5-trimethyl-1,3,4,6,7,8-hexahydronaphthalen-2-ol | 207 | 390.565 |
| cyclopentadec-4-en-1-one | 130 | 57.837 |
| (1~{S},4~{R},9~{S},10~{R},13~{S})-5,5,9,13-tetramethyl-14,16-dioxatetracyclo[11.2.1.0^{1,10}.0^{4,9}]hexadecane; (1~{S},4~{S},9~{R},10~{R},13~{R})-5,5,9,13-tetramethyl-14,16-dioxatetracyclo[11.2.1.0^{1,10}.0^{4,9}]hexadecane | 127 | 91.124 |
| (4-methyl-4-phenylpentan-2-yl) acetate | 119 | 61.999 |
| (3~{a}~{R},5~{a}~{R},9~{a}~{S},9~{b}~{R})-3~{a},6,6,9~{a}-tetramethyl-2,4,5,5~{a},7,8,9,9~{b}-octahydro-1~{H}-benzo[e][1]benzofuran | 105 | 101.246 |
| 1-(4-{tert}-butyl-2,6-dimethyl-3,5-dinitrophenyl)ethanone | 98 | 84.746 |
| [(1~{R},2~{S},5~{R},8~{S})-7,7-dimethyl-6-methylidene-2-tricyclo[6.2.1.0^{1,5}]undecanyl]methanol; 1$l^{2},2$l^{2},3$l^{2}-trinobelacyclopropane | 97 | 40.614 |
| Vetiver essential oil | 92 | 83.113 |
| 2,6,6,8-tetramethyl-9-oxatetracyclo[5.4.1.0^{1,5}.0^{8,10}]]dodecane | 91 | 85.571 |
| 3,7-dimethylocta-1,6-dien-3-yl 2-methylpropanoate | 88 | 57.139 |
| (1~{S},2~{R},3~{R},5~{R})-2,6,6-trimethylspiro[bicyclo[3.1.1]heptane-3,4'-cyclohex-2-ene]-1'-one | 87 | 12.490 |
| 4-[(1~{R},5~{S})-2,5,6,6-tetramethylcyclohex-2-en-1-yl]but-3-en-2-one; 4-[(1~{S},5~{S})-2,5,6,6-tetramethylcyclohex-2-en-1-yl]but-3-en-2-one; 4-(2,5,6,6-tetramethylcyclohexen-1-yl)but-3-en-2-one | 86 | 100.399 |
| 4,6,6,7,8,8-hexamethyl-1,3,4,7-tetrahydrocyclopenta[g]isochromene | 84 | 65.214 |
| CLEARWOOD ® | 82 | 100.242 |
| 4-(1-ethoxyethenyl)-3,3,5,5-tetramethylcyclohexan-1-one; 1-ethoxy-4-(1-ethoxyethenyl)-3,3,5,5-tetramethylcyclohexene | 81 | 106.077 |
| (4-{tert}-butylcyclohexyl) acetate | 79 | 93.846 |
| (3~{R})-3-methylcyclopentadec-5-en-1-one | 79 | 23.424 |
| (+−)-(3E)-4-(2,6,6-trimethyl-2-cyclohexen-1-yl)-3-buten-2-one | 79 | 461.612 |
| 4-(2,6,6-trimethylcyclohexen-1-yl)but-3-en-2-one; 4-(2,6,6-trimethylcyclohex-2-en-1-yl)but-3-en-2-one | 79 | 145.754 |
| Pine extract | 77 | 383.830 |
| guaiacwood oil | 77 | 26.913 |
| 4,5,6,7,8,9,10,11,12,13-decahydrocyclododeca[d][1,3]oxazole | 77 | 38.004 |
| 3-methylcyclopentadec-4-en-1-one; 3-methylcyclopentadec-5-en-1-one | 74 | 47.773 |
| 1-(2,6,6-trimethylcyclohexen-1-yl)but-2-en-1-one | 72 | 476.830 |
| (1~{S},3~{S},6~{R},7~{R},8~{S})-2,2,6,8-tetramethyltricyclo[5.3.1.0^{3,8}]undecan-3-ol | 70 | 80.993 |
| 3,5-diethyl-2,5-dimethylcyclohex-2-en-1-one; 3,5-diethyl-5,6-dimethylcyclohex-2-en-1-one | 67 | 193.734 |
| 4-(2,6,6-trimethylcyclohexen-1-yl)but-3-en-2-one | 66 | 268.660 |
| (6~{R},7~{R})-3,5,5,6,7,8,8-heptamethyl-6,7-dihydronaphthalene-2-carbaldehyde | 64 | 83.732 |
| Cedarwood oil | 63 | 159.480 |
| 1-(2,2-dimethyl-6-methylidenecyclohexyl)pent-1-en-3-one; 3-methyl-4-(2,6,6-trimethylcyclohex-2-en-1-yl)but-3-en-2-one; 1-(2,6,6-trimethylcyclohexen-1-yl)pent-1-en-3-one; 1-(2,6,6-trimethylcyclohex-2-en-1-yl)pent-1-en-3-one | 56 | 66.763 |
| Iris extract | 54 | 129.707 |
| (2,6,6,8-tetramethyl-8-tricyclo[5.3.1.0^{1,5}]undecanyl) acetate | 52 | 72.592 |
| 1-(2,6,6-trimethylcyclohexen-1-yl)hepta-1,6-dien-3-one; 1-(2,6,6-trimethylcyclohex-2-en-1-yl)hepta-1,6-dien-3-one | 49 | 35.930 |
| 1-indol-1-yl-3,7-dimethyloctane-1,7-diol | 46 | 175.126 |
| 4-(2,6,6-trimethylcyclohexen-1-yl)butan-2-one | 40 | 149.068 |
| (4R,4aS,6R)-4,4a-dimethyl-6-prop-1-en-2-yl-3,4,5,6,7,8-hexahydronaphthalen-2-one | 39 | 36.465 |
| 1,4-dioxacycloheptadecane-5,17-dione | 38 | 39.303 |
| 3-methyl-4-(2,6,6-trimethylcyclohex-2-en-1-yl)but-3-en-2-one | 37 | 120.418 |
| 2-(3-phenylpropyl)pyridine | 31 | 152.647 |
| (2~{S})-2-methyl-4-[(1~{R})-2,2,3-trimethylcyclopent-3-en-1-yl]pent-4-en-1-ol | 27 | 54.577 |
| 3-(2,2-dimethylpropyl)pyridine | 25 | 117.485 |
| Tuberose Fleur | 24 | 181.942 |

TABLE 19-continued

Antagonists of 1-octen-3-ol receptors OR2W1, Olfr93, Olfr120, Olfr398.

|  | Inhibition(%) | IC$_{50}$ (μM) |
|---|---|---|
| 4-(2,5,6,6-tetramethylcyclohexen-1-yl)but-3-en-2-one | 23 | 72.693 |
| 3,7-dimethylocta-2,6-dien-1-ol | 18 | 190.480 |
| 1-(2-{tert}-butylcyclohexyl)oxybutan-2-ol | 13 | 53.585 |
| (4E,8E)-4,8-cyclododecadien-1-one (A) + (4E,8Z)-4,8-cyclododecadien-1-one (B) + (4Z,8E)-4,8-cyclododecadien-1-one (C) |  | 195.571 |

TABLE 20

Spiro analogue antagonists of butyric acid receptor OR51E1

| IUPAC Name | IC50 | Inhibition (%) | Sensory Performance (%) |
|---|---|---|---|
| (2,3,9,9-tetramethylspiro[4.5]dec-2-en-10-yl) acetate | >600 | 116 | 40% |
| (1,5,10,10-tetramethylspiro[5.5]undec-3-en-11-yl) acetate | 72.33 | 72 | 43% |
| (2,3,9,9-tetramethylspiro[4.5]decan-10-yl) acetate | 51.40 | 62 | 50% |
| (5,10,10-trimethylspiro[5.5]undec-2-en-11-yl) formate | 44.37 | 129 |  |
| (3,5,10,10-tetramethylspiro[5.5]undec-2-en-11-yl) acetate | 71.39 | 104 |  |
| (9,9-dimethylspiro[4.5]dec-2-en-10-yl) acetate | 90.30 | 32 |  |
| 10-methoxy-9,9-dimethylspiro[4.5]dec-2-ene | 119.54 | 33 |  |
| 4,10,10,11-tetramethylspiro[5.5]undec-2-en-11-ol; 5,10,10,11-tetramethylspiro[5.5]undec-3-en-11-ol | 47.23 | 94 |  |
| 2,4,8-trimethylspiro[5.5]undec-3-en-11-ol; 2,9,11-trimethylspiro[5.5]undec-9-en-5-ol | 117.03 | 70 |  |
| 3-methyl-5-propan-2-ylspiro[5.5]undec-2-en-11-ol | 366.37 | 144 |  |
| 11-methylspiro[5.5]undecan-5-ol | 68.82 | 52 |  |
| 3,10,10-trimethylspiro[5.5]undec-3-en-11-ol; 4,10,10-trimethylspiro[5.5]undec-3-en-11-ol | >600 | 121 |  |
| [2,2-dimethyl-1-(2,4,6-trimethylcyclohex-3-en-1-yl)propyl] acetate | 52.56 | 89 |  |
| [2,2-dimethyl-1-(2,4,6-trimethylcyclohexyl)propyl] acetate | 241.99 | 101 |  |
| [(1~{R})-2,2-dimethyl-1-[(1~{S},2~{S})-2-methylcyclohexyl]propyl] acetate | 169.82 | 86 |  |
| 2,3,9,9-tetramethylspiro[4.5]dec-2-en-10-ol | 78.69 | 16 | 60% |
| 2,3,9,9-tetramethylspiro[4.5]dec-2-en-10-one |  |  | 56% |
| 2,2-dimethyl-6,6-bis(2-methylprop-2-enyl)cyclohexan-1-one | 46.59 | 103 | 50% |
| (2,3,9,9-tetramethylspiro[4.5]dec-2-en-10-yl) formate | 25.90 | 69 |  |
| (2,4,9,9-tetramethylspiro[4.5]dec-2-en-10-yl) acetate | 34.79 | 131 |  |
| 2,2-dimethyl-5,5-bis(2-methylprop-2-enyl)cyclopentan-1-ol | 35.11 | 119 |  |
| 9,9-dimethylspiro[4.5]dec-2-en-10-ol | 44.06 | 91 |  |
| (4,9,9-trimethylspiro[4.5]dec-2-en-10-yl) acetate | 48.52 | 106 |  |
| 2,2-dimethyl-5,5-bis(2-methylprop-2-enyl)cyclopentan-1-one | 51.71 | 82 |  |
| 1,1',1',5-tetramethyl-2'-methylidenespiro[6-oxabicyclo[3.1.0]hexane-3,3'-cyclohexane] | 75.67 | 37 |  |
| 2-but-3-en-2-yl-6,6-dimethyl-2-prop-2-enylcyclohexan-1-one | 76.42 | 115 |  |
| (4~{S},5~{R},6~{S},11~{S})-4,11-dimethylspiro[5.5]undecan-5-ol | 76.93 | 54 |  |
| 2,4,9,9-tetramethylspiro[4.5]dec-2-en-10-ol | 81.58 | 22 |  |
| 2,2-dimethyl-1-(2-methylcyclohexyl)propan-1-ol; 2,2-dimethyl-1-(3-methylcyclohexyl)propan-1-ol | 83.27 | 17 |  |
| 1-methoxy-2,6-dimethyl-1-prop-2-enylcyclohexane | 100.21 | 61 |  |
| 2,4,9,9-tetramethylspiro[4.5]dec-2-en-10-one | 109.82 | 63 |  |
| 2,3,9,9-tetramethylspiro[4.5]decan-10-ol | 119.78 | 12 |  |
| 2,2-dimethyl-6,6-bis(2-methylprop-2-enyl)cyclohexan-1-ol | 124.71 | 110 |  |
| 9,9-dimethylspiro[4.5]dec-2-en-10-one | 135.02 | 23 |  |

TABLE 20-continued

Spiro analogue antagonists of butyric acid receptor OR51E1

| IUPAC Name | IC50 | Inhibition (%) | Sensory Performance (%) |
|---|---|---|---|
| 2,3,8,8-tetramethylspiro[4.4]non-2-en-9-one | 198.38 | 10 | |
| 9-methoxy-8,8-dimethylspiro[4.4]non-2-ene | 237.96 | 100 | |
| 4,9,9-trimethylspiro[4.5]dec-2-en-10-one | 267.67 | 102 | |
| 1-(2,6-dimethylcyclohex-3-en-1-yl)-2,2-dimethylpropan-1-ol | 321.14 | 31 | |
| 4-methoxy-3,3-dimethylspiro[4.4]nonane | 337.13 | 105 | |
| (2,2,3,3,9,9-hexamethylspiro[4.5]decan-10-yl) acetate | 424.91 | 39 | |
| (8,8-dimethylspiro[4.4]non-2-en-9-yl) acetate | 488.31 | 107 | |
| methyl 1-(3-methylbut-2-enyl)cyclohex-2-ene-1-carboxylate; methyl 1-(3-methylbut-2-enyl)cyclohex-3-ene-1-carboxylate | 576.63 | 38 | |

TABLE 21

Antagonists of butyric acid receptor OR51E1

| IUPAC Name | IC50 | Inhibition (%) |
|---|---|---|
| 1-(2-methyl-4-tricyclo[5.2.1.0^{1,5}]decanyl)ethyl acetate | 97.01 | 23 |
| 1-(2,4-dimethyl-4-tricyclo[5.2.1.0^{1,5}]decanyl)ethyl acetate | 54.79 | 34 |
| 1-[(1~{S},2~{S},4~{S},7~{R})-2,3,4-trimethyl-4-tricyclo[5.2.1.0^{1,5}]decanyl]ethanone | 32.58 | 27 |
| 1-(2,4-dimethyl-4-tricyclo[5.2.1.0^{1,5}]decanyl)ethanone | 60.53 | 26 |
| 2,3,4-trimethyltricyclo[5.2.1.0^{1,5}]decane-4-carbaldehyde | 269.71 | 28 |
| (2,3,4-trimethyl-4-tricyclo[5.2.1.0^{1,5}]decanyl)methyl acetate | 60.80 | 27 |
| ~{N}-[[(1~{S},7~{R})-2,4-dimethyl-4-tricyclo[5.2.1.0^{1,5}]]decanyl]methylidene]hydroxylamine | 88.55 | 38 |
| ~{N}-[1-[(1~{R},7~{R})-2,3,4-trimethyl-4-tricyclo[5.2.1.0^{1,5}]decanyl]ethylidene]hydroxylamine | 79.71 | 81 |
| ~{N}-[1-[(1~{S},7~{R})-2,3-dimethyl-4-tricyclo[5.2.1.0^{1,5}]decanyl]ethylidene]hydroxylamine | 76.58 | 19 |

Example 12: Identification of Antagonists of an Indole/Skatole Olfactory Receptor Functional dose-response experiments were performed to identify compounds capable of antagonizing indole-sensitive receptors previously identified (U.S. Pat. No. 9,914,760 B2). Using a cell-based assay, mouse receptor Olfr738, Olfr739, Olfr740, Olfr741, Olfr742, Olfr743, Olfr744, Olfr746, Olfr748 and Olfr749 were tested in an HEK293T cell line wherein the endogenous RTP1 gene has been activated and the odorant receptor chaperone was expressed (described in WO2016201153A1). The receptor genes were tagged with a Flag-Rho tag combination. Receptor genes were co-transfected with the canonical olfactory human G-protein alpha subunit $G_{olf}$ gene. Co-expression of the human $G_{olf}$ activates the Gs transduction pathway that leads to an internal cAMP increase upon binding to the appropriate ligand (indole here). Odorant-induced activity was detected by measuring the cAMP increase in the cytosol using an HTRF based kit (CisBio, cAMP dynamic 2 kit, cat. 62AM4PEJ). The receptors were exposed to binary mixtures of increasing concentrations of the test compounds in the presence of a potent activation concentration of indole ($EC_{80}$) for each receptor. This generates a dose-dependent inhibition curve that can be characterized by $IC_{50}$ (the inhibitor concentration at which the receptor indole activity is inhibited by the half-maximal inhibition efficacy level) and % maximum inhibition (normalized to baseline indole $EC_{80}$ activity). The following tables summarize $IC_{50}$ and % inhibition for these compounds across all receptors (Table 22 and 23). All the compounds listed decreased the indole induced activity of at least one receptor. Representative dose-dependent inhibition curves are shown in FIGS. 6 to 9.

TABLE 22

| | Olfr738 | | Olfr739 | | Olfr740 | | Olfr741 | | Olfr742 | |
|---|---|---|---|---|---|---|---|---|---|---|
| Compound Name | IC50 | % Inhibition | IC50 | % Inhibition | IC50 | % Inhibition | IC50 | % Inhibition | IC50 | % Inhibition |
| (+−)-perhydro-5,5,8A-trimethyl-2-trans-naphthalenone | 2.74E−06 | 101.72 | 1.39E−05 | 68.44 | 1.96E−06 | 126.58 | 1.48E−04 | 96.86 | — | — |
| 1-(3,3-dimethylcyclohexen-1-yl)pent-4-en-1-one; 1-(5,5-dimethylcyclohexen-1-yl)pent-4-en-1-one | 6.29E−06 | 33.49 | 9.30E−06 | 64.23 | 1.68E−06 | 179.31 | 1.31E−04 | 124.57 | 4.30E−06 | 146.91 |

TABLE 22-continued

| Compound Name | Olfr738 IC50 | Olfr738 % Inhibition | Olfr739 IC50 | Olfr739 % Inhibition | Olfr740 IC50 | Olfr740 % Inhibition | Olfr741 IC50 | Olfr741 % Inhibition | Olfr742 IC50 | Olfr742 % Inhibition |
|---|---|---|---|---|---|---|---|---|---|---|
| 3-(4-hydroxy-4-methylpentyl)cyclohex-3-ene-1-carbaldehyde; 4-(4-hydroxy-4-methylpentyl)cyclohex-3-ene-1-carbaldehyde | 1.66E−04 | 14.67 | — | — | 1.85E−04 | 72.15 | — | — | 1.82E−04 | 41.42 |
| Amyl Phenylacetate | 8.27E−05 | 18.44 | — | — | 4.04E−05 | 61.04 | — | — | 1.41E−04 | 18.04 |
| 4-(2,6,6-trimethylcyclohexen-1-yl)but-3-en-2-one; 4-(2,6,6-trimethylcyclohex-2-en-1-yl)but-3-en-2-one | 2.62E−05 | 42.85 | 9.76E−05 | 3.23 | 1.87E−05 | 198.93 | 1.39E−04 | 150.11 | 1.00E−04 | 115.13 |
| 1,1,2,3,3-pentamethyl-2,5,6,7-tetrahydroinden-4-one | 2.13E−05 | 61.33 | — | — | 1.20E−05 | 217.11 | 2.56E−03 | 140.61 | 2.49E−04 | 119.64 |
| 4-t-butylcyclohexanone | 4.31E−05 | 52.44 | 6.99E−05 | 60.32 | 1.06E−05 | 213.12 | — | — | — | — |
| 3-phenylbutanal | — | — | — | — | — | — | — | — | 4.48E−05 | 113.30 |
| 2,4-dimethyl-4-phenyloxolane | — | — | — | — | 5.12E−05 | 100.25 | — | — | — | — |
| 1-(5,5-dimethylcyclohexen-1-yl)pent-4-en-1-one | — | — | — | — | 6.36E−05 | 91.15 | — | — | — | — |
| [1R-(1R*,4R*,6R*,10S*)]-4,12,12-trimethyl-9-methylene-5-oxatricyclo[8.2.0.04,6]dodecane | 1.81E−05 | 54.69 | 1.95E−05 | 102.21 | 1.34E−05 | 202.56 | 1.08E−04 | 59.56 | 9.91E−05 | 62.98 |
| 2-methyl-3-(4-methylphenyl) propanal | — | — | — | — | — | — | — | — | 8.82E−05 | 37.16 |
| 3-methyl-5-phenylpentanal | — | — | — | — | 1.61E−05 | 109.90 | — | — | — | — |
| Isopropyl Quinoline | 1.20E−04 | 20.66 | 6.13E−05 | 74.96 | 4.09E−05 | 148.06 | 9.16E−05 | 54.55 | 8.66E−05 | 72.34 |
| (+−)-(2E)-1-(2,6,6-trimethyl-2-cyclohexen-1-yl)-2-buten-1-one | 9.98E−05 | 12.19 | — | — | 1.37E−04 | 115.38 | 1.10E−04 | 75.65 | 9.54E−05 | 112.77 |
| 4-(2,6,6-trimethylcyclohexen-1-yl)but-3-en-2-one; 4-(2,6,6-trimethylcyclohex-2-en-1-yl)but-3-en-2-one | 4.33E−05 | 38.30 | 1.73E−04 | 68.34 | 2.09E−05 | 191.17 | 1.09E−04 | 171.50 | 1.01E−04 | 98.74 |
| 4,5,6,7,8,9,10,11,12,13-decahydrocyclododeca[d][1,3]oxazole | 9.26E−06 | 93.54 | 2.41E−05 | 61.91 | 5.52E−06 | 101.99 | 3.37E−05 | 62.10 | 2.68E−05 | 59.71 |

TABLE 23

| Compound Name | Olfr743 IC50 | Olfr743 % Inhibition | Olfr744 IC50 | Olfr744 % Inhibition | Olfr746 IC50 | Olfr746 % Inhibition | Olfr748 IC50 | Olfr748 % Inhibition | Olfr749 IC50 | Olfr749 % Inhibition |
|---|---|---|---|---|---|---|---|---|---|---|
| (+−)-perhydro-5,5,8A-trimethyl-2-trans-naphthalenone | 2.64E−04 | 123.10 | 7.47E−05 | 107.89 | 3.08E−04 | 81.36 | 1.06E−04 | 65.60 | 4.15E−05 | 96.98 |
| 1-(3,3-dimethylcyclohexen-1-yl)pent-4-en-1-one; 1-(5,5-dimethylcyclohexen-1-yl)pent-4-en-1-one | 2.10E−04 | 59.11 | 1.57E−04 | 44.92 | 8.94E−05 | 94.28 | 8.16E−05 | 66.47 | 4.62E−05 | 90.61 |
| 3-(4-hydroxy-4-methylpentyl)cyclohex-3-ene-1-carbaldehyde; 4-(4-hydroxy-4-methylpentyl)cyclohex-3-ene-1-carbaldehyde | — | — | — | — | 3.73E−04 | 43.95 | 2.13E−04 | 48.14 | 2.33E−04 | 62.05 |
| Amyl Phenylacetate | — | — | — | — | — | — | — | — | — | — |
| 4-(2,6,6-trimethylcyclohexen-1-yl)but-3-en-2-one; 4-(2,6,6-trimethylcyclohex-2-en-1-yl)but-3-en-2-one | 2.75E−04 | 114.78 | 1.25E−04 | 78.23 | — | — | — | — | 7.58E−05 | 127.38 |
| 1,1,2,3,3-pentamethyl-2,5,6,7-tetrahydroinden-4-one | — | — | — | — | — | — | — | — | — | — |
| 4-t-butylcyclohexanone | — | — | 1.75E−04 | 148.19 | — | — | — | — | — | — |
| 3-phenylbutanal | — | — | — | — | — | — | — | — | — | — |
| 2,4-dimethyl-4-phenyloxolane | — | — | — | — | — | — | — | — | — | — |
| 1-(5,5-dimethylcyclohexen-1-yl)pent-4-en-1-one | — | — | — | — | 2.24E−04 | 58.87 | — | — | — | — |
| [1R-(1R*,4R*,6R*,10S*)]-4,12,12-trimethyl-9-methylene-5-oxatricyclo[8.2.0.04,6]dodecane | 1.92E−04 | 38.36 | 1.13E−04 | 55.20 | 8.59E−05 | 13.17 | 1.21E−04 | 9.24 | 6.13E−05 | 91.71 |
| 2-methyl-3-(4-methylphenyl) propanal | — | — | — | — | — | — | — | — | — | — |
| 3-methyl-5-phenylpentanal | — | — | — | — | — | — | — | — | — | — |
| Isopropyl Quinoline | 1.19E−04 | 39.62 | 1.02E−04 | 116.59 | — | — | — | — | — | — |
| (+−)-(2E)-1-(2,6,6-trimethyl-2-cyclohexen-1-yl)-2-buten-1-one | — | — | — | — | — | — | — | — | 1.56E−04 | 47.86 |

TABLE 23-continued

| Compound Name | Olfr743 IC50 | Olfr743 % Inhibition | Olfr744 IC50 | Olfr744 % Inhibition | Olfr746 IC50 | Olfr746 % Inhibition | Olfr748 IC50 | Olfr748 % Inhibition | Olfr749 IC50 | Olfr749 % Inhibition |
|---|---|---|---|---|---|---|---|---|---|---|
| 4-(2,6,6-trimethylcyclohexen-1-yl)but-3-en-2-one; 4-(2,6,6-trimethylcyclohex-2-en-1-yl)but-3-en-2-one | 1.59E−04 | 112.64 | 1.59E−04 | 77.99 | — | — | — | — | 7.60E−05 | 51.48 |
| 4,5,6,7,8,9,10,11,12,13-decahydrocyclododeca[d][1,3]oxazole | 5.89E−05 | 31.68 | 1.17E−04 | 38.37 | — | — | 2.16E−04 | 12.61 | 7.00E−05 | 57.85 |

Publications cited throughout this document are hereby incorporated by reference in their entirety. Although the various aspects of the invention have been illustrated above by reference to examples and preferred aspects, it will be appreciated that the scope of the invention is defined not by the foregoing description but by the following claims properly construed under principles of patent law.

The invention claimed is:

1. A method to inhibit, reduce, or suppress the perception of a malodor in a subject, comprising contacting the subject with at least one compound having the structure:

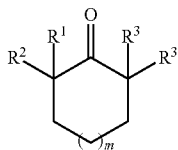

Formula (III)

in a form of any one of the stereoisomers or as a mixture thereof,
wherein the index m represents 0 or 1;
wherein $R^1$ and $R^2$ represent, independently from each other, a hydrogen atom or a methyl group;
wherein each $R^3$ represent, independently from each other, a hydrogen atom or a $C_{1-4}$ alkyl or alkenyl group,
wherein the at least one compound is contacted in an amount sufficient to inhibit, reduce, or suppress the subject's perception of the malodor.

2. The method of claim 1, wherein the contacting inhibits at least one olfactory receptor in the subject.

3. A method to inhibit at least one olfactory receptor in a subject, comprising contacting the subject with at least one compound having the structure:

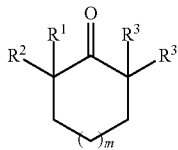

Formula (III)

in a form of any one of the stereoisomers or as a mixture thereof,
wherein the index m represents 0 or 1;
wherein $R^1$ and $R^2$ represent, independently from each other, a hydrogen atom or a methyl group;
wherein each $R^3$ represent, independently from each other, a hydrogen atom or a Ci-4 alkyl or alkenyl group,
wherein the at least one olfactory receptor is a butyric acid olfactory receptor, and
wherein the at least one compound is contacted in an amount sufficient to inhibit the at least one olfactory receptor.

4. The method of claim 2, wherein the inhibition of the at least one olfactory receptor inhibits, reduces, suppresses, the perception of a malodor in a subject.

5. The method of claim 1, wherein the malodor is selected from the group consisting of: latrine malodor, laundry malodor, moldy malodor, and sweat malodor.

6. The method of claim 2, wherein the at least one olfactory receptor is a butyric acid olfactory receptor.

7. The method of claim 6, wherein the butyric acid olfactory receptor is selected from the group consisting of: the OR51E1 olfactory receptor and the Olfr558 olfactory receptor.

8. The method of claim 6, wherein the at least one compound that inhibits the butyric acid olfactory receptor is selected from the group consisting of: 2,2-dimethyl-6,6-bis(2-methylprop-2-enyl)cyclohexan-1-one, 2,2-dimethyl-5,5-bis(2-methylprop-2-enyl)cyclopentan-1-one, 2-but-3-en-2-yl-6,6-dimethyl-2-prop-2-enylcyclohexan-1-one, a mixture of 2,2-dimethyl-5,5-bis(2-methylprop-2-enyl)cyclopentan-1-one and 2-but-3-en-2-yl-6,6-dimethyl-2-prop-2-enylcyclohexan-1-one, 2,2-bis(2-methyl-2-propen-1-yl)cyclohexanone, and combinations thereof.

9. The method of claim 1, wherein the at least one compound is incorporated into a perfuming composition.

10. The method of claim 9, wherein the perfuming composition comprises a malodor receptor antagonist system comprising at least one perfuming ingredient and a non-functional perfume accord.

11. The method of claim 9, wherein the perfuming composition comprises:
(i) from about 2 wt % to about 85 wt %, of a malodor receptor antagonist system comprising at least one ingredient perfuming;
(ii) from about 15 wt % to 98 wt % of a functional perfume accord comprising at least 2 perfuming ingredient(s) wherein, the accord has a tonality selected from floral, citrus and jasmine; and
(iii) optionally a non-functional perfume accord.

* * * * *